United States Patent
Edwards et al.

(10) Patent No.: US 10,576,206 B2
(45) Date of Patent: Mar. 3, 2020

(54) AUTO-INJECTORS FOR ADMINISTRATION OF A MEDICAMENT WITHIN A PREFILLED SYRINGE

(71) Applicant: kaleo, Inc., Richmond, VA (US)

(72) Inventors: Eric S. Edwards, Moseley, VA (US); Evan T. Edwards, Charlottesville, VA (US); Paul F. Meyers, Fishers, IN (US)

(73) Assignee: kaleo, Inc., Richmond, VA (US)

( * ) Notice: Subject to any disclaimer, the term of this patent is extended or adjusted under 35 U.S.C. 154(b) by 149 days.

(21) Appl. No.: 15/738,008

(22) PCT Filed: Jun. 30, 2016

(86) PCT No.: PCT/US2016/040333
§ 371 (c)(1),
(2) Date: Dec. 19, 2017

(87) PCT Pub. No.: WO2017/004345
PCT Pub. Date: Jan. 5, 2017

(65) Prior Publication Data
US 2018/0304017 A1  Oct. 25, 2018

Related U.S. Application Data

(60) Provisional application No. 62/186,939, filed on Jun. 30, 2015, provisional application No. 62/194,599, (Continued)

(51) Int. Cl.
*A61M 5/20* (2006.01)
*A61M 5/24* (2006.01)
(Continued)

(52) U.S. Cl.
CPC .......... *A61M 5/2046* (2013.01); *A61M 5/178* (2013.01); *A61M 5/20* (2013.01);
(Continued)

(58) Field of Classification Search
CPC .. A61M 5/2033; A61M 5/30; A61M 5/14284; A61M 5/20; A61M 5/3202;
(Continued)

(56) References Cited

U.S. PATENT DOCUMENTS 2,409,656 A   10/1946   Austin
2,960,087 A   11/1960   Uytenbogaart
(Continued)

FOREIGN PATENT DOCUMENTS

DE   2019296   11/1971
EP   1287840 A1   3/2003
(Continued)

OTHER PUBLICATIONS

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.
(Continued)

*Primary Examiner* — Manuel A Mendez
(74) *Attorney, Agent, or Firm* — ReavesColey PLLC

(57) ABSTRACT

An apparatus includes a housing, a carrier, and an expandable assembly. The housing defines an opening configured to selectively place a gas chamber of the housing in fluid communication with an exterior volume. The carrier is movably disposed within the housing and is coupled to a medicament container. A proximal surface of the carrier defines a portion of a boundary of the gas chamber. The expandable assembly has a first member and a second member. The first member is coupled to an elastomeric member disposed within the medicament container, and the second member includes a valve portion. The expandable assembly transitions from a collapsed configuration to an expanded configuration when the elastomeric member
(Continued)

moves within the medicament container. The valve portion moves relative to the opening when the expandable assembly transitions from the first to the second configuration, placing the gas chamber in fluid communication with the exterior volume.

20 Claims, 75 Drawing Sheets

Related U.S. Application Data filed on Jul. 20, 2015, provisional application No. 62/249,056, filed on Oct. 30, 2015.

(51) Int. Cl.
*A61M 5/32* (2006.01)
*A61M 5/31* (2006.01)
*A61M 5/178* (2006.01)

(52) U.S. Cl.
CPC ............ *A61M 5/2066* (2013.01); *A61M 5/24* (2013.01); *A61M 5/31* (2013.01); *A61M 5/3204* (2013.01); *A61M 5/326* (2013.01); *A61M 5/3221* (2013.01); *A61M 5/3234* (2013.01); *A61M 2005/206* (2013.01); *A61M 2005/2013* (2013.01); *A61M 2005/2073* (2013.01); *A61M 2005/3139* (2013.01); *A61M 2205/581* (2013.01)

(58) Field of Classification Search
CPC .... A61M 5/3204; A61M 5/2066; A61M 5/24; A61M 5/2448; A61M 5/3234; A61M 5/31596; A61M 5/2053; A61M 5/19; A61M 5/31511; A61M 5/326; A61M 5/284; A61M 5/31501; A61M 5/31513; A61M 5/1454; A61M 5/3157; A61M 5/1452; A61M 5/2046; A61M 5/2466; A61M 5/148; A61M 5/3257; A61M 5/002; A61J 1/2096; A61J 1/2089; A61J 1/20
See application file for complete search history.

(56) References Cited

U.S. PATENT DOCUMENTS

| | | |
|---|---|---|
| 3,055,362 A | 9/1962 | Uytenbogaart |
| 3,115,133 A | 12/1963 | Morando |
| 3,426,448 A | 2/1969 | Sarnoff |
| 3,563,373 A | 2/1971 | Paulson |
| 3,565,070 A | 2/1971 | Hanson et al. |
| 3,688,765 A | 9/1972 | Gasaway |
| 3,768,472 A | 10/1973 | Hodosh et al. |
| 3,795,061 A | 3/1974 | Sarnoff et al. |
| 3,797,489 A | 3/1974 | Sarnoff |
| 3,941,130 A | 3/1976 | Tibbs |
| 3,945,379 A | 3/1976 | Pritz et al. |
| 4,031,889 A | 6/1977 | Pike |
| 4,108,177 A | 8/1978 | Pistor |
| 4,124,024 A | 11/1978 | Schwebel et al. |
| 4,226,235 A | 10/1980 | Sarnoff et al. |
| 4,227,528 A | 10/1980 | Wardlaw |
| 4,258,713 A | 3/1981 | Wardlaw |
| 4,360,019 A | 11/1982 | Portner et al. |
| 4,378,015 A | 3/1983 | Wardlaw |
| 4,394,863 A | 7/1983 | Bartner |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,664,653 A | 5/1987 | Sagstetter et al. |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,755,169 A | 7/1988 | Sarnoff et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,820,286 A | 4/1989 | van der Wal |
| 4,822,340 A | 4/1989 | Kamstra |
| 4,826,489 A | 5/1989 | Haber |
| 4,853,521 A | 8/1989 | Claeys et al. |
| 4,874,381 A | 10/1989 | Vetter |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,080,649 A | 1/1992 | Vetter |
| 5,085,642 A | 2/1992 | Sarnoff et al. |
| 5,092,842 A | 3/1992 | Bechtold et al. |
| 5,092,843 A | 3/1992 | Monroe et al. |
| 5,104,380 A | 4/1992 | Holman et al. |
| 5,125,898 A | 6/1992 | Kaufhold, Jr. et al. |
| 5,139,490 A | 8/1992 | Vetter et al. |
| 5,147,311 A | 9/1992 | Pickhard |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,244,465 A | 9/1993 | Michel |
| 5,271,527 A | 12/1993 | Haber et al. |
| 5,281,198 A | 1/1994 | Haber et al. |
| 5,286,258 A | 2/1994 | Haber et al. |
| 5,295,965 A | 3/1994 | Wilmot |
| 5,298,023 A | 3/1994 | Haber et al. |
| 5,298,024 A | 3/1994 | Richmond |
| 5,312,326 A | 5/1994 | Myers et al. |
| 5,314,412 A | 5/1994 | Rex |
| 5,318,544 A | 6/1994 | Drypen et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,358,489 A | 10/1994 | Wyrick |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,394,866 A | 3/1995 | Ritson et al. |
| 5,395,345 A | 3/1995 | Gross |
| 5,399,163 A | 3/1995 | Peterson et al. |
| 5,405,362 A | 4/1995 | Kramer et al. |
| 5,417,660 A | 5/1995 | Martin |
| 5,451,210 A | 9/1995 | Kramer et al. |
| 5,466,217 A | 11/1995 | Myers et al. |
| 5,478,316 A | 12/1995 | Bitdinger et al. |
| 5,514,097 A | 5/1996 | Knauer |
| 5,514,135 A | 5/1996 | Earle |
| 5,527,287 A | 6/1996 | Miskinyar |
| 5,540,664 A | 7/1996 | Wyrick |

(56) References Cited

U.S. PATENT DOCUMENTS

| | | |
|---|---|---|
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,658,259 A | 8/1997 | Pearson et al. |
| 5,681,291 A | 10/1997 | Galli |
| 5,681,292 A | 10/1997 | Tober et al. |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,772,635 A | 6/1998 | Dastur et al. |
| 5,779,677 A | 7/1998 | Frezza |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,814,020 A | 9/1998 | Gross |
| 5,823,346 A | 10/1998 | Weiner |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,990 A | 12/1998 | Cirelli et al. |
| 5,852,590 A | 12/1998 | de la Huerga |
| 5,853,292 A | 12/1998 | Eggert et al. |
| 5,858,001 A | 1/1999 | Tsals et al. |
| 5,865,795 A | 2/1999 | Schiff et al. |
| 5,868,711 A * | 2/1999 | Kramer ............ A61B 17/3472 604/136 |
| 5,868,713 A | 2/1999 | Klippenstein |
| 5,868,721 A | 2/1999 | Marinacci |
| D407,487 S | 3/1999 | Greubel et al. |
| 5,876,380 A | 3/1999 | Manganini et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,050,977 A | 4/2000 | Adams |
| 6,056,728 A | 5/2000 | von Schuckmann |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,120,786 A | 9/2000 | Cheikh |
| 6,123,685 A * | 9/2000 | Reynolds ............ A61M 5/155 604/191 |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,223,936 B1 | 5/2001 | Jeanbourquin |
| 6,245,046 B1 | 6/2001 | Sibbitt |
| 6,258,063 B1 | 7/2001 | Haar et al. |
| 6,258,068 B1 | 7/2001 | Kirchhofer et al. |
| 6,259,654 B1 | 7/2001 | de la Huerga |
| 6,264,629 B1 | 7/2001 | Landau |
| 6,270,479 B1 | 8/2001 | Bergens et al. |
| 6,280,421 B1 | 8/2001 | Kirchhofer et al. |
| 6,312,412 B1 | 11/2001 | Saied et al. |
| 6,317,630 B1 | 11/2001 | Gross et al. |
| 6,334,070 B1 | 12/2001 | Nova et al. |
| 6,364,866 B1 | 4/2002 | Furr et al. |
| 6,371,939 B2 | 4/2002 | Bergens et al. |
| 6,383,168 B1 | 5/2002 | Landau et al. |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,419,656 B1 | 7/2002 | Vetter et al. |
| 6,425,897 B2 | 7/2002 | Overes et al. |
| 6,427,684 B2 | 8/2002 | Ritsche et al. |
| 6,428,517 B1 | 8/2002 | Hochman et al. |
| 6,428,528 B2 | 8/2002 | Sadowski |
| 6,454,746 B1 | 9/2002 | Bydlon et al. |
| 6,475,181 B1 | 11/2002 | Potter et al. |
| 6,478,771 B1 | 11/2002 | Lavi et al. |
| 6,482,186 B1 | 11/2002 | Douglas et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,599,272 B1 | 7/2003 | Hjertman et al. |
| 6,613,010 B2 | 9/2003 | Castellano |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,656,150 B2 | 12/2003 | Hill et al. |
| 6,656,163 B1 | 12/2003 | Marshall et al. |
| 6,659,980 B2 | 12/2003 | Moberg et al. |
| 6,673,035 B1 | 1/2004 | Rice et al. |
| 6,676,630 B2 | 1/2004 | Landau et al. |
| 6,679,862 B2 | 1/2004 | Diaz et al. |
| 6,689,093 B2 | 2/2004 | Landau |
| 6,692,469 B1 | 2/2004 | Weekes et al. |
| 6,702,778 B2 | 3/2004 | Hill et al. |
| 6,706,019 B1 | 3/2004 | Parker et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,657 B1 | 4/2004 | Dedig et al. |
| 6,726,661 B2 | 4/2004 | Munk et al. |

(56) References Cited

U.S. PATENT DOCUMENTS

| | | | |
|---|---|---|---|
| 6,736,796 | B2 | 5/2004 | Shekalim |
| 6,743,203 | B1 | 6/2004 | Pickhard |
| 6,743,635 | B2 | 6/2004 | Neel et al. |
| 6,749,437 | B2 | 6/2004 | Chan |
| 6,752,781 | B2 | 6/2004 | Landau et al. |
| 6,764,469 | B2 | 7/2004 | Broselow |
| 6,767,336 | B1 | 7/2004 | Kaplan |
| 6,770,052 | B2 | 8/2004 | Hill et al. |
| 6,770,056 | B2 | 8/2004 | Price et al. |
| 6,783,509 | B1 | 8/2004 | Landau et al. |
| 6,786,875 | B2 | 9/2004 | Barker et al. |
| 6,786,885 | B2 | 9/2004 | Hochman et al. |
| 6,793,646 | B1 | 9/2004 | Giambattista et al. |
| 6,803,856 | B1 | 10/2004 | Murphy et al. |
| 6,805,686 | B1 | 10/2004 | Fathallah et al. |
| 6,808,514 | B2 | 10/2004 | Schneider et al. |
| 6,809,653 | B1 | 10/2004 | Mann et al. |
| 6,817,986 | B2 | 11/2004 | Slate et al. |
| 6,830,560 | B1 | 12/2004 | Gross et al. |
| 6,839,304 | B2 | 1/2005 | Niemiec et al. |
| 6,872,200 | B2 | 3/2005 | Mann et al. |
| 6,875,195 | B2 | 4/2005 | Choi |
| 6,883,222 | B2 | 4/2005 | Landau |
| 6,923,764 | B2 | 8/2005 | Aceti et al. |
| 6,936,029 | B2 | 8/2005 | Mann et al. |
| 6,936,032 | B1 | 8/2005 | Bush, Jr. et al. |
| 6,937,150 | B2 | 8/2005 | Medema et al. |
| 6,942,646 | B2 | 9/2005 | Langley et al. |
| 6,946,299 | B2 | 9/2005 | Neel et al. |
| 6,949,082 | B2 | 9/2005 | Langley et al. |
| 6,952,604 | B2 | 10/2005 | DeNuzzio et al. |
| 6,953,445 | B2 | 10/2005 | Wilmot et al. |
| 6,953,693 | B2 | 10/2005 | Neel et al. |
| 6,958,691 | B1 | 10/2005 | Anderson et al. |
| 6,959,247 | B2 | 10/2005 | Neel et al. |
| 6,961,285 | B2 | 11/2005 | Niemiec et al. |
| 6,964,650 | B2 | 11/2005 | Alexandre et al. |
| 6,969,259 | B2 | 11/2005 | Pastrick et al. |
| 6,979,316 | B1 | 12/2005 | Rubin et al. |
| 6,979,326 | B2 | 12/2005 | Mann et al. |
| 6,985,870 | B2 | 1/2006 | Martucci et al. |
| 6,997,911 | B2 | 2/2006 | Klitmose |
| 7,014,470 | B2 | 3/2006 | Vann |
| 7,074,211 | B1 | 7/2006 | Heiniger et al. |
| 7,104,972 | B2 | 9/2006 | Moller et al. |
| 7,113,101 | B2 | 9/2006 | Peterson et al. |
| 7,116,233 | B2 | 10/2006 | Zhurin |
| 7,118,553 | B2 | 10/2006 | Scherer |
| 7,126,879 | B2 | 10/2006 | Snyder |
| 7,158,011 | B2 | 1/2007 | Brue |
| 7,299,981 | B2 | 11/2007 | Hickle et al. |
| 7,329,241 | B2 | 2/2008 | Horvath et al. |
| 7,357,790 | B2 | 4/2008 | Hommann et al. |
| 7,416,540 | B2 | 8/2008 | Edwards et al. |
| 7,465,294 | B1 | 12/2008 | Vladimirsky |
| 7,500,963 | B2 | 3/2009 | Westbye et al. |
| 7,500,967 | B2 | 3/2009 | Thorley et al. |
| 7,503,907 | B1 | 3/2009 | Lesch, Jr. |
| 7,544,188 | B2 | 6/2009 | Edwards et al. |
| 7,611,491 | B2 | 11/2009 | Pickhard |
| 7,611,495 | B1 | 11/2009 | Gianturco |
| 7,637,891 | B2 | 12/2009 | Wall |
| 7,648,482 | B2 | 1/2010 | Edwards et al. |
| 7,648,483 | B2 | 1/2010 | Edwards et al. |
| 7,654,983 | B2 | 2/2010 | De La Sema et al. |
| 7,674,246 | B2 | 3/2010 | Gillespie et al. |
| 7,678,073 | B2 | 3/2010 | Griffiths et al. |
| 7,686,788 | B2 * | 3/2010 | Freyman .......... A61M 5/14526 604/124 |
| 7,708,719 | B2 | 5/2010 | Wilmot et al. |
| 7,731,686 | B2 | 6/2010 | Edwards et al. |
| 7,731,690 | B2 | 6/2010 | Edwards et al. |
| 7,749,194 | B2 | 7/2010 | Edwards et al. |
| 7,758,550 | B2 | 7/2010 | Bollenbach et al. |
| 7,771,397 | B1 | 8/2010 | Olson |
| 7,806,866 | B2 | 10/2010 | Hommann et al. |
| 7,850,662 | B2 | 12/2010 | Veasey et al. |
| 7,871,393 | B2 | 1/2011 | Monroe |
| 7,901,377 | B1 | 3/2011 | Harrison et al. |
| 7,901,384 | B2 | 3/2011 | Kleyman et al. |
| 7,918,823 | B2 | 4/2011 | Edwards et al. |
| 7,918,832 | B2 | 4/2011 | Veasey et al. |
| 7,931,614 | B2 | 4/2011 | Gonnelli et al. |
| 7,938,802 | B2 | 5/2011 | Bicknell et al. |
| 7,938,808 | B2 | 5/2011 | Pessin |
| 7,947,017 | B2 | 5/2011 | Edwards et al. |
| 8,016,788 | B2 | 9/2011 | Edwards et al. |
| 8,021,335 | B2 | 9/2011 | Lesch, Jr. |
| 8,105,281 | B2 | 1/2012 | Edwards et al. |
| 8,105,293 | B2 | 1/2012 | Pickhard |
| 8,123,719 | B2 | 2/2012 | Edwards et al. |
| 8,162,886 | B2 | 4/2012 | Sadowski et al. |
| 8,172,082 | B2 | 5/2012 | Edwards et al. |
| 8,177,749 | B2 | 5/2012 | Slate et al. |
| 8,206,360 | B2 | 6/2012 | Edwards et al. |
| 8,221,347 | B2 | 7/2012 | Toles et al. |
| 8,231,573 | B2 | 7/2012 | Edwards et al. |
| 8,251,947 | B2 | 8/2012 | Kramer et al. |
| 8,276,583 | B2 | 10/2012 | Farieta et al. |
| 8,313,466 | B2 | 11/2012 | Edwards et al. |
| 8,361,029 | B2 | 1/2013 | Edwards et al. |
| 8,409,141 | B2 | 4/2013 | Johansen et al. |
| 8,425,462 | B2 | 4/2013 | Edwards et al. |
| 8,574,214 | B2 | 11/2013 | Kühn et al. |
| 8,608,698 | B2 | 12/2013 | Edwards et al. |
| 8,613,720 | B2 | 12/2013 | Bendek et al. |
| 8,632,504 | B2 | 1/2014 | Young |
| 8,647,306 | B2 | 2/2014 | Schwirtz et al. |
| 8,684,968 | B2 | 4/2014 | Genosar |
| 8,690,827 | B2 | 4/2014 | Edwards et al. |
| 8,728,042 | B2 | 5/2014 | Pickhard |
| 8,734,394 | B2 | 5/2014 | Adams et al. |
| 8,747,357 | B2 | 6/2014 | Stamp et al. |
| 8,900,197 | B2 | 12/2014 | Crow |
| 8,920,377 | B2 | 12/2014 | Edwards et al. |
| 8,945,048 | B2 | 2/2015 | Thorley et al. |
| 8,961,455 | B2 | 2/2015 | Holmqvist et al. |
| 8,992,477 | B2 | 3/2015 | Raday et al. |
| 9,022,980 | B2 | 5/2015 | Edwards et al. |
| 9,044,549 | B2 | 6/2015 | Niklasson |
| 9,056,170 | B2 | 6/2015 | Edwards et al. |
| 9,084,849 | B2 | 7/2015 | Edwards et al. |
| 9,149,579 | B2 | 10/2015 | Edwards et al. |
| 9,173,999 | B2 | 11/2015 | Edwards et al. |
| 9,289,563 | B2 | 3/2016 | Pickhard et al. |
| 9,345,831 | B2 | 5/2016 | Raday et al. |
| 9,352,099 | B2 | 5/2016 | Roberts et al. |
| 9,586,010 | B2 | 3/2017 | Mesa et al. |
| 9,586,011 | B2 | 3/2017 | Roberts et al. |
| 10,105,499 | B2 | 10/2018 | Schwirtz et al. |
| 2001/0005781 | A1 | 6/2001 | Bergens et al. |
| 2001/0037087 | A1 | 11/2001 | Knauer |
| 2002/0016567 | A1 | 2/2002 | Hochman et al. |
| 2002/0042596 | A1 | 4/2002 | Hartlaub et al. |
| 2002/0055711 | A1 | 5/2002 | Lavi et al. |
| 2002/0076679 | A1 | 6/2002 | Aman |
| 2002/0079326 | A1 | 6/2002 | Fuchs |
| 2002/0095120 | A1 | 7/2002 | Larsen et al. |
| 2002/0096543 | A1 | 7/2002 | Juselius |
| 2003/0028145 | A1 | 2/2003 | Duchon et al. |
| 2003/0040717 | A1 | 2/2003 | Saulenas et al. |
| 2003/0105430 | A1 | 6/2003 | Lavi et al. |
| 2003/0106824 | A1 | 6/2003 | Wilmot et al. |
| 2003/0120222 | A1 | 6/2003 | Vaillancourt |
| 2003/0132128 | A1 | 7/2003 | Mazur |
| 2003/0233070 | A1 | 12/2003 | De La Serna et al. |
| 2004/0015125 | A1 | 1/2004 | Alexandre et al. |
| 2004/0019326 | A1 | 1/2004 | Gilbert et al. |
| 2004/0024361 | A1 | 2/2004 | Fago et al. |
| 2004/0024367 | A1 | 2/2004 | Gilbert |
| 2004/0039336 | A1 | 2/2004 | Amark et al. |
| 2004/0039337 | A1 | 2/2004 | Letzing |
| 2004/0039368 | A1 | 2/2004 | Reilly et al. |
| 2004/0054327 | A1 | 3/2004 | Gillespie, III |

(56) References Cited

U.S. PATENT DOCUMENTS

| | | |
|---|---|---|
| 2004/0073169 A1 | 4/2004 | Amisar et al. |
| 2004/0092874 A1 | 5/2004 | Mazidji |
| 2004/0094146 A1 | 5/2004 | Schiewe et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1 | 10/2004 | Atterbury et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0049561 A1 | 3/2005 | Hommann et al. |
| 2005/0062603 A1 | 3/2005 | Fuerst et al. |
| 2005/0090781 A1 | 4/2005 | Baba et al. |
| 2005/0090782 A1 | 4/2005 | Marshall et al. |
| 2005/0101912 A1 | 5/2005 | Faust et al. |
| 2005/0134433 A1 | 6/2005 | Sweeney, II |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0192530 A1 | 9/2005 | Castellano |
| 2005/0192534 A1 | 9/2005 | Wolbring et al. |
| 2005/0197654 A1 | 9/2005 | Edman et al. |
| 2005/0203466 A1 | 9/2005 | Hommann et al. |
| 2005/0222539 A1 | 10/2005 | Gonzales et al. |
| 2005/0261742 A1 | 11/2005 | Nova et al. |
| 2005/0267403 A1 | 12/2005 | Landau et al. |
| 2005/0273059 A1 | 12/2005 | Mernoe et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129089 A1 | 6/2006 | Stamp |
| 2006/0129090 A1 | 6/2006 | Moberg et al. |
| 2006/0173408 A1 | 8/2006 | Wyrick |
| 2006/0184133 A1 | 8/2006 | Pessin |
| 2006/0189938 A1 | 8/2006 | Hommann et al. |
| 2006/0200077 A1 | 9/2006 | Righi et al. |
| 2006/0223027 A1 | 10/2006 | Smith et al. |
| 2006/0235354 A1 | 10/2006 | Kaal et al. |
| 2006/0247578 A1 | 11/2006 | Arguendas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0021720 A1 | 1/2007 | Guillermo |
| 2007/0074722 A1 | 4/2007 | Giroux et al. |
| 2007/0100288 A1 | 5/2007 | Bozeman et al. |
| 2007/0129686 A1 | 6/2007 | Daily et al. |
| 2007/0135767 A1 | 6/2007 | Gillespie, III et al. |
| 2007/0173772 A1 | 7/2007 | Liversidge |
| 2007/0184847 A1 | 8/2007 | Hansen et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0265568 A1 | 11/2007 | Tsals et al. |
| 2008/0111685 A1 | 5/2008 | Olson et al. |
| 2008/0147006 A1 | 6/2008 | Brunnberg et al. |
| 2008/0154200 A1 | 6/2008 | Lesch |
| 2008/0171995 A1 | 7/2008 | Vitullo et al. |
| 2008/0188798 A1 | 8/2008 | Weber |
| 2008/0208114 A1 | 8/2008 | Landau et al. |
| 2008/0228143 A1 | 9/2008 | Stamp |
| 2008/0255513 A1 | 10/2008 | Kaal et al. |
| 2008/0262443 A1 | 10/2008 | Hommann et al. |
| 2009/0093759 A1 | 4/2009 | Judd et al. |
| 2009/0192486 A1 | 7/2009 | Wilmot et al. |
| 2009/0209939 A1 | 8/2009 | Verespej et al. |
| 2009/0221962 A1 | 9/2009 | Kaal et al. |
| 2009/0240200 A1 | 9/2009 | Heneveld et al. |
| 2009/0318361 A1 | 12/2009 | Noera et al. |
| 2010/0010454 A1 | 1/2010 | Marshall et al. |
| 2010/0049125 A1 | 2/2010 | James et al. |
| 2010/0137808 A1 | 6/2010 | Wilmot et al. |
| 2010/0152659 A1 | 6/2010 | Streit et al. |
| 2010/0160894 A1 | 6/2010 | Julian et al. |
| 2010/0185148 A1 | 7/2010 | Gillespie, III et al. |
| 2010/0185178 A1 | 7/2010 | Sharp et al. |
| 2010/0280460 A1 | 11/2010 | Markussen |
| 2011/0046565 A1 | 2/2011 | Radmer et al. |
| 2011/0060274 A1 | 3/2011 | Kuhn |
| 2011/0092954 A1 | 4/2011 | Jennings |
| 2011/0098655 A1 | 4/2011 | Jennings et al. |
| 2011/0144594 A1 | 6/2011 | Sund et al. |
| 2011/0201999 A1 | 8/2011 | Cronenberg |
| 2011/0202011 A1 | 8/2011 | Wozencroft |
| 2011/0213314 A1 | 9/2011 | Guillermo |
| 2011/0270220 A1 | 11/2011 | Genosar |
| 2011/0319864 A1 | 12/2011 | Beller et al. |
| 2012/0046613 A1 | 2/2012 | Plumptre |
| 2012/0056019 A1 | 3/2012 | Renz et al. |
| 2012/0101446 A1 | 4/2012 | Heald |
| 2012/0101475 A1 | 4/2012 | Wilmot et al. |
| 2012/0103328 A1 | 5/2012 | Smith et al. |
| 2012/0107783 A1 | 5/2012 | Julian et al. |
| 2012/0116319 A1 | 5/2012 | Grunhut |
| 2012/0125951 A1 | 5/2012 | Leak et al. |
| 2012/0130318 A1 | 5/2012 | Young |
| 2012/0143144 A1 | 6/2012 | Young |
| 2012/0172804 A1 | 7/2012 | Plumptre |
| 2012/0172817 A1 | 7/2012 | Bruggemann et al. |
| 2012/0191049 A1 | 7/2012 | Harms et al. |
| 2012/0209200 A1 | 8/2012 | Jones et al. |
| 2012/0233834 A1 | 9/2012 | Szechinski et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2012/0283648 A1 | 11/2012 | Veasey et al. |
| 2012/0283651 A1 | 11/2012 | Veasey et al. |
| 2012/0283662 A1 | 11/2012 | MacDonald et al. |
| 2012/0289906 A1 | 11/2012 | Jones et al. |
| 2012/0289929 A1 | 11/2012 | Boyd et al. |
| 2012/0310168 A1 | 12/2012 | Plumptre et al. |
| 2012/0310206 A1 | 12/2012 | Kouyoumjian et al. |
| 2012/0323186 A1 | 12/2012 | Karlsen et al. |
| 2012/0325865 A1 | 12/2012 | Forstreuter et al. |
| 2012/0330244 A1 | 12/2012 | Helmer et al. |
| 2013/0060231 A1 | 3/2013 | Adlon et al. |
| 2013/0060232 A1 | 3/2013 | Adlon et al. |
| 2013/0079718 A1 | 3/2013 | Shang et al. |
| 2013/0079725 A1 | 3/2013 | Shang et al. |
| 2013/0096512 A1 | 4/2013 | Ekman et al. |
| 2013/0110050 A1 | 5/2013 | Boyd et al. |
| 2013/0131602 A1 | 5/2013 | Kemp et al. |
| 2013/0138049 A1 | 5/2013 | Kemp et al. |
| 2013/0150800 A1 | 6/2013 | Kemp et al. |
| 2013/0172822 A1 | 7/2013 | Ekman et al. |
| 2013/0204199 A1 | 8/2013 | Hourmand et al. |
| 2013/0218074 A1 | 8/2013 | Holmqvist et al. |
| 2013/0226084 A1 | 8/2013 | Samandi et al. |
| 2013/0236872 A1 | 9/2013 | Laurusonis et al. |
| 2013/0245562 A1 | 9/2013 | Kouyoumjian et al. |
| 2013/0266919 A1 | 10/2013 | Baker et al. |
| 2013/0274662 A1 | 10/2013 | Hourmand et al. |
| 2013/0274707 A1 | 10/2013 | Wilmot et al. |
| 2013/0296796 A1 | 11/2013 | Hourmand et al. |
| 2013/0317427 A1 | 11/2013 | Brereton et al. |
| 2013/0317477 A1 | 11/2013 | Edwards et al. |
| 2013/0317480 A1 | 11/2013 | Reber et al. |
| 2014/0025014 A1 | 1/2014 | Radmer et al. |
| 2014/0031760 A1 | 1/2014 | Mercer et al. |
| 2014/0046259 A1 | 2/2014 | Reber et al. |
| 2014/0081234 A1 | 3/2014 | Eggert et al. |

(56) References Cited

U.S. PATENT DOCUMENTS

| | | | |
|---|---|---|---|
| 2014/0103075 A1 | 4/2014 | Bennison et al. |
| 2014/0114250 A1 | 4/2014 | DeSalvo et al. |
| 2014/0128840 A1 | 5/2014 | Rao et al. |
| 2014/0135705 A1 | 5/2014 | Hourmand et al. |
| 2014/0257185 A1 | 9/2014 | Bachmann et al. |
| 2014/0257241 A1 | 9/2014 | Sutkin et al. |
| 2015/0051538 A1 | 2/2015 | Hata et al. |
| 2015/0165129 A1 | 6/2015 | Row et al. |
| 2015/0174325 A1 | 6/2015 | Young et al. |
| 2015/0238695 A1 | 8/2015 | Edwards et al. |
| 2015/0283323 A1 | 10/2015 | Young et al. |
| 2016/0015907 A1 | 1/2016 | Edwards et al. |
| 2016/0022909 A1 | 1/2016 | Edwards et al. |
| 2016/0045670 A1 | 2/2016 | Edwards et al. |
| 2016/0074584 A1 | 3/2016 | Carmel et al. |
| 2016/0114110 A1 | 4/2016 | Kerns |
| 2016/0184521 A1 | 6/2016 | Edwards et al. |
| 2016/0193412 A1 | 7/2016 | Cereda et al. |
| 2016/0250414 A1 | 9/2016 | Edwards et al. |
| 2016/0354556 A1 | 12/2016 | Zucker et al. |
| 2017/0246393 A1 | 8/2017 | Genosar |
| 2017/0290982 A1 | 10/2017 | Edwards et al. |
| 2018/0008774 A1 | 1/2018 | Edwards et al. |
| 2018/0204636 A1 | 7/2018 | Edwards et al. |
| 2018/0296760 A1 | 10/2018 | Csenar et al. |
| 2018/0304018 A1 | 10/2018 | Blondino et al. |
| 2019/0009025 A1 | 1/2019 | Chakrabarti et al. |
| 2019/0009027 A1 | 1/2019 | Edwards et al. |
| 2019/0151548 A1 | 5/2019 | Edwards et al. |
| 2019/0175837 A1 | 6/2019 | Edwards et al. |
| 2019/0275253 A1 | 9/2019 | Edwards et al. |
| 2019/0282763 A1 | 9/2019 | Edwards et al. |

FOREIGN PATENT DOCUMENTS

| | | |
|---|---|---|
| EP | 1462134 A1 | 9/2004 |
| EP | 1518575 A1 | 3/2005 |
| EP | 1712178 A2 | 10/2006 |
| FR | 1514210 | 2/1968 |
| FR | 2506161 | 11/1982 |
| FR | 2509615 | 1/1983 |
| FR | 2700959 | 2/1993 |
| GB | 2490807 | 11/2012 |
| MX | PA04009276 | 1/2005 |
| WO | WO 91/04760 | 4/1991 |
| WO | WO 93/02720 | 2/1993 |
| WO | WO 95/13838 | 5/1995 |
| WO | WO 95/26009 | 9/1995 |
| WO | WO 95/35126 | 12/1995 |
| WO | WO 98/52632 | 11/1998 |
| WO | WO 99/10031 | 3/1999 |
| WO | WO 2001/024690 | 4/2001 |
| WO | WO 2001/026020 | 4/2001 |
| WO | WO 2001/041849 | 6/2001 |
| WO | WO 2001/088828 | 11/2001 |
| WO | WO 2001/093926 | 12/2001 |
| WO | WO 2002/083205 | 10/2002 |
| WO | WO 2002/083212 | 10/2002 |
| WO | WO 2003/011378 | 2/2003 |
| WO | WO 2003/013632 | 2/2003 |
| WO | WO 2003/095001 | 11/2003 |
| WO | WO 2003/097133 | 11/2003 |
| WO | WO 2004/047890 | 6/2004 |
| WO | WO 2004/047891 | 6/2004 |
| WO | WO 2004/047892 | 6/2004 |
| WO | WO 2004/047893 | 6/2004 |
| WO | WO 2004/054644 | 7/2004 |
| WO | WO 2005/050526 | 6/2005 |
| WO | WO 2005/070481 | 8/2005 |
| WO | WO 2005/077441 | 8/2005 |
| WO | WO 2006/058426 | 6/2006 |
| WO | WO 2006/109778 | 10/2006 |
| WO | WO 2006/125692 | 11/2006 |
| WO | WO 2008/005315 | 1/2008 |
| WO | WO 2008/148864 | 12/2008 |
| WO | WO 2009/095735 | 8/2009 |
| WO | WO 2010/033806 | 3/2010 |
| WO | WO 2011/157930 | 12/2011 |
| WO | WO 2013/044172 | 3/2013 |
| WO | WO 2016/160341 A1 | 10/2016 |
| WO | WO 2017/033193 A2 | 3/2017 |
| WO | WO 2017/034618 A1 | 3/2017 |
| WO | WO 2017/210011 | 12/2017 |
| WO | WO 2018/078121 | 5/2018 |

OTHER PUBLICATIONS

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.

Examination Report for British Patent Application No. GB 0708523.6, dated Dec. 8, 2008.

Office Action for JP2007-543005, dated Feb. 1, 2010.

Examination Report for British Patent Application No. GB 0822532.8, dated Jan. 21, 2009.

Examination Report for British Patent Application No. GB 0822532.8, dated May 21, 2009.

Office Action for U.S. Appl. No. 11/562,061, dated Feb. 3, 2009.

Office Action for U.S. Appl. No. 11/758,393, dated May 13, 2009.

Search Report and Written Opinion for International Patent Application No. PCT/US07/84891 dated Sep. 15, 2008, 7 pages.

Office Action for U.S. Appl. No. 12/138,987, dated Oct. 5, 2009.

Office Action for U.S. Appl. No. 13/053,451, dated Nov. 15, 2012.

Office Action for U.S. Appl. No. 13/090,392, dated Feb. 29, 2012.

International Search Report and Written Opinion for International Patent Application No. PCT/US06/03415, dated Jul. 13, 2006, 10 pages.

Office Action for U.S. Appl. No. 12/119,016, dated Nov. 3, 2011.

Examination Report for Australian Patent Application No. 2012211307, dated Mar. 3, 2014, 3 pages.

Supplementary Search Report for European Patent Application No. 12740010.9, dated Aug. 5, 2014.

International Search Report and Written Opinion for International Application No. PCT/US2012/022675, dated May 25, 2012.

Third Party Observations filed in European Patent Application No. 07864490.3, dated Aug. 22, 2016.

International Search Report and Written Opinion for International Application No. PCT/US2016/40333 dated Dec. 12, 2016.

Office Action for Canadian Patent Application No. 2,825,600, dated Feb. 1, 2018.

Extended European Search Report for European Patent Application No. 16818770.6, dated Jul. 3, 2019.

\* cited by examiner

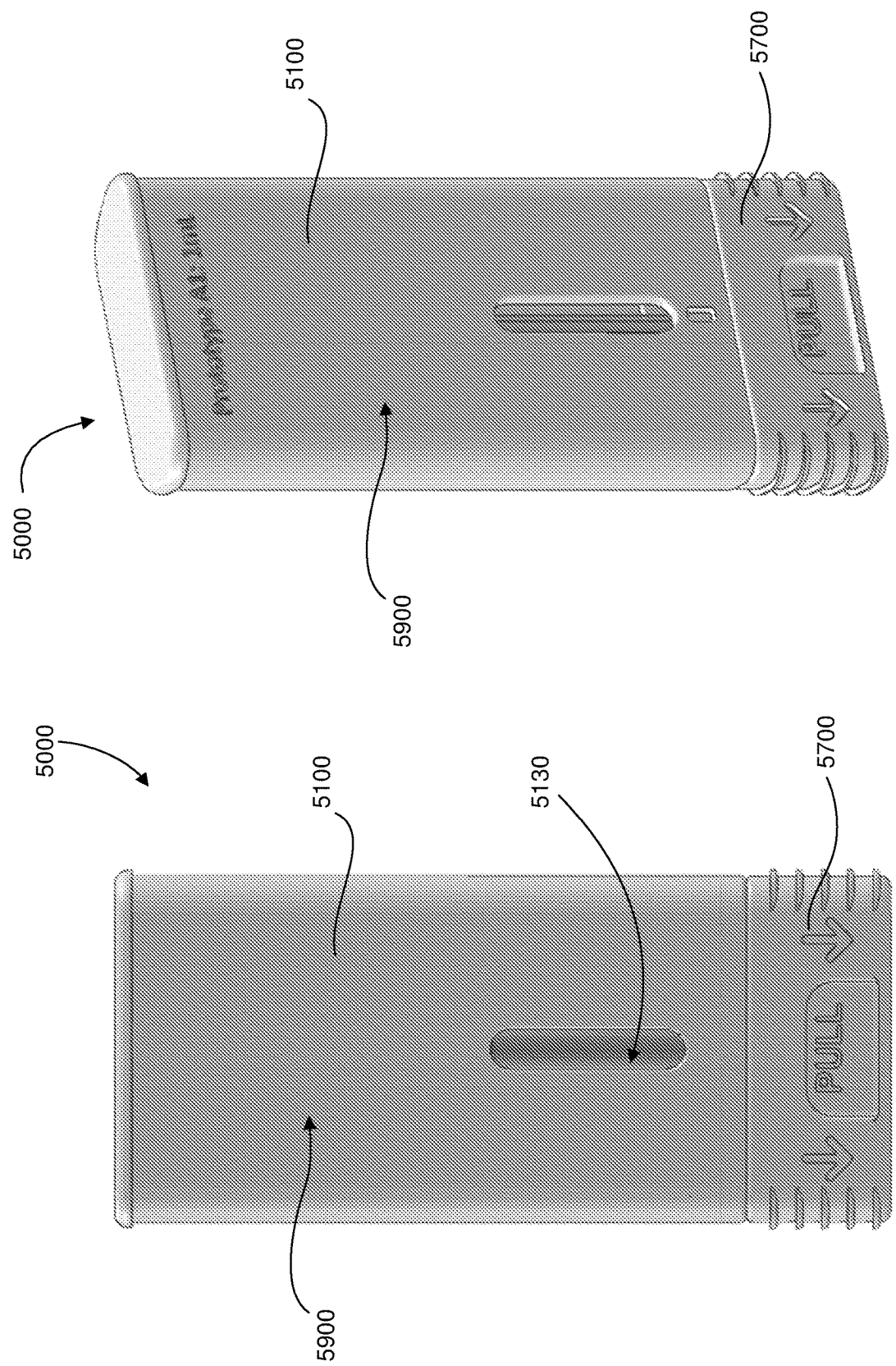

AUTO-INJECTORS FOR ADMINISTRATION OF A MEDICAMENT WITHIN A PREFILLED SYRINGE

CROSS-REFERENCE TO RELATED APPLICATIONS

This application is a U.S. national stage filing under 35 U.S.C. § 371 of International. Application No. PCT/US2016/40333, entitled "AUTO-INJECTORS FOR ADMINISTRATION OF A MEDICAMENT WITHIN A PREFILLED SYRINGE," filed Jun. 30, 2016, which claims benefit of priority to U.S. Provisional Application Ser. No. 62/186,939, entitled "Auto-Injectors for Administration of a Medicament Within a Prefilled Syringe," filed Jun. 30, 2015, 62/194,599, entitled "Auto-Injectors for Administration of a Medicament Within a Prefilled Syringe," filed Jul. 20, 2015, and 62/249,056, entitled "Auto-Injectors for Administration of a Medicament Within a Prefilled Syringe," filed Oct. 30, 2015, each of which is incorporated herein by reference in its entirety.

BACKGROUND

The embodiments described herein relate to medicament delivery devices. More particularly, the embodiments described herein relate to medicament delivery devices for delivery of medicaments contained within a prefilled syringe.

Known prefilled syringes are commonly used to contain and inject medicaments. Known prefilled syringes include a syringe body, often constructed from glass, within which a medicament is contained. The distal end portion of some known prefilled syringes includes a staked needle (i.e., a needle that is permanently coupled to the syringe body during manufacture), the end of which is disposed within a needle cover to maintain the sterility of the needle prior to use. Other known prefilled syringes include a Luer fitting or adapted such that the distal end portion of the syringe body can be coupled to a needle. The proximal end portion of the syringe body of known prefilled syringes includes a plunger (usually constructed from an elastomer) that defines a portion of the container closure, and that can be moved within the syringe body to inject the medicament. The proximal end portion also includes a flange to allow the user to grasp the syringe body and manually apply a force to a piston to move the plunger, thereby causing injection of the medicament.

Although prefilled syringes can be cost effective devices for storing and delivering medicaments, known methods for using prefilled syringes include manually inserting the needle into the body followed by manually applying the injection force. Moreover, upon completion of the injection, known methods include covering the needle to avoid needle sticks. Thus, known prefilled syringes are often used by healthcare professionals that are trained in such procedures. To facilitate the self-administration of medicaments contained in prefilled syringes, some known autoinjectors have been adapted to contain prefilled syringes. In this manner, the autoinjector provides a source of stored energy for inserting the needle and/or injecting the medicament.

Known autoinjectors, however, are often designed for a medicament container having a specific size and/or shape, and are therefore often not configured to receive known prefilled syringes. For example, using a prefilled syringe within a known autoinjector can often result in high forces being applied to the flange of the syringe body during the insertion operation, which can lead to breakage of the syringe flange or body. Moreover, because many known prefilled syringes include a staked needle that is in fluid communication with the medicament, applying a force to the plunger during storage and/or during an insertion operation is undesirable. For example, the application of a force against the plunger during storage, which can result, for example, when a spring-loaded member is placed in contact with the plunger, can cause in leakage of the medicament. As another example, the application of a force against the plunger during a needle insertion event can result in the injection of the medicament before the needle is inserted to the desired location. Similarly stated, some known auto-injectors are not configured to control the force applied to the plunger within the syringe body during storage and/or needle insertion.

Known autoinjectors configured to incorporate a prefilled syringe often include a spring-based actuation system that moves a piston rod to insert the needle and inject the medicament. The size (e.g., length) of such known systems, however, can be larger than desired because of the need to incorporate the piston rod.

Moreover, known medicaments or therapeutic substances are formulated to include high molecular weight compounds, compounds with complex molecular structures, living cells, and/or biologics. Such medicaments often have a very high viscosity (e.g., greater than about 100 centipoise at room temperature), which must be accommodated by the delivery system. Accordingly, many know auto-injectors that accommodate a prefilled syringe may not be able to provide sufficient force and/or develop the desired flow rate for effective delivery.

Thus, a need exists for improved methods and devices for delivering medicaments contained within a prefilled syringe.

SUMMARY

Medicament delivery devices for administration of medicaments contained within a prefilled syringe are described herein. In some embodiments, an apparatus includes a housing, a carrier, and an expandable assembly. A side wall of the housing defines an opening configured to selectively place a gas chamber defined by the housing in fluid communication with an exterior volume. The carrier is configured to be movably disposed within the housing and coupled to a medicament container. A proximal surface of the carrier defines a portion of a boundary of the gas chamber. The expandable assembly has a first member and a second member. The first member is coupled to an elastomeric member disposed within the medicament container, and the second member includes a valve portion. The expandable assembly is configured to transition from a collapsed configuration to an expanded configuration when the elastomeric member moves within the medicament container. The valve portion moves relative to the opening when the expandable assembly transitions from the first configuration to the second configuration to place the gas chamber in fluid communication with the exterior volume.

In some embodiments, an apparatus includes a housing, an energy storage member, a medicament container, and a carrier. The housing has a housing length along a longitudinal axis. The energy storage member is disposed within the housing, and is configured to produce a force when the actuated. The medicament container is disposed within the housing, and has a container length. The medicament container has an elastomeric member disposed therein, and is coupled to a needle. The carrier is coupled to the medicament container. The carrier is configured to move from a first carrier position to a second carrier position in response to the force produced by the energy storage member such that the needle moves from a first needle position, in which the needle is disposed within the housing, to a second needle position, in which a portion of the needle extends from the housing. The elastomeric member is configured to move within the medicament container from a first position to a second position to convey a medicament from the medicament container when the carrier is in the second carrier position. A ratio of the housing length to the container length is less than about 1.5. In some embodiments, the medicament container and needle are further configured to be moved from the second position to a third position whereby the needle is retracted up within the housing.

BRIEF DESCRIPTION OF THE DRAWINGS

FIGS. 45-48 are various views of a medicament delivery device (or models thereof) according to an embodiment.

DETAILED DESCRIPTION

Figure 1:
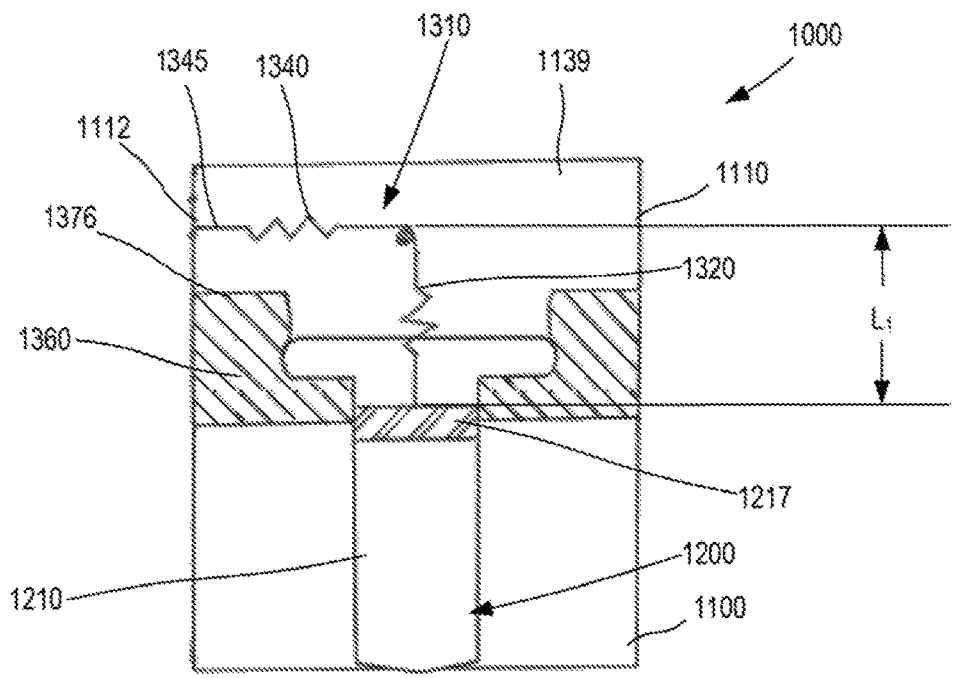
FIGS. 1-3 are schematic illustrations of a medicament delivery device according to an embodiment, in a first configuration, a second configuration, and a third configuration, respectively.

Medicament delivery devices for administration of medicaments contained within a prefilled syringe are described herein. In some embodiments, an apparatus includes an apparatus includes a housing, a carrier, and an expandable assembly. A side wall of the housing defines an opening configured to selectively place a gas chamber defined by the housing in fluid communication with an exterior volume. The carrier is configured to be movably disposed within the housing and coupled to a medicament container. A proximal surface of the carrier defines a portion of a boundary of the gas chamber. The expandable assembly has a first member and a second member. The first member is coupled to an elastomeric member disposed within the medicament container, and the second member includes a valve portion. The expandable assembly is configured to transition from a collapsed configuration to an expanded configuration when the elastomeric member moves within the medicament container. The valve portion moves relative to the opening when the expandable assembly transitions from the first configuration to the second configuration to place the gas chamber in fluid communication with the exterior volume.

In some embodiments, an apparatus includes a housing, an energy storage member, a medicament container, and a carrier. The housing has a housing length along a longitudinal axis. The energy storage member is disposed within the housing, and is configured to produce a force when the actuated. The medicament container is disposed within the housing, and has a container length. The medicament container has an elastomeric member disposed therein, and is coupled to a needle. The carrier is coupled to the medicament container. The carrier is configured to move from a first carrier position to a second carrier position in response to the force produced by the energy storage member such that the needle moves from a first needle position, in which the needle is disposed within the housing, to a second needle position, in which a portion of the needle extends from the housing. The elastomeric member is configured to move within the medicament container from a first position to a second position to convey a medicament from the medicament container when the carrier is in the second carrier position. A ratio of the housing length to the container length is less than about 1.5.

In some embodiments, an apparatus includes a housing, a medicament container, and a gas vent assembly. The housing defines a gas chamber, and has a side wall that defines an opening that selectively places the gas chamber in fluid communication with an exterior volume. The medicament container has an elastomeric member disposed therein. The elastomeric member is configured to move within the medicament container from a first position to a second position to convey a medicament from the medicament container in response to a pressurized gas being conveyed into the gas chamber. A proximal surface of the elastomeric member defines a portion of a boundary of the gas chamber. The gas vent assembly has a first member and a second member. The first member is coupled to the elastomeric member, and the second member coupled within the opening. The first member of the gas vent assembly is configured to move with the elastomeric member such that the second member moves relative to the opening to fluidically couple the gas chamber with the exterior volume when the elastomeric member is in the second position.

In some embodiments, an apparatus includes a housing defining a gas chamber, a medicament container assembly disposed within the housing, a retraction spring, an expandable assembly, and an energy storage member. The medicament container assembly includes a needle fluidically coupled to the medicament container. The medicament container assembly is configured to move between a first needle position, in which the needle is disposed within the housing, and a second needle position in which a portion of the needle extends from the housing. The retraction spring is configured to bias the medicament container assembly towards the first needle position. The expandable assembly is configured to transition between a collapsed configuration and an expanded configuration. The expandable assembly includes a proximal member and a distal member. The energy storage member is configured to produce a pressurized gas within the gas chamber. The pressurized gas exerts a force to move the medicament container assembly from the first needle position to the second needle position and to move an elastomeric member within the medicament container to convey a medicament from the medicament container via the needle. The proximal member of the expandable assembly is configured to actuate a valve to release the pressurized gas from the gas chamber when the expandable assembly is transitioned from the collapsed configuration to the expanded configuration.

In some embodiments, an apparatus includes a housing (that defines a gas chamber), an energy storage member, a first medicament container assembly, and a second medicament container assembly. The energy storage member is disposed within the housing, and is configured to produce a pressurized gas within the gas chamber. Each of the first medicament container assembly and the second medicament container assembly is disposed within the housing. The first medicament container assembly includes a first container body and a first elastomeric member disposed within the first container body. The first medicament container assembly includes a first needle coupled to a distal end portion of the first container body. The first medicament container assembly is configured to move within the housing in response to a force exerted by the pressurized gas such that the first needle moves from within the housing to an exterior volume outside of the housing. The first elastomeric member is configured to move within the first container body to convey a first medicament contained therein in response to the force. The second medicament container assembly includes a second container body and a second elastomeric member disposed within the second container body. The second medicament container assembly includes a second needle coupled to a distal end portion of the second container body. The second medicament container assembly is configured to move within the housing in response to the force such that the second needle moves from within the housing to the exterior volume. The second elastomeric member is configured to move within the second container body to convey a second medicament contained therein in response to the force.

In some embodiments, an apparatus includes a housing (that defines a gas chamber), an energy storage member, a first medicament container assembly, and a second medicament container assembly. The energy storage member is disposed within the housing, and is configured to produce a pressurized gas within the gas chamber. Each of the first medicament container assembly and the second medicament container assembly is disposed within the housing. The first medicament container assembly includes a first carrier and a first container body. The first carrier is coupled to the first container body, and is configured to move within the housing to convey a first medicament in response to a force exerted by the pressurized gas. A proximal surface of the first carrier defines a first portion of a boundary of the gas chamber. The second medicament container assembly includes a second carrier and a second container body. The second carrier is coupled to the second container body and is configured to move within the housing to convey a second medicament in response to the force exerted by the pressurized gas. A proximal surface of the second carrier defines a second portion of the boundary of the gas chamber.

In some embodiments, an apparatus includes a housing, a first medicament container, a second medicament container, and a movable member. The first medicament container and the second medicament container are configured to move within the housing between a first position and a second position in response to a force produced by an energy storage member. The first medicament container includes a first plunger disposed therein and a first needle. The second medicament container includes a second plunger disposed therein and a second needle. The movable member is configured to move within the housing in response to the force to insert the first needle and the second needle into a target tissue in the same operation. A portion of the movable member is configured to deform when the first needle and the second needle are inserted such that at least a portion of the force is exerted upon the first plunger and the second plunger. In response to the portion of the force, the first plunger is configured to move within the first medicament container to convey a first medicament from the first medicament container via the first needle, and the second plunger is configured to move within the second medicament container to convey a second medicament from the second medicament container via the second needle.

In some embodiments, an apparatus includes a housing (that defines a gas chamber), an energy storage member, a medicament container assembly, and a carrier. The energy storage member is disposed within the housing, and is configured to produce a pressurized gas within the gas chamber. The medicament container assembly is disposed within the housing, and includes a container body and an elastomeric member disposed within the container body. The medicament container assembly includes a needle coupled to a distal end portion of the container body. The carrier is coupled to the medicament container assembly. A proximal surface of the carrier defines a portion of a boundary of the gas chamber. The carrier is configured to move within the housing from a first carrier position to a second carrier position in response to a force exerted by the pressurized gas on the proximal surface of the carrier. The carrier includes a first seal member and a second seal member. The first seal member is in sliding contact with an inner surface of the housing to fluidically isolate the gas chamber. The second seal member is in contact with a proximal end portion of the container body to fluidically isolate the gas chamber. The first seal member in a fixed position relative to the second seal member.

In some embodiments, a method includes placing a housing of a medical injector into contact with a target location. The housing defines a gas chamber, and encloses an energy storage member, a first medicament container assembly, and a second medicament container assembly. The first medicament container assembly includes a first container body, a first elastomeric member disposed within the first container body, and a first needle coupled to a distal end portion of the first container body. The first needle is disposed within the housing. The second medicament container assembly includes a second container body, a second elastomeric member disposed within the second container body, and a second needle coupled to a distal end portion of the second container body. The second needle is disposed within the housing. The method includes actuating the energy storage member to produce a pressurized gas within the gas chamber of the housing. The first medicament container assembly moves within the housing in response to a force exerted by the pressurized gas such that the first needle moves from within the housing to an exterior volume outside of the housing. The first elastomeric member moves within the first container body to convey a first medicament contained therein in response to the force. The second medicament container assembly moves within the housing in response to the force exerted by the pressurized gas such that the second needle moves from within the housing to the exterior volume. The second elastomeric member moves within the second container body to convey a second medicament contained therein in response to the force.

As used herein, the term "medicament" includes any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like.

The term "about" when used in connection with a referenced numeric indication means the referenced numeric indication plus or minus up to 10 percent of that referenced numeric indication. For example, "about 100" means from 90 to 110.

In a similar manner, term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10% of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

As used in this specification and the appended claims, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

The term "fluid-tight" is understood to encompass hermetic sealing (i.e., a seal that is gas-impervious) as well as a seal that is only liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at pressures of less than about 5 psig, less than about 10 psig, less than about 20 psig, less than about 30 psig, less than about 50 psig, less than about 75 psig, less than about 100 psig, and all values in between. Any residual fluid layer that may be present on a portion of a wall of a container after component defining a "substantially-fluid tight" seal are moved past the portion of the wall are not considered as leakage.

Figure 2:
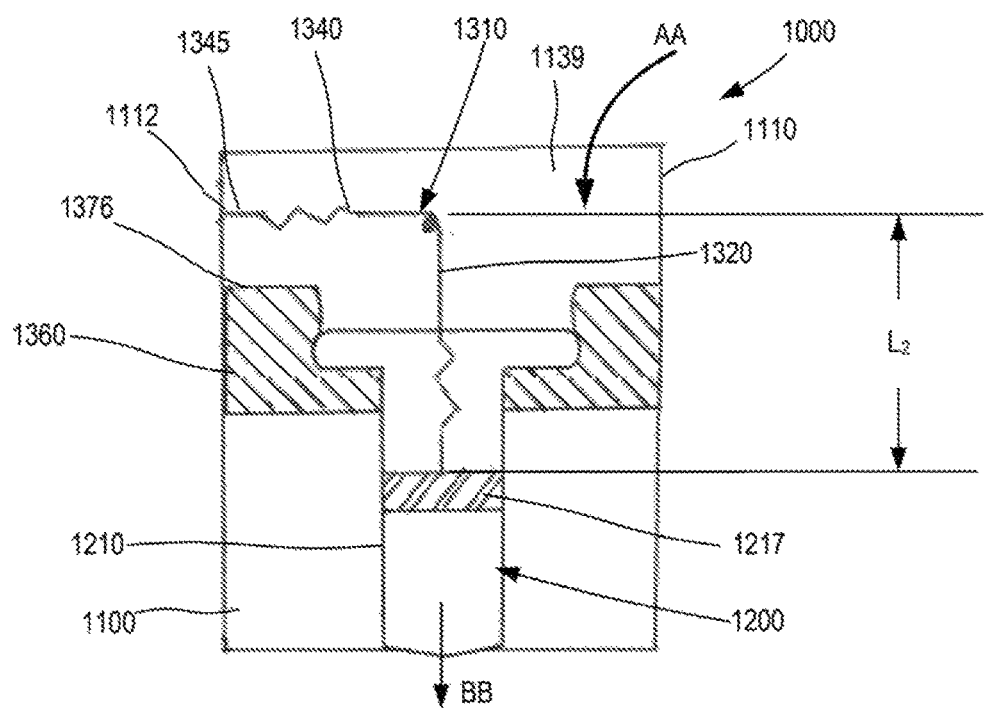
Figure 3:
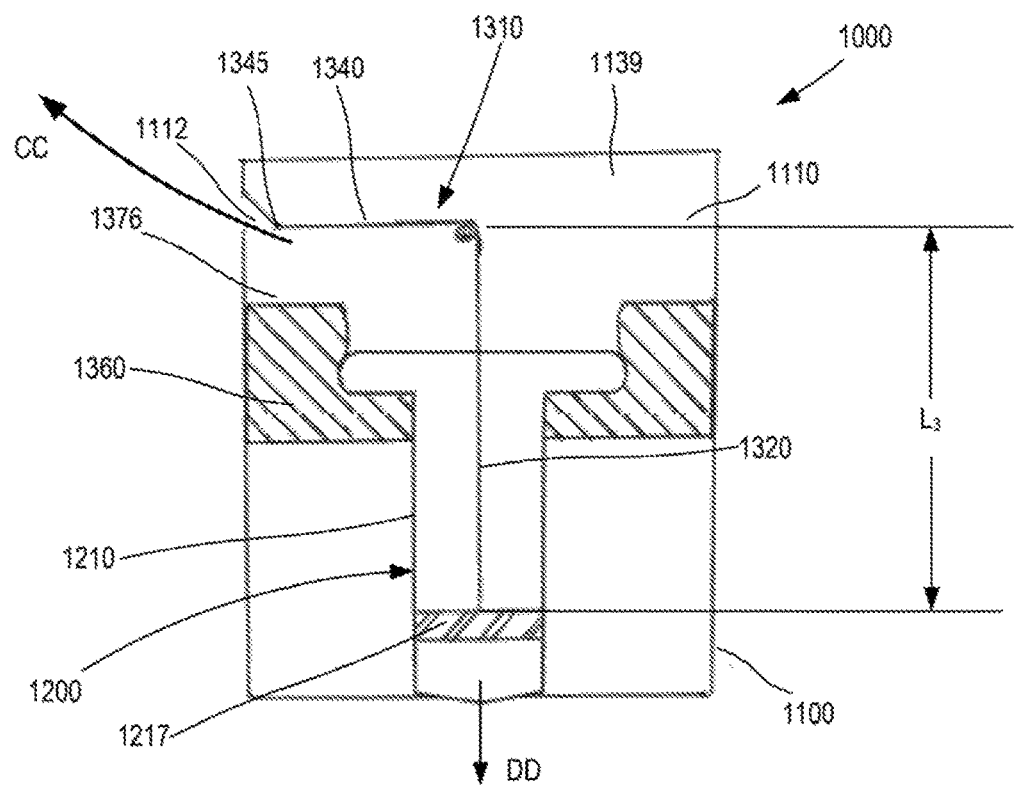

FIGS. 1-3 are schematic illustrations of a medicament delivery device 1000 according to an embodiment. The medicament delivery device 1000 includes a housing 1100, a carrier 1360 disposed within the housing 1100, a medicament container assembly 1200, and an expandable assembly 1320. The housing 1100 defines a gas chamber 1139 that receives a pressurized gas from a suitable energy storage member (not shown). The gas chamber 1139 can be of any suitable size and shape, and can be, for example, a portion of the volume defined by the housing 1100 within which a portion of the medicament container assembly 1200 and/or the carrier 1360 is disposed. The housing includes a side wall 1110 that defines an opening 1112 (see FIG. 3) that can selectively place the gas chamber 1139 in fluid communication with an exterior volume. As described in more detail below, the opening 1112 and the valve portion 1145 of the expandable assembly allow the gas pressure within the gas chamber 1139 to be reduced upon completion of the injection event.

The housing 1100 can be any suitable size, shape, or configuration and can be made of any suitable material. For example, in some embodiments, the housing 1100 is an assembly of multiple parts formed from a plastic material and defines a substantially rectangular shape when assembled. In other embodiments, the housing 1100 can have a substantially cylindrical shape.

The medicament container assembly 1200 has a container body 1210 that defines a volume that contains (i.e., is filled with or partially filled with) a medicament. The distal end portion of the medicament container body 1210 includes a neck or opening through which the medicament can be delivered. In some embodiments, the medicament container assembly 1200 can include a delivery member coupled to the container body 1210, and through which the medicament is delivered. For example, in some embodiments, the medicament container assembly 1200 includes a needle, a nozzle, a mouthpiece, or the like. In some embodiments, the medicament container assembly 1200 can be a prefilled syringe having a needle staked thereto, of the types shown and described herein.

The medicament container assembly 1200 includes an elastomeric member 1217 (i.e., a plunger) that seals the medicament within the container body 1210. The elastomeric member 1217 is configured to move within the container body to inject the medicament from the medicament container assembly 1200. The elastomeric member 1217 can be of any design or formulation suitable for contact with the medicament. For example, the elastomeric member 1217 can be formulated to minimize any reduction in the efficacy of the medicament that may result from contact (either direct or indirect) between the elastomeric member 1217 and the medicament. For example, in some embodiments, the elastomeric member 1217 can be formulated to minimize any leaching or out-gassing of compositions that may have an undesired effect on the medicament. In other embodiments, the elastomeric member 1217 can be formulated to maintain its chemical stability, flexibility and/or sealing properties when in contact (either direct or indirect) with the medicament over a long period of time (e.g., for up to six months, one year, two years, five years or longer).

The carrier 1360 is disposed within the housing, and is configured to be coupled to a medicament container assembly 1200. The carrier 1360 can be coupled to the medicament container assembly 1200 in any suitable manner. For example, as shown, in some embodiments, the carrier 1360 can define an opening within which a portion of the container body 1210 can be received. The carrier 1360 can define, for example, a shoulder, protrusion, or other structure that couples to a portion of the container body 1210 (e.g., a flange, a side wall or the like). In other embodiments, the carrier 1360 can surround only a portion of the container body 1210. In yet other embodiments, the carrier 1360 can be constructed from multiple components that are joined together (e.g., via a hinged joint, a mechanical fastener or the like) to surround and/or be coupled to the medicament container assembly 1200.

The carrier 1360 includes a proximal surface 1376 that defines a portion of a boundary of the gas chamber 1139. In this manner, when a pressurized gas is conveyed into the gas chamber 1139, the pressure therein will produce a force on the proximal surface 1376 and/or the elastomeric member 1217. As described below, by selectively venting the gas chamber 1139 via the opening 1112, movement of the carrier 1360 within the housing 1100 and/or the elastomeric member 1217 within the container body 1210 can be controlled. In some embodiments, the carrier 1360 includes a seal portion or a seal member that produces a fluid-tight seal between the carrier 1360 and the housing 1100. Accordingly, when pressurized gas flows into gas chamber 1139, the volume between the proximal surface 1376 of the carrier 1360 and the proximal end portion of the housing 1100 is sealed (i.e., is fluidically isolated from the exterior volume).

In some embodiments, the carrier 1360 is configured to move within the housing 1100 from a first carrier position to a second carrier position in response to a pressurized gas being conveyed into the gas chamber 1139. In such embodiments, movement of the carrier 1360 can produce movement of the medicament container assembly 1200 to facilitate delivery of the medicament therein.

The expandable assembly 1310 includes a first member 1320 and a second member 1340. The first member 1320 is coupled to the elastomeric member 1217. In this manner, movement of the elastomeric member 1217 within the container body 1210 (i.e., to expel the medicament therefrom) produces movement of at least a portion of the first member 1320. Similarly stated, when the elastomeric member 1217 is exposed to a force (e.g., produced by the pressurized gas within the gas chamber 1139 acting directly on a proximal surface of the elastomeric member 1217), movement of the elastomeric member 1217 exerts a force on the first member 1320 of the expandable assembly 1310. Specifically, distal movement of the elastomeric member 1217 can produce a tensile force on the first member 1320.

The first member 1320 can be coupled to the elastomeric member 1217 in any suitable manner. For example, in some embodiments, the first member 1320 can be threadedly coupled to the elastomeric member 1217. In other embodiments, the first member 1320 can be press fit into a bore of or about a protrusion of the elastomeric member 1217. In yet other embodiments, the first member 1320 can be bonded to the elastomeric member 1217 via an adhesive, a weld process, or the like.

The second member 1340 includes a valve portion 1345. In some embodiments, the valve portion 1345 can be coupled within and/or in proximity to the opening 1112. Thus, as described below, when the expandable assembly 1310 transitions from a first (or collapsed) configuration to a second (or expanded) configuration, the valve portion 1345 can move relative to the opening 1112 to place the gas chamber 1139 in fluid communication with the exterior volume. Specifically, prior to use the medicament delivery device 1000 is in a first configuration, as shown in FIG. 1. When the medicament delivery device 1000 is in its first configuration, the elastomeric member 1217 is disposed proximally within the container body 1210, and the medicament container assembly 1200 contains a dose of medicament. Further, the expandable assembly 1310 is in its first (or collapsed) configuration. When in its collapsed configuration the expandable assembly 1310 has a first size, as indicated by the length $L_1$ of the first member 1320.

When the medicament delivery device 1000 is actuated, a pressurized gas flows into the gas chamber 1139, as shown by the arrow AA in FIG. 2. The pressure within the gas chamber 1139 exerts a force on the proximal surface of the carrier 1360 and on the elastomeric member 1217. The force causes the elastomeric member 1217 to move distally within the container body 1210, as shown by the arrow BB, thereby expelling the medicament therefrom. As the elastomeric member 1217 moves, the attachment between the first member 1320 and the elastomeric member 1217 begins to expand the expandable assembly 1310. As shown, as the expandable assembly 1310 transitions from its first configuration, it has a second size, as indicated by the length $L_2$ of the first member 1320. The second size is larger than the first size.

The continued movement of the elastomeric member 1217, as shown by the arrow DD in FIG. 3, causes the expandable assembly 1310 to transition from its first (or collapsed) configuration to its second (or expanded) configuration. As shown, when the expandable assembly 1310 is in its second configuration, it has a third size, as indicated by the length $L_3$ of the first member 1320. The third size is larger than the second size. During this transition, the valve portion 1345 of the second member 1340 moves relative to the opening 1112, thereby placing the gas chamber 1139 in fluid communication with the exterior volume. In this manner, the pressurized gas (and thus the pressure) within the gas chamber 1139 can be released, as shown by the arrow CC, as a function of the position of the elastomeric member 1217 within the container body 1210. In this manner, further movement of the elastomeric member 1217 within the container body 1210 (produced by the pressurized gas) can be stopped when a desired dose volume has been expelled.

Each of the first member 1320 or the second member 1340 can be constructed from any suitable material to accommodate the desired expansion of the expandable member 1310. For example, in some embodiments, each of the first member 1320 or the second member 1340 can be constructed from a resilient material (i.e., a material that elastically deforms and stores energy therein when exposed to a force). For example, in some embodiments, each of the first member 1320 or the second member 1340 can be a spring. In other embodiments, each of the first member 1320 or the second member 1340 can be constructed from rigid (i.e., substantially non-deformable) material. In such embodiments, the expansion of the expandable assembly 1310 can be achieved by relative movement between the first member 1320 and the second member 1340. In some embodiments, for example, the first member 1320 and the second member 1340 can be in a nested configuration.

Although the medicament delivery device 1000 is shown as including the carrier 1360 to facilitate coupling the medicament container assembly 1200 within the housing 1100, in other embodiments, a medicament delivery device can be devoid of a carrier. For example, in some embodiments, the medicament container assembly 1200 (e.g., a prefilled syringe) can be sealingly coupled within the housing 1100 without a carrier.

In some embodiments, a gas-powered medicament delivery device can produce a compact device, in which the outer dimensions of the housing is not substantially larger than the length of the medicament container disposed therein. For example, as shown and described herein, in some embodiments, a medicament delivery device can be devoid of a mechanical linkage that exerts or transfers a force to an elastomeric member to expel a medicament from a medicament container therein. Similarly stated, in some embodiments, a medicament delivery device can be devoid of mechanical linkages (rams, rods) that transfer force to the elastomeric member. Rather, as shown above with respect to the device 1000, in some embodiments, the elastomeric member can exert a force onto a member (e.g., an expandable member) to provide control over the delivery. Such medicament delivery devices (or medicament delivery mechanisms) are considered to be "pistonless" systems. As one example, in a pistonless, gas-powered auto-injector, the force exerted by the gas can move the medicament container relative to the housing and similarly, can move the elastomeric member relative to (e.g., within) the medicament container. In some embodiments, by not including a movable mechanism, a piston, and/or the like, a height of the medical injector 1000 can be reduced relative to, for example, the height of a device that includes a rigid, single length piston.

For example, any of the medicament delivery devices described herein can include any suitable "pistonless" design, such as those described in International Patent Application No. PCT/US16/23995, entitled "DEVICES AND METHODS FOR DELIVERING A LYOPHILIZED MEDICAMENT," filed on Mar. 24, 2016, which is incorporated herein by reference in its entirety.

In some embodiments, the characteristics of the medicament, the medicament container and the needle are such that the force required to achieve the desired injection is not possible via manual injection. Accordingly, in some embodiments a device can include an energy storage member configured to produce the desired force (and/or pressure within the medicament container) to deliver the medicament. For example, in certain circumstances, the pressure of the medicament within a needle-based medicament container can be modeled by the Hagen-Poiseuille law, as indicated below:

$$P = (8 * \mu * L * Q)/(\Pi * R^4) \quad (1)$$

where P is the pressure of the medicament within the medicament container, $\mu$ is the viscosity of the medicament, L is the length of the needle (not shown), Q is the flow rate of the medicament through the needle, and R is the radius of the lumen defined by the needle. Because the pressure (and/or force) required to inject a high viscosity fluid through a small-bore needle is proportional to the inverse of the radius of the lumen of the needle to the fourth power, the pressure of the medicament within the medicament container necessary to achieve the desired flow rate can, at times, be relatively high. By including a gas-based energy storage member, the desired pressure can be achieved.

In some embodiments, the energy storage member can be configurable to include various amounts of stored energy without changing the size of the energy storage member. In such embodiments, therefore, a high force (e.g., to inject viscous medicaments) can be achieved in the same packaging that is used for lower viscosity medicaments. For example, in some embodiments, the energy storage member can be a compressed gas cylinder having any desired pressure (and thus, mass) of gas therein. Accordingly, the pressure and/or force can be achieved to complete the operations described herein, regardless of the medicament.

In such embodiments, the use of a non-mechanical energy storage member (e.g., gas, propellant, magnetic, electronic or the like) can produce a sufficiently high force to produce the desired pressure within the medicament container to produce the desired injection. For example, in such embodiments having a larger diameter, the amount of force needed to produce a desired internal pressure increases significantly. In some embodiments, any of the medicament delivery devices shown herein can include a gas-based energy storage system configured to produce a gas pressure (e.g., within the gas chamber) of between about 200 psi and about 2700 psi. In some embodiments, any of the injectors shown herein can include a gas-based energy storage system configured to produce a gas pressure of about 200 psi, 300 psi, 400 psi, 500 psi, 600 psi, 700 psi, 800 psi, 900 psi, 1100 psi, 1200 psi, 1300 psi, 1500 psi, 1700 psi, 1900 psi, 2100 psi, 2300 psi, 2500 psi, or 2700 psi. The gas pressure can be produced by any suitable mechanism, such as, for example, by puncturing a compressed gas container, releasing a propellant (e.g., hydrofluoroalkane), releasing a liquefied gas, triggering a chemical reaction, or the like.

Figure 4:
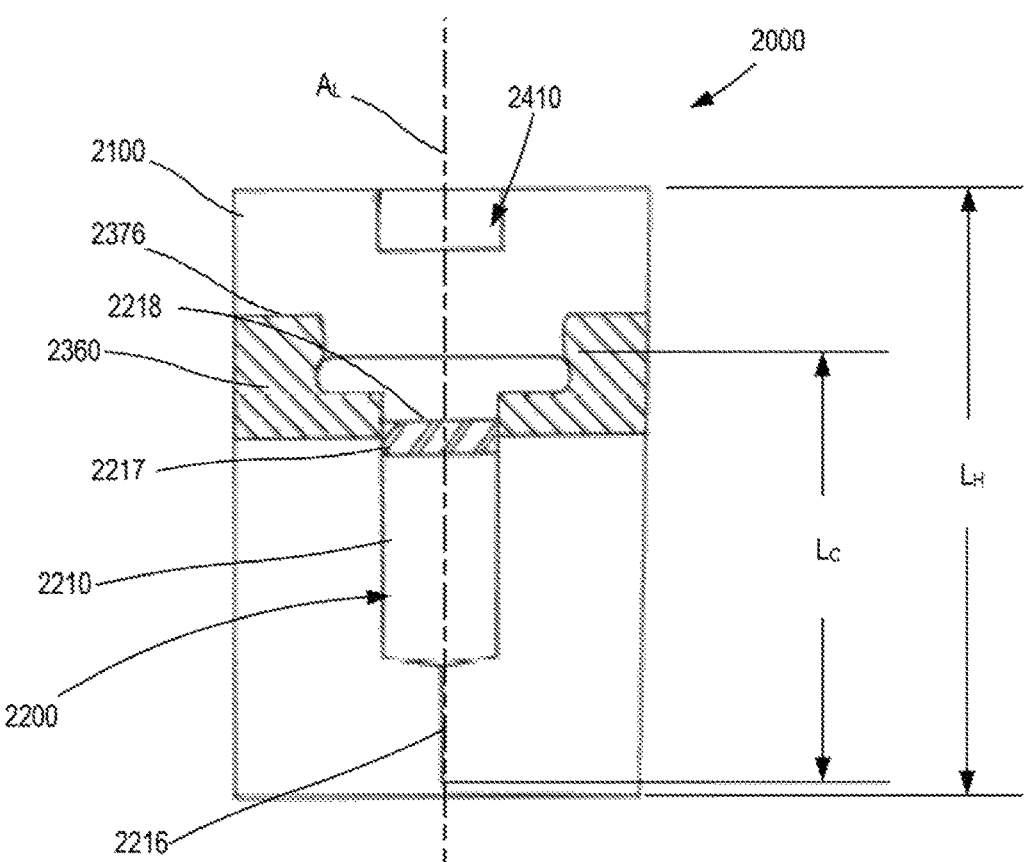
FIGS. 4-6 are schematic illustrations of a medicament delivery device according to an embodiment, in a first configuration, a second configuration, and a third configuration, respectively.
Figure 5:
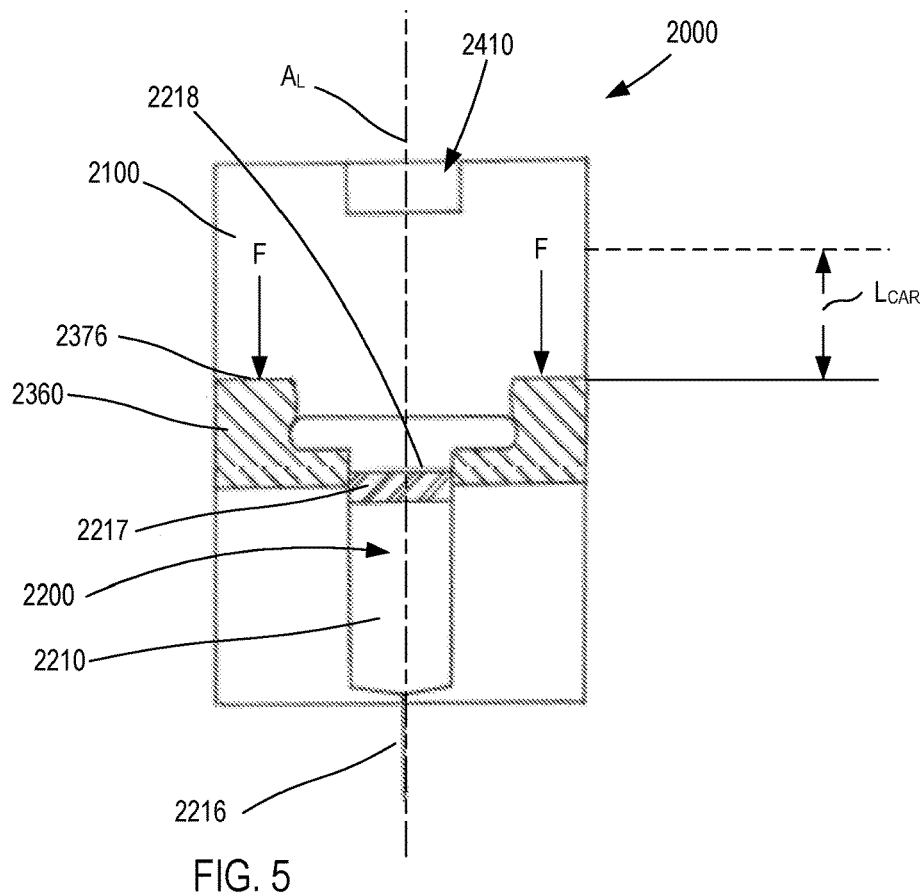
Figure 6:
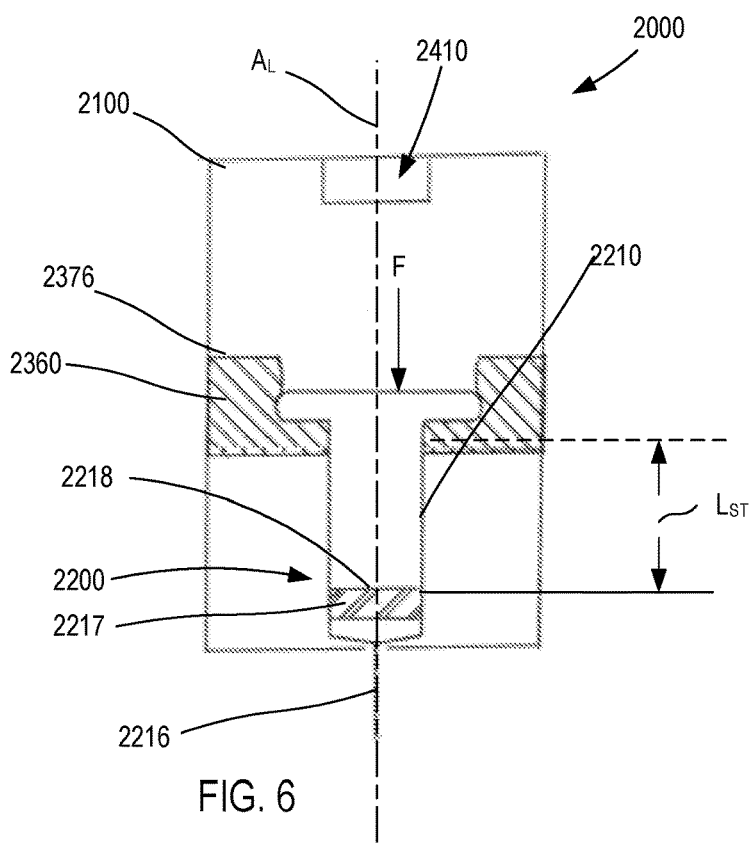

FIGS. 4-6 are schematic illustrations of a medicament delivery device 2000 according to an embodiment. The medicament delivery device 2000 includes a housing 2100, an energy storage member 2410, a carrier 2360, and a medicament container assembly 2200. The housing 2100 contains the energy storage member 2410, the carrier 2360, and at least a portion of the medicament container assembly 2200. The housing 2100 can be any suitable size, shape, or configuration. As shown, the housing 2100 has housing length $H_L$ defined along a longitudinal axis $A_L$ of the housing. Moreover, the housing 2100 can be made of any suitable material. For example, in some embodiments, the housing 2100 is an assembly of multiple parts formed from a plastic material and defines a substantially rectangular shape when assembled. In other embodiments, the housing 2100 can have a substantially cylindrical shape.

The energy storage member 2410 is disposed within the housing 2100, and is configured to produce a force F (see FIGS. 5 and 6) to convey the contents of the medicament container assembly 2200 when the energy storage member 2410 is actuated to release a potential energy stored therein. The energy storage member 2410 can be any suitable member or device that stores potential energy and, when actuated, releases the energy to produce a force. For example, the energy storage member 2410 (and any of the energy storage members described herein) can be any of a gas container, a chemical energy storage member, a spring, a magnetic, or an electrical energy storage member.

The medicament container assembly 2200 has a container body 2210 that defines a volume that contains (i.e., is filled with or partially filled with) a medicament. The distal end portion of the medicament container body 2210 includes a needle 2216 through which the medicament can be delivered. The needle 2216 can be any suitable needle having any suitable diameter and length. For example, in some embodiments, the needle 2216 is a 29-gauge needle having a length of approximately 0.5 inches. In some embodiments, the medicament container assembly 2200 can be a prefilled syringe having the needle 2216 staked thereto. As shown in FIG. 4, the medicament container assembly has a length $L_C$ (from the flange to the distal tip of the needle 2216).

The medicament container assembly 2200 includes an elastomeric member 2217 (i.e., a plunger) that seals the medicament within the container body 2210. The elastomeric member 2217 is configured to move within the container body to inject the medicament from the medicament container assembly 2200. The elastomeric member 2217 can be of any design or formulation suitable for contact with the medicament. For example, the elastomeric member 2217 can be formulated to minimize any reduction in the efficacy of the medicament that may result from contact (either direct or indirect) between the elastomeric member 2217 and the medicament. For example, in some embodiments, the elastomeric member 2217 can be formulated to minimize any leaching or out-gassing of compositions that may have an undesired effect on the medicament. In other embodiments, the elastomeric member 2217 can be formulated to maintain its chemical stability, flexibility and/or sealing properties when in contact (either direct or indirect) with the medicament over a long period of time (e.g., for up to six months, one year, two years, five years or longer).

The carrier 2360 is movably disposed within the housing, and is configured to be coupled to the medicament container assembly 2200. The carrier 2360 can be coupled to the medicament container assembly 2200 in any suitable manner. For example, as shown, in some embodiments, the carrier 2360 can define an opening within which a portion of the container body 2210 can be received. The carrier 2360 can define, for example, a shoulder, protrusion, or other structure that couples to a portion of the container body 2210 (e.g., a flange, a side wall or the like). In other embodiments, the carrier 2360 can surround only a portion of the container body 2210. In yet other embodiments, the carrier 2360 can be constructed from multiple components that are joined together (e.g., via a hinged joint, a mechanical fastener or the like) to surround and/or be coupled to the medicament container assembly 2200.

The carrier 2360 includes a proximal surface 2376 upon which a force F produced by the energy storage member 2410 can act. In this manner, when the medicament delivery device 2000 is actuated, the carrier 2360 moves within the housing 2100 from a first carrier position (FIG. 4) to a second carrier position (FIG. 5). As shown in FIG. 5, movement of the carrier 2360 in the distal direction moves the medicament container assembly 2200 in a like manner and distance. Specifically, when the carrier 2360 is in the first carrier position (FIG. 4), the needle 2216 is in a first needle position, in which the needle 2216 is disposed within the housing 2100. When the carrier 2360 is in the second carrier position (FIG. 5), the needle 2216 is in a second needle position, in which a portion of the needle 2216 is disposed outside of the housing 2100. The length of the exposed portion of the needle 2216 is dependent on the distance the carrier 2360 moves. As shown in FIG. 5, the distance between the first carrier position and the second carrier position (the carrier distance) is $L_{CAR}$.

After the carrier 2360 is in the second carrier position (and the needle 2216 is exposed), continued application of the force F from the energy storage member 2410 causes movement of the elastomeric member 2217 within the container body 2210. In the manner, the medicament can be expelled from the container body 2210. Similarly stated, when the proximal surface 2218 of the elastomeric member 2217 is exposed to the force F movement of the elastomeric member 2217 conveys the medicament from the container body 2210.

Moreover, the medicament container assembly 2200 and the energy storage member 2410 can be collectively configured such that the elastomeric member 2217 travels a desired distance within the container body 2210 during a delivery event. This distance is referred to as the "stroke," and is shown as $L_{ST}$ in FIG. 6. In some embodiments, the travel of the elastomeric member 2217 can be controlled or limited by deactivating the energy storage member 2410 (e.g., for an electronic- or magnetic-based energy storage member). In other embodiments, the travel of the elastomeric member 2217 can be controlled or limited by releasing a pressure from within the housing 2100, similar the gas vent mechanisms described herein. In this manner, the medicament delivery device 2200 can be configured to provide a desired fill volume and delivery volume. For example, in some embodiments the medicament container assembly 2200 can be a prefilled syringe and can be purchased and/or acquired with a given fill volume.

In some embodiments, the device 2000 is configured as a compact device such that a ratio of the housing length $H_L$ to the container length $H_C$ is less than about 1.5. In other embodiments, the device 2000 is configured such that a ratio of the housing length $H_L$ to the container length $H_C$ is less than about 1.25. In yet other embodiments, the device 2000 is configured such that a ratio of the housing length $H_L$ to the container length $H_C$ is less than about 1.1.

In some embodiments, the device 2000 is configured as a compact device such that a ratio of the housing length $H_L$ to a sum of the container length $H_C$, the carrier distance $L_{CAR}$, and the stroke $L_{ST}$ is less than about 1.1. In other embodiments, the device 2000 is configured such that a ratio of the housing length $H_L$ to a sum of the container length $H_C$, the carrier distance $L_{CAR}$, and the stroke $L_{ST}$ is less than about 1.0. In yet other embodiments, the device 2000 is configured such that a ratio of the housing length $H_L$ to a sum of the container length $H_C$, the carrier distance $L_{CAR}$, and the stroke $L_{ST}$ is less than about 0.9.

In some embodiments, the medicament delivery device 2000 includes a retraction mechanism coupled to any one of the carrier 2360 or the medicament container assembly 2200 to retract the needle 2216 back into the housing 2100 after delivery of the medicament. For example, in some embodiments, the medicament delivery device 2000 includes a spring (not shown) that moves the carrier 2360, and thus the medicament container assembly 2200 back towards the first needle position after delivery of the medicament.

Figure 7:
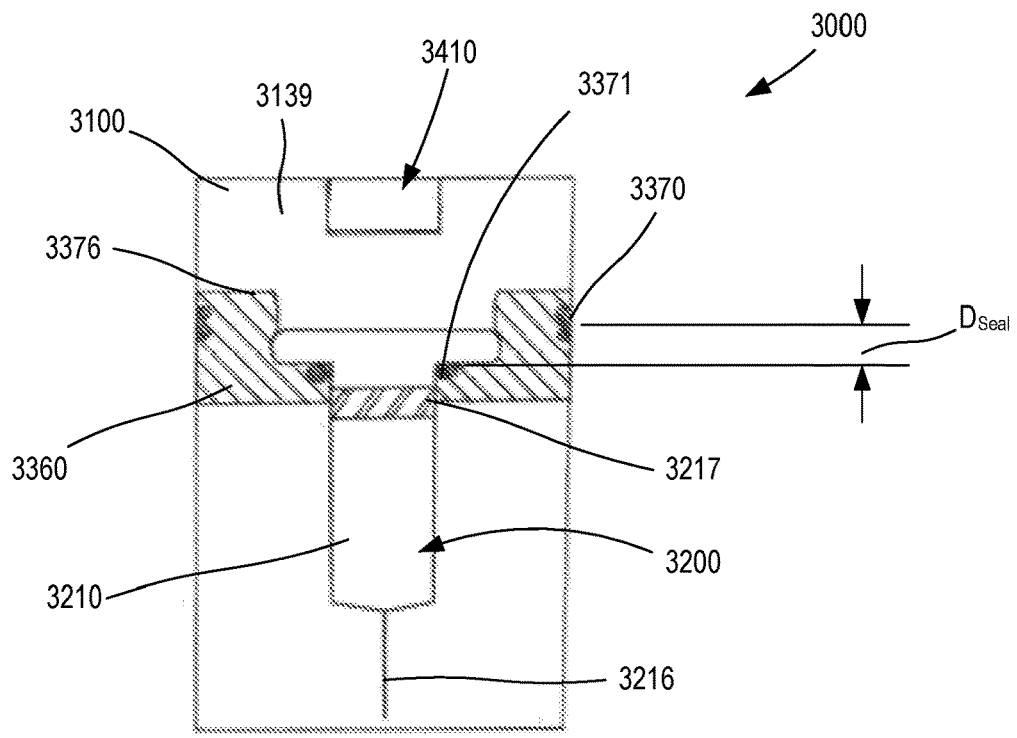
FIGS. 7 and 8 are schematic illustrations of a medicament delivery device according to an embodiment, in a first configuration and a second configuration, respectively.
Figure 8:
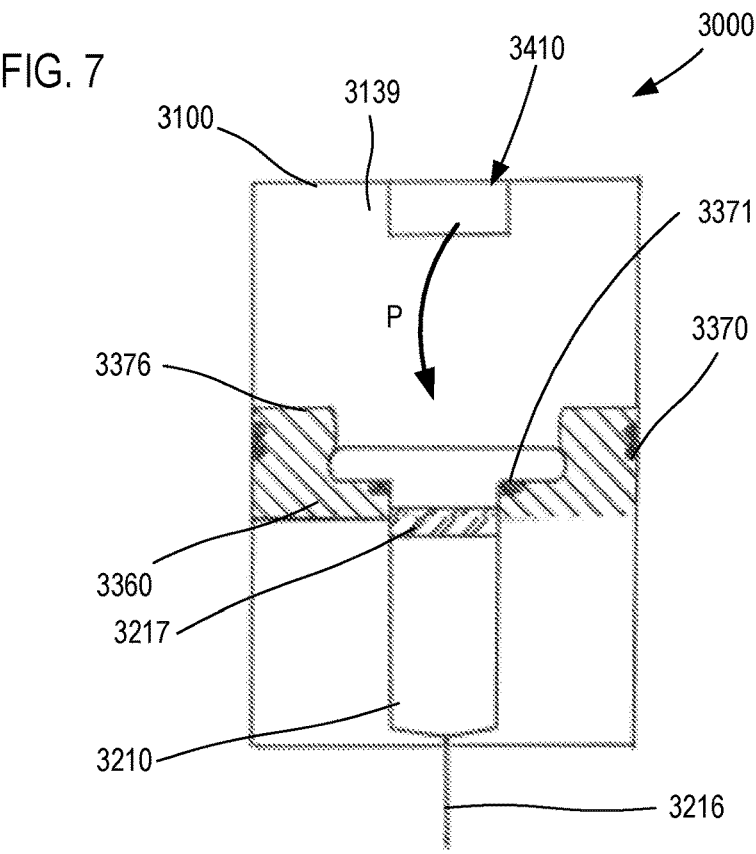
Figure 9:
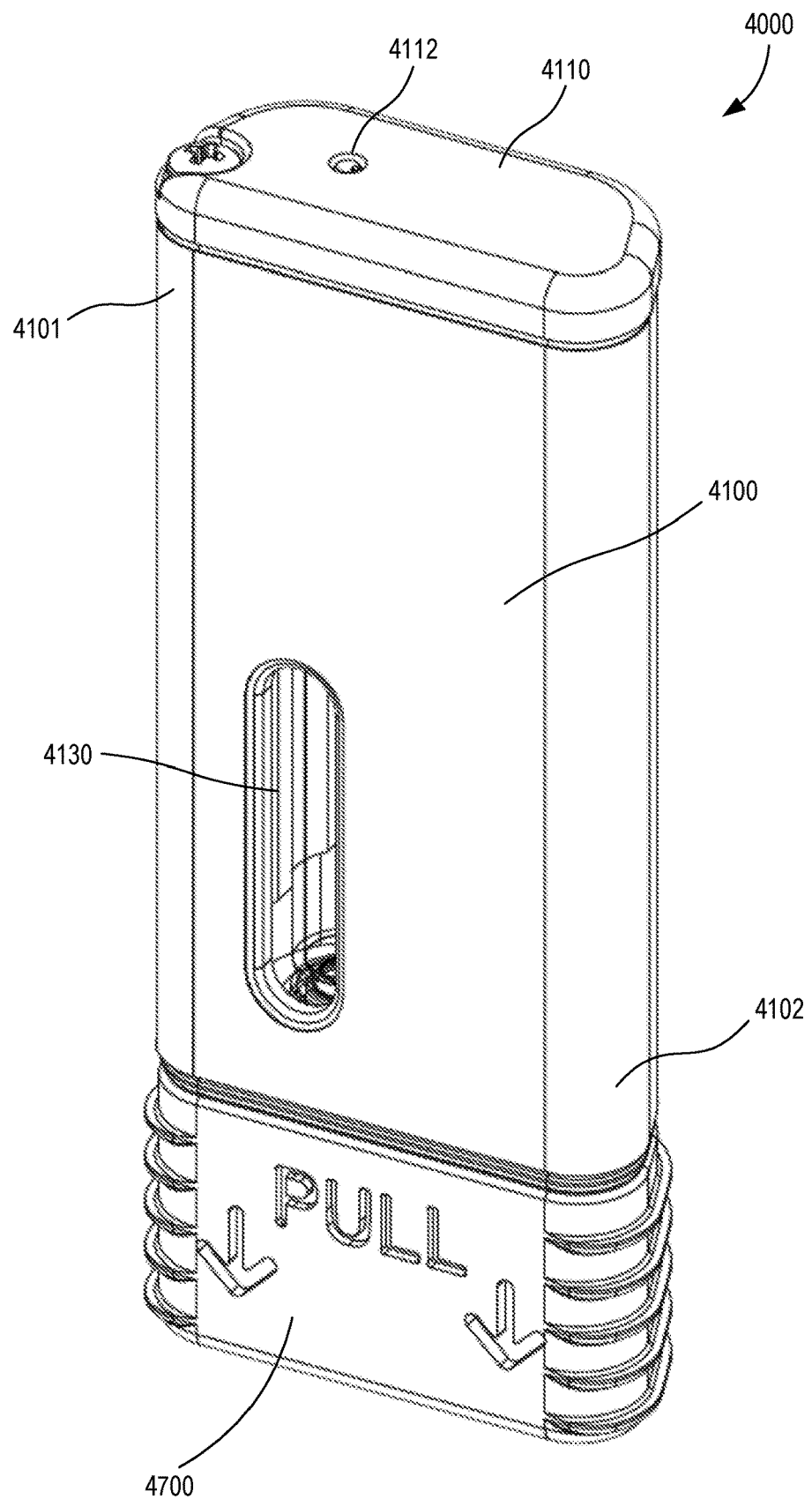
FIGS. 9 and 10 are perspective front and rear views, respectively, of a medical injector according to an embodiment, in a first configuration.
Figure 10:
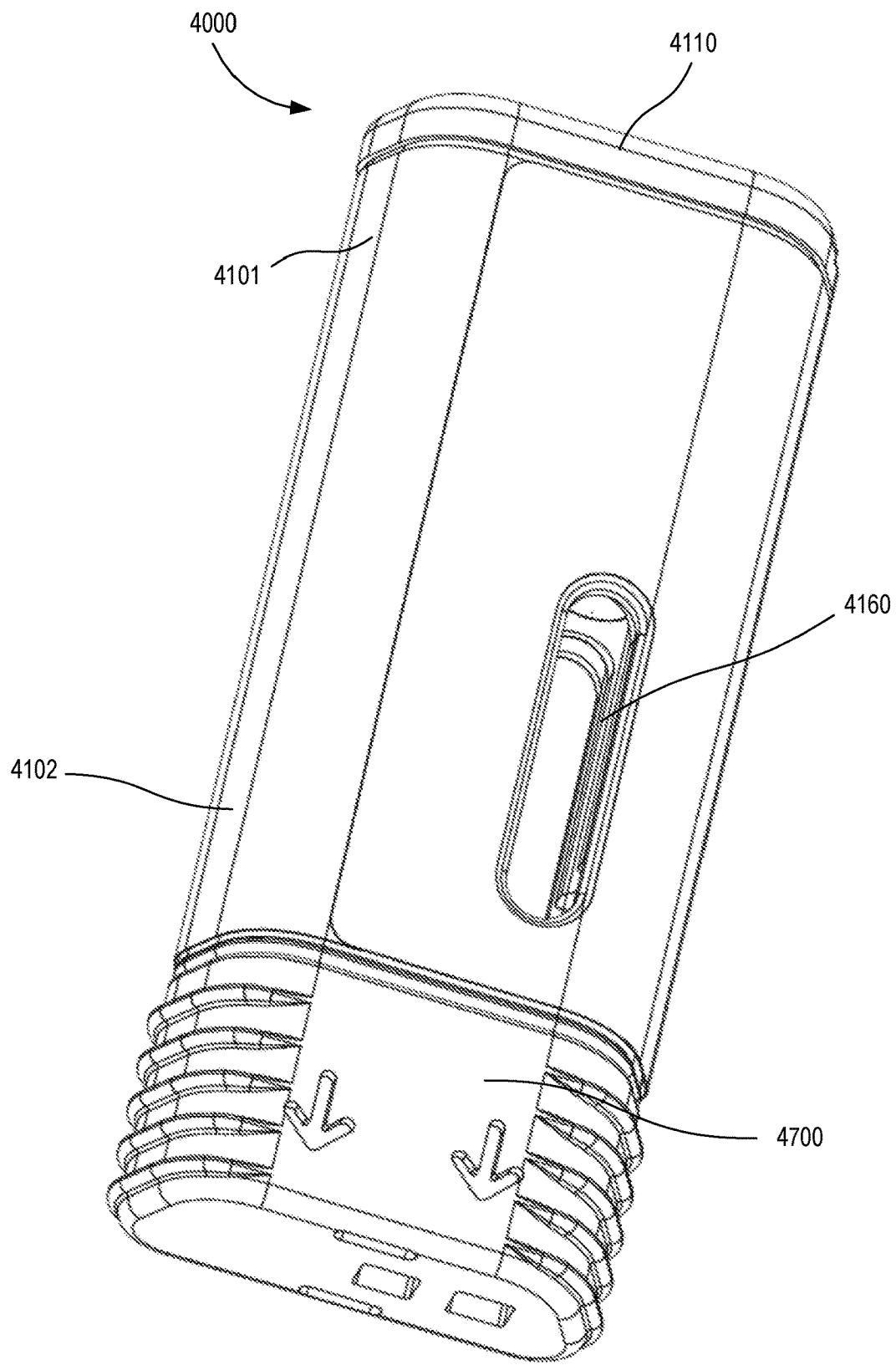
Figure 11:
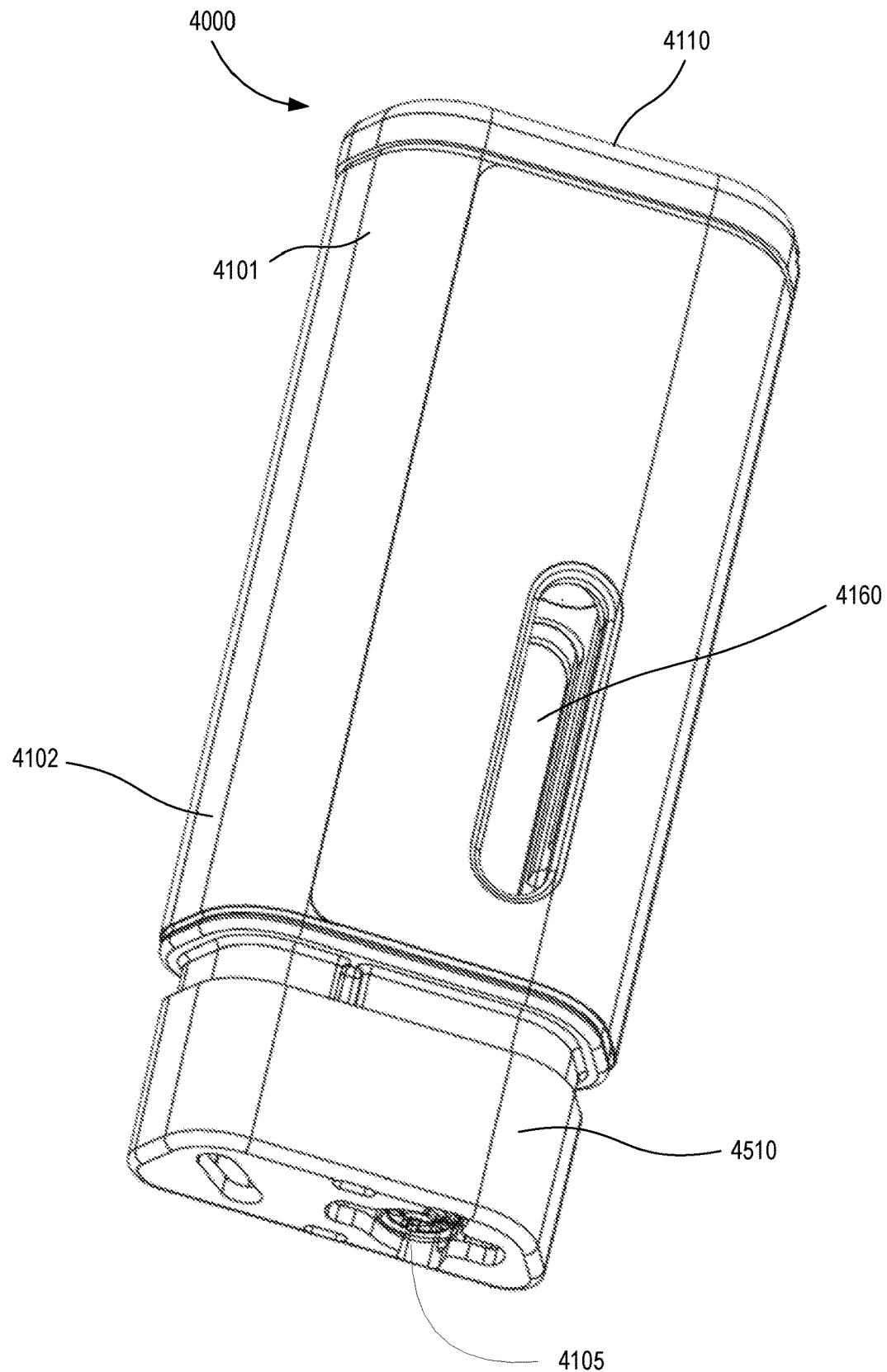
FIG. 11 is a perspective rear view of the medical injector illustrated in FIGS. 9 and 10, with the safety lock removed.

In some embodiments, the carrier 2360 (and any of the carriers shown and described herein) can include one or more seals to facilitate movement within the housing while also maintaining isolation of an internal volume of the housing. For example, in some embodiments, a carrier can include a seal to maintain a pressurized gas chamber during a delivery event. In this manner, high pressures can be employed to deliver a range of volumes of a variety of medicaments (having a wide range of viscosity). FIGS. 7 and 8 are schematic illustrations of a medicament delivery device 3000 according to an embodiment. The medicament delivery device 3000 includes a housing 3100, an energy storage member 3410, a carrier 3360, and a medicament container assembly 3200. The housing 3100 defines a gas chamber 3139 that receives a pressurized gas from the energy storage member 3410. The gas chamber 3139 can be of any suitable size and shape, and can be, for example, a portion of the volume defined by the housing 3100 within which a portion of the medicament container assembly 3200 and/or the carrier 3360 is disposed. Although not shown, in some embodiments, the housing includes a vent mechanism, such as an opening or valve, of the types shown and described herein (e.g., with respect to the device 1000 and the device 4000). In this manner, the gas pressure within the gas chamber 3139 can be reduced upon completion of the injection event.

The housing 3100 can be any suitable size, shape, or configuration and can be made of any suitable material. For example, in some embodiments, the housing 3100 is an assembly of multiple parts formed from a plastic material and defines a substantially rectangular shape when assembled. In other embodiments, the housing 3100 can have a substantially cylindrical shape.

The energy storage member 3410 is disposed within the housing 3100, and is configured to produce a force F (see FIGS. 5 and 6) to convey the contents of the medicament container assembly 3200 when the energy storage member 3410 is actuated to release a potential energy stored therein. The energy storage member 3410 can be any suitable member or device that stores potential energy and, when actuated, releases the energy to produce a force. For example, the energy storage member 3410 (and any of the energy storage members described herein) can be any of a gas container, a chemical energy storage member, a spring, a magnetic, or an electrical energy storage member.

The medicament container assembly 3200 has a container body 3210 that defines a volume that contains (i.e., is filled with or partially filled with) a medicament. The distal end portion of the medicament container body 3210 includes a needle 3216 through which the medicament can be delivered. The needle 3216 can be any suitable needle having any suitable diameter and length. For example, in some embodiments, the needle 3216 is a 39-gauge needle having a length of approximately 0.5 inches. In some embodiments, the medicament container assembly 3200 can be a prefilled syringe having the needle 3216 staked thereto.

The medicament container assembly 3200 includes an elastomeric member 3217 (i.e., a plunger) that seals the medicament within the container body 3210. The elastomeric member 3217 is configured to move within the container body to inject the medicament from the medicament container assembly 3200. The elastomeric member 3217 can be of any design or formulation suitable for contact with the medicament. For example, the elastomeric member 3217 can be formulated to minimize any reduction in the efficacy of the medicament that may result from contact (either direct or indirect) between the elastomeric member 3217 and the medicament. For example, in some embodiments, the elastomeric member 3217 can be formulated to minimize any leaching or out-gassing of compositions that may have an undesired effect on the medicament. In other embodiments, the elastomeric member 3217 can be formulated to maintain its chemical stability, flexibility and/or sealing properties when in contact (either direct or indirect) with the medicament over a long period of time (e.g., for up to six months, one year, two years, five years or longer).

The carrier 3360 is disposed within the housing, and is configured to be coupled to a medicament container assembly 3200. The carrier 3360 can be coupled to the medicament container assembly 3200 in any suitable manner. For example, as shown, the carrier 3360 can define an opening within which a portion of the container body 3210 can be received. The carrier 3360 can define, for example, a shoulder, protrusion, or other structure that couples to a portion of the container body 3210 (e.g., a flange, a side wall or the like). In other embodiments, the carrier 3360 can surround only a portion of the container body 3210. In yet other embodiments, the carrier 3360 can be constructed from multiple components that are joined together (e.g., via a hinged joint, a mechanical fastener or the like) to surround and/or be coupled to the medicament container assembly 3200.

The carrier 3360 includes a proximal surface 3376 that defines a portion of a boundary of the gas chamber 3139. In this manner, when a pressurized gas P (see FIG. 8) is conveyed into the gas chamber 3139, the pressure therein will produce a force on the proximal surface 3376 and/or the elastomeric member 3217. In this manner, when the medicament delivery device 3000 is actuated, the carrier 3360 moves within the housing 3100 from a first carrier position (FIG. 7) to a second carrier position (FIG. 8). As shown in FIG. 8, movement of the carrier 3360 in the distal direction moves the medicament container assembly 3200 in a like manner and distance. Specifically, when the carrier 3360 is in the first carrier position (FIG. 7), the needle 3216 is in a first needle position, in which the needle 3216 is disposed within the housing 3100. When the carrier 3360 is in the second carrier position (FIG. 8), the needle 3216 is in a second needle position, in which a portion of the needle 3216 is disposed outside of the housing 3100.

As shown, the carrier 3360 includes a first seal member 3370 and a second seal member 3371. The first (or outer) seal member 3370 is in sliding contact with an inner surface of the housing 3100 to fluidically isolate the gas chamber 3139 from an exterior volume. Similarly stated, the outer seal member 3370 is configured to form a substantially fluid tight seal with the inner surface of the housing 3100 defining the gas chamber (or medicament cavity) 3139. The first seal member 3370 can be any suitable seal, such as an O-ring, a strip seal or the like.

The second seal member 3371 is in contact with a proximal end portion of the container body 3210. For example, in some embodiments, the second (or inner) seal member 3371 is disposed between an inner surface of a flange of the container body 3210 and a shoulder of the carrier 3360. The inner seal member 3371 forms a substantially fluid tight seal between the container body 3210 and the carrier 3360. In this manner, the fluid leakage paths associated with (or caused by) the medicament container within the housing 3100 can be minimized.

As shown in FIG. 7, the first seal member 3370 is spaced apart from the second seal member 3371 by a distance $D_{Seal}$. In some embodiments, the carrier 3360 is constructed such that the first seal member 3370 remains in a fixed position relative to the second seal member 3371 during use. Although the second seal member 3371 is shown as being disposed distally from the first seal member 3370, in other embodiments, the second seal member 3371 can be longitudinally aligned with, or disposed proximally from, the first seal member 3370.

In some embodiments, a medicament delivery can be an auto-injector having a pistonless delivery system in which the force exerted by the gas can move the medicament container relative to the housing and the elastomeric member relative to (e.g., within) the medicament container. For example, FIGS. 9-43 show a medical injector 4000 (also referred to as "auto-injector," "injector," or "device"), according to an embodiment. The medical injector 4000 is a gas-powered auto-injector configured to deliver a medicament contained within a prefilled syringe 4200, as described herein. A discussion of the components of the medical injector 4000 will be followed by a discussion of the operation of the medical injector 4000. Certain aspects of the medical injector 4000 can be similar to or substantially the same to the medical injectors described in U.S. patent application Ser. No. 13/357,935 (now U.S. Pat. No. 9,084, 849) entitled, "MEDICAMENT DELIVERY DEVICES FOR ADMINISTRATION OF A MEDICAMENT WITHIN A PREFILLED SYRINGE," filed on Jan. 25, 2012 (referred to henceforth as the "'849 patent"), the disclosure of which is incorporated herein by reference in its entirety.

Figure 12:
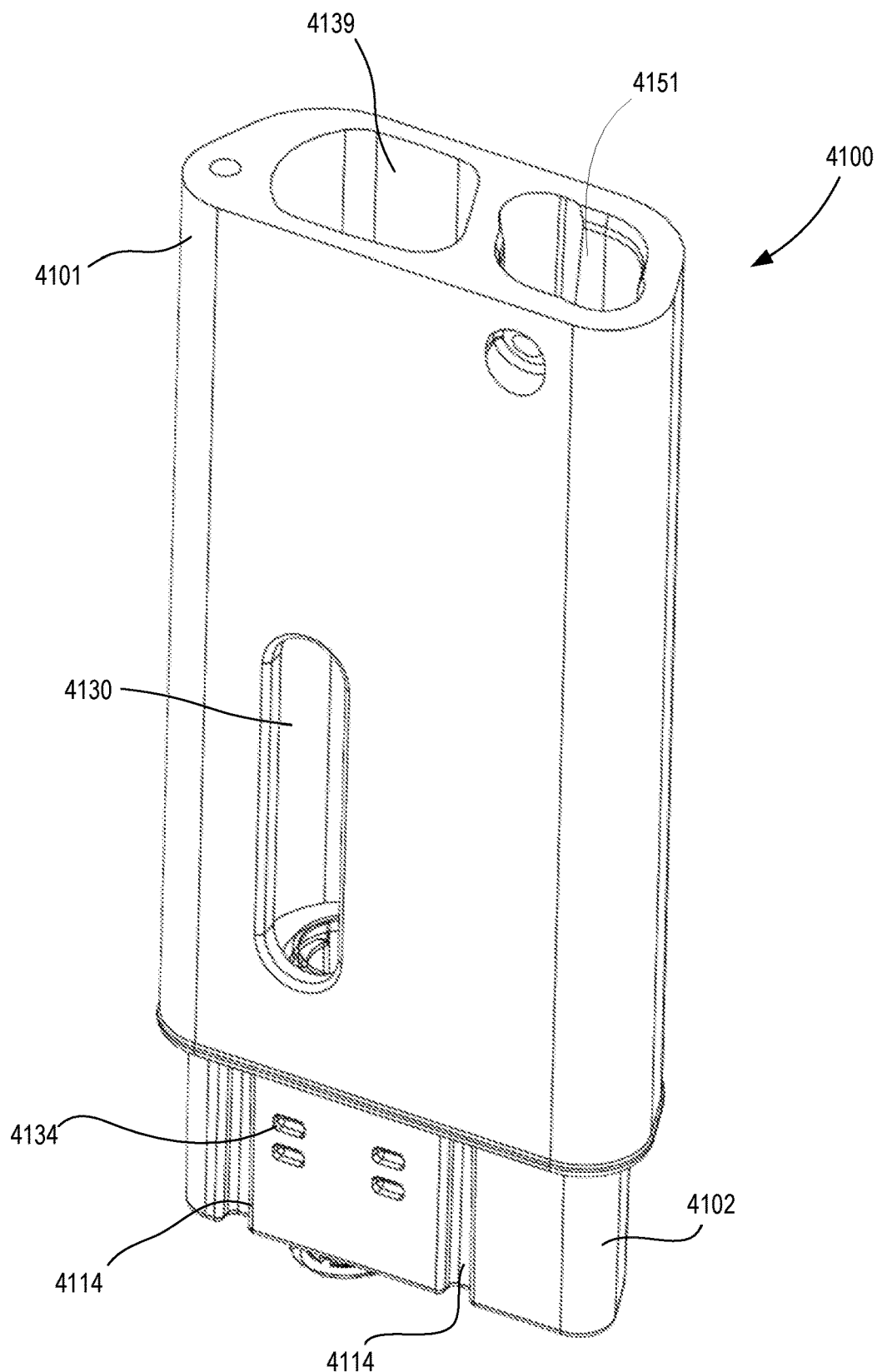
FIG. 12 is a perspective view of a housing of the medical injector illustrated in FIGS. 9 and 10.
Figure 13:
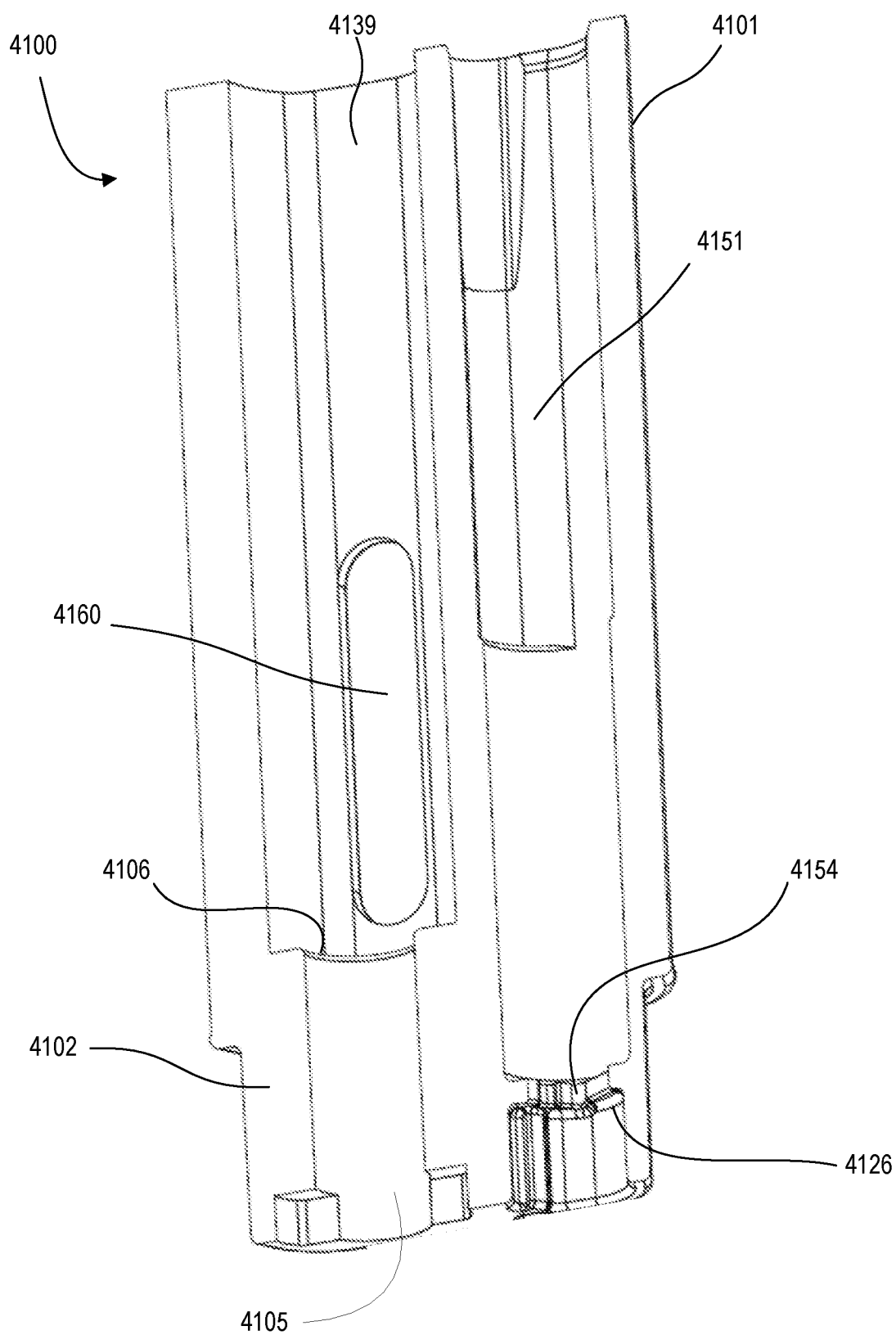
FIG. 13 is a cross-sectional view of the housing illustrated in FIG. 12.
Figure 29:
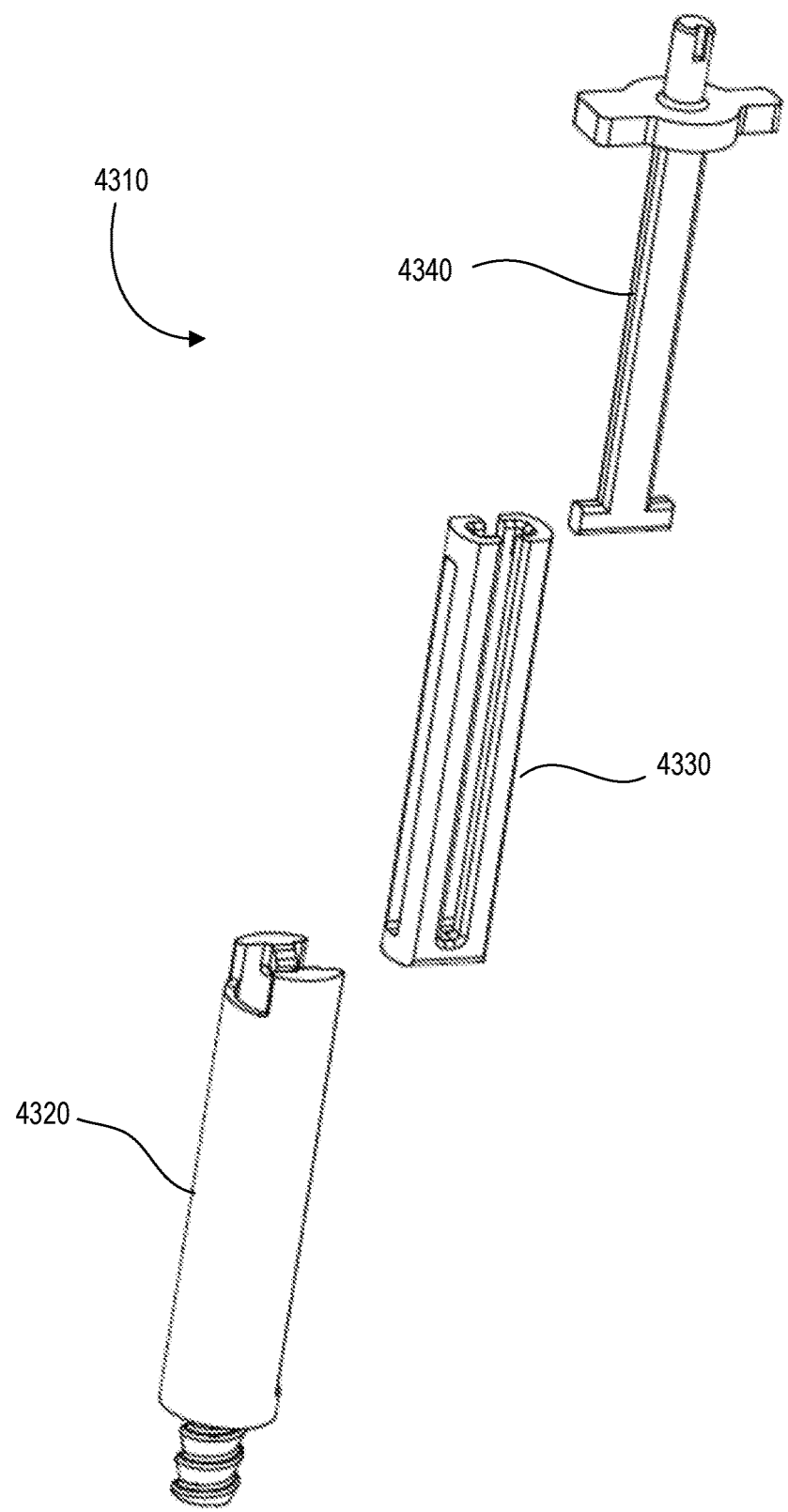
Figure 30:
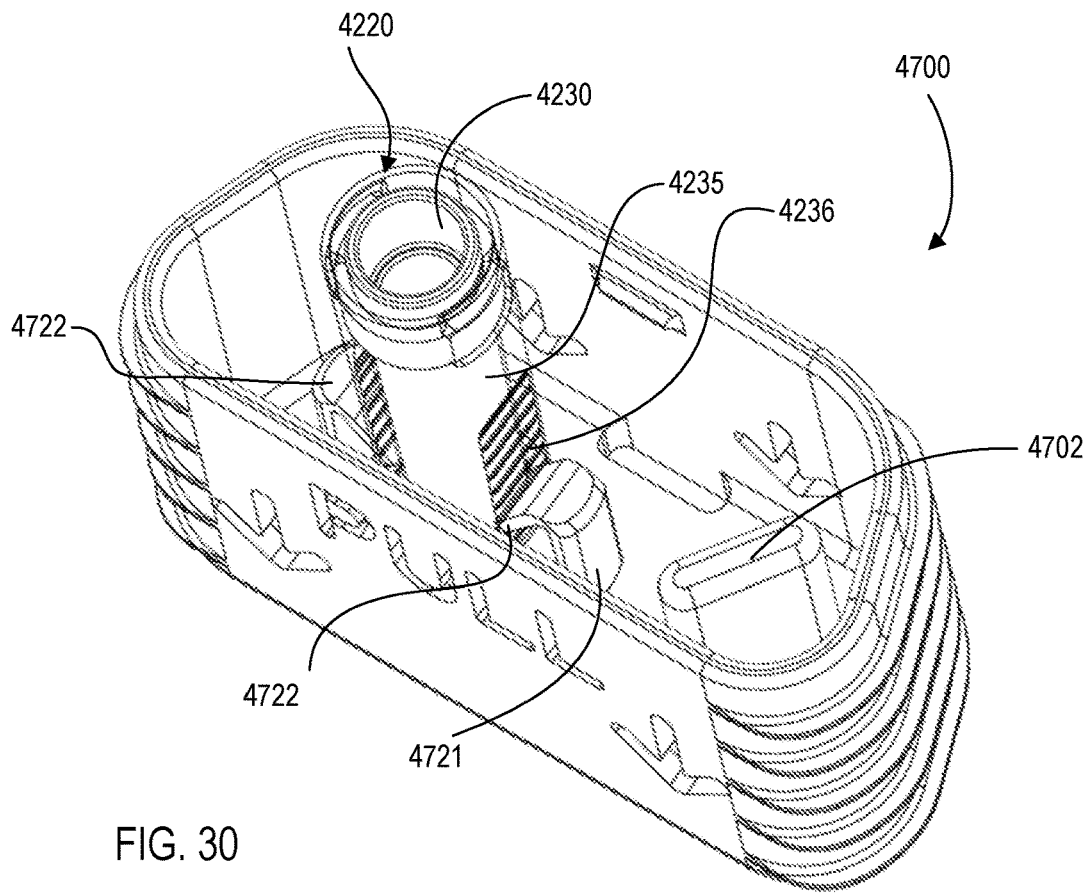
FIGS. 30 and 31 are perspective views of a safety lock of the medical injector shown in FIGS. 9 and 10.
Figure 31:
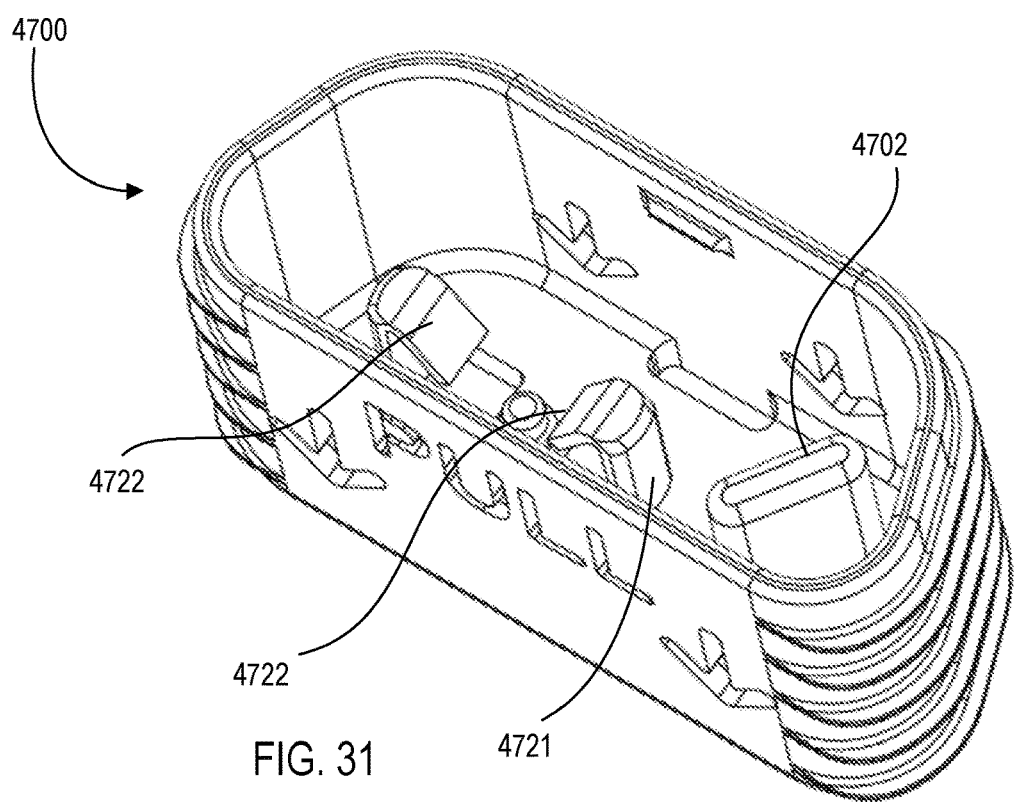

The medical injector 4000 includes a housing 4100 (see e.g., FIGS. 12-13), a system actuation assembly 4500 (see e.g., FIGS. 16-17), a medicament container assembly 4200 (see FIG. 26), a medicament delivery mechanism 4300 (see e.g., FIGS. 22-29), a base 4510 (or actuator, see FIGS. 32 and 33); and a safety lock 4700 (see FIGS. 30-31). As shown in FIGS. 12-13, the housing 4100 has a proximal end portion 4101 and a distal end portion 4102. The housing 4100 defines a first status indicator aperture 4130 and a second status indicator aperture 4160. The first status indicator aperture 4130 defined by the housing 4100 is located on a first side of the housing 4100, and the second status indicator aperture 4160 of the housing 4100 is located on a second side of the housing 4100. The status indicator apertures 4130, 4160 can allow a patient to monitor the status and/or contents of the medicament container 4200, the carrier 4360, and the medicament contained within the housing 4100. For example, by visually inspecting the status indicator apertures 4130, 4160, a patient can determine whether the medicament container 4200 contains a medicament and/or whether the medicament has been dispensed.

In some embodiments, the housing 4100 can include a label or indicia that mask or otherwise accentuates the status indicator apertures 4130, 4160 and/or the contents viewed therethrough. For example, in some embodiments, the housing 4100 can include a label (not shown) having border that surrounds at least a portion of the status indicator aperture 4130, the status indicator apertures 4160 (or both). In some embodiments, a label can include indicator colors that alert user (or assist a user in determining) whether the medicament is properly colored, whether a portion of the carrier 4360 is visible through the window or the like.

Figure 16:
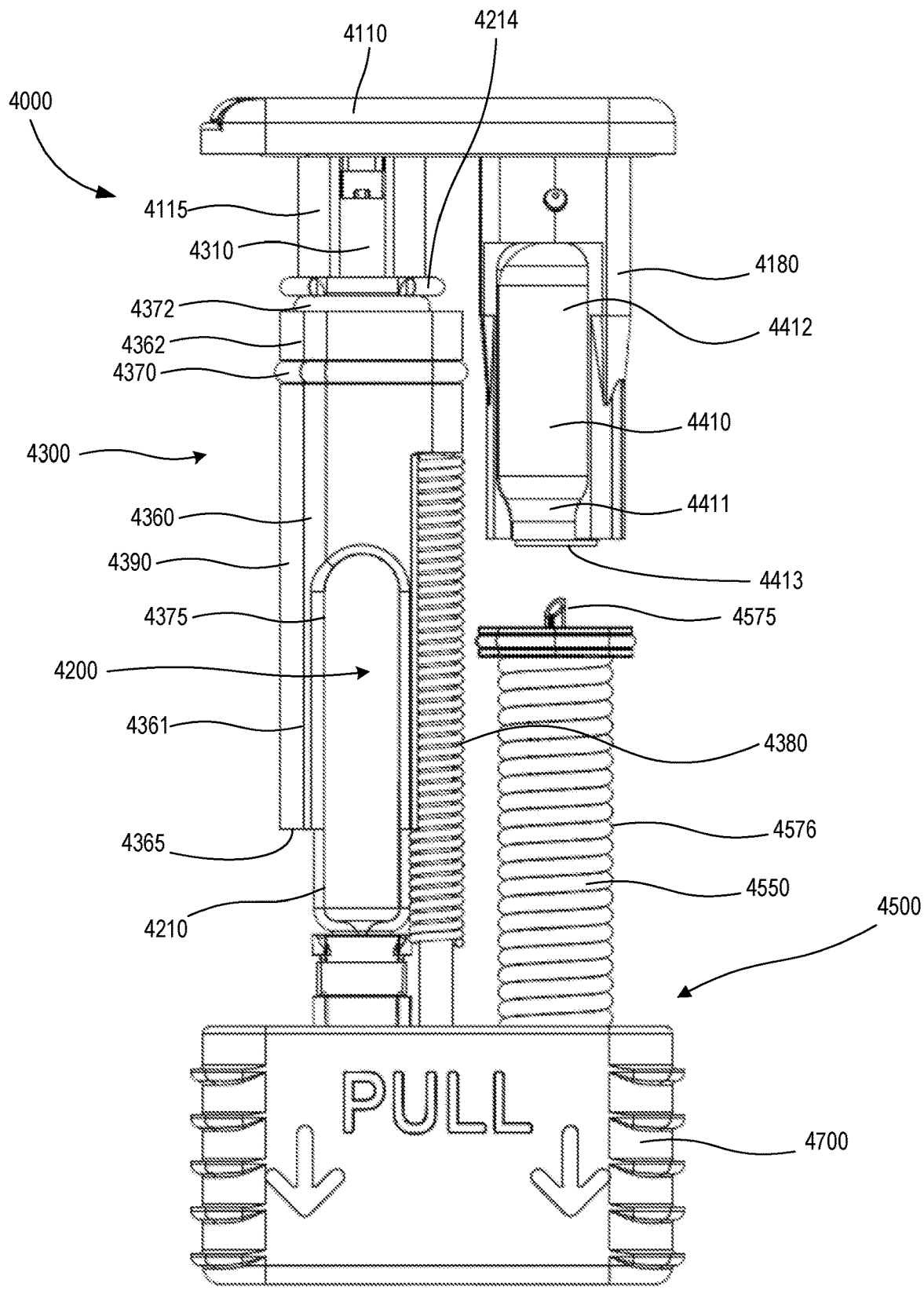
FIGS. 16 and 17 are front views of a medicament delivery mechanism of the medical injector shown in FIGS. 9 and 10.
Figure 17:
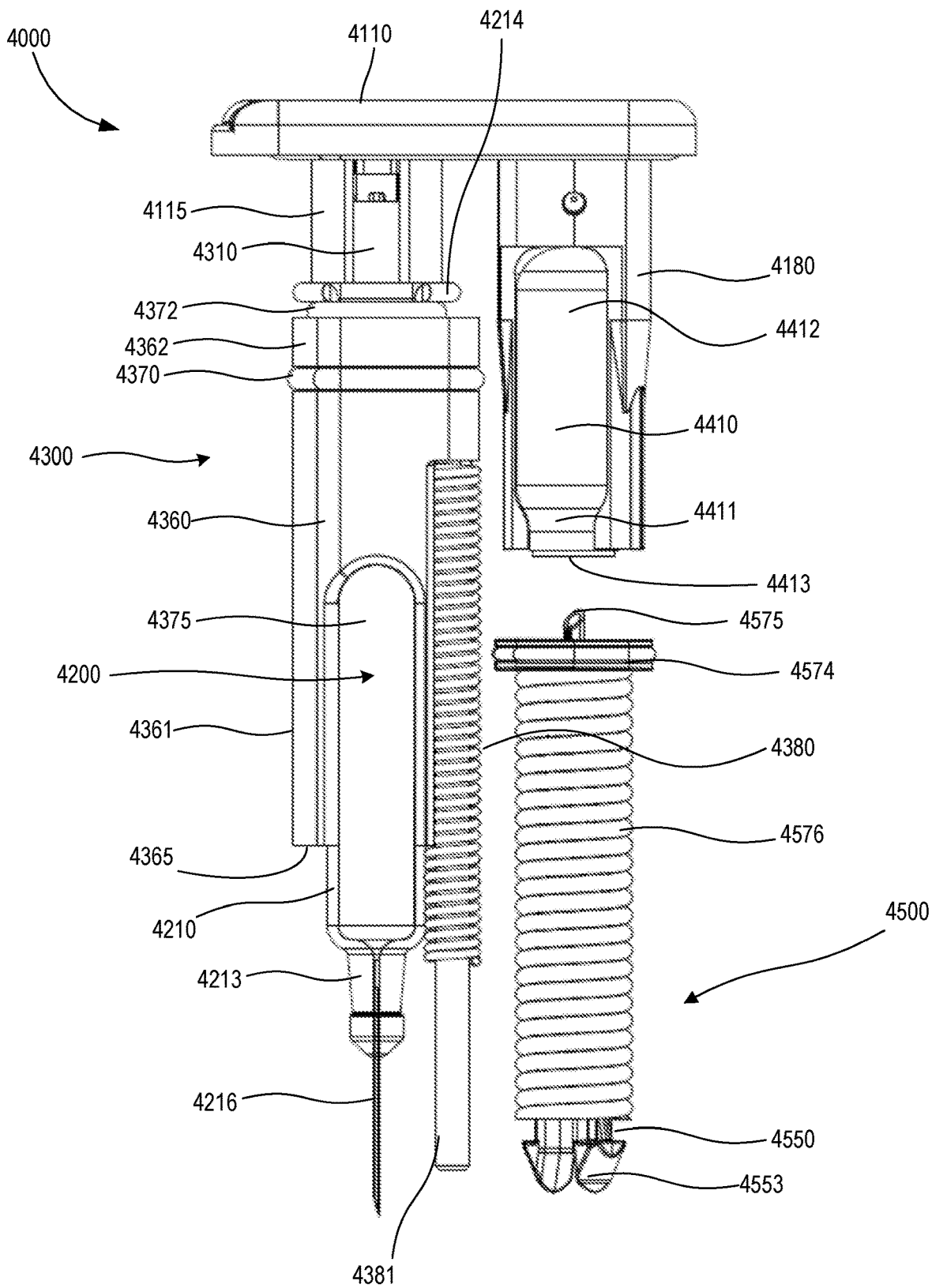

As shown in FIGS. 12 and 13, the housing 4100 defines a gas container cavity 4151 and a medicament cavity 4139. The gas container cavity 4151 is configured to receive the gas container 4410 and a portion of the system actuator assembly 4500 (e.g., a release member 4550 and the spring 4576, as shown in FIGS. 16 and 17). The proximal end portion 4152 of the gas container cavity 4151 is configured to receive the gas container retention member 4580 of a proximal cap 4103 of the housing 4100, as described in further detail herein. The gas container cavity 4151 is in fluid communication with the medicament cavity 4139 via a gas passageway (not shown), as described in further detail herein.

The medicament cavity 4139 is configured to receive the medicament container assembly 4200 and at least a portion of the medicament delivery mechanism 4300. In particular, as described below, the medicament delivery mechanism 4300 includes a carrier assembly 4390 and a gas vent assembly 4310 movably disposed in the medicament cavity 4139. The medicament cavity 4139 is in fluid communication with a region outside the housing 4100 via a needle aperture 4105 (see e.g., FIGS. 45 and 46) and also a vent opening 4112.

Figure 15:
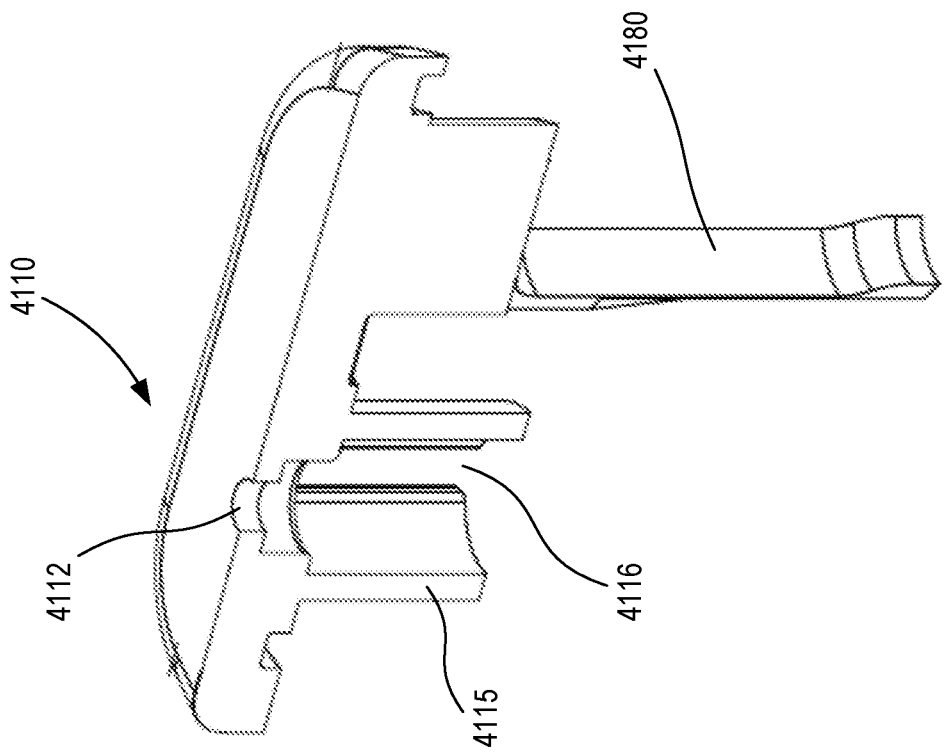
FIGS. 14 and 15 are a perspective view and a cross-sectional view, respectively, of a proximal cap of the medical injector illustrated in FIG. 9.
Figure 14:
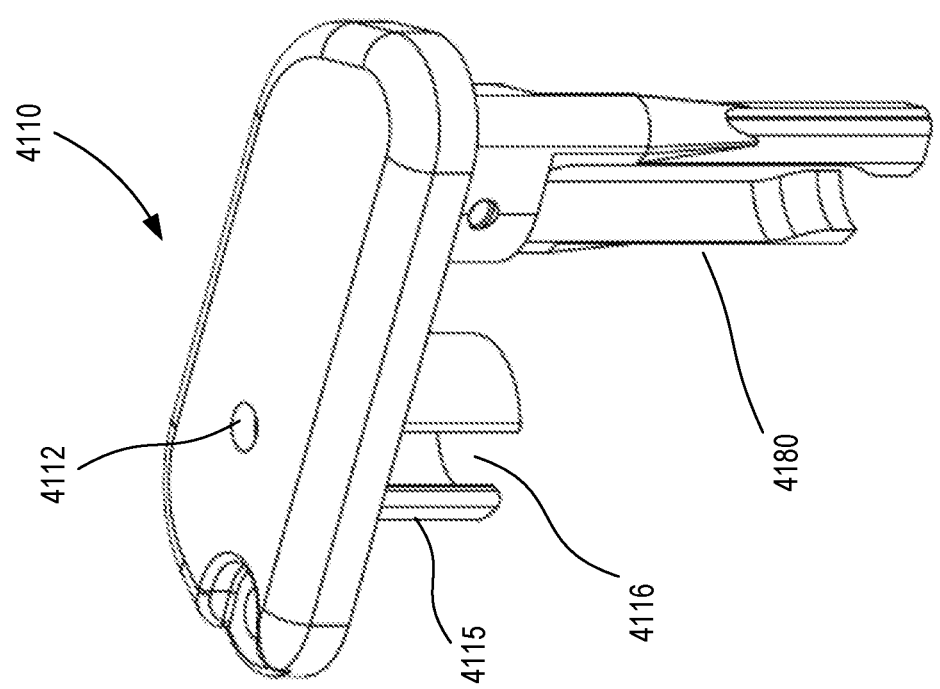
Figure 20:
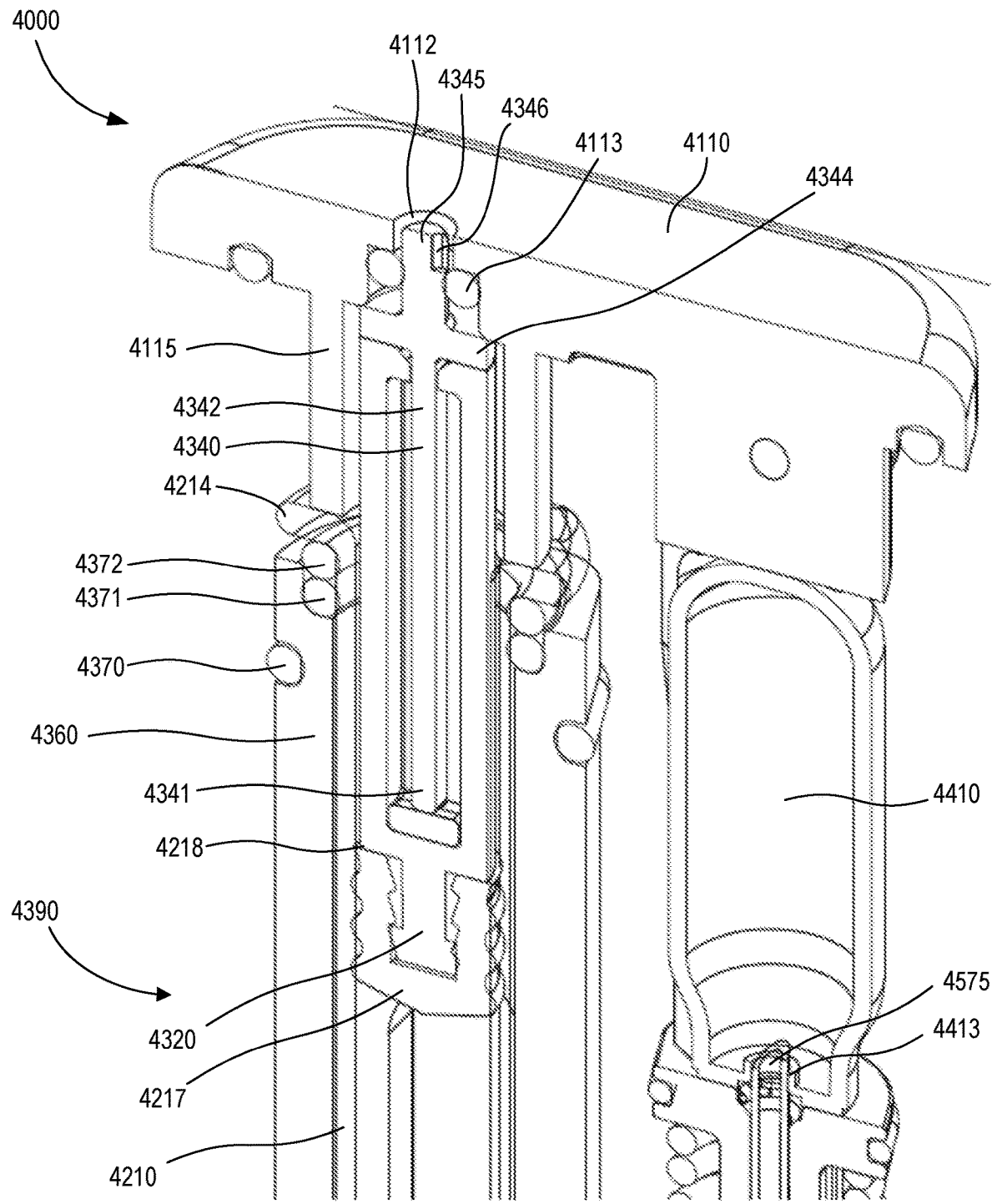
FIG. 20 is an enlarged cross-sectional view of a portion of the medical injector shown in FIGS. 9 and 10, in the first configuration.

The proximal end portion 4101 of the housing 4100 includes a proximal cap 4110 (see e.g., FIGS. 14, 15 and 20). The proximal cap 4110 includes a gas container retention member 4180 and defines a gas passageway between the medicament cavity 4139 and the gas container cavity 4151. The gas container retention member 4180 is configured to receive and/or retain a gas container 4410 that contains a pressurized gas, as shown in FIGS. 16 and 17. When the medical injector 4000 is actuated, pressurized gas from the gas container 4410 is conveyed from the gas container cavity 4151 to the medicament cavity 4139 via the gas passageway. Said another way, the gas passageway places the gas container cavity 4151 in fluid communication with the medicament cavity 4139. Thus, the proximal portion of the medicament cavity 4139 can be referred to as a gas chamber. Similarly stated, the proximal portion of the medicament cavity 4139 is a volume within which a pressurized gas is conveyed to move the carrier 4360 and inject the medicament, as described herein.

The proximal cap 4110 also includes an O-ring 4113 and defines the vent opening 4112. As described herein, the vent opening 4112 provides the passageway through which pressurized gas is conveyed from the medicament cavity 4139 (or gas chamber portion of the medicament cavity 4139) to a volume outside of the medical injector 4000. In this manner, the force produced by the pressurized gas on the medicament delivery mechanism 4300 and/or the medicament container assembly 4200 can be reduced to allow needle retraction after the injection is completed. As shown in FIG. 20, the O-ring 4113, in conjunction with the valve portion 4345 of the gas vent assembly 4310, selectively seals the vent opening 4112 during needle insertion and delivery of the medicament.

Although the vent opening 4112 is shown as being defined by the proximal cap 4110, and being in a proximal surface thereof, in other embodiments, the vent opening 4112 (and any of the vent openings described herein, including the vent opening 8112) can be defined within any suitable portion of the proximal cap or side wall. For example, in some embodiments, the vent opening 4112 (and any of the vent openings described herein, including the vent opening 8112) can be defined by the proximal cap, but can have a centerline that is nonparallel to a longitudinal axis of the medical injector 4000. Said another way, in some embodiments, the vent opening 4112 (and any of the vent openings described herein, including the vent opening 8112) can open towards a side of the medical injector, rather than opening towards the proximal end, as shown. In other embodiments, the vent opening 4112 (and any of the vent openings described herein, including the vent opening 8112) can be defined by any wall and/or surface of the housing 4100.

The proximal cap 4110 includes a guide wall 4115 within which the first (or proximal) member 4340 of the gas vent assembly 4310 moves. Specifically, the guide wall defines a pair of slots 4116 within which the guide surface 4344 of the first member 4340 (see e.g., FIGS. 27, 28) slide during operation. The guide wall 4115 also includes an end surface 4117 against which a flange 4214 of the container body 4210 rests when the medical injector 4000 is in its first configuration (i.e., the "storage" state).

As shown in FIG. 13, the distal end portion 4102 of the housing 4100 includes a shoulder 4106 and defines a needle aperture 4105. The distal end portion 4102 also includes base rail grooves 4114 and base retention recesses 4134 (see FIG. 12). The shoulder 4106 is configured to contact a corresponding surface 4365 of the carrier body 4360 (see e.g., FIG. 20) when the needle 4216 has been inserted a desired distance. In this manner the shoulder 4016 can act as an "end stop" or insertion limiting mechanism. The needle aperture 4105 is the opening through which the needle 4216 is disposed when the medical injector 4000 is actuated, as described in further detail herein.

Figure 21:
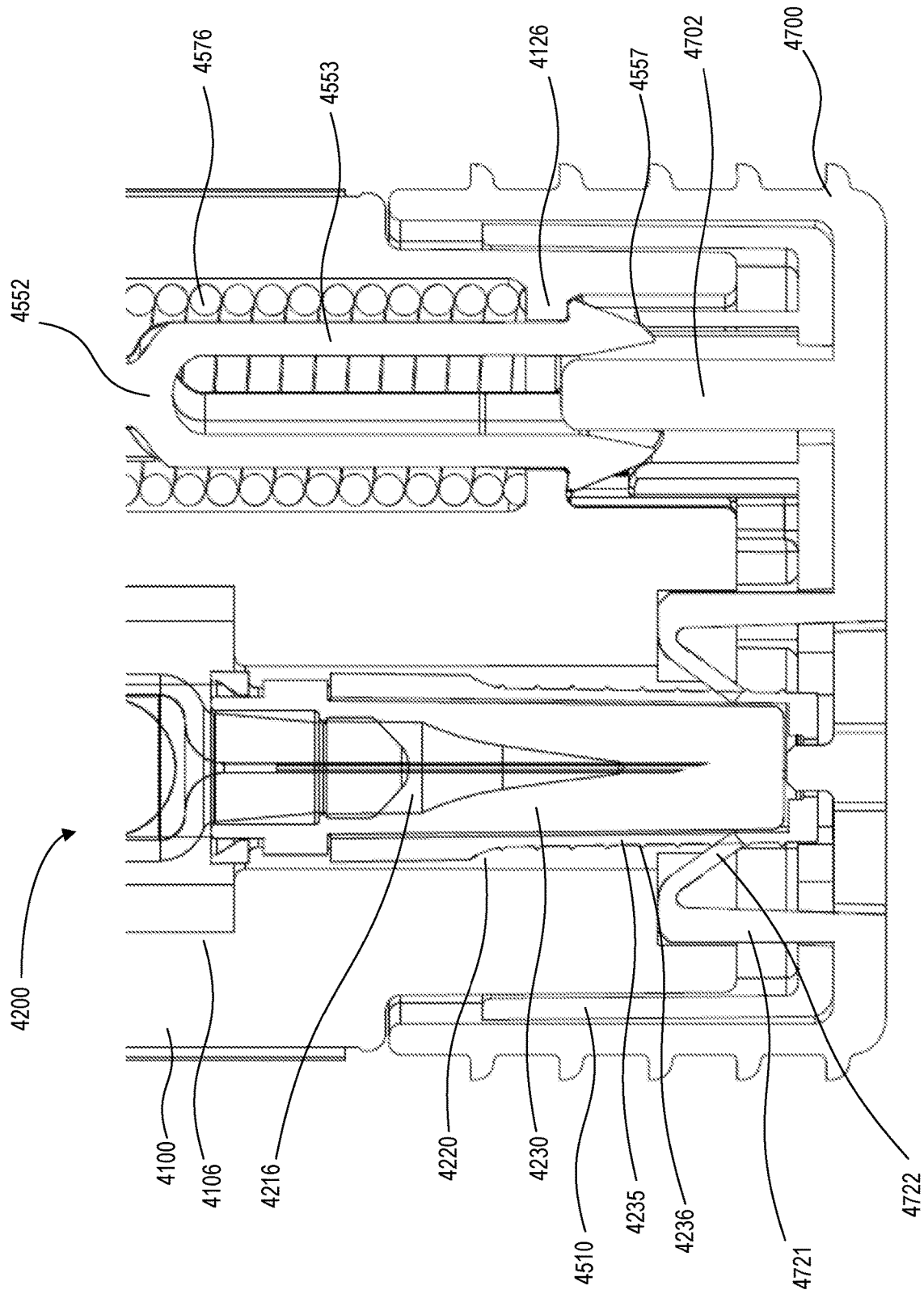
FIG. 21 is an enlarged cross-sectional view of a portion of the medical injector shown in FIGS. 9 and 10, in the first configuration.

The distal end portion 4102 of the housing also include a release member contact surface 4126, and defines the release member aperture. As shown in FIG. 21, the release member aperture 4145 receives a distal end portion 5152 of a release member 4550, such that the extensions 4553 of the release member 4550 engage with the release member contact surface to prevent activation of the medical injector 4000. The safety lock 4700, its components and functions are described in more detail below.

The distal base retention recesses 4134 are configured to receive the base connection knobs 4518 of the actuator 4510 (also referred to herein as "base 4510," see e.g., FIGS. 32 and 33) when the base 4510 is in a first position relative to the housing 4100. The proximal-most pair of base retention recesses 4134 are configured to receive the base connection knobs 4518 of the base 4510 when the base 4510 is in a second (i.e., actuated) position relative to the housing 4100. The base retention recesses 4134 have a tapered proximal sidewall and a non-tapered distal sidewall. This allows the base retention recesses 4134 to receive the base connection knobs 4518 such that the base 4510 can move proximally relative to the housing 4100, but cannot move distally relative to the housing 4100. Said another way, the distal-most set of base retention recesses 4134 are configured to prevent the base 4510 from moving distally when the base 4510 is in a first position and the proximal-most set of base retention recesses 4134 are configured to prevent the base 4510 from moving distally when the base 4510 is in a second position. Similarly stated, the proximal base retention recesses 4134 and the base connection knobs 4518 cooperatively to limit movement of the base to prevent undesirable movement of the base 4510 after the medical injector 4000 is actuated. The proximal base retention recesses 4134 and the base connection knobs 4518 also provide a visual cue to the user that the medical injector 4000 has been used.

Figure 32:
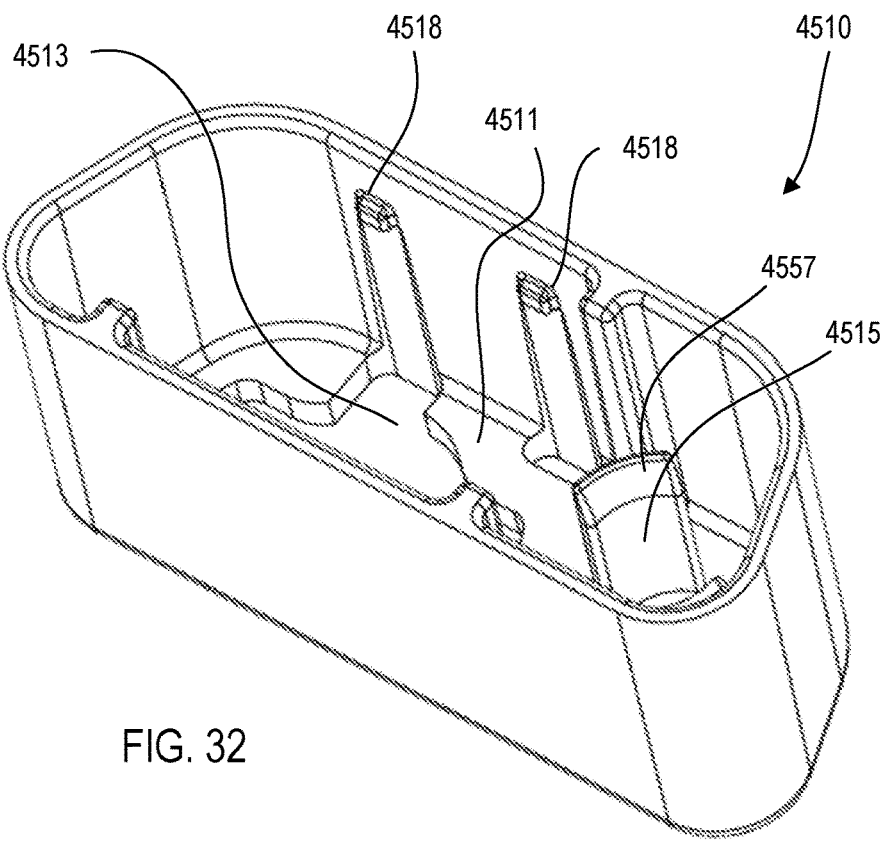
FIGS. 32 and 33 are perspective views of a system actuator of the medical injector shown in FIGS. 9 and 10.
Figure 33:
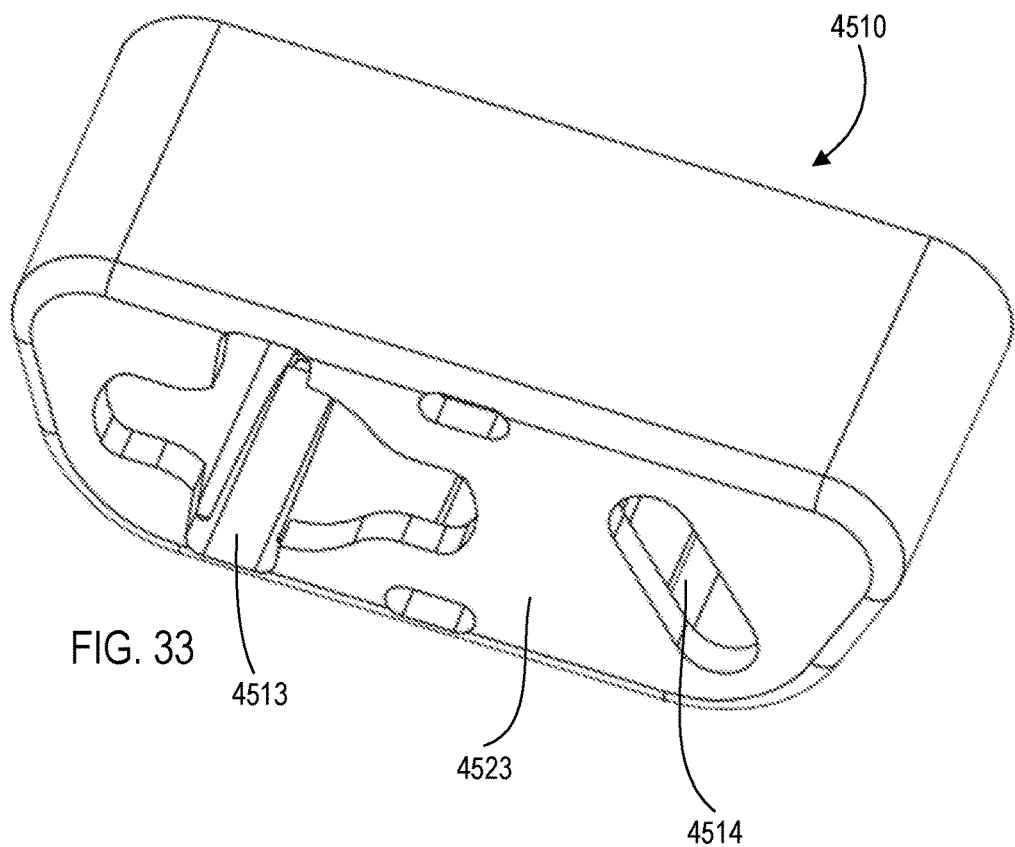

The base rail grooves 4114 receive the guide members 4517 of the base 4510 (see FIGS. 32 and 33). The guide members 4517 of the base 4510 and the base rail grooves 4114 of the housing 4100 engage each other in a way that allows the guide members 4517 of the base 4510 to slide in a proximal and/or distal direction within the base rail grooves 4114 while limiting lateral movement of the guide members 4517. This arrangement allows the base 4510 to move in a proximal and/or distal direction with respect to the housing 4100 but prevents the base 4510 from moving in a lateral direction with respect to the housing 4100.

Figure 26:
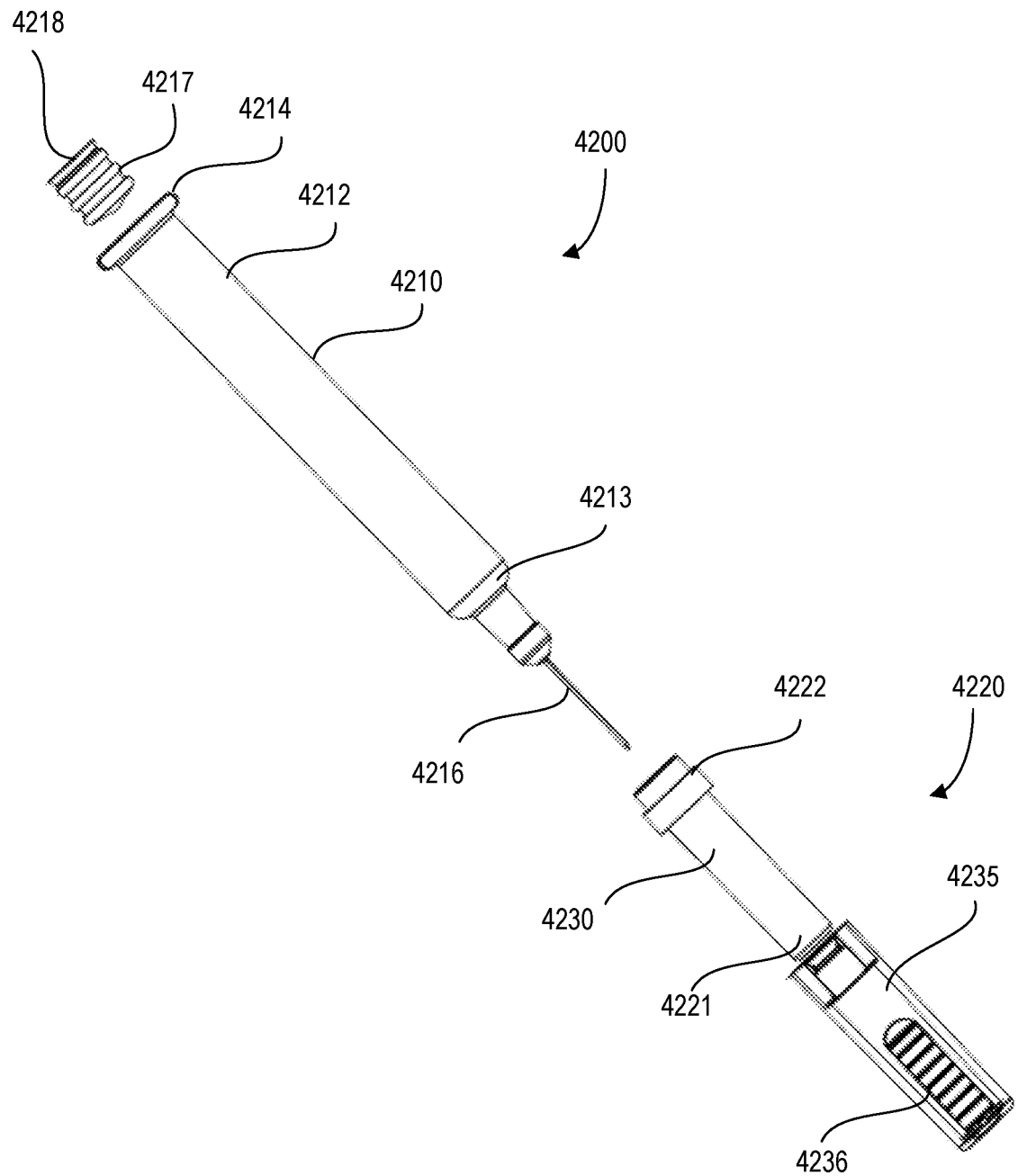
FIG. 26 is an exploded view of a medicament container assembly of the medical injector shown in FIGS. 9 and 10.

FIGS. 16-17 provide an overview of the medicament container assembly 4200, the system actuator assembly 4500, and the medicament delivery mechanism 4300 of the medical injector 4000. Referring to FIG. 26, the medicament container assembly 4200 has a container body 4210 with a distal end portion 4213 and a proximal end portion 4212. The container body 4210 defines a volume that contains (i.e., is filled with or partially filled with) a medicament. The distal end portion 4213 of the medicament container assembly 4200 includes a neck that is coupled to the needle 4216, as described below. The proximal end portion 4212 of the medicament container assembly 4200 includes an elastomeric member 4217 (i.e., a plunger) that seals the medicament within the container body 4210. The elastomeric member 4217 is configured to move within the container body to inject the medicament from the medicament container assembly 4200.

More particularly, as shown in FIG. 20, the elastomeric member 4217 includes a proximal surface 4218 and is coupled to the distal member 4320 of the gas venting assembly 4310. In this manner, as described below, when the pressurized gas is conveyed into the medicament cavity 4139 (or "gas chamber"), the pressure exerts a force on the proximal surface 4218 to move the elastomeric member 4217 within the container body 1210 (i.e., to expel the medicament therefrom). Further, because the elastomeric member 4217 is coupled to the gas venting assembly 4310, movement of the elastomeric member 4217 within the container body 4210 produces movement of at least a portion of the distal member 4320. Similarly stated, when the elastomeric member 4217 is exposed to a force (e.g., produced by the pressurized gas within the gas chamber 4139 acting directly on the proximal surface 4218), movement of the elastomeric member 4217 exerts a force on the distal member 4320. Specifically, distal movement of the elastomeric member 4217 can produce a tensile force on the distal member 4320.

The distal member 4320 can be coupled to the elastomeric member 4217 in any suitable manner. For example, as shown, the proximal surface 4218 receives and/or couples to a protrusion 4323 of the distal member 4320 of the gas venting assembly 4310. In other embodiments, the distal member 4320 can be threadedly coupled to the elastomeric member 4217. In yet other embodiments, the distal member 4320 can be bonded to the elastomeric member 4217 via an adhesive, a weld process, or the like The elastomeric member 4217 can be of any design or formulation suitable for contact with the medicament. For example, the elastomeric member 4217 can be formulated to minimize any reduction in the efficacy of the medicament that may result from contact (either direct or indirect) between the elastomeric member 4217 and the medicament. For example, in some embodiments, the elastomeric member 4217 can be formulated to minimize any leaching or out-gassing of compositions that may have an undesired effect on the medicament. In other embodiments, the elastomeric member 4217 can be formulated to maintain its chemical stability, flexibility and/or sealing properties when in contact (either direct or indirect) with the medicament over a long period of time (e.g., for up to six months, one year, two years, five years or longer).

In some embodiments, the elastomeric member 4217 can be constructed from multiple different materials. For example, in some embodiments, at least a portion of the elastomeric member 4217 can be coated. Such coatings can include, for example, polydimethylsiloxane. In some embodiments, at least a portion of the elastomeric member 4217 can be coated with polydimethylsiloxane in an amount of between approximately 0.02 mg/cm$^2$ and approximately 0.80 mg/cm$^2$.

The proximal end portion 4212 of the container body 4210 includes a flange 4214 configured to be disposed within a portion of the carrier body 4360, as described in further detail herein. The flange 4214 can be of any suitable size and/or shape. Although shown as substantially circumscribing the container body 4210, in other embodiments, the flange 4214 can only partially circumscribe the container body 4210.

The medicament container assembly 4200 can have any suitable size (e.g., length and/or diameter) and can contain any suitable volume of the medicament. In some embodiments, the medicament container assembly 4200 (and any of the medicament container assemblies described herein) can be a prefilled (or prefillable) syringe, such as those manufactured by Becton Dickinson, Gerresheimer, Ompi Pharma or others. For example, in some embodiments, the medicament container assembly 4200 (and any of the medicament container assemblies described herein) can be a Becton Dickinson "BD Hypak Physiolis" prefillable syringe containing any of the medicaments described herein. The medical injector 4000 can be configured to inject any suitable dosage such as, for example, a dose of up to 4 mL of any of the medicaments described herein. In other embodiments, the medical injector 4000 can be configured to inject a dose of up to 2 mL, 3 mL, 4 mL, 5 mL, or more of any of the medicaments described herein.

The container body 4210 can be constructed from glass, and can be fitted and/or coupled to any suitable needle. For example, in some embodiments, the container body 4210 can be coupled to a needle having any suitable size. Any of the medicament container assemblies and/or prefilled syringes described herein can be coupled to a needle having a gauge size of 21 gauge, 22 gauge, 23 gauge, 24 gauge, 25 gauge, 26 gauge, 27 gauge, 28 gauge, 29 gauge, 30 gauge, or 31 gauge. Any of the medicament container assemblies and/or prefilled syringes described herein can be coupled to a needle having any suitable length, such as, for example, a length of about 0.2 inches, about 0.27 inches, about 0.38 inches, about 0.5 inches, about 0.63 inches, about 0.75 inches, or more. In some embodiments, for example, any of the medicament containers and/or prefilled syringes described herein can be coupled to a 29 gauge, needle having a length of approximately 0.5 inches.

As shown in FIG. 26, the medicament container assembly 4200 includes a needle sheath assembly 4220, that includes a sheath body 4230 and a sheath cover 4235. The needle sheath assembly 4220 includes a distal end portion 4221 and a proximal end portion 4222. The sheath body 4230 defines a bore that receives the needle 4216 and/or a distal end portion of the 4213 of the medicament container body 4210. The inner portion of the sheath body 4230 defines a friction fit with the distal end portion 4213 of the medicament container body 4210. In this manner, the needle sheath assembly 4220 can protect the user from the needle 4216 and/or can keep the needle 4216 sterile before the user actuates the medical injector 4000.

The sheath cover 4235 is disposed about (and surrounds) the sheath body 4230. The sheath cover 4235 includes a series of ribs 4236 that engage the tabs 4722 of the safety lock 4700 (see e.g., FIGS. 19 and 21). Specifically, the distal end portion 4812 of the sheath assembly 4220 is configured to be inserted into a space defined between the tabs 4722 of the engagement members 4721 of the safety lock 4700. The tabs 4722 are angled and/or bent towards the distal direction to allow the distal end portion 4812 of the sheath assembly 4220 to move between the engagement members 4721 in a distal direction, but not in a proximal direction. Similarly stated, the tabs 4722 include an edge that contacts the ribs 4236 of the sheath cover 4235 to prevent the safety lock 4700 from moving in a distal direction relative to the needle sheath 4810. In this manner, the needle sheath assembly 4220 is removed from the needle 4216 when the safety lock 4700 is moved in a distal direction with respect to the housing 4100.

The delivery mechanism 4300 includes a gas vent assembly 4310 (also referred to as an expandable assembly), but does not rely on a piston or rigid member to move the elastomeric member 4217 within the container body 4210 to inject the medicament. Rather, the elastomeric member 4217 is moved by the force produced by the pressurized gas within the gas chamber (or medicament cavity 4139). Accordingly, the stroke length and/or the dosage amount can be set by the expanded length of the gas vent assembly 4310. In this manner, the length of the medicament container assembly 4200 and the length of the gas vent assembly 4310 can be configured such the desired dosage amount is delivered. Moreover, because the gas vent assembly 4310 moves from a collapsed to an expanded configuration, the medicament delivery mechanism 4300 can fit within the same housing 4100 regardless of the fill volume, the delivery volume and/or the ratio of the fill volume to the delivery volume. In this manner, the same housing and production tooling can be used to produce devices having various dosages of the medicament. For example, in a first embodiment (e.g., having a fill volume to delivery volume ratio of 0.4), the medicament container has a first length and the second movable member has a first length. In a second embodiment (e.g., having a fill volume to delivery volume ratio of 0.6), the medicament container has a second length shorter than the first length, and the second movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

In some embodiments, the device 4000 is configured such that a ratio of the housing length $H_L$ to the container length $H_C$ is less than about 1.5. In other embodiments, the device 4000 is configured such that a ratio of the housing length $H_L$ to the container length $H_C$ is less than about 1.25. In yet other embodiments, the device 4000 is configured such that a ratio of the housing length $H_L$ to the container length $H_C$ is less than about 1.1.

In some embodiments, the device 4000 is configured such that a ratio of the housing length $H_L$ to a sum of the container length $H_C$, the carrier distance, and the stroke is less than about 1.1. In other embodiments, the device 4000 is configured such that a ratio of the housing length $H_L$ to a sum of the container length $H_C$, the carrier distance, and the stroke is less than about 1.0. In yet other embodiments, the device 4000 is configured such that a ratio of the housing length $H_L$ to a sum of the container length $H_C$, the carrier distance, and the stroke is less than about 0.9.

Figure 34:
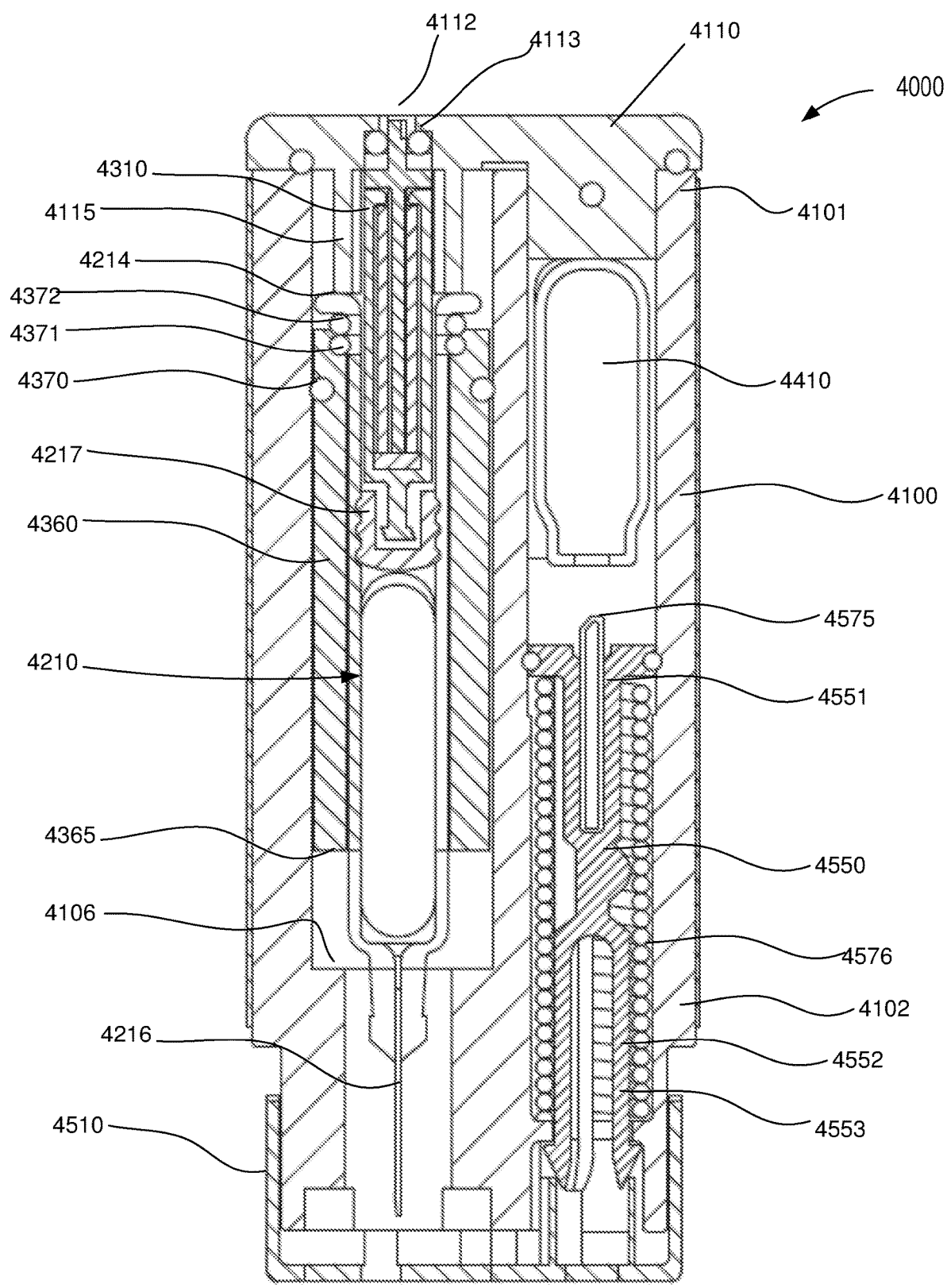
FIG. 34 is a front cross-sectional view of the medical injector shown in FIGS. 9 and 10, in a second configuration (safety lock removed).
Figure 35:
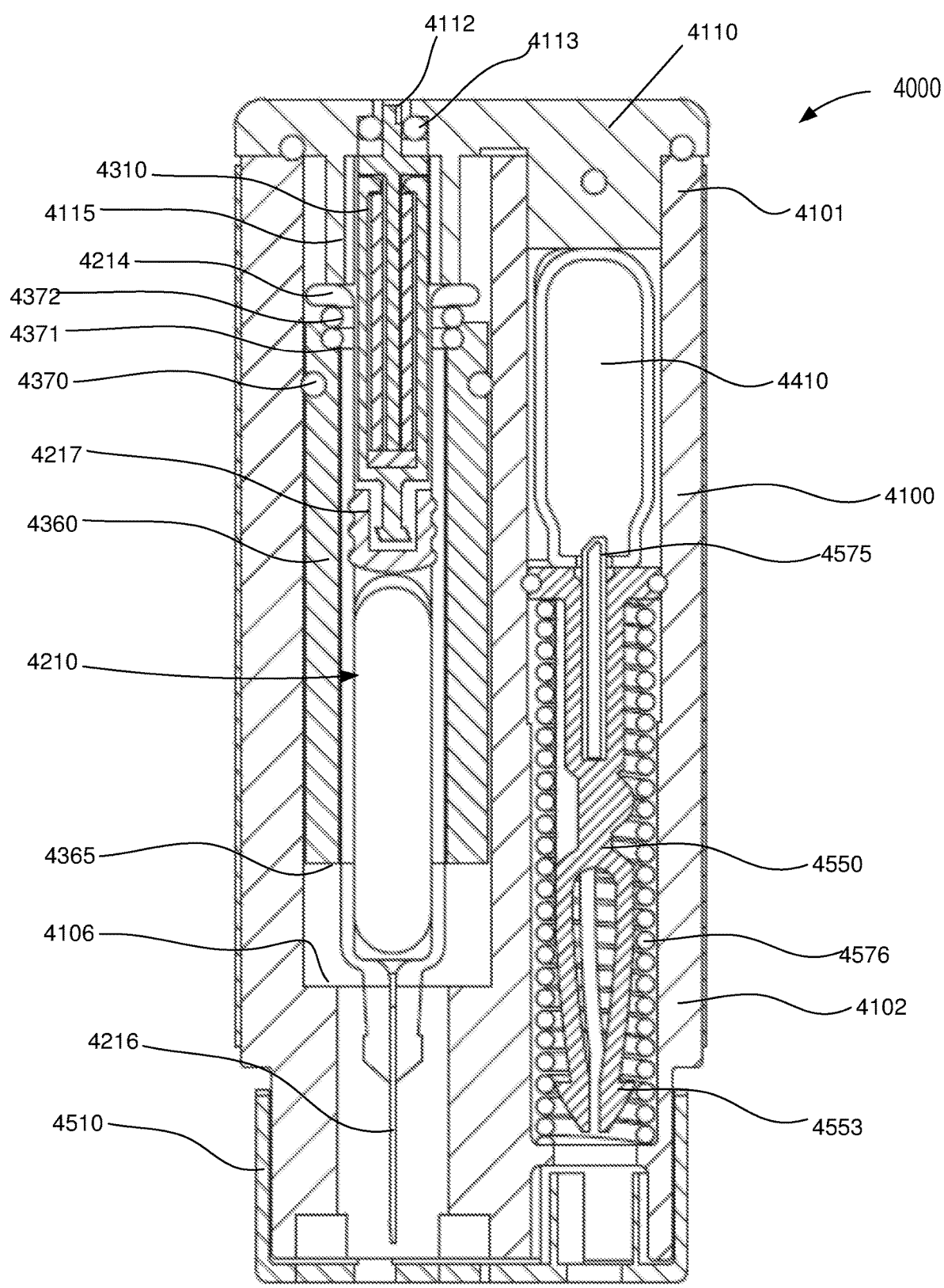
FIG. 35 is a front cross-sectional view of the medical injector shown in FIGS. 9 and 10, in a third configuration (actuated).

As shown in FIGS. 16, 17 and 34, the system actuator assembly 4500 includes the base 4510, a release member 4550 and a spring 4576. FIG. 17 shows certain internal components of the medical injector 4000 without the base 4510 and the safety lock 4700 so that the release member 4550 can be more clearly shown. The release member 4550 has a proximal end portion 4551 and a distal end portion 4552, and is movably disposed within the distal end portion of the gas container cavity 4151. The proximal end portion of the release member 4550 includes a sealing member 4574 and a puncturer 4575. The sealing member 4574 is configured to engage the sidewall of the housing 4100 defining the gas container cavity 4151 such that the proximal end portion of the gas container cavity 4151 is fluidically isolated from the distal end portion of the gas container cavity 4151. In this manner, when gas is released from the gas container 4410, the gas contained in the proximal end portion of the gas container cavity 4151 is unable to enter the distal end portion of the gas container cavity 4151. The puncturer 4575 of the release member 4550 is configured to contact and puncture a frangible seal 4413 on the gas container 4410 when the release member 4550 moves proximally within the gas container cavity 4151.

The distal end portion 4552 of the release member 4550 includes extensions 4553. The extensions 4553 have projections that include tapered surfaces and engagement surfaces. Further, the extensions 4553 define an opening between the adjacent extensions 4553. The engagement surfaces are configured to extend through the release member aperture and contact the release member contact surface of the housing 4100, as shown in FIG. 34. In this manner, the engagement surfaces limit proximal movement of the release member 4550.

The opening defined by the extensions 4553 is configured to receive the safety lock protrusion 4702 of the safety lock 4700 (see e.g., FIGS. 19 and 21) when the safety lock 4700 is coupled to the housing 4100 and/or the base 4510. The safety lock protrusion 4702 is configured to prevent the extensions 4553 from moving closer to each other. Said another way, the safety lock protrusion 4702 is configured to ensure that the extensions 4553 remain spaced apart and the engagement surfaces remain in contact with the release member contact surface of the housing 4100. In some embodiments, for example, the release member 4550 and/or the extensions 4553 can be constructed from any suitable material configured to withstand deformation that may occur when exposed to a load over an extended period of time.

The tapered surfaces of the extensions 4553 are configured to contact corresponding tapered surfaces 4557 of the base 4510 when the base 4510 is moved proximally relative to the housing 4100. Accordingly, when the base 4510 is moved proximally relative to the housing 4100, the extensions 4553 are moved together by the tapered surfaces. The inward movement of the extensions 4553 causes the release member 4550 to disengage the release member contact surface 4126 of the housing 4100, thereby allowing the release member 4550 to be moved proximally along its longitudinal axis as the spring 4576 expands (see FIG. 37).

The gas container 4410 includes a distal end portion 4411 and a proximal end portion 4412, and is configured to contain and/or produce a pressurized gas. The distal end portion 4411 of the gas container 4410 contains a frangible seal 4413 configured to break when the puncturer 4575 of the release member 4550 contacts the frangible seal 4413. The gas container retention member 4180 of the proximal cap 4110 of the housing 4100 is configured to receive and/or retain the proximal end portion 4412 of the gas container 4410. Said another way, the position of the gas container 4410 within the gas container cavity 4151 is maintained by the gas container retention member 4180. As shown in FIGS. 16 and 17, the length of the gas container retention member 4180 and the length of the release member 4550 collectively determine the distance between the puncturer 4575 and the frangible seal 4413 when the medical injector 4000 is in the storage configuration. Accordingly, this distance, which is the distance through which the puncturer 4575 travels when the medical injector 4000 is actuated, can be adjusted by changing the length of the gas container retention member 4180 and/or the length of the release member 4550. In some embodiments, the actuation time and/or the force exerted by the puncturer 4575 on the frangible seal 4413 can be adjusted by changing the distance between the puncturer 4575 and the frangible seal 4413.

Figure 23:
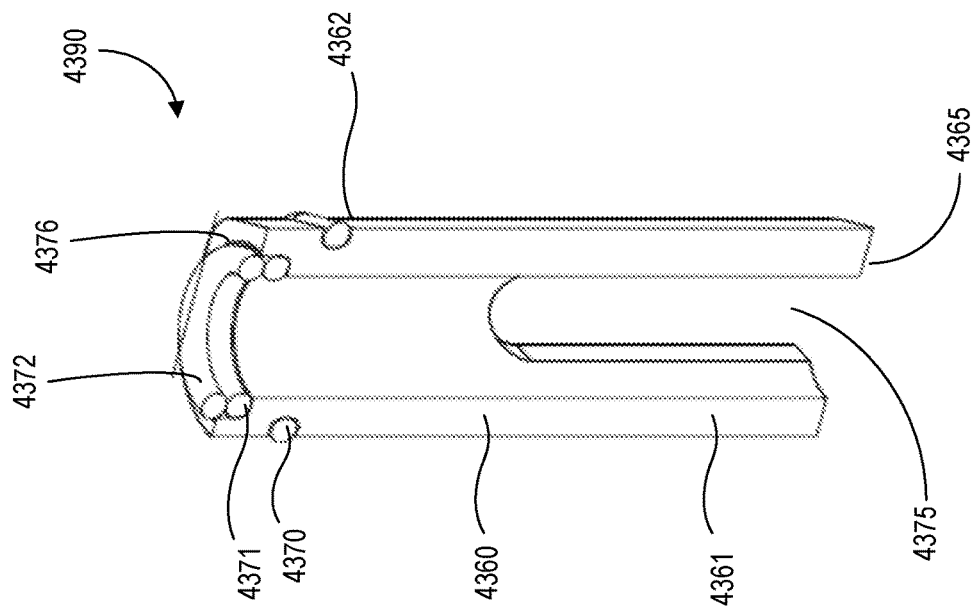
FIGS. 22 and 23 are a perspective view and a cross-sectional view, respectively, of a carrier assembly of the medical injector shown in FIGS. 9 and 10.
Figure 22:
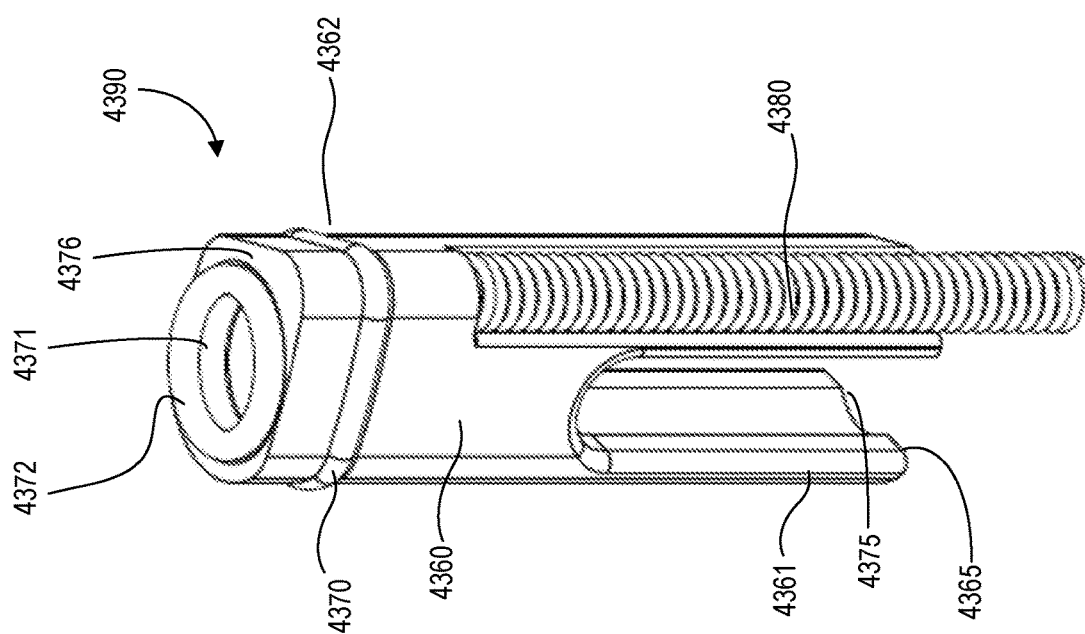
Figure 24:
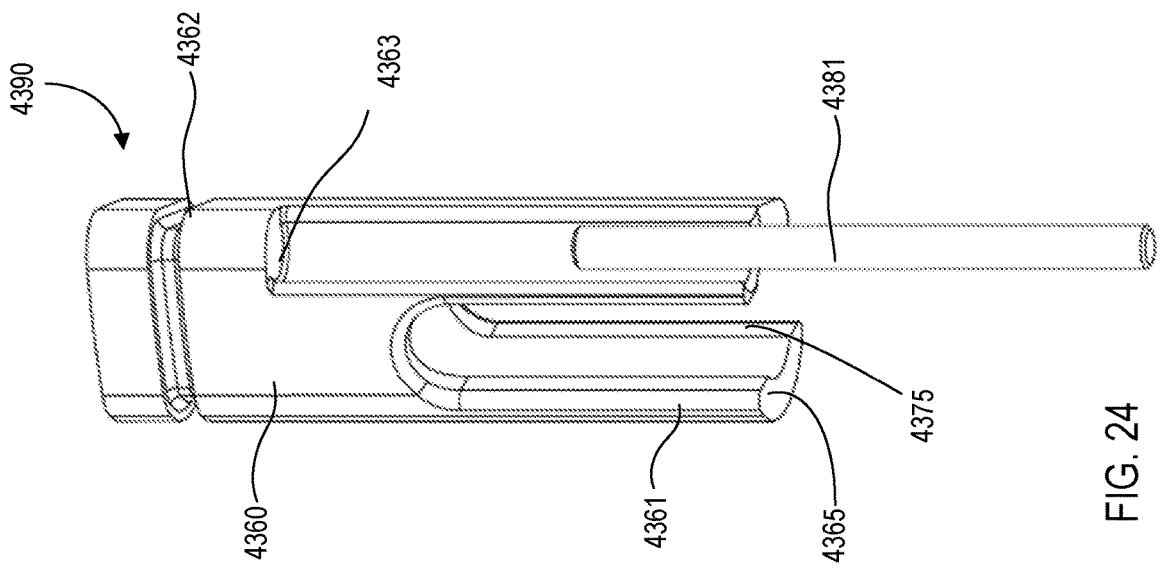
FIG. 24 is a perspective view of the carrier assembly of the medical injector shown in FIGS. 9 and 10.

The medicament delivery mechanism 4300 includes a carrier assembly 4390 and a gas vent assembly 4310. The carrier assembly 4390 and the gas vent assembly 4310 are each movably disposed within the medicament cavity 4139 of the housing 4100. As shown in FIGS. 22-24, the carrier assembly 4390 includes a carrier body 4360 and a retraction spring 4380. The carrier body 4360 includes a proximal end portion 4362 and a distal end portion 4361. The proximal end portion 4362 of the carrier body 4360 defines an opening within which the medicament container body 4210 is disposed. The proximal end portion 4362 also includes a proximal surface 4376, forms a portion of the boundary of the gas chamber (i.e., the portion of the medicament cavity 1139 within which the pressurized gas flows). In this manner, the pressurized gas produces a force on the proximal surface 4376, which moves the carrier assembly 4390 distally within the housing 4110.

An inner surface of the proximal end portion 4362 defines a groove within which a first O-ring 4371 and a second O-ring 4372 are disposed. The first O-ring 4371 and the second O-ring 4372 are disposed between a top surface of the carrier body 4360 and the flange 4214 of the medicament container body 4210. In this manner, the first O-ring 4371 and the second O-ring 4372 form a substantially fluid-tight seal. Accordingly, when pressurized gas flows into the proximal portion of the medicament cavity 4139 (i.e., the gas chamber), the area between the inner surface of the carrier body 4360 and the medicament container body 4210 is sealed. The first O-ring 4371 and the second O-ring 4372 also dampen any impact on the flange 4214.

An outer surface of the carrier body 4360 defines an O-ring groove and includes an outer O-ring 4370. The outer surface is configured to slide within the medicament cavity 4139, and the O-ring 4370 and an inner surface of the housing 4100 define a form a substantially fluid-tight seal. Accordingly, when pressurized gas flows into the proximal portion of the medicament cavity 4139, the area between the outer surface of the carrier body 4360 and the inner surface of the housing 4100 is sealed. The outer O-ring 4370 is in a fixed location relative to each of the inner O-rings 4371, 4372. In other embodiments, however, a carrier assembly can include components that move relative to each other such that an outer seal member moves relative to an inner seal member.

Figure 25:
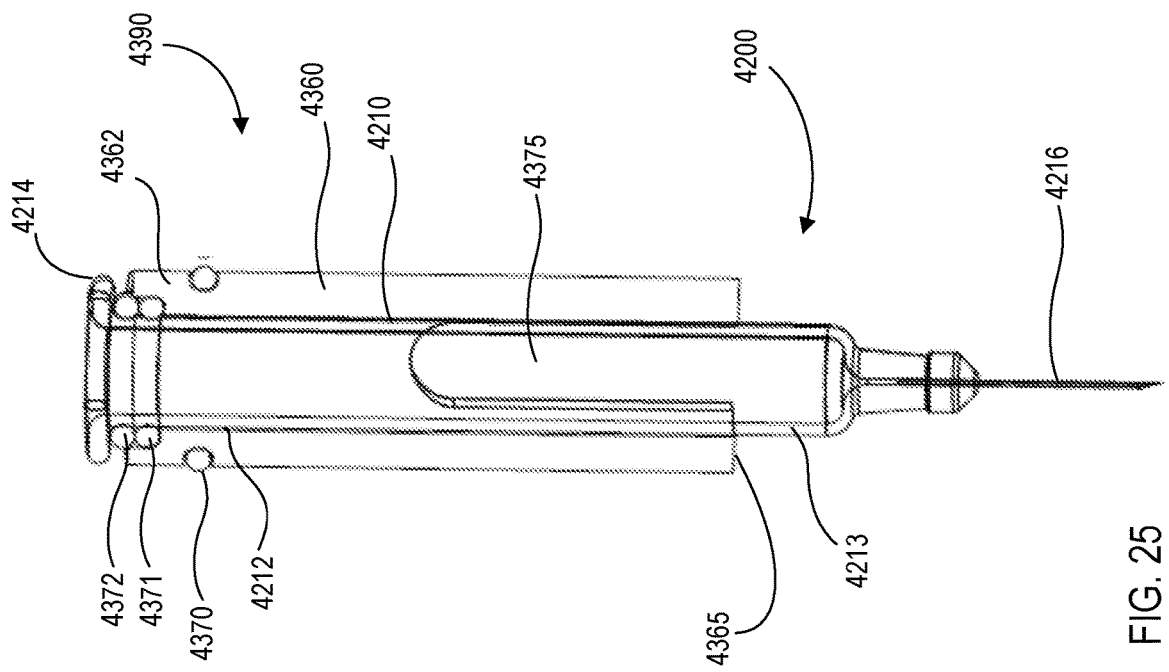
FIG. 25 is a cross-sectional view of the carrier assembly and a medicament container of the medical injector shown in FIGS. 9 and 10.

The distal end portion 4361 of the carrier body 4360 has an open end. Thus, as shown in FIGS. 24 and 25, the distal end portion 4213 of the medicament container body 4210 extends beyond the carrier body 4360. Additionally, the distal end portion 4361 of the carrier body 4360 includes two extensions (or "legs") that collectively define an opening 4375. This opening is configured to align with the status apertures 4130, 4160 of the housing to allow viewing of the medicament within the medicament container assembly, the elastomeric member 4217 or the like. The distal end portion 4361 also includes an end surface 4365 configured to contact the shoulder 4106 of the housing 4100 (see e.g., FIG. 37) when the needle 4216 has been inserted a desired distance.

The retraction spring 4380 is disposed within a spring pocket 4363 defined by the outer surface of the carrier body 4360, as shown in FIG. 24. The retraction spring 4380 is disposed about a spring pin 4381 that limits buckling or other lateral movement of the retraction spring 4380 during use.

The gas vent assembly 4310 is configured to expand and/or change configurations during operation of the medical injector 4100, and selectively produces a pathway through which pressurized gas escapes the medicament cavity 4139 after delivery of the medicament. By releasing or removing the force from the carrier body 4360 and/or the medicament container assembly 4200, the retraction spring 4380 can move the carrier body 4360 proximally to retract the needle 4216. Notably, the gas vent assembly 4310 does not exert a distal force on the elastomeric member 4217, but rather, is carried distally by the elastomeric member 4217 during delivery of the medicament. Thus, this arrangement is considered a "pistonless" delivery system, because the force for insertion and medicament delivery is provided by the pressurized gas acting directly upon the medicament container assembly 4200 (e.g., the proximal surface 4218 of the elastomeric member 4217) and/or the carrier assembly 4390 (e.g., the proximal surface 4376 of the carrier body 4360).

Figure 27:
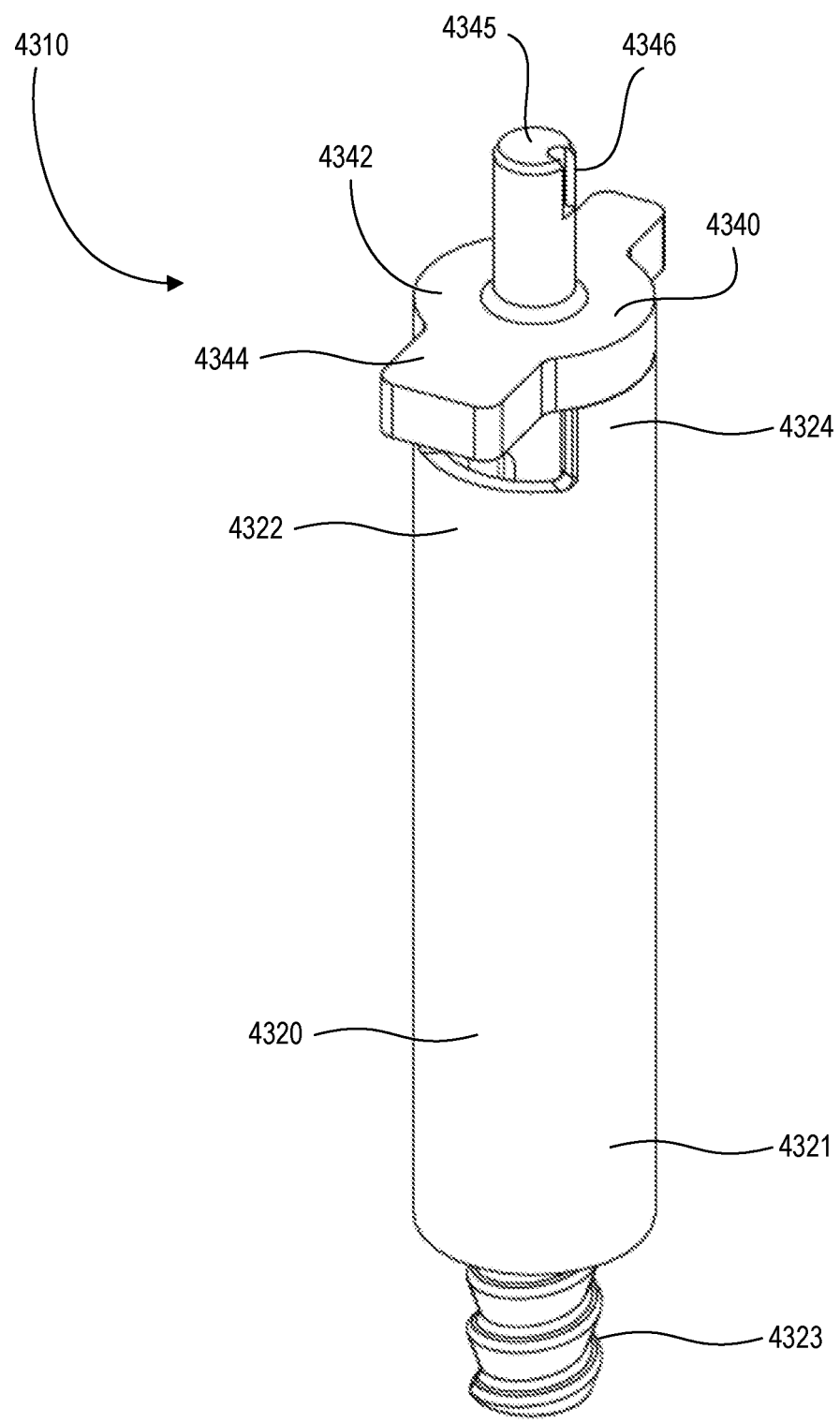
FIG. 27 is a perspective view of a gas vent assembly of the medical injector shown in FIGS. 9 and 10.
Figure 28:
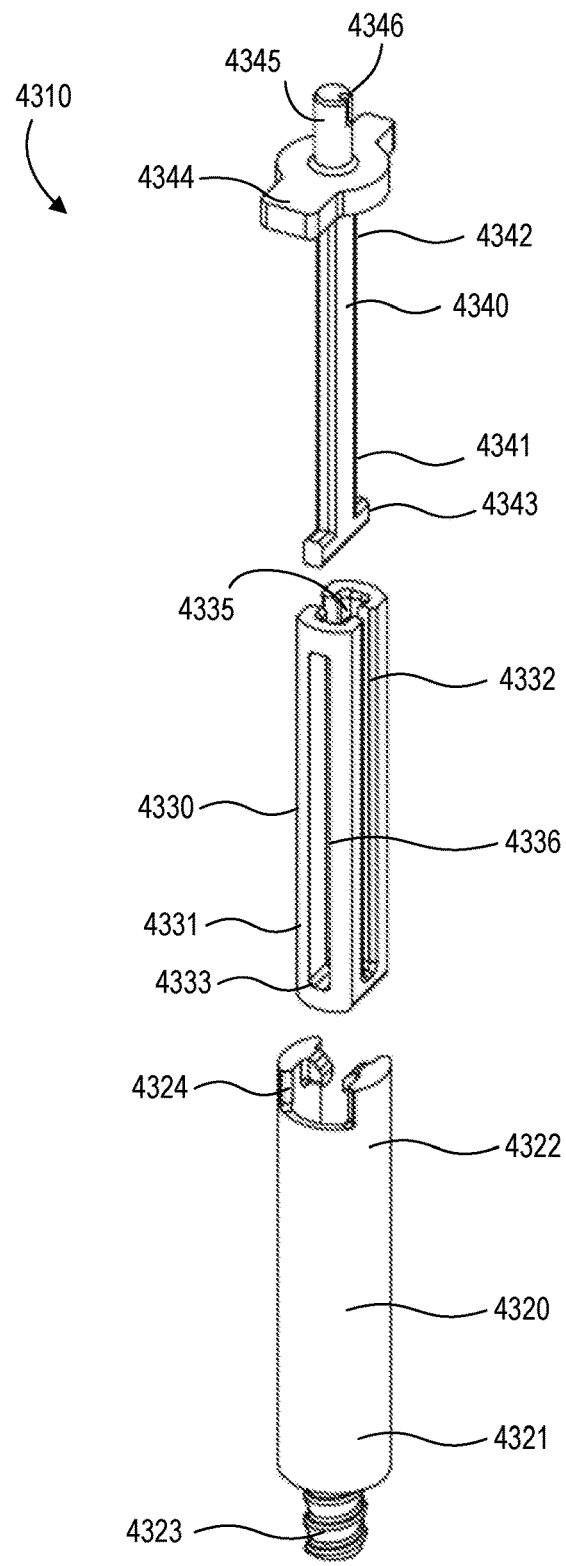
FIGS. 28 and 29 are exploded views of the gas vent assembly of the medical injector shown in FIGS. 9 and 10.

As shown in FIGS. 27-29, the gas vent assembly 4310 includes a first (or distal) member 4320, a second (or central) member 4330 and a third (or proximal) member 4340. These components are nested together such that the gas vent assembly 4310 can be transitioned from a collapsed configuration (FIG. 19) to an expanded configuration (FIG. 40), and a series of partially expanded configurations therebetween. When the gas vent assembly 4310 is in the expanded configuration (FIG. 40, after delivery of the medicament), the opening 4112, the O-ring 4113 and the passageway 4346 collectively allow the gas to escape the medicament cavity 4139, such that needle retraction can occur.

The first member 4320 includes a proximal end portion 4322 and a distal end portion 4321. The distal end portion 4321 includes a protrusion 4323 configured to matingly engage the elastomeric member 4217. In this manner, movement of the elastomeric member 4217 distally causes movement of first member 4320 distally. The proximal end portion 4322 includes a pair of retention walls 4324 configured to engage a corresponding distal end surface 4333 of the second (or central) member 4330. More particularly, the first member 4320 defines an opening within which the second member 4330 can slide. The retention walls 4324 limit movement of the second member 4330.

The second member 4330 includes a proximal end portion 4332 and a distal end portion 4331. The distal end portion 4331 includes the distal end surface 4333 that engages the first member 4320. The second member defines an opening 4335 and a pair of side grooves 4336. The third (or proximal) member 4340 is movably disposed within the opening 4335. In particular, the distal protrusions 4343 of the third member 4340 slide within the side grooves 4336 and contact the proximal end portion 4332 to limit movement of the third member 4340 within the second member 4330.

The third member 4340 includes a proximal end portion 4342 and a distal end portion 4341. The distal end portion 4341 includes the distal protrusions 4343 that engage the second member 4320. The proximal end portion 4342 includes a guide surface 4344 and a valve portion 4345. The guide surface 4344 slides within the slots 4116 of the guide wall 4115. The valve portion 4345 defines a passageway 4346.

Figure 19:
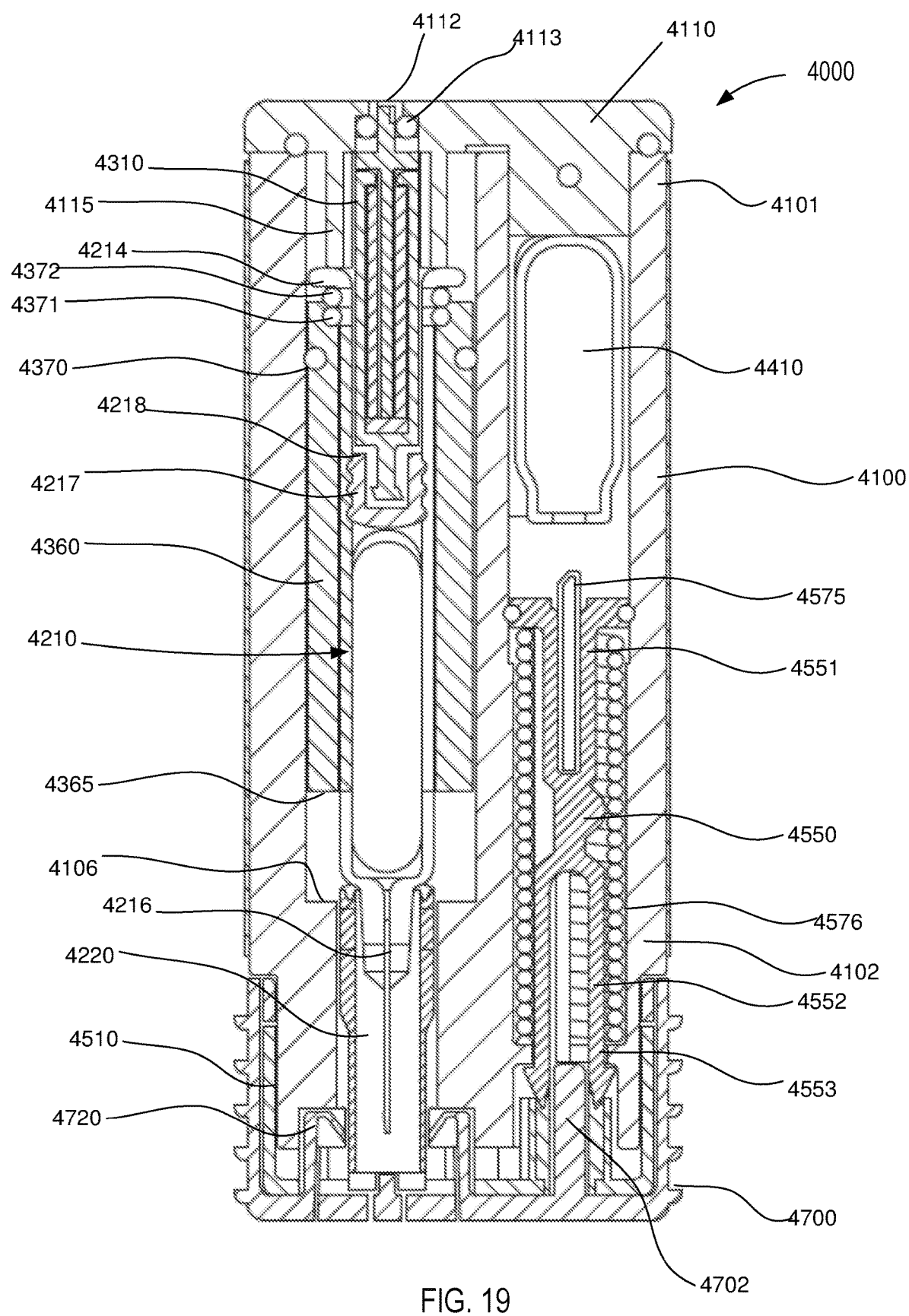
FIG. 19 is a front cross-sectional view of the medical injector shown in FIGS. 9 and 10, in the first configuration.

As shown in FIGS. 19, 30 and 31, the safety lock 4700 includes a safety lock protrusion 4702 and an engagement portion 4720. As described above, when the safety lock 4700 is in a first (locked) position, the safety lock protrusion 4702 is configured to be disposed in the opening defined by the extensions 4553 of the release member 4550. Accordingly, the safety lock protrusion 4702 is configured to prevent the extensions 4553 from moving closer to each other, thereby preventing proximal movement of the release member 4550 and/or delivery of the medicament.

The engagement portion 4720 of the safety lock 4700 includes engagement members 4721 that extend in a proximal direction. The engagement members 4721 have tabs 4722 that extend from a surface of the engagement members. The tabs 4722 engage the ribs 4236 of the sheath cover 4235 to limit relative movement between the safety lock 4700 and the needle sheath assembly 4220, as described above. In this manner, the needle sheath assembly 4220 can protect the user from the needle 4216 and/or can keep the needle 4216 sterile before the user actuates the medical injector 4000, and the needle sheath assembly 4220 can be removed from about the needle 4216 when the safety lock 4700 is removed.

The outer surface of the safety lock 4700 include a grip portion (lateral ribs) and indicia thereon. The grip portion provides an area for the user to grip and/or remove the safety lock 4700 from about the housing 4100. The indicia provide instruction on how to remove the safety lock 4700. In some embodiments, for example, indicia can indicate the direction the user should pull the safety lock 4700 to remove the safety lock 4700.

FIGS. 32 and 33 show the base (or actuator) 4510 of the medical injector 4000. The base 4510 includes a proximal (or inner) surface 4511, a distal (or outer) surface 4523 and base connection knobs 4518. The distal surface 4523 is disposed against a target surface (not shown) during use of the injector 4000. As described below, the housing 4100 is moved distally relative to the base 4510 and/or the distal surface 4523, thereby causing the base 4510 to move proximally relative to the housing 4100 to actuate the medical injector 4000. The base 4510 defines a needle aperture 4513 and a safety lock protrusion aperture 4514. The needle aperture 4513 is configured to receive the needle 4216 when the medical injector 4000 is actuated. The safety lock protrusion aperture 4514 of the base 4510 receives the safety lock protrusion 4702 of the safety lock 4700 when the safety lock 4700 is coupled to the housing 4100 and/or the base 4510.

The proximal surface 4511 of the base 4510 includes guide members (not shown) and protrusions 4515. The guide members of the base 4510 engage and/or slide within the base rail grooves 4114 of the housing 4100, as described above. The protrusions 4515 of the base 4510 engage the tapered surfaces of the extensions 4553 of the release member 4550. As described in further detail herein, when the safety lock 4700 is removed and the base 4510 is moved in a proximal direction with respect to the housing 4100, the protrusions 4515 of the base 4510 are configured to move the extensions 4553 of the release member 4550 closer to each other, actuating the medicament delivery mechanism 4300. As described above, the base connection knobs 4518 engage the base retention recesses 4134 in a way that allows proximal movement of the base 4510 but limits distal movement of the base 4510.

Figure 18:
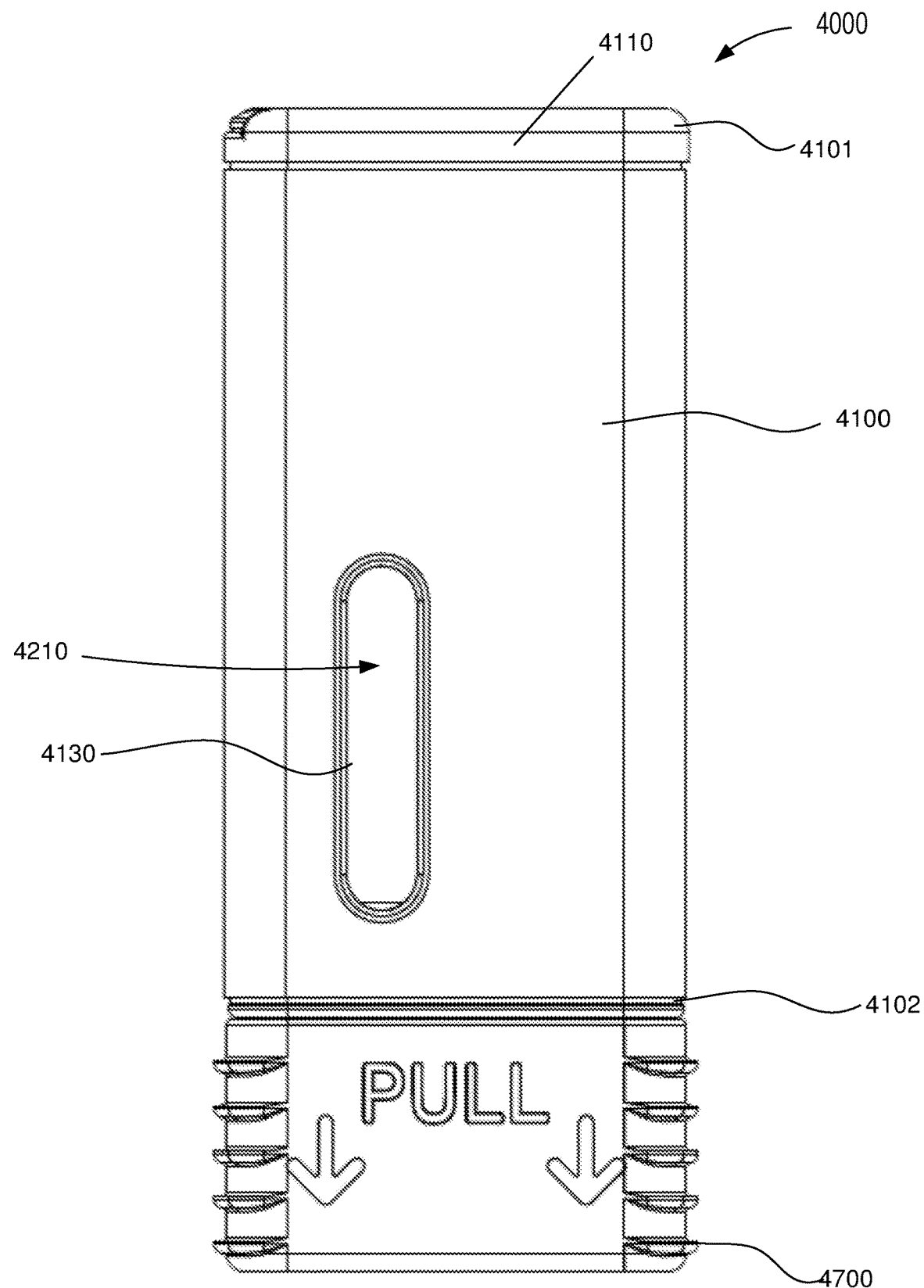
FIG. 18 is a front view of the medical injector shown in FIGS. 9 and 10, in the first configuration.

The medical injector 4000 can be moved from the first configuration (FIGS. 18 and 19) to a second configuration (FIG. 34) by moving the safety lock 4700 from a first position to a second position. The safety lock 4700 is moved from a first position to a second position by moving and/or removing the safety lock 4700 distally with respect to the housing 4100. When the safety lock 4700 is moved from the first position to the second position, the safety lock protrusion 4702 is removed from between the extensions 4553 of the release member 4550, thereby enabling the medicament delivery mechanism 4300. As shown in FIG. 18, prior to actuation, a portion of the medicament container assembly 4200 can be viewed via the status aperture 4130. Specifically, the container body 4210 and the contents therein (e.g., the medicament) can be viewed. As described above, in some embodiments, the housing 4100 can include a label or other indicia providing a color strip (against which the medicament can be compared), instructions for viewing or the like. Although not shown in FIG. 18, in some embodiments, a portion of the elastomeric member 4217 is visible via the status aperture 4130.

After the safety lock 4700 is moved from the first position to the second position, the medical injector 4000 can be moved from the second configuration (FIG. 34) to a third configuration (FIG. 35) by moving the base 4510 from a first position to a second position. Similarly stated, the medical injector 4000 can be actuated by the system actuator assembly 4500 by moving the base 4510 proximally relative to the housing 4100. The base 4510 is moved from its first position to its second position by placing the medical injector 4000 against the body of the patient and moving the base 4510 with respect to the housing 4100. Specifically, as described above the base includes a "contact portion" (i.e., the distal surface 4523) that can be placed against and/or in contact with the target location. Moving the base 4510 from the first position to the second position causes the base 4510 to engage the extensions 4553 of the release member 4550, thereby moving the extensions 4553 together. The inward movement of the extensions 4553 causes engagement surface of the release member 4550 to become disengaged from the housing 4100, thereby allowing the release member 4550 to be moved proximally along its longitudinal axis as the spring 4576 expands.

Figure 36:
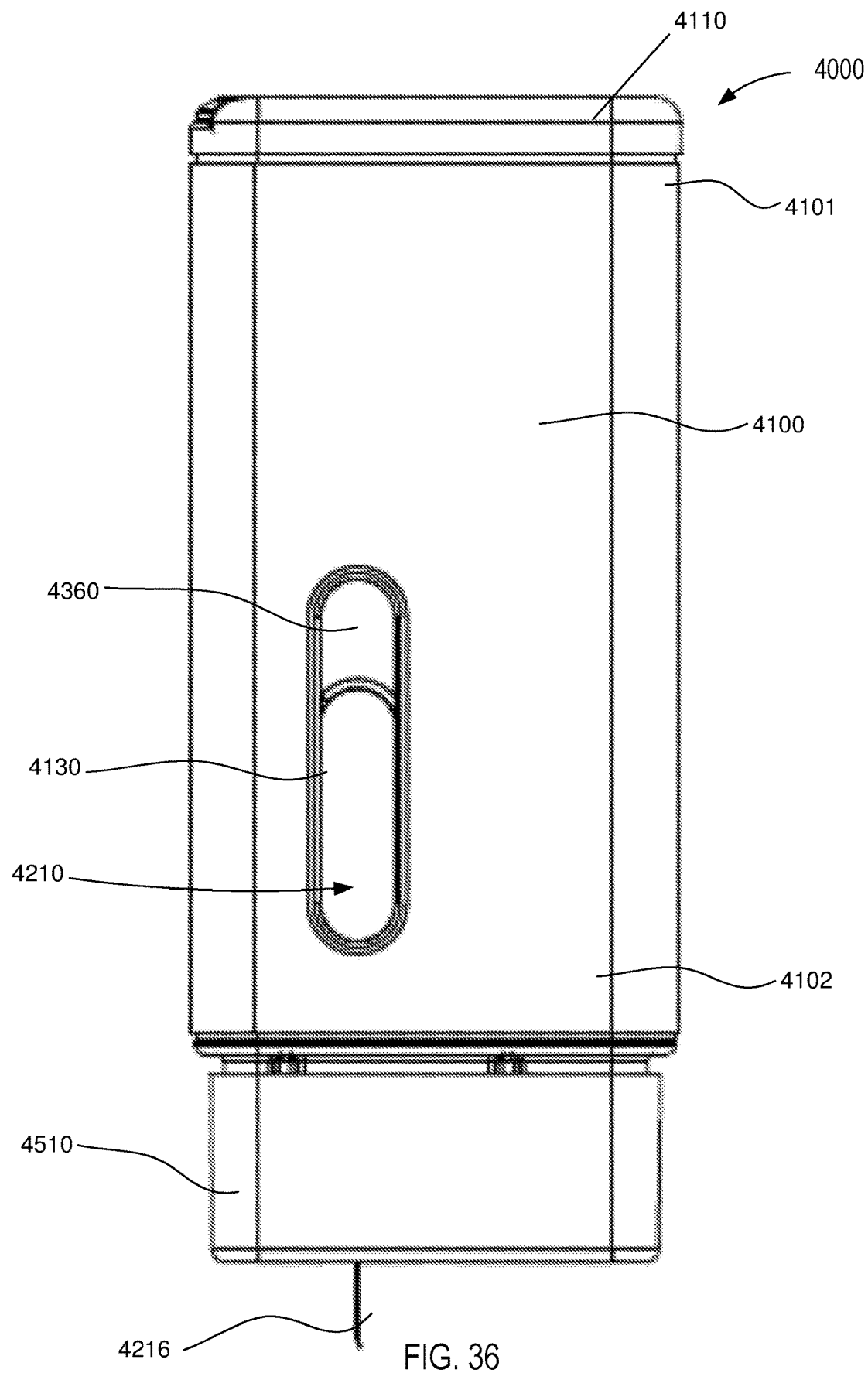
FIG. 36 is a front view of the medical injector shown in FIGS. 9 and 10, in a fourth configuration (needle inserted).
Figure 37:
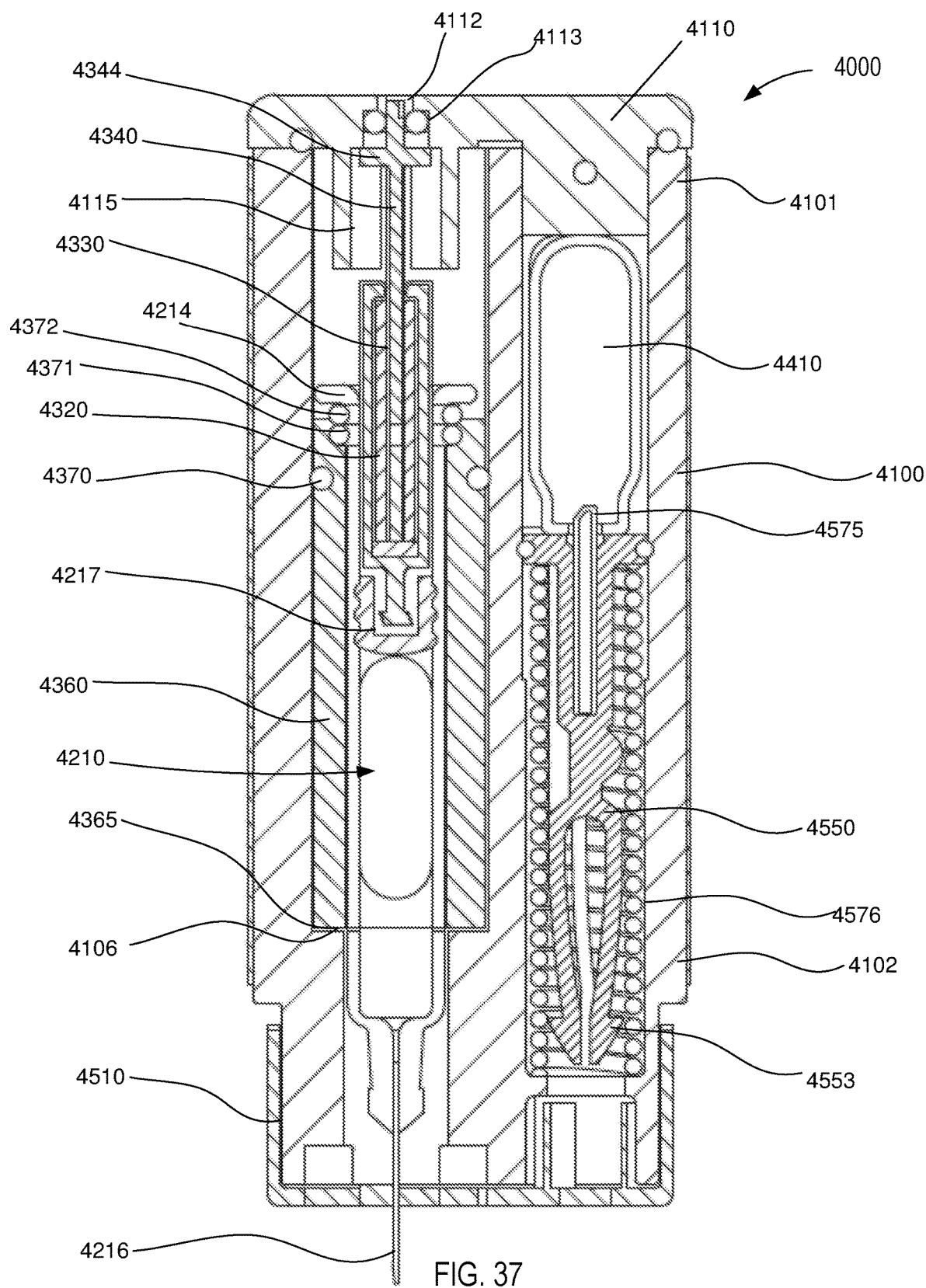
FIG. 37 is a front cross-sectional view of the medical injector shown in FIGS. 9 and 10, in the fourth configuration (needle inserted).
Figure 38:
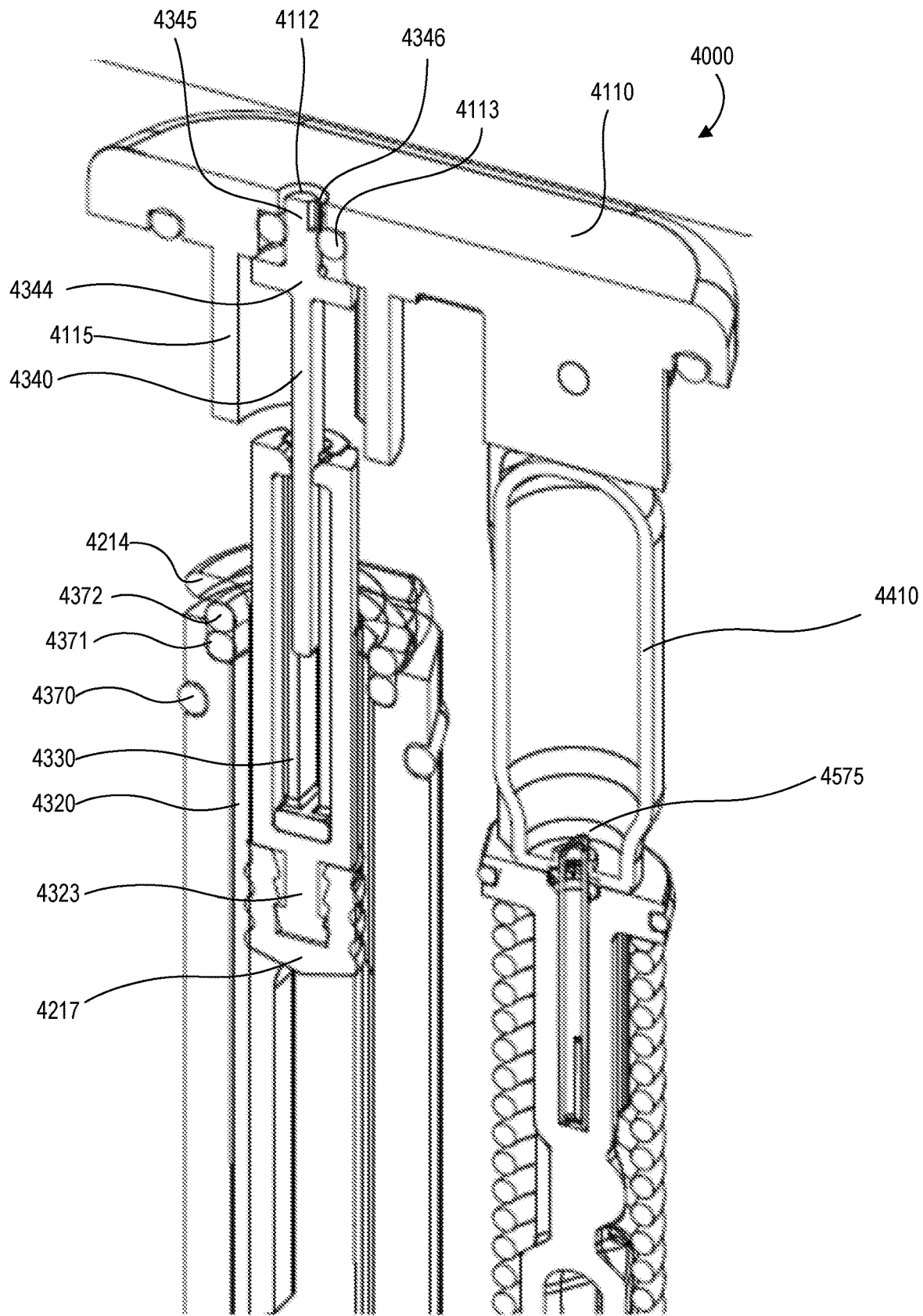
FIG. 38 is an enlarged cross-sectional view of the medical injector shown in FIGS. 9 and 10, in the fourth configuration.

When the base 4510 is moved from the first position to the second position, the system actuator assembly 4500 actuates the medicament delivery mechanism 4300, thereby placing the medical injector 4000 in its fourth configuration (i.e., the needle insertion configuration), as shown in FIGS. 36 and 37. More particularly, when the medical injector 4000 is in its fourth configuration, the puncturer 4575 of the release member 4550 is in contact with and/or disposed through the frangible seal 4413 of the gas container 4410.

After the frangible seal 4413 has been punctured, an actuating portion of a compressed gas flows from the gas container 4410, via the gas passageway and into the medicament cavity 4139. The gas applies gas pressure to flange 4214 of the medicament container and/or the top surface of the carrier body 4360. Because the seals 4371, 4372 and the outer seal 4370 maintain the medicament cavity 4139 fluidically isolated from the exterior of the device, the gas pressure exerts a force to move the carrier assembly 4390 distally within the medicament cavity 4139, as shown in FIG. 37. In this manner, the movement of the needle 4216 in a distal direction causes the distal end portion of the needle 4216 to exit the housing 4100 and enter the body of a patient prior to administering the medicament.

As shown in FIG. 37, when the device moves from the third configuration to the fourth configuration, the gas vent assembly expands from its collapsed configuration (FIGS. 18, 34) to a partially expanded configuration. Notably, in the partially expanded configuration, the valve portion 4345 is maintained in a sealed position within the opening 4112 and the O-ring 4113. Thus, the medicament cavity 4139 is maintained in fluidic isolation.

When the needle 4216 has extended by a desired distance, the distal surface 4365 of the carrier body 4360 contacts the surface 4106 of the housing 4100 to limit further distal movement of the carrier assembly 4390 within the housing 4100. When the distal movement of the carrier assembly 4390 is prevented, the gas within the medicament cavity 4139 (i.e., the gas chamber) continues to apply gas pressure to the elastomeric member 4217. This causes the elastomeric member 4217 (and therefore the first member 4320 of the gas vent assembly 4310) to move in the distal direction with the medicament container body 4210. Distal movement of the elastomeric member 4217 generates a pressure upon the medicament contained within the medicament container assembly 4200, thereby allowing at least a portion of the medicament to flow out of the medicament container 4200 via the needle 4216. The medicament is delivered to a body of a user via the medicament delivery path defined by the medicament container 4200 and the needle 4216. At the end of injection, the medical injector is in its fifth configuration (FIG. 40).

Figure 39:
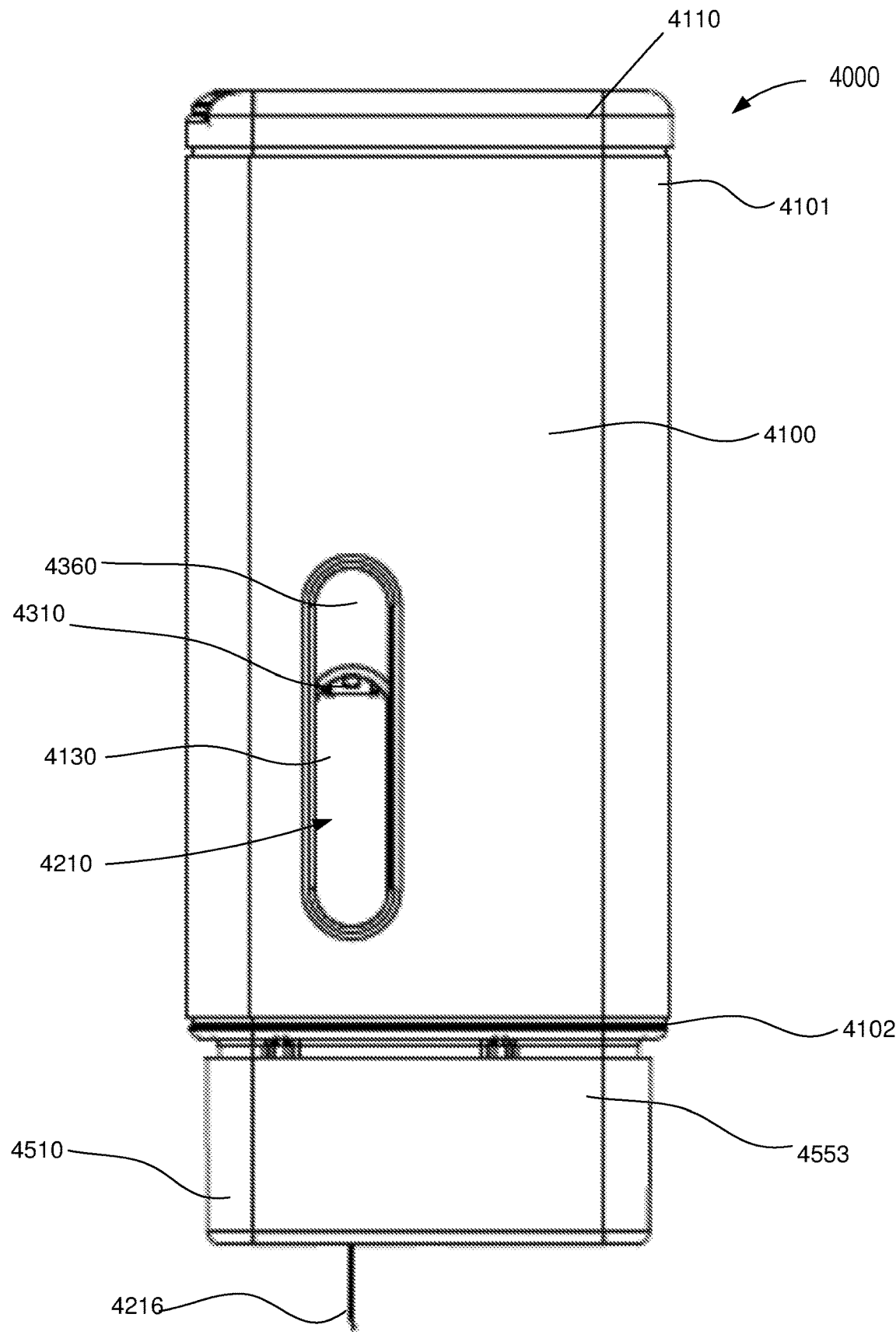
FIG. 39 is a front view of the medical injector shown in FIGS. 9 and 10, in a fifth configuration (medicament delivered).

As shown in FIG. 39, when the medical injector 4000 is in its fifth configuration, a portion of the medicament container assembly 4200, a portion of the carrier body 4360, and a portion of the gas vent assembly 4310 can be viewed via the status aperture 4130. As described above, in some embodiments, the housing 4100 can include a label or other indicia providing a color strip to assist the user in identifying the carrier, providing instructions for viewing, or the like. Although not shown in FIG. 18, in some embodiments, a portion of the elastomeric member 4217 is visible via the status aperture 4130 when the medical injector 4000 is in its fifth configuration.

Figure 40:
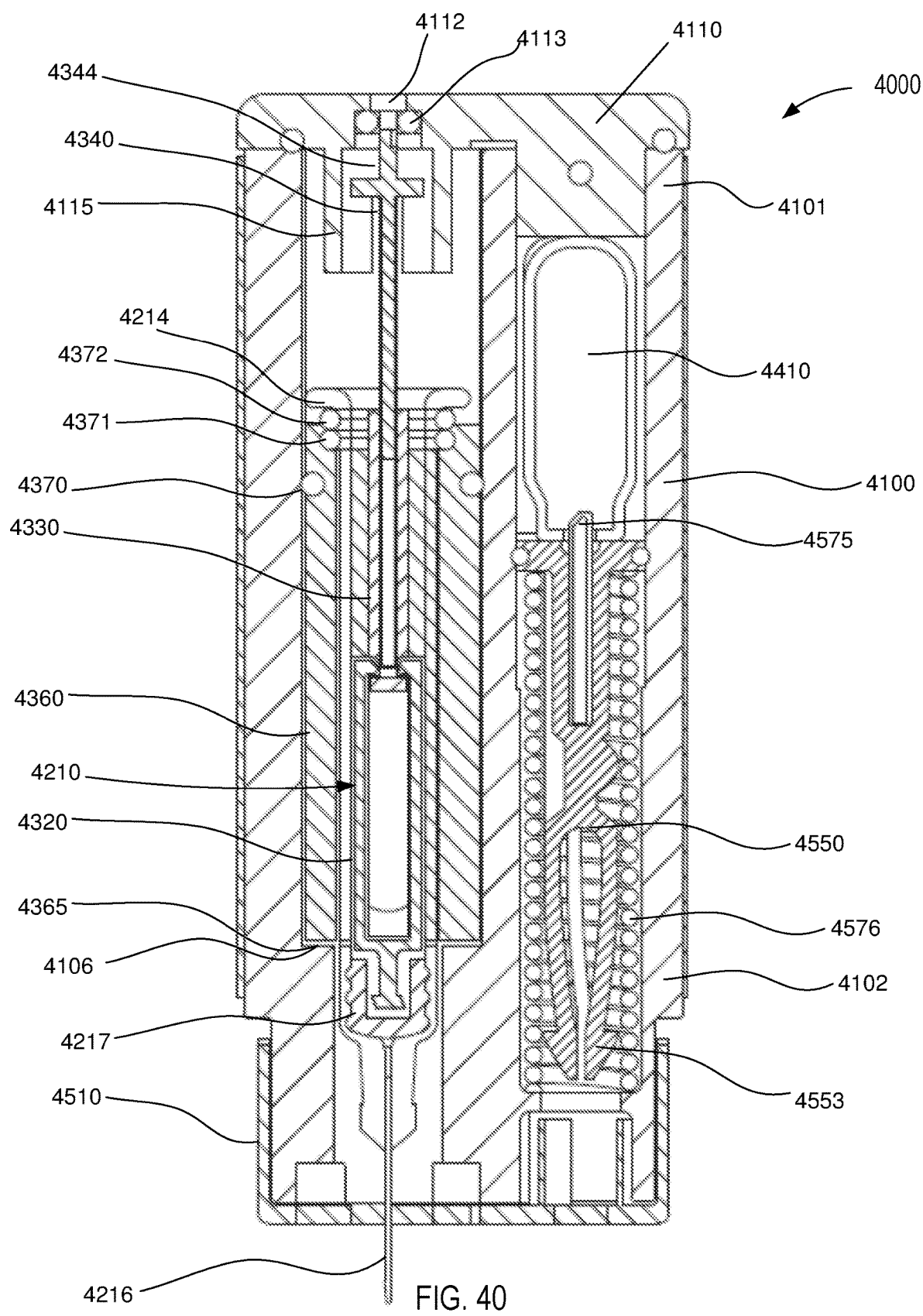
FIG. 40 is a front cross-sectional view of the medical injector shown in FIGS. 9 and 10, in the fifth configuration (medicament delivered).
Figure 41:
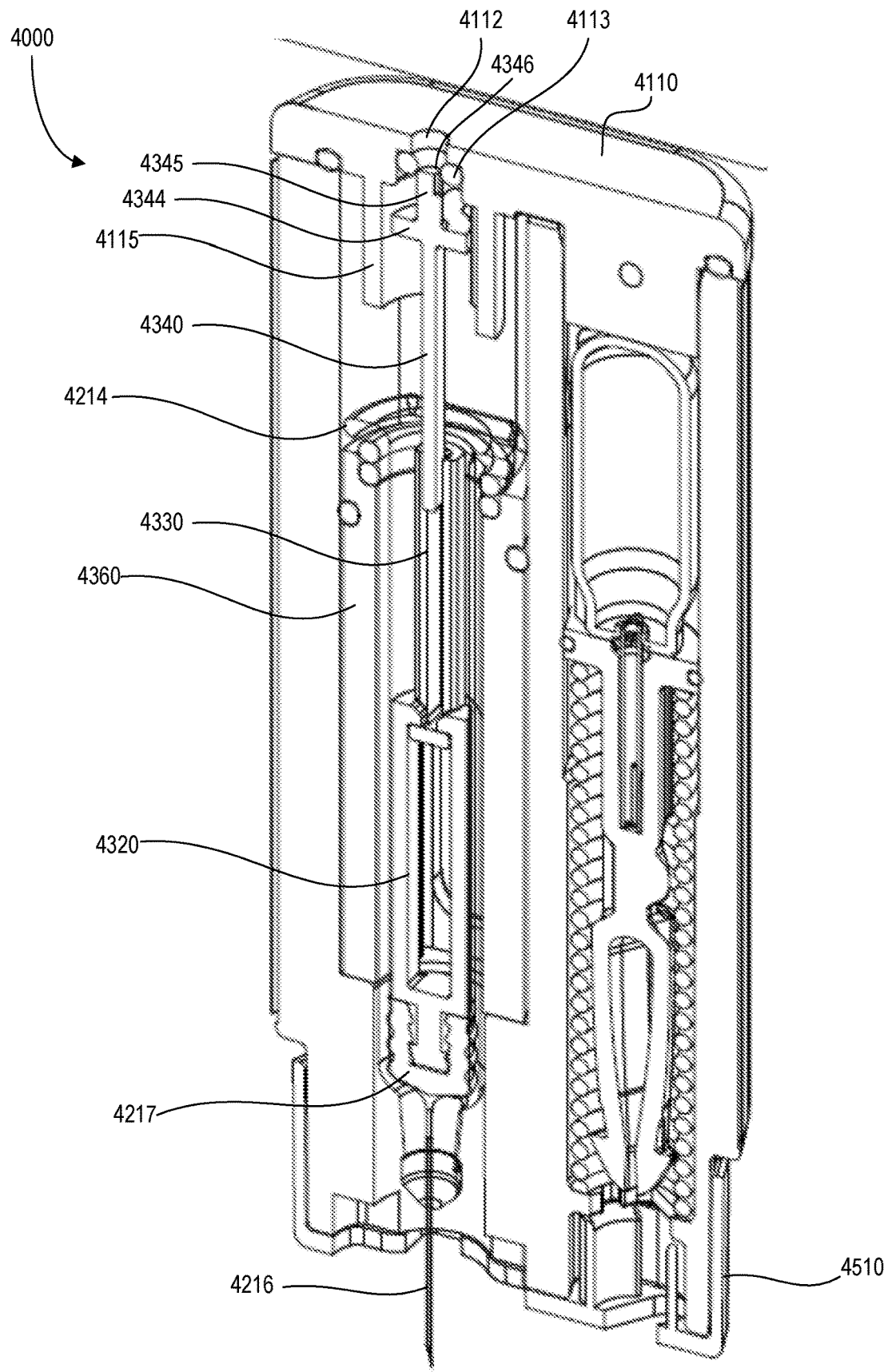
FIG. 41 is a perspective cross-sectional view of the medical injector shown in FIGS. 9 and 10, in the fifth configuration (medicament delivered).

As shown in FIGS. 40 and 41, as the elastomeric member 4217 moves distally, the gas vent assembly 4310 continues to move to its fully expanded configuration. After the elastomeric member 4217 has moved a predetermined distance within the medicament container body 4210 (corresponding to the desired dose), the valve portion 4345 is moved from within the opening 4112 thereby allowing the pressurized gas contained within the gas chamber (i.e., the volume within the medicament cavity 4139 between the proximal end of the housing 4100 and the surface of the carrier 4360) to escape via the passageway 4346 and the opening 4112. After the gas pressure within the medicament cavity 4139 decreases below a certain level, the force exerted by the retraction spring 4380 on the carrier body 4360 is sufficient to cause the carrier body 4360 to move proximally within the housing 4100 (i.e., to retract). This places the medical injector in its sixth configuration (FIGS. 42 and 43).

Figure 42:
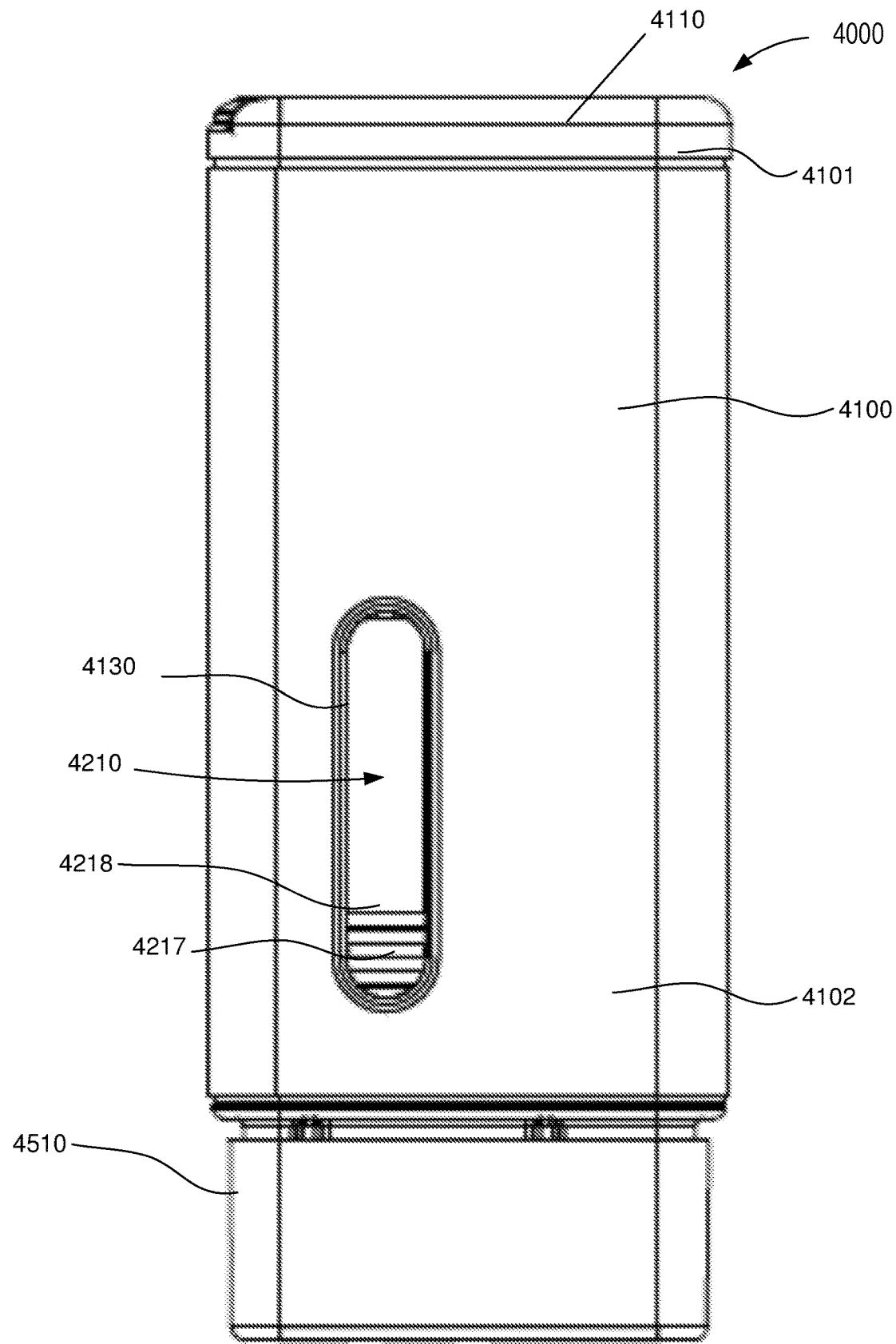
FIG. 42 is a front view of the medical injector shown in FIGS. 9 and 10, in a sixth configuration (needle retracted).
Figure 43:
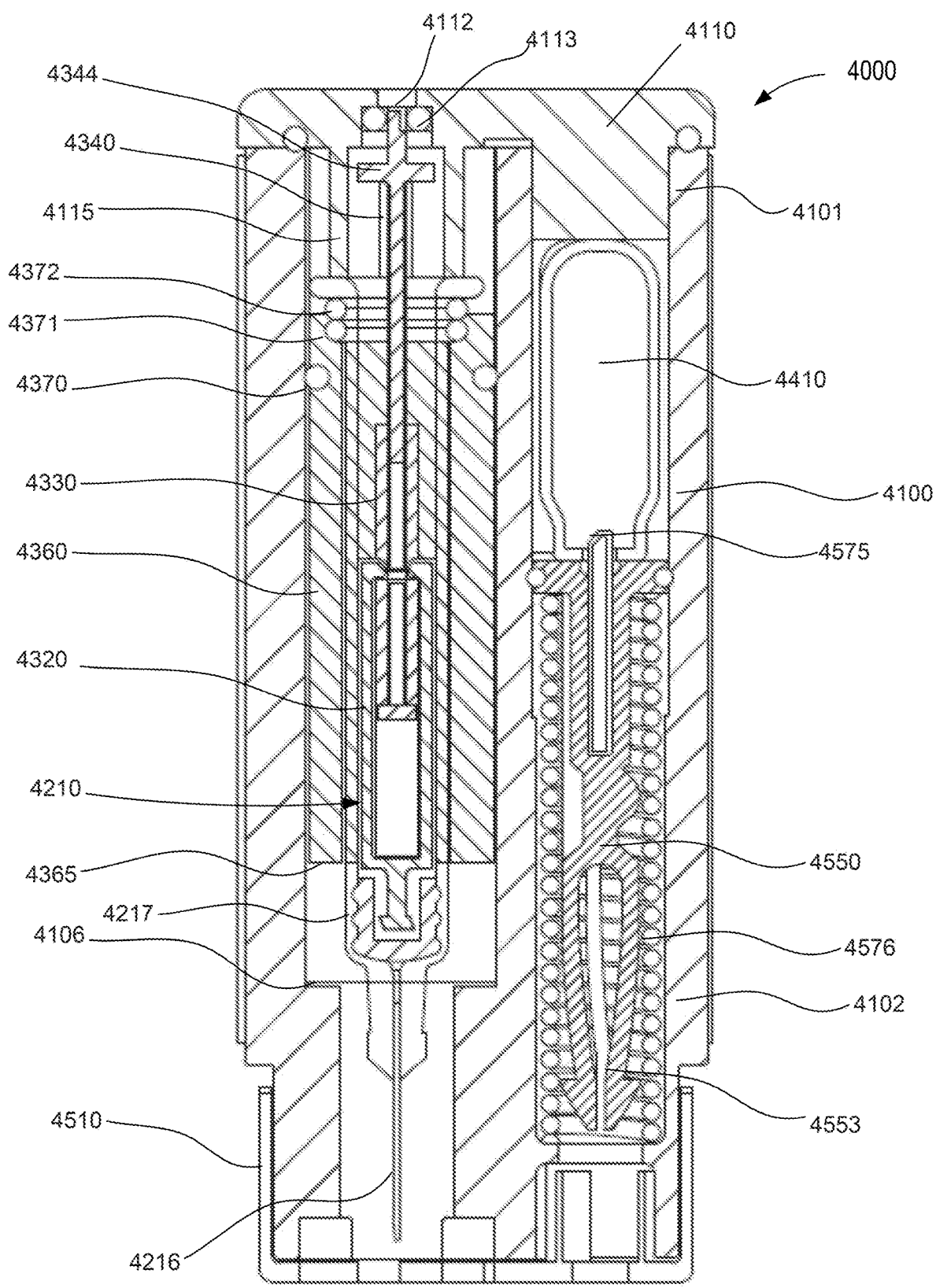
FIG. 43 is a front cross-sectional view of the medical injector shown in FIGS. 9 and 10, in a sixth configuration (needle retracted).

As shown in FIG. 42, when the medical injector 4000 is in its sixth configuration, a portion of the medicament container assembly 4200 can be viewed via the status aperture 4130. Specifically, as shown, the container body 4210 and a portion of the elastomeric member 4217 are visible via the status aperture 4130. As described above, in some embodiments, the housing 4100 can include a label or other indicia providing a color strip to assist the user in identifying the elastomeric member, providing instructions for viewing, or the like. Although not shown in FIG. 18, in some embodiments, a portion of the carrier 4360 is visible via the status aperture 4130 when the medical injector 4000 is in its sixth configuration.

As described above, the medicament delivery mechanism 4300 is considered to be a "pistonless" system. With a pistonless gas-powered auto-injector, the force exerted by the gas can move the medicament container relative to the housing and similarly, can move the elastomeric member 4217 relative to (e.g., within) the container body 4210. In some embodiments, by not including a movable mechanism, a piston, and/or the like, a height of the medical injector 4000 can be reduced relative to, for example, the height of a device that includes a rigid, single length piston.

Figure 44:
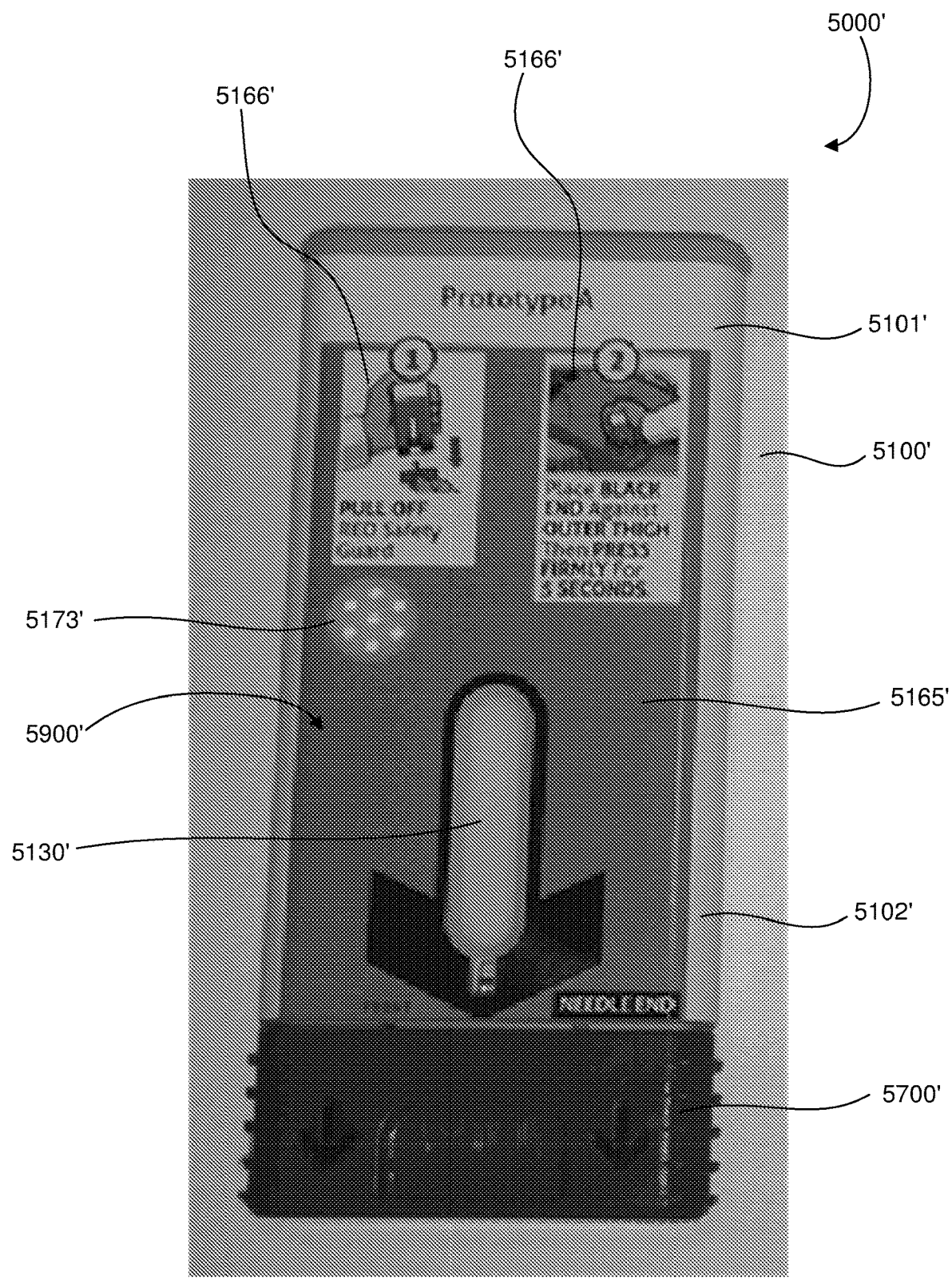
FIG. 44 is a photograph of a medicament delivery device (or model thereof) according to an embodiment.
Figure 48:
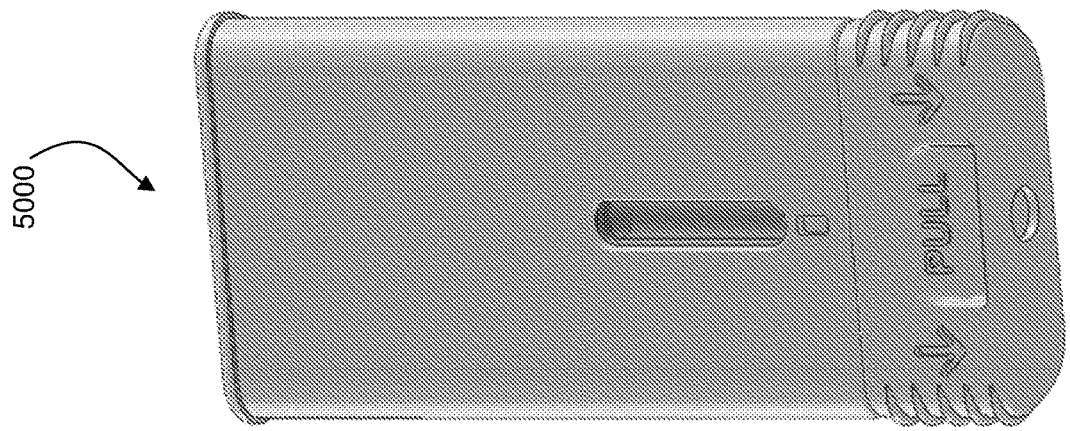
Figure 47:
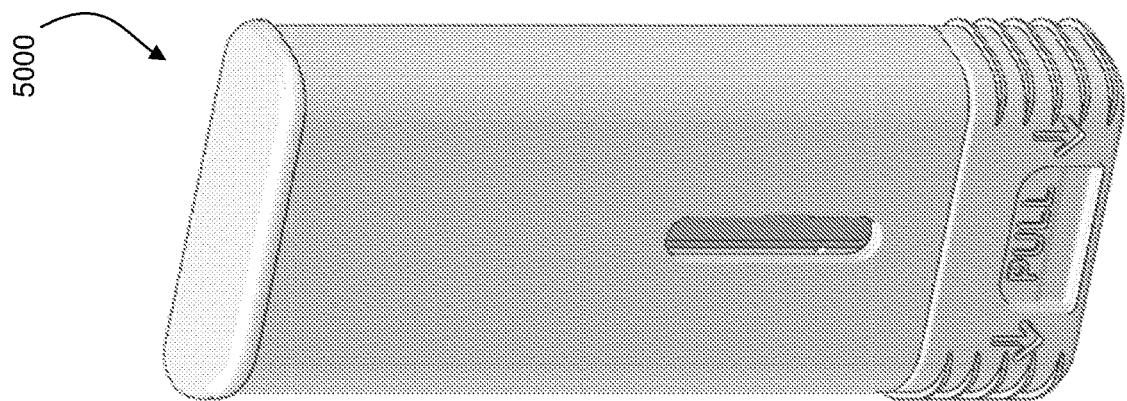

In some embodiments, any of the devices shown and described herein can include an electronic circuit system to provide user instruction and/or feedback. In some embodiments the electronic circuit system can be integral to the device (e.g., included within the housing, such as the housing 4100). In other embodiments, the electronic circuit system can be an external, discrete component that is affixed to the device. For example, FIG. 44 shows a photograph of a medical injector 5000' that includes an electronic circuit system 5900'.

The medical injector 5000' includes a housing 5100', a system actuation assembly (not shown), a medicament container assembly (not shown), a medicament delivery mechanism (not shown), a base', a safety lock 5700', and an electronic circuit system 5900'. Although not shown in FIG. 44, the system actuation assembly is similar to the system actuation assembly 4500 described above with respect to the medical injector 4000 (see FIGS. 16-17). Thus, the system actuation assembly of the medical injector 5000' is not described in detail herein. Although not shown in FIG. 44, the medicament container assembly is similar to the medicament container assembly 4200 described above with respect to the medical injector 4000 (see FIG. 26). Thus, the medicament container assembly of the medical injector 5000' is not described in detail herein. Although not shown in FIG. 44, the medicament delivery mechanism is similar to the medicament delivery mechanism 4300 described above with respect to the medical injector 4000 (see FIGS. 22-29). Thus, the medicament delivery mechanism of the medical injector 5000' is not described in detail herein.

As shown, the housing 5100' has a proximal end portion 5101' and a distal end portion 5102'. The housing 5100' defines a first status indicator aperture 5130' (on the first or front side) and a second status indicator aperture (not shown, on the second or back side). The status indicator aperture 5130' can allow a patient to monitor the status and/or contents of the medicament container, the carrier, and the medicament contained within the housing 5100. For example, by visually inspecting the status indicator apertures 5130', a patient can determine whether the medicament container contains a medicament and/or whether the medicament has been dispensed.

As shown, the housing 5100' includes a label 5165' that includes a series of indicia 5166'. The indicia 5166' include the colored portions that mask or otherwise accentuate the status indicator aperture 5130' and/or the contents viewed therethrough. The indicia 5166' also include instructions for use, descriptions of the device 5000', and the like. The label 5165' also defines an opening through which the sound apertures 5173' can be exposed.

The medical injector 5000' includes an electronic circuit system configured to control, actuate, and/or otherwise produce an output associated with a portion of the medical injector 5000'. Although not shown in FIG. 44, the safety lock 5700' includes a battery isolation tab, which functions similar to a battery isolation protrusion of the cover, described in detail in the '849 patent. In particular, the safety lock 5700' can include a protrusion that extends into the housing 5100' and selectively isolates a power source (e.g., a battery) from the remaining portions of the electronic circuit system 5900'. Thus, removal of the safety lock 5700' results in (1) removal of a needle sheath (similar to the sheath assembly 4220 described above), and (2) electrically connecting a battery to a remainder of an electronic circuit system, thus producing an initial electronic output. In some embodiments, the removal of the safety lock can also engage a switch to produce an electronic output instructing a user in the operation of the medical injector 5000'. Specifically, in some embodiments, the safety lock 5700' includes a protrusion that engages a circuit board or otherwise contacts a switch or sensor (not shown) to produce an electronic output. The electronic circuit system of the medical injector 5000' can be similar to any of the electronic circuit systems shown and described herein and in the '849 patent.

In some embodiments, the electronic circuit system 5900' (and any of the electronic circuit systems described herein) can include an audio output device configured to output audible sound to a user in response to use of the medical injector 5000'. In some embodiments, the audible output device can be a speaker. In some embodiments, the audible sound can be, for example, associated with a recorded message and/or a recorded speech. In other embodiments, the audible instructions can be an audible beep, a series of tones and/or or the like.

In some embodiments, the electronic circuit system 5900' (and any of the electronic circuit systems described herein) can include a light output device configured to output a visual signal to a user in response to use of the medical injector 5000'. In some embodiments, the light output device can be a light emitting diode (LED). In some embodiments, the visual signal can be, for example, a series of flashes, a sequence of lights, or the like.

In some embodiments, the electronic circuit system 5900' (and any of the electronic circuit systems described herein) can include a network interface device (not shown) configured to operatively connect the electronic circuit system 5900' to a remote device (not shown) and/or a communications network (not shown). In this manner, the electronic circuit system 5900' can send information to and/or receive information from the remote device. The remote device can be, for example, a remote communications network, a computer, a compliance monitoring device, a cell phone, a personal digital assistant (PDA) or the like. Such an arrangement can be used, for example, to download replacement processor-readable code from a central network to the electronic circuit system 5900'. In some embodiments, for example, the electronic circuit system 5900' can download information associated with a medical injector 5000', such as an expiration date, a recall notice, updated use instructions or the like. Similarly, in some embodiments, the electronic circuit system 5900, can upload information associated with the use of the medical injector 5000' via the network interface device (e.g., compliance information or the like).

In addition to providing user instruction and/or feedback via the electronic circuit system, the medical injector 5000' can also provide user feedback and/or instruction via a visual status window 5130'. The status window 5130' and/or a portion of the housing are configured such that various portions of the medicament delivery mechanism and/or the medicament container are visible therethrough during various stages of operation. For example, in some embodiments, all or portions of a medicament container assembly and/or movable mechanism (e.g., a prefilled syringe, an elastomeric member or plunger, a carrier, a movable mechanism, etc., as shown and described in the '849 patent) can be visible through the status window 5130'.

In some embodiments, the medical injector 5000' can provide non-electronic user feedback and/or instruction via a sound produced by the pressurized gas, by the interface between components during actuation, or the like. In this manner, the medical injector 5000' can include both electronic outputs (e.g., via lights and/or sound) and non-electronic outputs (e.g., via the status window and/or an acoustic noise output). In some embodiments, for example, the gas release valve (similar to the gas relief opening 4112 and the gas venting assembly 4310 described above) can include an orifice or chamber such that the escaping gas produces a sound or "whistle." In some embodiments, the orifice or flow path can be configured such that the sound is within a desired frequency range or loudness. In other embodiments, the non-electronic output can be a clicking sound, a snapping sound, a clapping sound, a cracking sound, and/or any other suitable audible output. In other embodiments, the base can produce a distinct snapping sound when it contacts a locking feature of the housing during actuation. In yet other embodiments, one or more prefilled syringes within the medical injector 5000' can be disposed within a carrier inside of the housing (not shown in FIG. 1). The carrier can produce a desired sound when it impacts an internal surface of the housing during actuation. In other embodiments, a component inside the housing can produce an audible output only after the needle is inserted into the patient, only after the drug is delivered into the patient, or only after the needle retracts into the housing. This output may be different then the activation sound or output.

FIGS. 45-48 are perspective views of a medical injector 5000 that includes an electronic circuit system 5900. The medical injector 5000 includes a housing 5100, a system actuation assembly (not shown), a medicament container assembly (not shown), a medicament delivery mechanism (not shown), a base', a safety lock 5700. Although not shown, the system actuation assembly is similar to the system actuation assembly 4500 described above with respect to the medical injector 4000 (see FIGS. 16-17). Thus, the system actuation assembly of the medical injector 5000 is not described in detail herein. Although not shown, the medicament container assembly is similar to the medicament container assembly 4200 described above with respect to the medical injector 4000 (see FIG. 26). Thus, the medicament container assembly of the medical injector 5000 is not described in detail herein. Although not shown, the medicament delivery mechanism is similar to the medicament delivery mechanism 4300 described above with respect to the medical injector 4000 (see FIGS. 22-29). Thus, the medicament delivery mechanism of the medical injector 5000 is not described in detail herein. The electronic circuit system 5900 of the medical injector 5000 is similar to that of the medical injector 5000' and is therefore not described in detail.

Although the medical injector 5000' and the medical injector 5000 are shown as being devoid of an outer cover, in other embodiments, the medical injector 5000', the medical injector 5000, and any of the medicament delivery devices shown and described herein can include an outer cover that covers and/or surrounds at least a portion of the housing, the safety lock and/or the base. Such covers can also cover the status apertures to limit the light that is transmitted into the medicament container. Such covers can also interact with an electronic circuit system (e.g., the electronic circuit systems 5900' and 5900), causing the production of an electronic output when the cover and/or a safety lock is removed.

Figure 49:
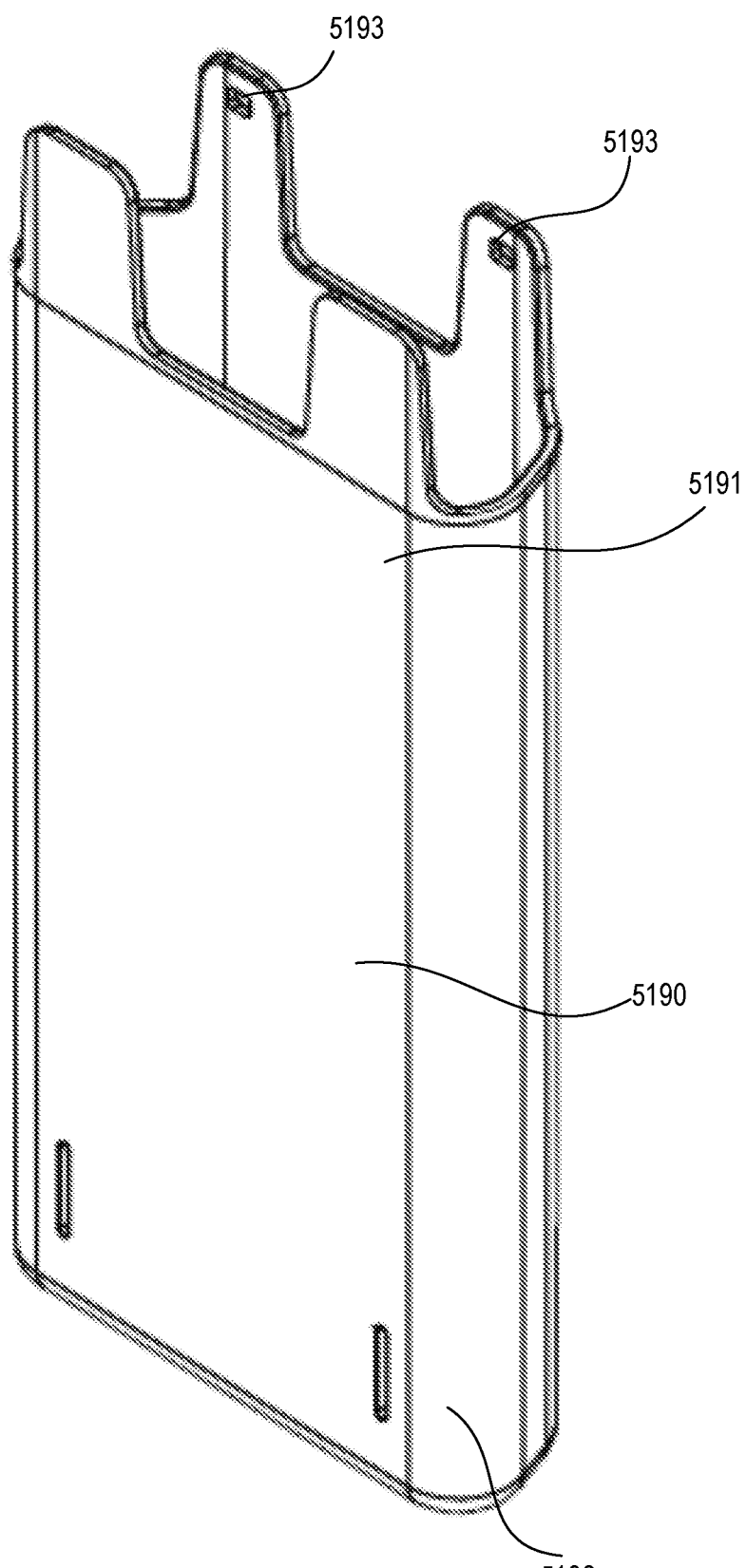
FIGS. 49 and 50 are perspective views of a cover of a medical injector, according to an embodiment.
Figure 50:
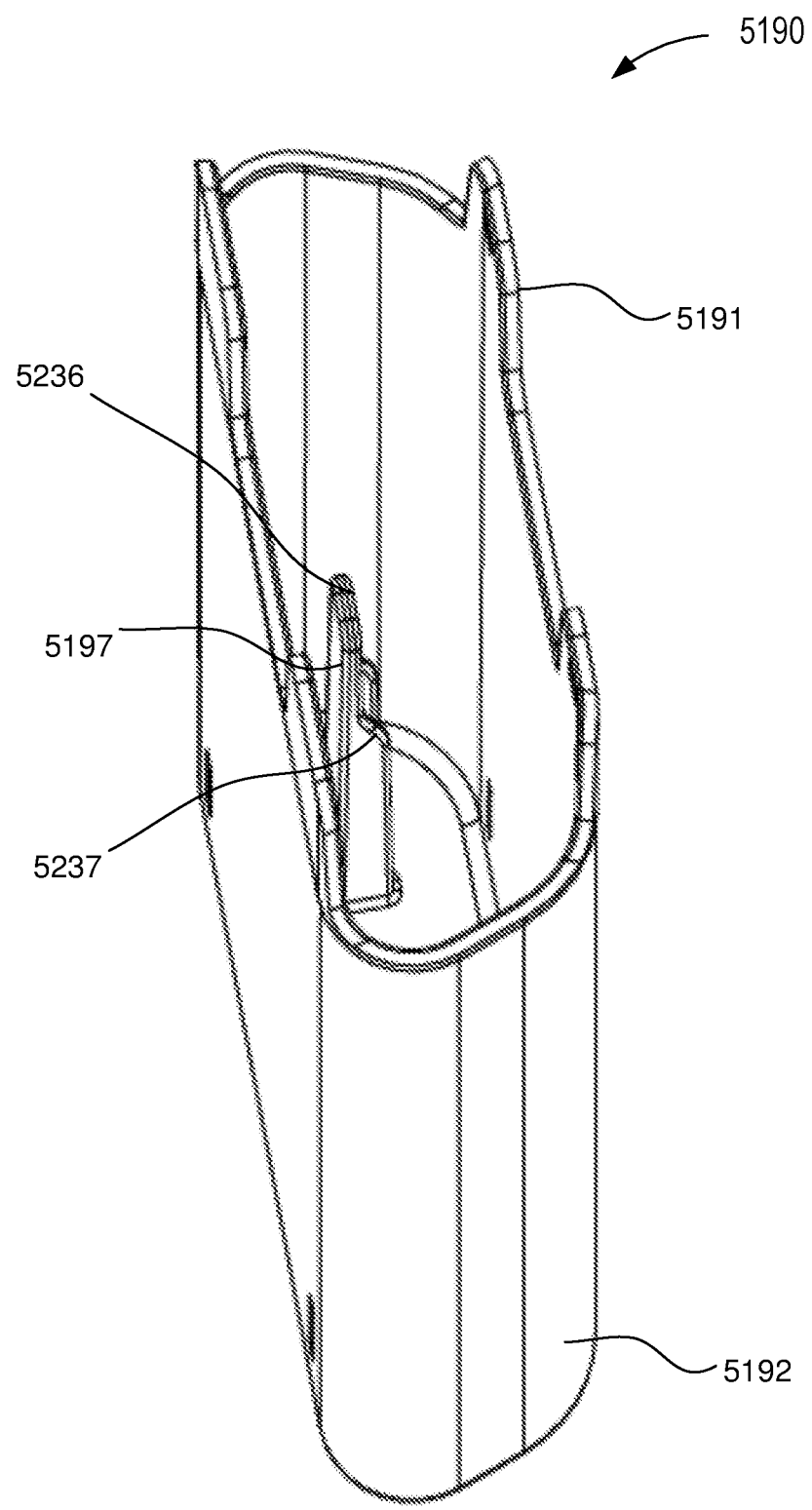
Figure 51:
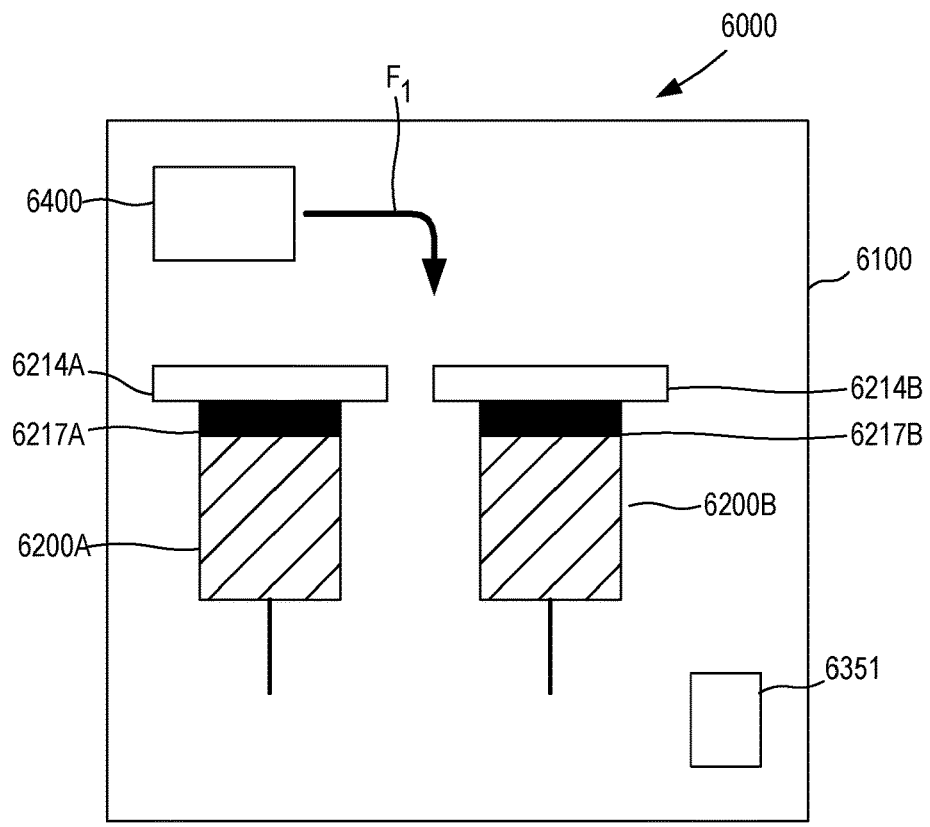
FIGS. 51-54 are schematic illustrations of a medicament delivery device according to an embodiment, in a first, second, third and fourth configuration, respectively.

For example, FIGS. 49-50 show an example of a cover 5190 that can be used with and/or included in the medical injector 5000 or any of the medicament delivery devices described herein. The cover 5190 includes a proximal end portion 5191 and a distal end portion 5192, and defines a cavity 5196. The cavity 5196 of the cover 5190 is configured to receive at least a portion of the housing 5100. Thus, when the portion of the housing 5100 is disposed within the cover 5190, the cover 5190 blocks an optical pathway between the medicament container and a region outside of the housing 5100. Similarly stated, when the portion of the housing 5100 is disposed within the cover 5190, the cover 5190 obstructs the first status indicator aperture 5130 to reduce the amount of light transmitted to the medicament. In this manner, the life of the medicament can be extended by the prevention and/or reduction of degradation to the medicament that may be caused by ultra-violet radiation. In other embodiments, however, such those containing a medicament that is not sensitive to ultraviolet (UV) radiation, the cover 5190 can include viewing windows and/or openings that substantially correspond to the aperture 5130.

The proximal end portion 5191 of the cover 5190 defines apertures 5193 configured to receive the retention protrusions (not shown) of the housing 5100. In this manner, the apertures 5193 and the retention protrusions of the housing 5100 removably retain the cover 5190 about at least a portion of the housing 5100.

As described above, the electronic circuit system 5900 can be actuated when the housing 5100 is at least partially removed from the cover 5190. More particularly, the distal end portion 5192 of the cover 5190 includes the battery isolation protrusion 5197. The battery isolation protrusion 5197 includes a proximal end portion 5236 and a tapered portion 5237. The proximal end portion 5236 of the battery isolation protrusion 5197 is configured to be removably disposed between a portion of a power source.

While the medical injectors 5000' and 5000 are shown as having the status windows (e.g., window 5130') disposed substantially at or near a latitudinal center of the medical injectors 5000' and 5000, in other embodiments, a medical injector can be configured to include a medicament container such as a prefilled syringe or the like disposed off-centered or otherwise in a non-coaxial arrangement with an energy storage member. For example, the medical injector 4000 includes the medicament container assembly 4200 that is disposed in a substantially off-center position relative to a width of the medical injector 4000. In other words, the medicament container is non-coaxial with the energy storage member. Moreover, because the medicament container is off-center relative to the width of the medical injector 4000, the status aperture 4130 defined by the housing is similarly off-center relative to the width of the medical injector 4000.

In some embodiments, a medicament delivery device can include two or more medicament containers, each having a delivery member through which the medicament therein can be delivered. Such embodiments can accommodate the delivery of viscous medicaments and/or large volumes of medicament (e.g. >1 mL dose) by delivering portions of the overall dose in parallel. Specifically, as discussed above with respect to Eq. 1, the needle length (L) and the needle gauge (identified as the radius R of the needle lumen) can have a profound impact on the pressure needed to deliver a desired volume of medicament therethrough. Thus, by using a "parallel delivery" device of the types shown and described herein, delivery of viscous medicaments, such as certain large or macromolecular injectables that include carbohydrate-derived formulations, lipids, nucleic acids, proteins/peptides (e.g. monoclonal antibodies) and other biotechnologically-derived medicaments, can be facilitated.

For example, FIGS. 51-54 show schematic illustrations of a "dual container" device 6000 according to an embodiment in a first, second, third and fourth configuration, respectively. The medicament delivery device 6000 includes a housing 6100, two medicament containers 6200A and 6200B, an energy storage member 6400, and a retraction member 6351. The housing 6100 defines a gas chamber 6139 that receives a pressurized gas from the energy storage member 6400. The gas chamber 6139 can be of any suitable size and shape, and can be, for example, a portion of the volume defined by the housing 6100 within which a portion of the first medicament container 6200A and/or the second medicament container 6200B are disposed. Although not shown, in some embodiments, the housing includes a vent mechanism, such as an opening or valve, of the types shown and described herein (e.g., with respect to the device 1000 and the device 4000). In this manner, the gas pressure within the gas chamber 6139 can be reduced upon completion of the injection event.

The housing 6100 can be any suitable size, shape, or configuration and can be made of any suitable material. For example, in some embodiments, the housing 6100 is an assembly of multiple parts formed from a plastic material and defines a substantially rectangular shape when assembled. In other embodiments, the housing 6100 can have a substantially cylindrical shape.

The medicament containers 6200A, 6200B each have a container body that defines a volume that contains (i.e., is filled with or partially filled with) a medicament. The distal end portion of each medicament container 6200A, 6200B is coupled to a needle 6216A, 6216B, respectively, through which the medicament can be delivered. In some embodiments, the medicament container 6200A and the medicament container 6200B can each be a prefilled syringe having the needle 6216A, 6216B, respectively, staked thereto. Such prefilled syringes can be any of the types shown and described herein.

The medicament container 6200A and the medicament container 6200B each include an elastomeric member 1217A, 1217B, respectively, that seals the medicament within the container body. The elastomeric members 1217A, 1217B are configured to move within the container body to inject the medicament from the medicament container assembly 1200. The elastomeric members 1217A, 1217B can be of any design or formulation suitable for contact with the medicament, of the types shown and described herein.

Although the medicament container 6200A and the medicament container 6200B are shown as being parallel to and noncoaxial with each other, in other embodiments, the medicament container 6200A and the medicament container 6200B can be arranged in any suitable manner within the housing 6100. Moreover, although the medicament container 6200A and the medicament container 6200B are shown as being disposed within the housing 6100 without a carrier, in other embodiments, the medicament container 6200A and the medicament container 6200B can each be disposed within a carrier (or set of carriers) to facilitate movement within the housing 6100.

The energy storage member 6400 is disposed within the housing 6100, and is configured to convey a pressurized gas into the gas chamber 6139 produce a force $F_1$ (see FIGS. 51-53) to convey the contents of the two medicament containers 6200A and 6200B when the energy storage member 6400 is actuated. The energy storage member 6400 can be any suitable member or device that stores potential energy and, when actuated, produces the pressurized gas. For example, the energy storage member 6400 (and any of the energy storage members described herein) can be any of a device containing compressed gas, a device containing a vapor pressure-based propellant or the like.

Thus, when actuated the energy storage member 6400 produces a force $F_1$ to deliver the medicament contained within the medicament containers 6200A, 6200B. More specifically, the energy storage member 6400 produces the force $F_1$ that moves the medicament containers 6200A, 6200B from a first position to a second position in a first direction indicated by the arrow AA in FIG. 52 and/or that moves the plungers 6217A, 6217B from a first plunger position to a second plunger position as shown by the arrows BB in FIG. 53. By employing the energy storage member 6400 to produce the force $F_1$ rather than relying on a user to manually produce the delivery force, the medicament can be delivered into the body at the desired pressure and/or flow rate, and with the desired delivery characteristics. Moreover, this arrangement reduces the likelihood of partial delivery (e.g., that may result if the user is interrupted or otherwise rendered unable to manually produce the force to complete the delivery). Moreover, by including a single energy storage member 6400, a user can initiate delivery from both medicament containers via a single actuation operation.

In some embodiments, the energy storage member 6400 can be configurable to include various amounts of stored energy without changing the size of the energy storage member. In such embodiments, therefore, a high force (e.g., to inject viscous medicaments) can be achieved in the same packaging that is used for lower viscosity medicaments. For example, in some embodiments, the energy storage member 6400 can be a compressed gas cylinder having any desired pressure (and thus, mass) of gas therein. Accordingly, the pressure and/or force (e.g., force $F_1$) can be achieved to complete the operations described herein, regardless of the medicament.

As shown, the energy storage member 6400 is operably coupled (e.g., via the gas chamber 6139) to the medicament containers 6200A, 6200B and/or the medicament therein such that the force $F_1$ delivers the medicament. In some embodiments, for example, the force $F_1$ can be transmitted to the medicament containers and/or the medicament therein via a carrier or movable member (not shown). When the medicament delivery device 6000 is actuated to produce the force $F_1$, the medicament containers 6200A, 6200B move from the first position (see FIG. 51, which corresponds to the first configuration of the medicament delivery device 6000) to the second position (see FIG. 52, which corresponds to the second configuration of the medicament delivery device 6000). As shown, the movement of the medicament containers 6200A, 6200B within the housing 6100 results in a needle insertion operation.

When the medicament containers 6200A, 6200B are in their respective second positions, the pressure within the gas chamber 6139 continues to exert a force on the elastomeric members 6217A, 6217B. This causes each elastomeric member 6217A, 6217B to move within its respective container body to expel the medicament therefrom, as shown by the arrows BB in FIG. 53. The movement of the elastomeric member 6217A, 6217B places the medicament delivery device 6000 in a third configuration.

Although shown as moving substantially simultaneously, in other embodiments, the medicament container 6200A and the medicament container 6200B can move within the housing 6100 at different times. Further, in other embodiments, the elastomeric member 6217A and the elastomeric member 6217B can move within their respective container bodies at different times. In some embodiments, the medicament delivery device 6000 includes a gas vent assembly, such as the gas vent assembly 4310, to release the pressure within the gas chamber 6139 as a function of the position of the elastomeric member 6217A and/or the elastomeric member 6217B.

Figure 52:
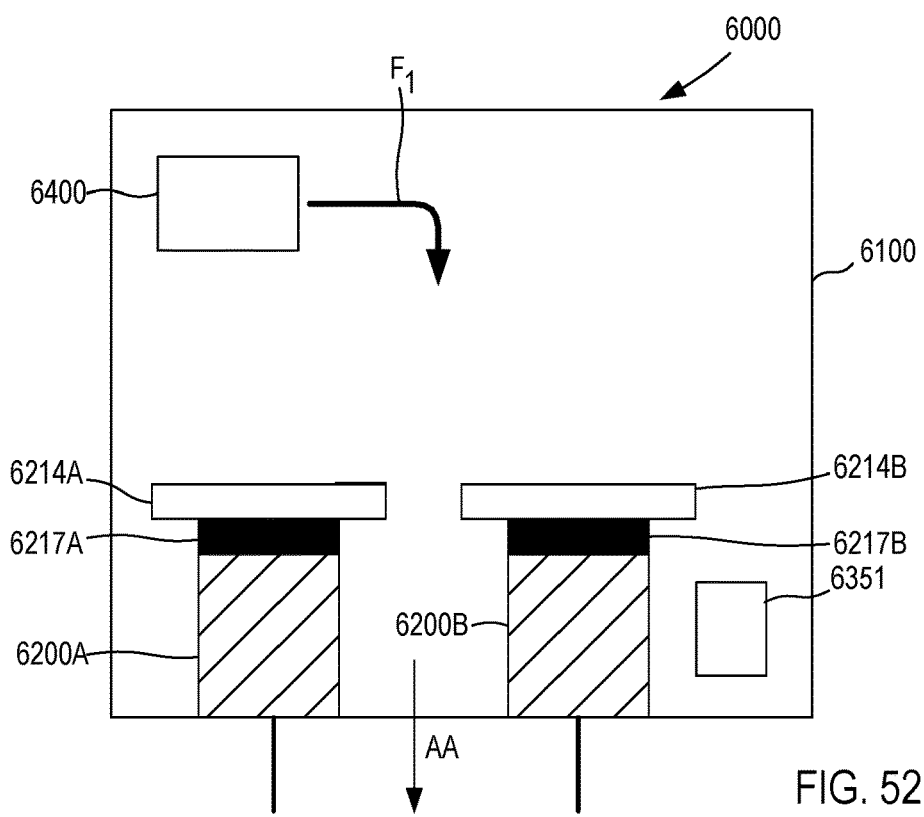
Figure 53:
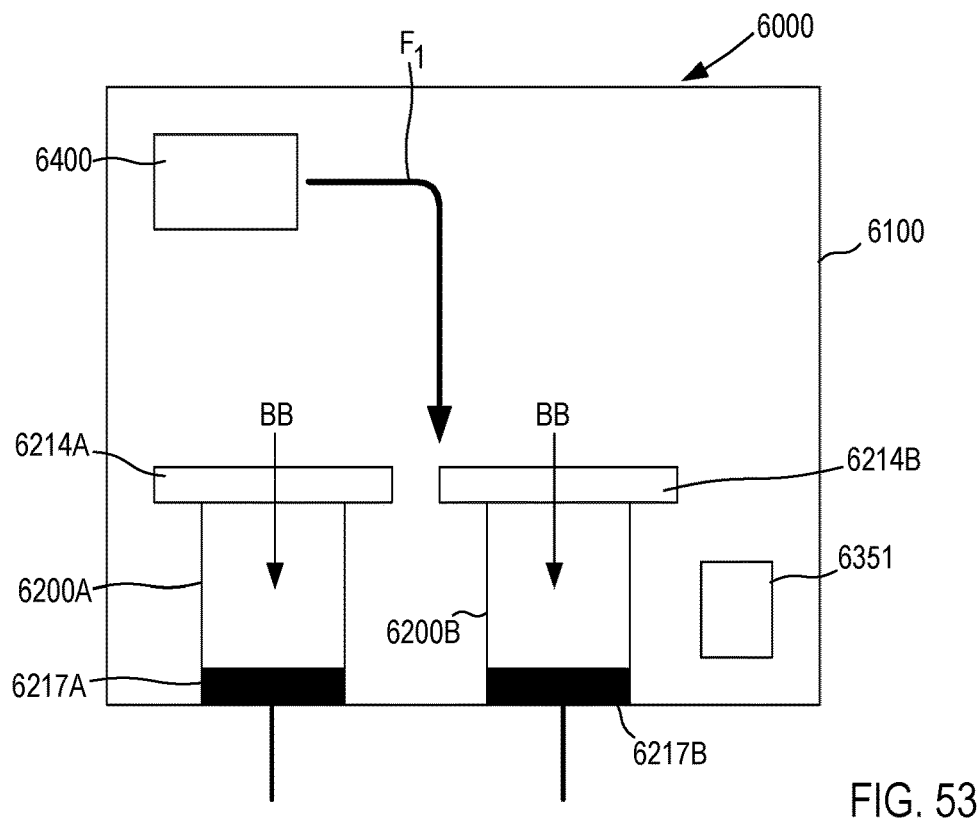
Figure 54:
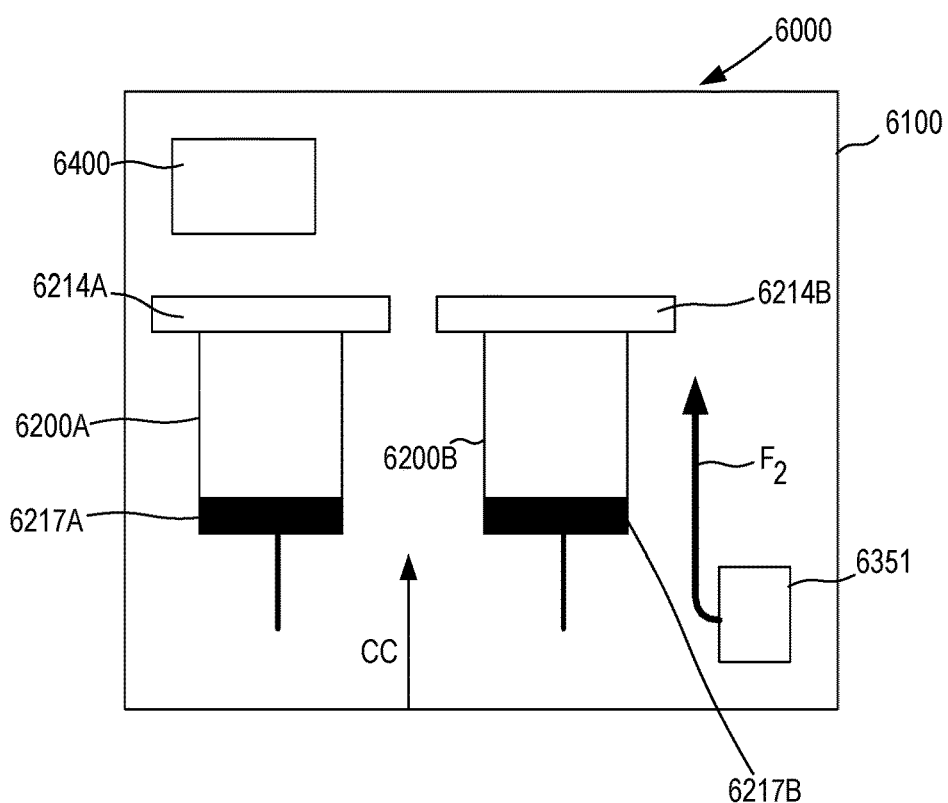

After the medicament is delivered, the retraction member 6351 exerts a retraction force $F_2$ on the medicament container 6200A and the medicament container 6200B. The force $F_2$ is applied in a second direction, opposite the first direction. The retraction force $F_2$ moves the medicament containers from the second position (e.g., the second and third configuration, as shown in FIGS. 52 and 53) in the direction of the arrow CC toward the first position, as shown in FIG. 54. In this manner, the retraction member 6351 produces the retraction force $F_2$ and moves the medicament containers 6200A, 6200B (and their respective needles) away from the body of the patient and into the housing 6100 of the medicament delivery device 6000.

The retraction member 6351 can be any suitable device or mechanism that, when actuated, produces a force $F_2$ to move the medicament containers in the second direction as indicated by the arrow CC in FIG. 54. In some embodiments, the retraction member 6351 can be a mechanical energy storage member, such as a spring, a device containing compressed gas, a device containing a vapor pressure-based propellant or the like. In other embodiments, the retraction member 6351 can be an electrical energy storage member, such as a battery, a capacitor, a magnetic energy storage member or the like. In yet other embodiments, the retraction member 6351 can be a chemical energy storage member, such as a container containing two substances that, when mixed, react to produce energy. Although the retraction member 6351 is shown as being separate and distinct from the energy storage member 6400, in some embodiments, the energy storage member 6400 can be configured to produce the retraction force $F_2$.

FIGS. 55-58 show schematic illustrations of a "dual container" device 7000 according to an embodiment in a first, second, third and fourth configuration, respectively. The medicament delivery device 7000 includes a housing 7100, two medicament containers 7200A and 7200B, two movable members 7300A and 7300B, an energy storage member 7400, and a retraction member 7351. The housing 7100 can be any suitable size, shape, or configuration and can be made of any suitable material. For example, in some embodiments, the housing 7100 is an assembly of multiple parts formed from a plastic material and defines a substantially rectangular shape when assembled. The housing 7100 can define any suitable status apertures (or windows) as shown herein.

The medicament containers 7200A, 7200B are disposed within the housing 7100, and contains (i.e., is filled or partially filled with) a medicament of the types described herein. For example, each medicament container 7200A, 7200B can be a prefilled syringe of the types described herein, and can include a proximal end portion having a flange (6214A, 7214B), and a distal end portion that is coupled to a needle (not shown in FIGS. 55-58). Each medicament container 7200 includes an elastomeric member 7217A, 7217B (also referred to herein as a "plunger").

The energy storage member 7400 can be any suitable device or mechanism that, when actuated, produces a force $F_1$ to deliver the medicament contained within the medicament containers 7200A, 7200B. Similarly stated, the energy storage member 7400 can be any suitable device or mechanism that produces the force $F_1$ such that the medicament is conveyed from the medicament containers into a body of a patient. More specifically, the energy storage member 7400 produces the force $F_1$ that moves the medicament containers 7200A, 7200B from a first position to a second position in a first direction indicated by the arrow AA in FIG. 55 and/or that moves the plungers 7217A, 7217B from a first plunger position to a second plunger position as shown by the arrows BB in FIG. 56. By employing the energy storage member 7400 to produce the force $F_1$ rather than relying on a user to manually produce the delivery force, the medicament can be delivered into the body at the desired pressure and/or flow rate, and with the desired delivery characteristics. Moreover, this arrangement reduces the likelihood of partial delivery (e.g., that may result if the user is interrupted or otherwise rendered unable to manually produce the force to complete the delivery).

In some embodiments, the energy storage member 7400 can be a mechanical energy storage member, such as a spring, a device containing compressed gas, a device containing a vapor pressure-based propellant or the like. In other embodiments, the energy storage member 7400 can be an electrical energy storage member, such as a battery, a capacitor, a magnetic energy storage member or the like. In yet other embodiments, the energy storage member 7400 can be a chemical energy storage member, such as a container containing two substances that, when mixed, react to produce energy.

In some embodiments, the energy storage member 7400 can be configurable to include various amounts of stored energy without changing the size of the energy storage member. In such embodiments, therefore, a high force (e.g., to inject viscous medicaments) can be achieved in the same packaging that is used for lower viscosity medicaments. For example, in some embodiments, the energy storage member 7400 can be a compressed gas cylinder having any desired pressure (and thus, mass) of gas therein. Accordingly, the pressure and/or force (e.g., force $F_1$) can be achieved to complete the operations described herein, regardless of the medicament.

Figure 55:
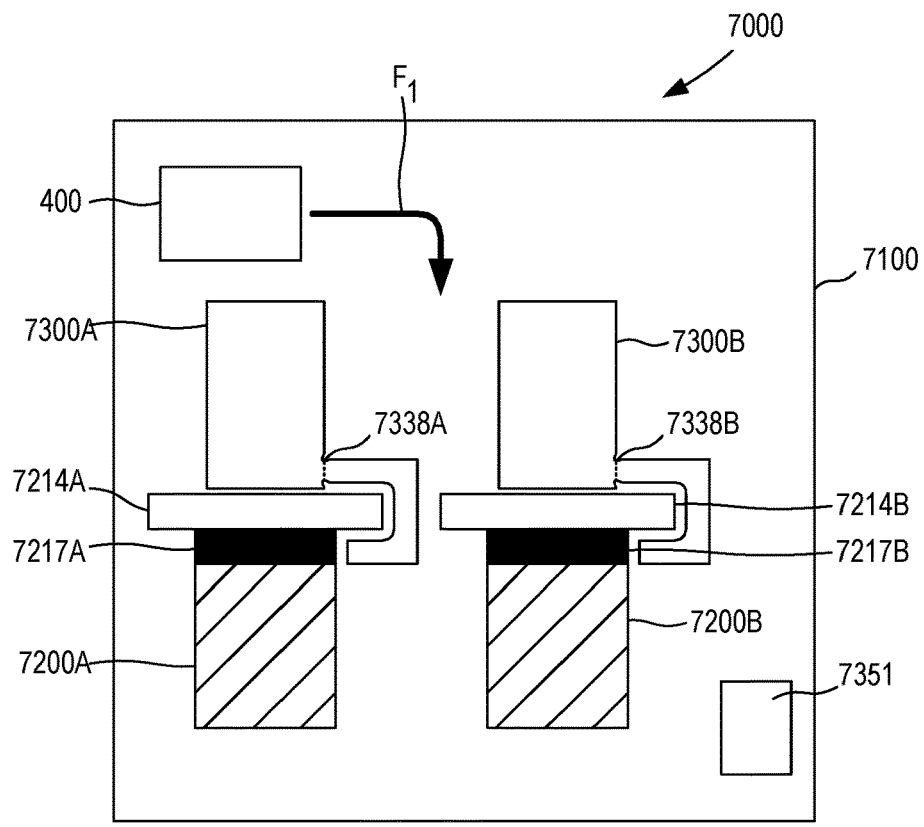
FIGS. 55-58 are schematic illustrations of a medicament delivery device according to an embodiment, in a first, second, third and fourth configuration, respectively.

As shown in FIG. 55, the energy storage member 7400 is operably coupled to the movable members 7300A, 7300B, the medicament containers 7200A, 7200B and/or the medicament therein such that the force $F_1$ delivers the medicament. In some embodiments, for example, the force $F_1$ can be transmitted to the medicament containers and/or the medicament therein via the movable members. The movable members 7300A, 7300B can be any suitable member, device, assembly or mechanism configured to move within the housing 7100. As shown in FIGS. 55-58, the movable members 7300A, 7300B include a piston portion configured to transmit the force $F_1$ to the plungers 7217A, 7217B disposed within each medicament container.

Figure 56:
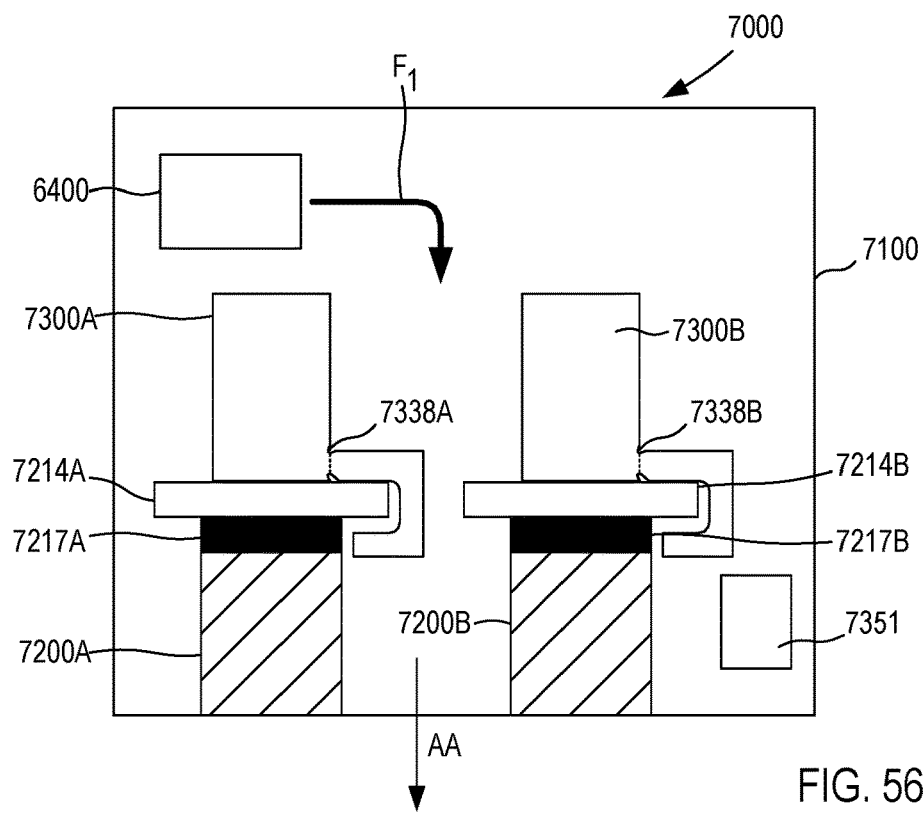

As shown, when the medicament delivery device 7000 is actuated to produce the force $F_1$, the movable members 7300A, 7300B move the medicament containers 7200A, 7200B from the first position (see FIG. 55, which corresponds to the first configuration of the medicament delivery device 7000) to the second position (see FIG. 56, which corresponds to the second configuration of the medicament delivery device 7000). In some embodiments, the movement of the medicament containers within the housing 7100 results in a needle insertion operation.

In some embodiments, a shoulder of each movable member 7300A, 7300B can be configured to maintain a distance between the piston portion of the movable member and the plunger when the medicament delivery device 7000 is in the first configuration (FIG. 55). Similarly stated, in some embodiments, each movable member and its respective medicament container are collectively configured such that the piston portion is spaced apart from the respective plunger when the medicament delivery device 7000 is in its storage configuration and/or when the medicament containers 7200A, 7200B are moving between its first position and its second position. In this manner, any preload or residual force produced by the energy storage member 7400 on the movable members 7300A, 7300B is not transferred to the plungers 7217A, 7217B.

Figure 57:
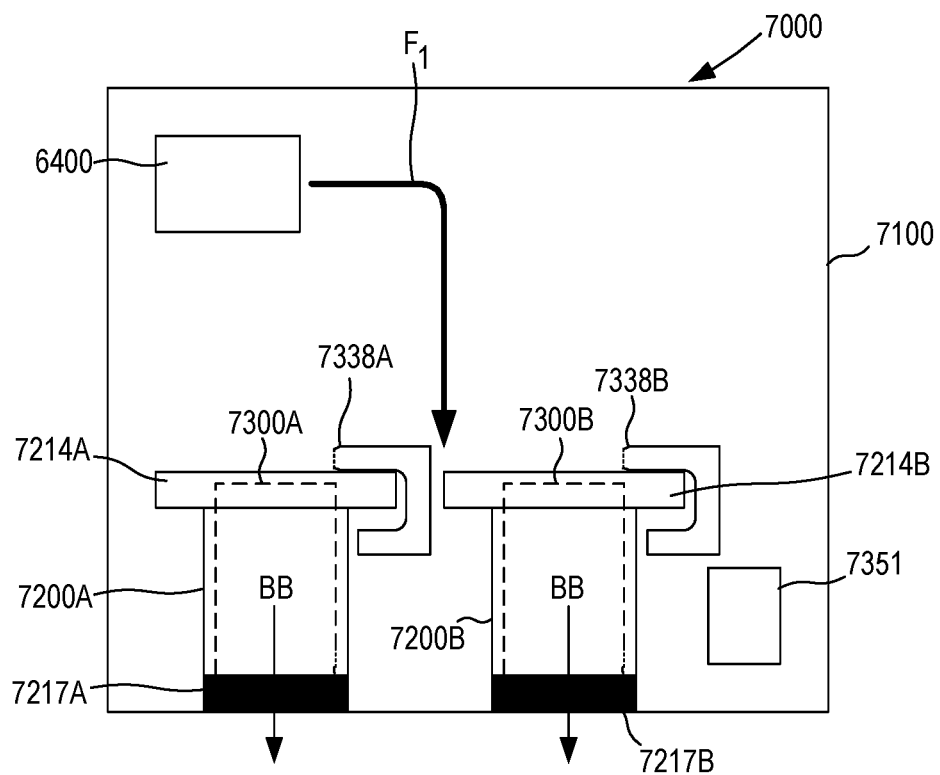

As shown in FIGS. 55-58, each movable member 7300A, 7300B includes a deformable portion 7338A, 7338B configured to deform when the medicament container 7200 is in the second position such that at least a portion of the force $F_1$ is exerted upon the plungers 7217A, 7217B. In some embodiments, the deformable portions 7338A, 7338B can be separated from the movable member 7300A, 7300B. In this manner, the piston portion of each movable member 7300A, 7300B transmits at least a portion of the force $F_1$ to is respective plunger 7217A, 7217B, thereby placing the medicament container 7200 into the third configuration (FIG. 57). More specifically, when the deformable portions 7338A, 7338B deform, the piston portions each move within the respective medicament container in the direction of the arrow BB (FIG. 57) and moves each plunger within the medicament container to deliver the medicament contained therein.

Figure 58:
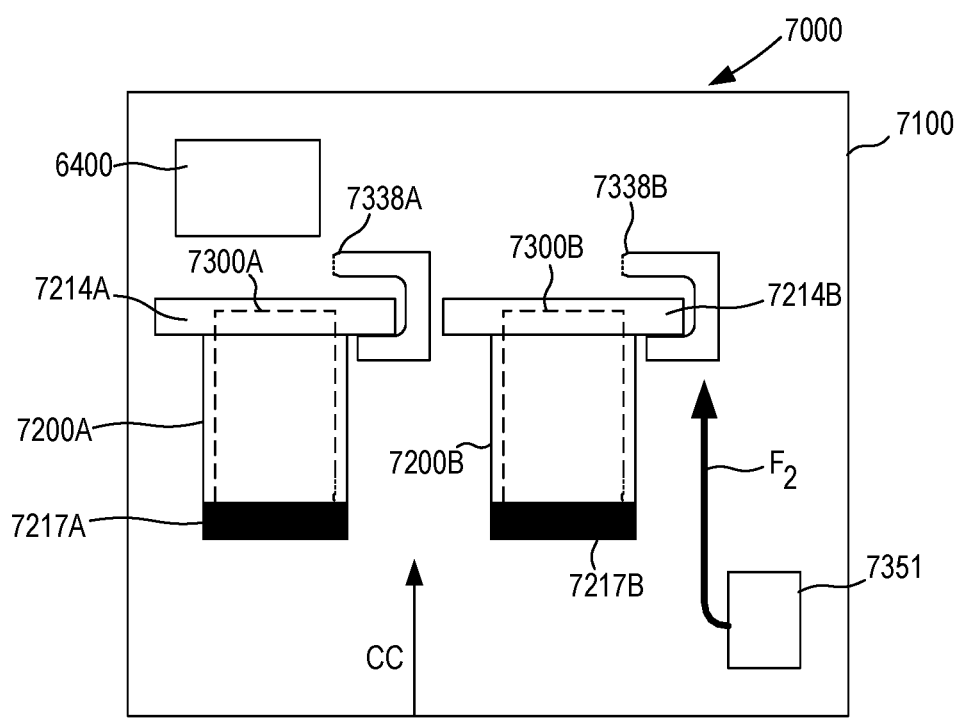
Figure 59:
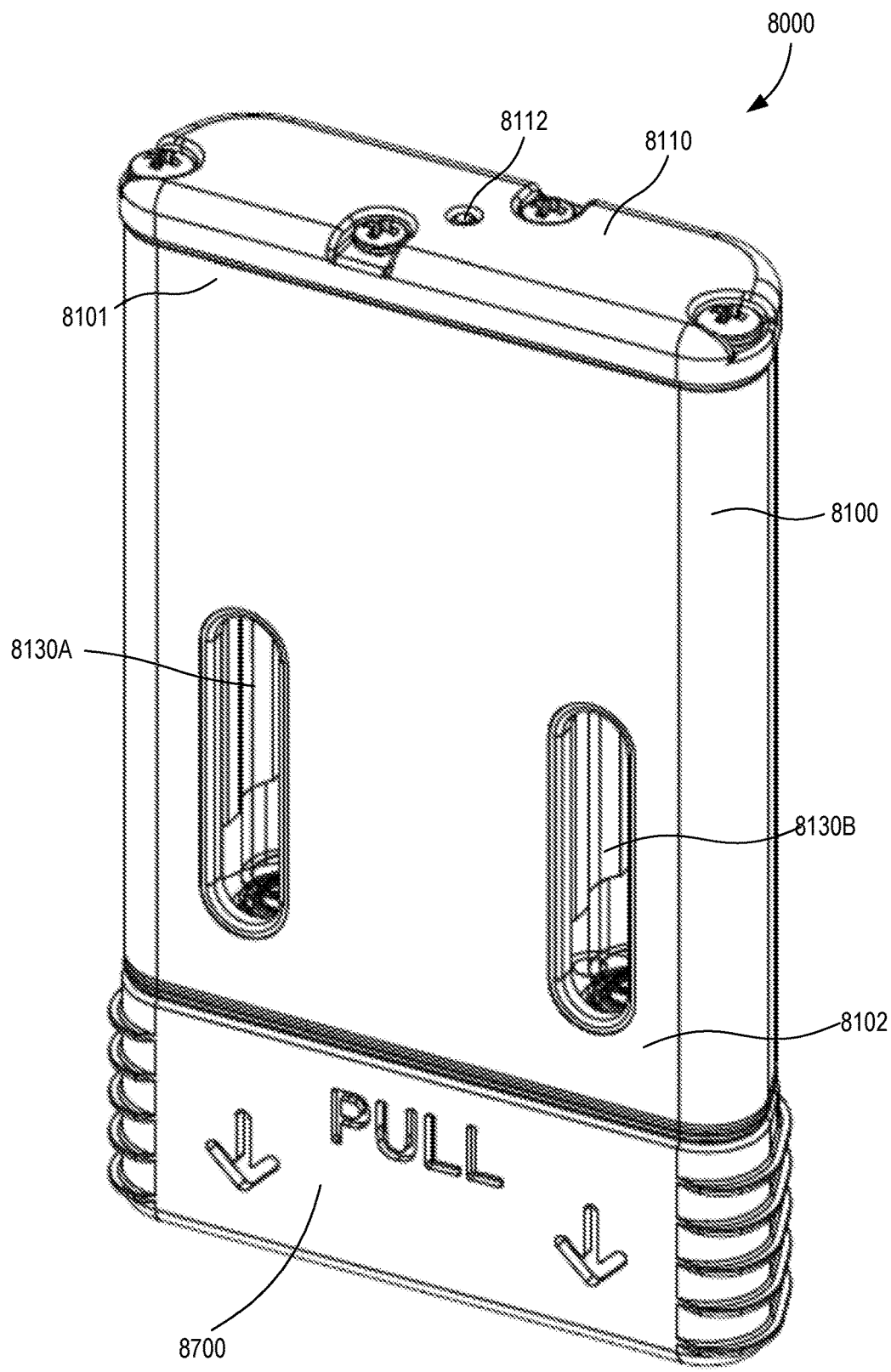
FIGS. 59 and 60 are perspective front and rear views, respectively, of a medical injector according to an embodiment, in a first configuration.
Figure 60:
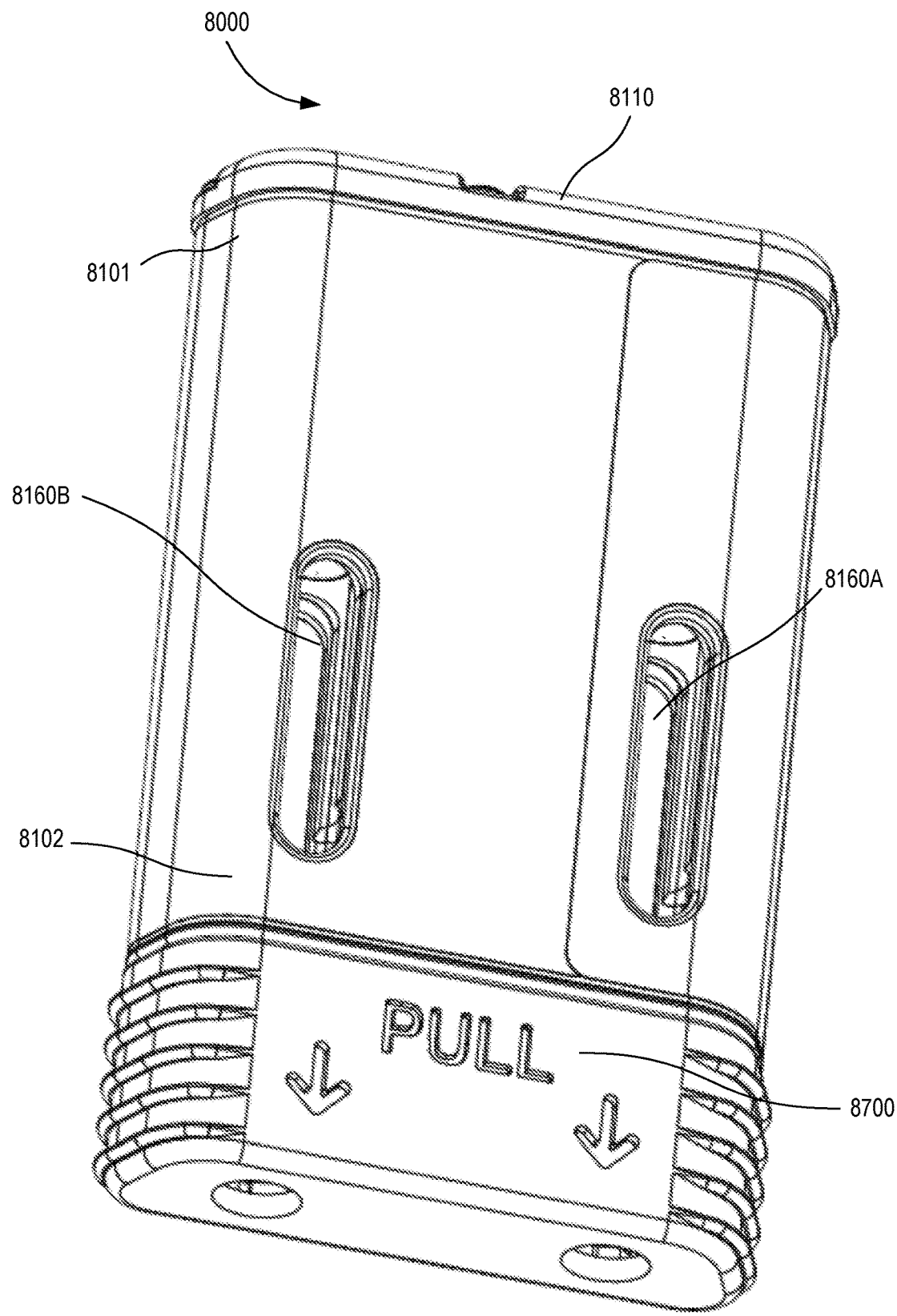
Figure 61:
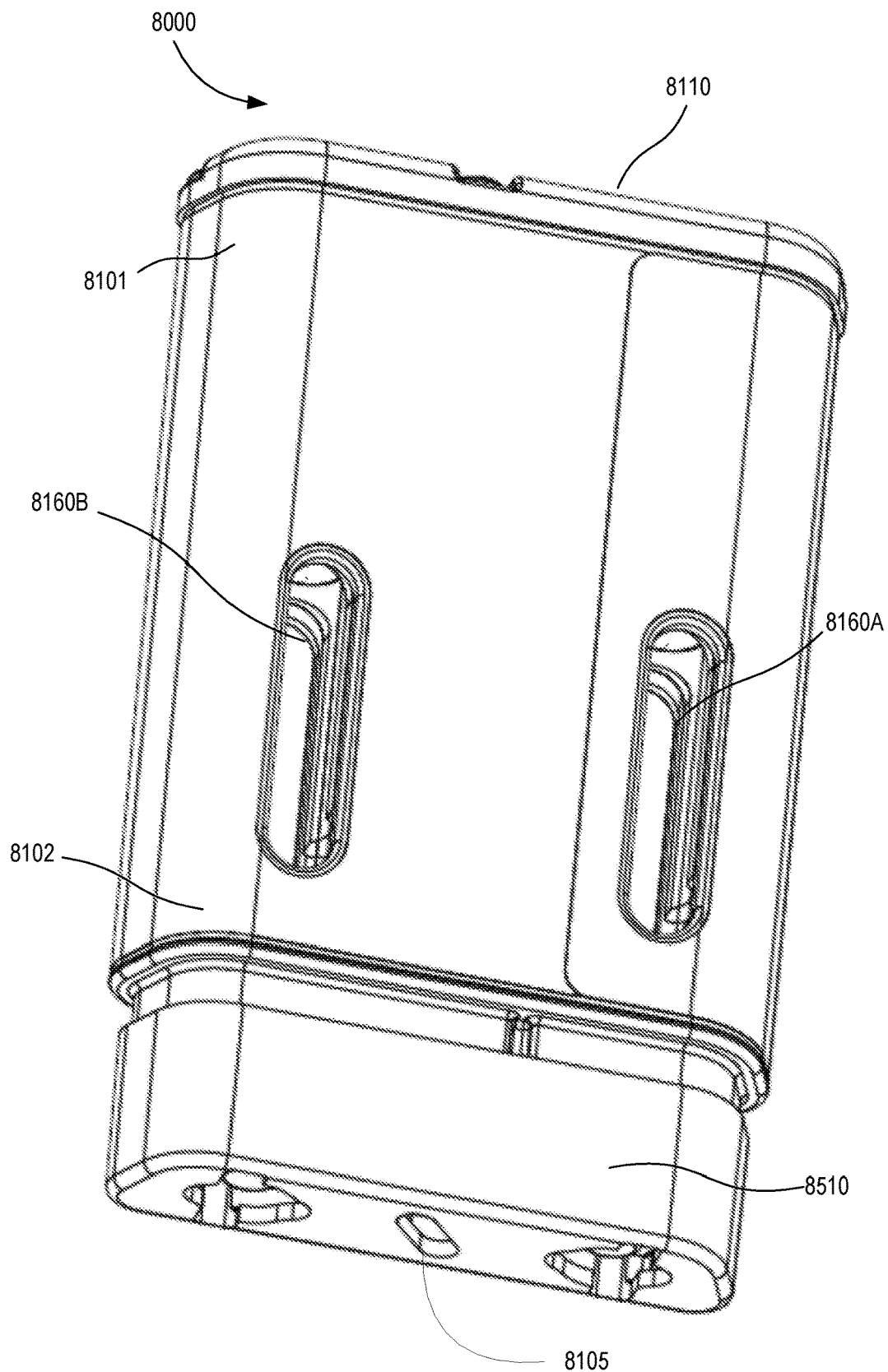
FIG. 61 is a perspective rear view of the medical injector illustrated in FIGS. 59 and 60, with the safety lock removed.

After the medicament is delivered, the retraction member 7351 exerts a retraction force $F_2$ on each movable member 7300A, 7300B in a second direction, opposite the first direction. When the retraction force $F_2$ is exerted, a second shoulder of each movable member 7300A, 7300B engages a distal surface of each flange 7214A, 7214B, thereby exerting at least a portion of the retraction force $F_2$ thereon. The exertion of the retraction force $F_2$ on the flanges 7214A, 7214B moves the medicament containers from the second position (e.g., the second and third configuration, as shown in FIGS. 56 and 57) in the direction of the arrow CC toward the first position, as shown in FIG. 58. In this manner, the retraction member 7351 produces the retraction force $F_2$ and moves the medicament container 7200 (and a needle) away from the body of the patient and into the housing 7100 of the medicament delivery device 7000.

The retraction member 7351 can be any suitable device or mechanism that, when actuated, produces a force $F_2$ to move the medicament containers in the second direction as indicated by the arrow CC in FIG. 58. In some embodiments, the retraction member 7351 can be a mechanical energy storage member, such as a spring, a device containing compressed gas, a device containing a vapor pressure-based propellant or the like. In other embodiments, the retraction member 7351 can be an electrical energy storage member, such as a battery, a capacitor, a magnetic energy storage member or the like. In yet other embodiments, the retraction member 7351 can be a chemical energy storage member, such as a container containing two substances that, when mixed, react to produce energy. Although the retraction member 7351 is shown as being separate and distinct from the energy storage member 7400, in some embodiments, the energy storage member 7400 can be configured to produce the retraction force $F_2$.

Although shown as including two distinct movable members 7300A, 7300B, in other embodiments, a dual container medical injector can include a single structure or movable member that acts upon both medicament containers.

In some embodiments, a medical injector can include two prefilled syringes, each containing up to 1 mL of medicament (or more), and each having a needle. Upon actuation of the device (as described above), a single energy storage member (e.g., a compressed gas container) can release energy to move the two containers within the housing in substantially the same operation to inject the two needles. The force produced by the energy storage member can further inject the medicament from each container. In some embodiments, a single retraction member (e.g., a spring) can retract the two medicament containers thereby withdrawing the two needles into the housing. In other embodiments, a device can include separate retraction members associated with each medicament container.

Figure 62:
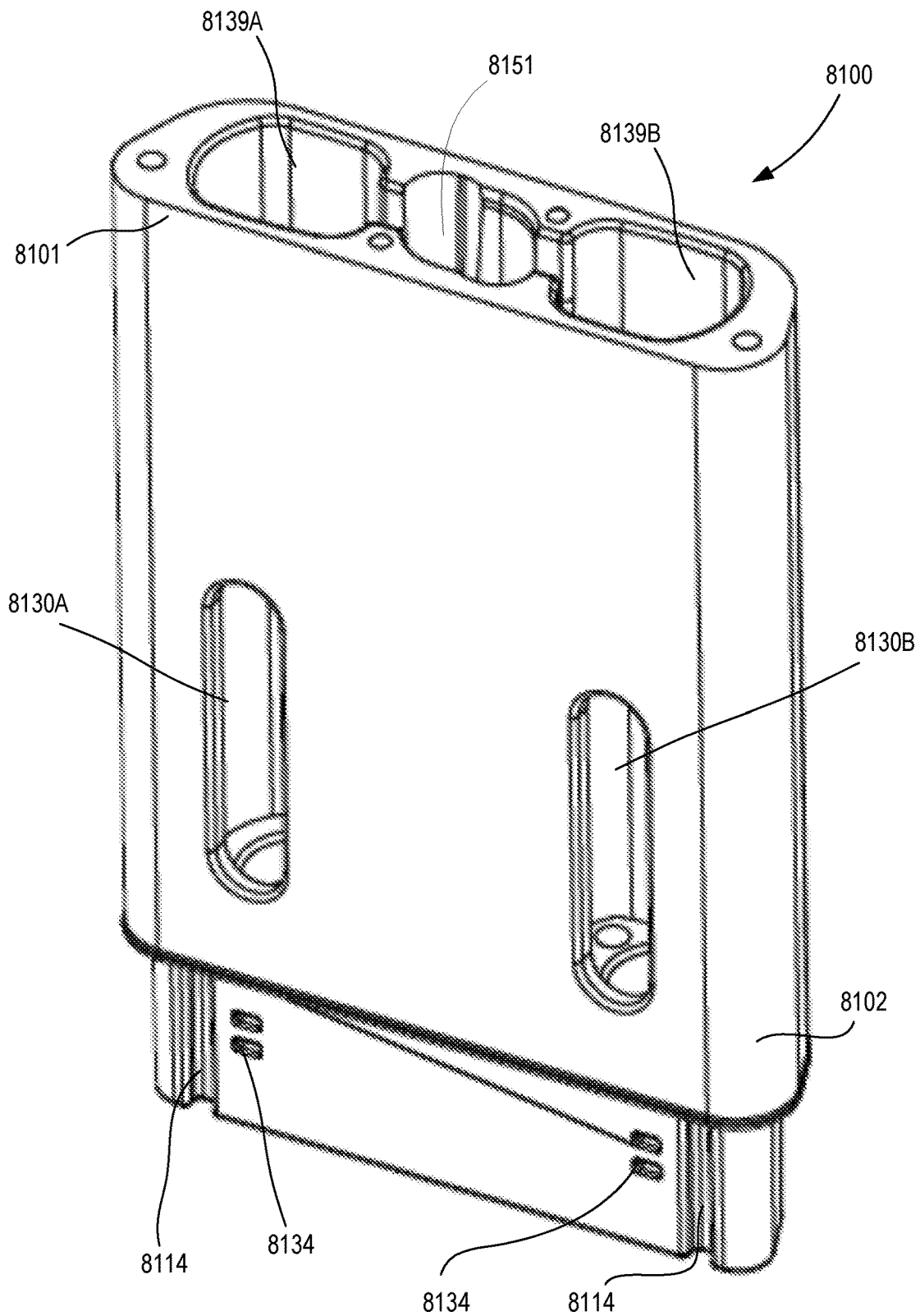
FIG. 62 is a perspective view of a housing of the medical injector illustrated in FIGS. 59 and 60.
Figure 63:
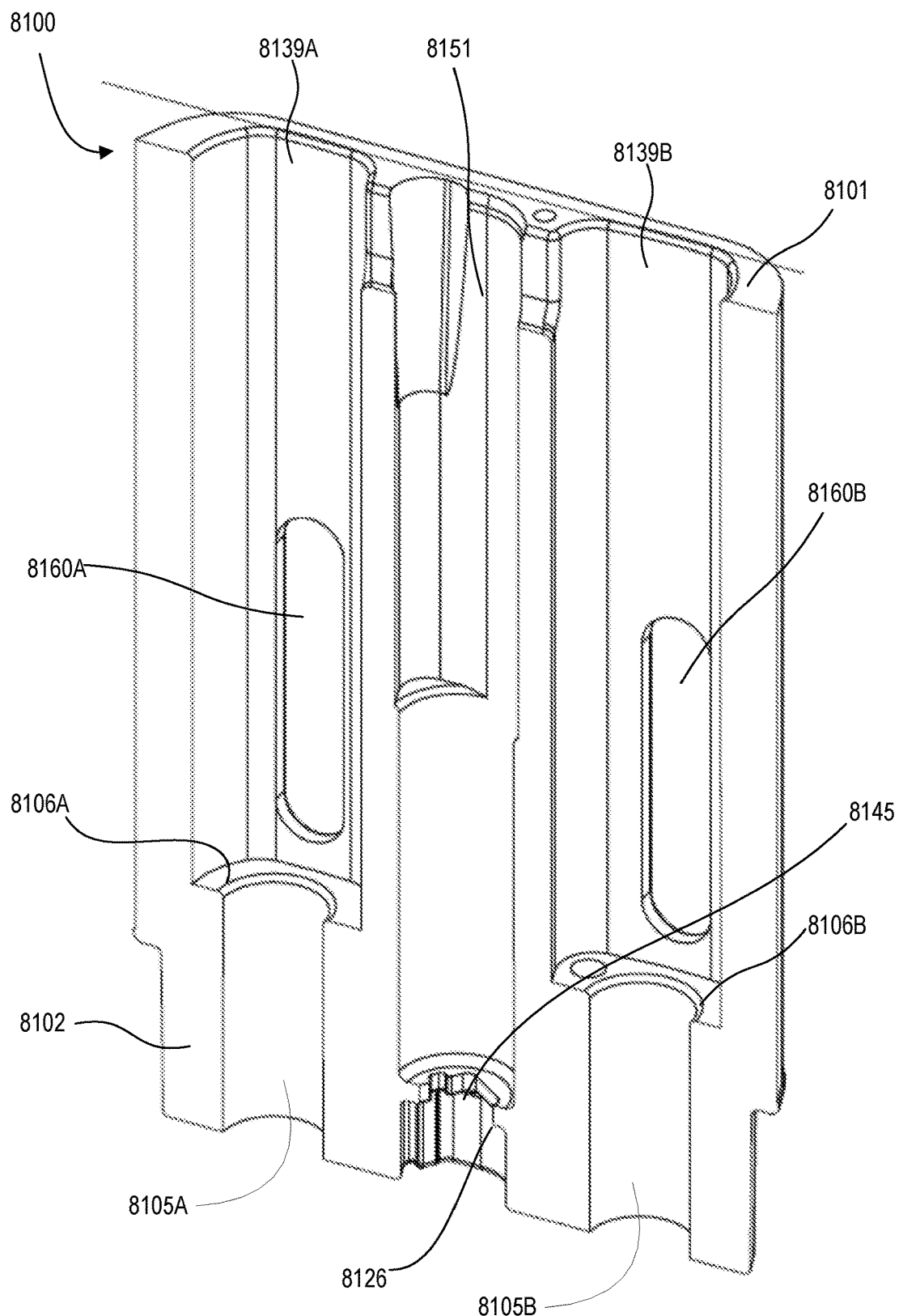
FIG. 63 is a cross-sectional view of the housing illustrated in FIG. 62.

FIGS. 59-78 show a dual-container medical injector 8000 (also referred to as "auto-injector," "injector," or "device"), according to an embodiment. The medical injector 8000 is a gas-powered auto-injector configured to deliver a medicament contained within two prefilled syringe assemblies 4200, as described herein. The medical injector 8000 includes a housing 8100 (see e.g., FIGS. 62-63), a system actuation assembly 8500 (see e.g., FIG. 65), two medicament container assemblies 4200, a medicament delivery mechanism 8300 (see e.g., FIG. 70), a base 8510 (or actuator, see FIG. 73); and a safety lock 8700 (see FIGS. 71-72). As shown in FIGS. 62-63, the housing 8100 has a proximal end portion 8101 and a distal end portion 8102. The operation of, and certain components within, the medical injector 8000 are similar in many respects to that of the medical injector 4000, and thus certain aspects are not described in detail herein. For example, as described herein, the medicament container assembly within the medical injector 8000 is the same as the medicament container assembly 4200 shown and described above. One way that the medical injector 8000 differs from the medical injector 4000 is that the dual-container medical injector includes a gas vent mechanism that actuates a single release valve, as discussed in more detail below.

The housing 8100 defines a pair of front status indicator apertures 8130A, 8130B and a pair of rear status indicator apertures 8160A, 8160B. The front status indicator apertures 8130A, 8130B are defined by the housing 8100 and are located on a first side of the housing 8100, and the rear status indicator apertures 8160A, 8160B are located on a second side of the housing 8100. The status indicator apertures 8130A, 8160A can allow a patient to monitor the status and/or contents of the first medicament container assembly 4200, the first carrier 4360, and the medicament contained therein. The status indicator apertures 8130B, 8160B can allow a patient to monitor the status and/or contents of the second medicament container assembly 4200, the second carrier 4360, and the medicament contained therein.

In some embodiments, the housing 8100 can include a label or indicia that mask or otherwise accentuates the status indicator apertures 8130A, 8130B, 8160A, 8160B and/or the contents viewed therethrough. For example, in some embodiments, the housing 8100 can include a label (not shown) having border that surrounds at least a portion of the status indicator apertures. In some embodiments, a label can include indicator colors that alert user (or assist a user in determining) whether the medicament is properly colored, whether a portion of the carrier 8360A, 8360B is visible through the window or the like.

Figure 65:
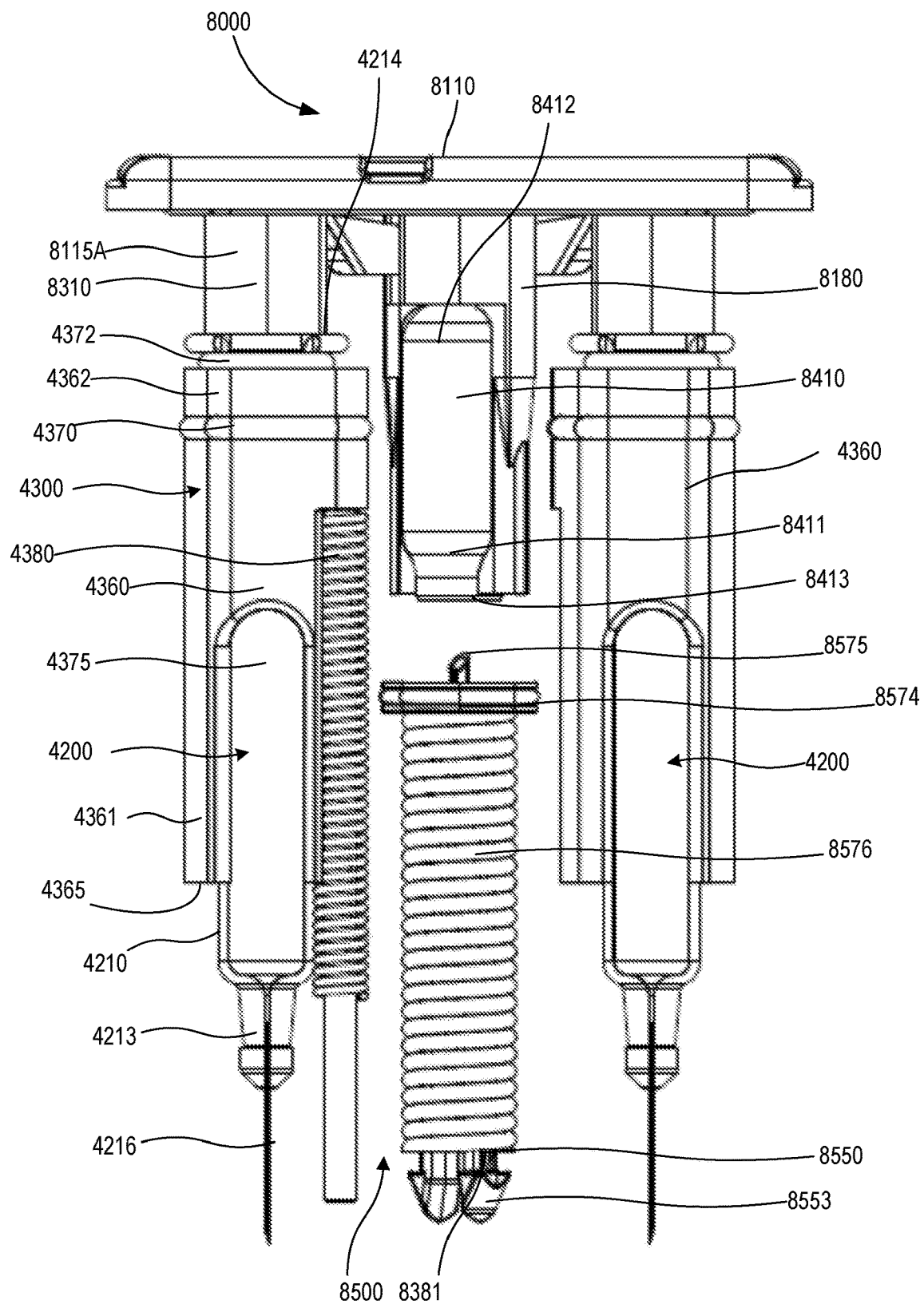
FIG. 65 is a front view of a medicament delivery mechanism of the medical injector shown in FIGS. 59 and 60.

As shown in FIGS. 62 and 63, the housing 8100 defines a gas container cavity 8151 and a first medicament cavity 8139A, and a second medicament cavity 8139B. The gas container cavity 8151 is configured to receive the gas container 8410 and a portion of the system actuator assembly 8500 (e.g., a release member 8550 and the spring 8576, as shown in FIG. 65). The proximal end portion 8152 of the gas container cavity 8151 is configured to receive the gas container retention member 8580 of a proximal cap 8103 of the housing 8100, as described in further detail herein. The gas container cavity 8151 is in fluid communication with the first medicament cavity 8139A and the second medicament cavity 8139B via gas passageways (not shown).

The first medicament cavity 8139A is configured to receive the first medicament container assembly 4200 and at least a portion of the medicament delivery mechanism 8300. In particular, as described below, the medicament delivery mechanism 8300 includes a first carrier assembly 4390 and a gas vent assembly 8310 movably disposed in the housing 8100. The first medicament cavity 8139A is in fluid communication with a region outside the housing 8100 via a first needle aperture 8105A (see e.g., FIG. 63) and also the vent opening 8112.

The second medicament cavity 8139B is configured to receive the second medicament container assembly 4200 and at least a portion of the medicament delivery mechanism 8300. The second medicament cavity 8139B is in fluid communication with a region outside the housing 8100 via a second needle aperture 8105B (see e.g., FIG. 63) and also the vent opening 8112.

Figure 64:
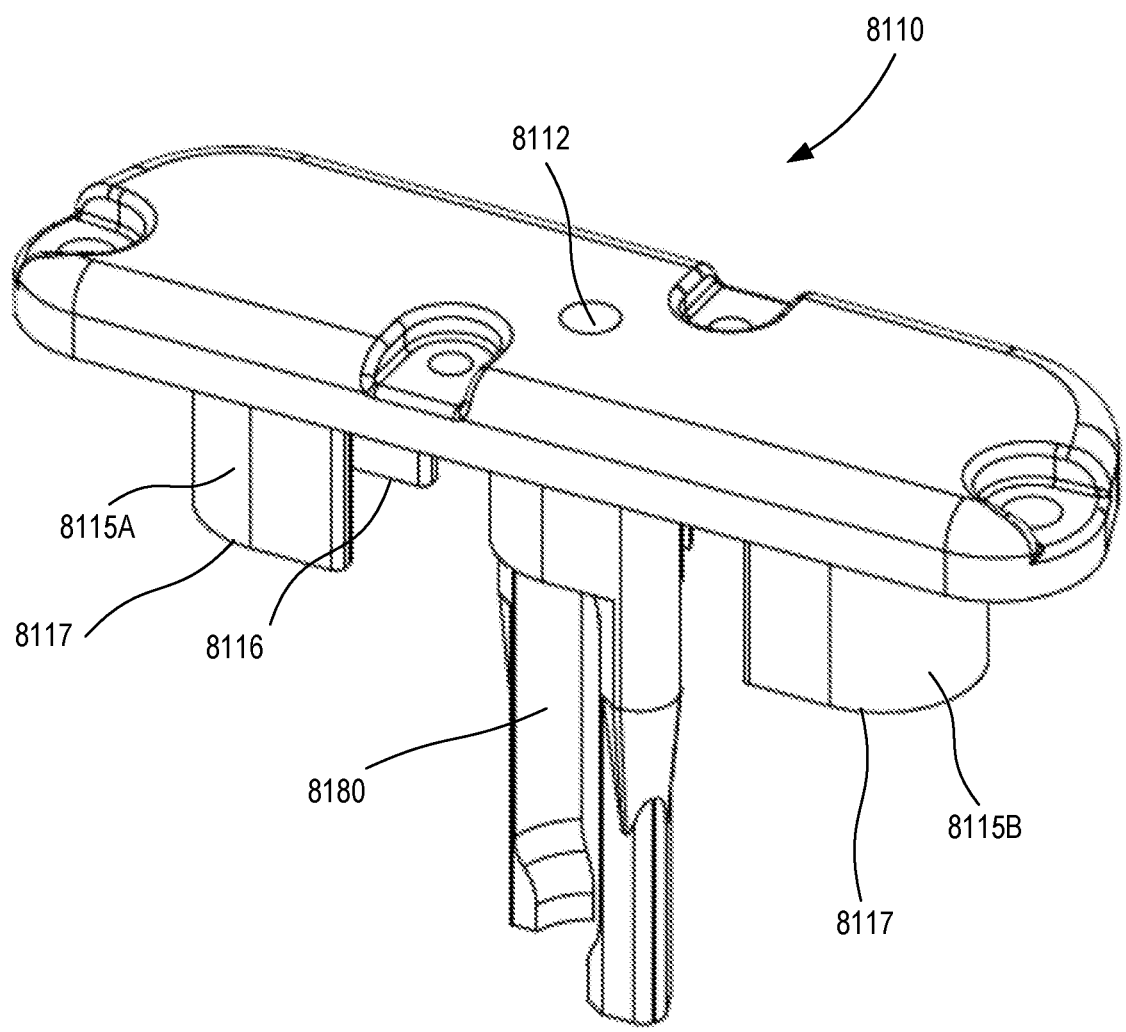
FIG. 64 is a perspective view of a proximal cap of the medical injector illustrated in FIG. 59.
Figure 68:
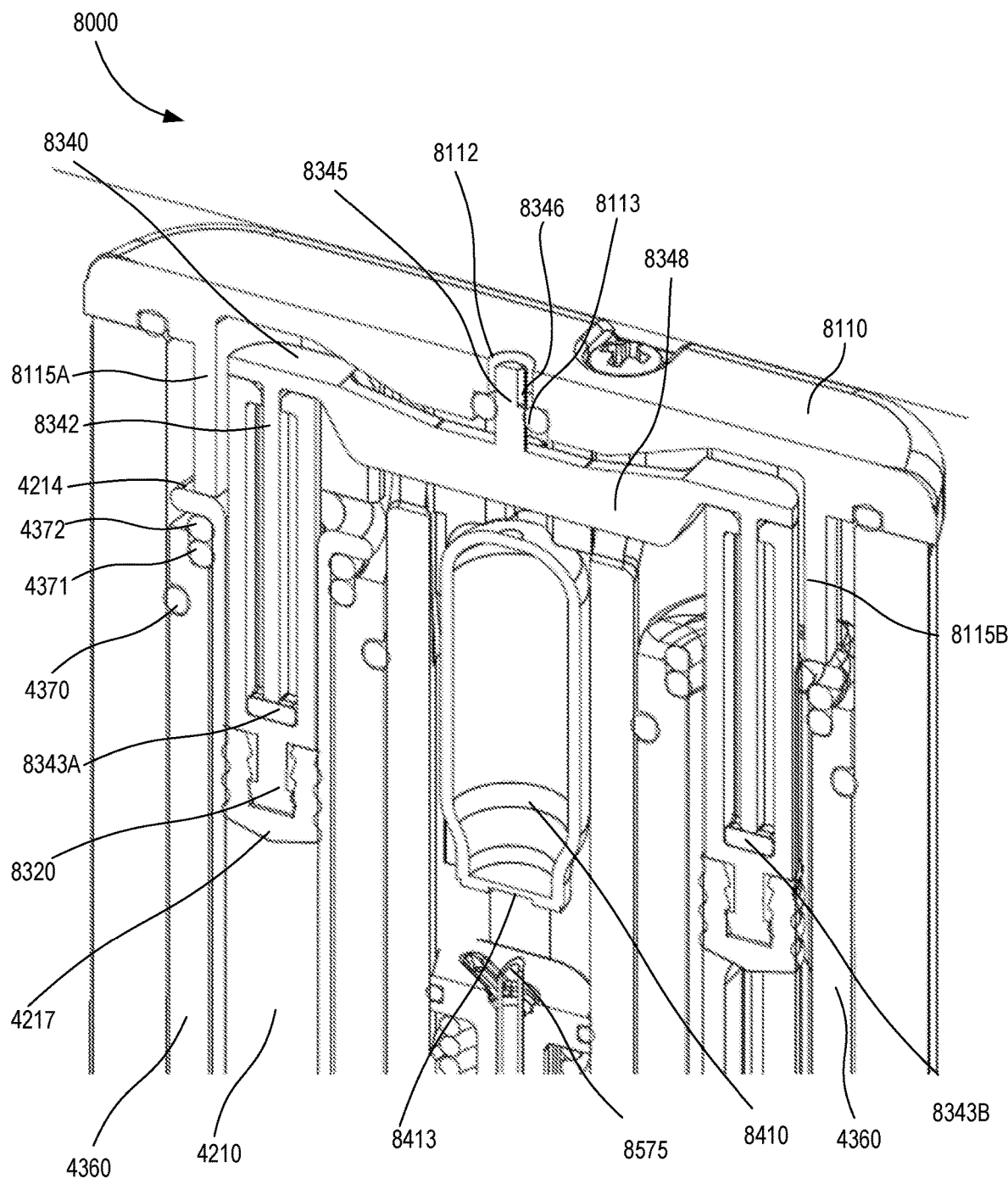
FIG. 68 is an enlarged cross-sectional view of a portion of the medical injector shown in FIGS. 59 and 60, in the first configuration.

The proximal end portion 8101 of the housing 8100 includes a proximal cap 8110 (see e.g., FIGS. 64 and 68). The proximal cap 8110 includes a gas container retention member 8180 and defines a gas passageway between the medicament cavities 8139A, 8139B and the gas container cavity 8151. The gas container retention member 8180 is configured to receive and/or retain a gas container 8410 that contains a pressurized gas, as shown in FIG. 65. When the medical injector 8000 is actuated, pressurized gas from the gas container 8410 is conveyed from the gas container cavity 8151 to the medicament cavities 8139A, 8139B via the gas passageways. Said another way, the gas passageways place the gas container cavity 8151 in fluid communication with the medicament cavities 8139A, 8139B. Thus, the proximal portion of the medicament cavity 8139A and the medicament cavity 8139B can be referred to as a gas chamber.

Figure 67:
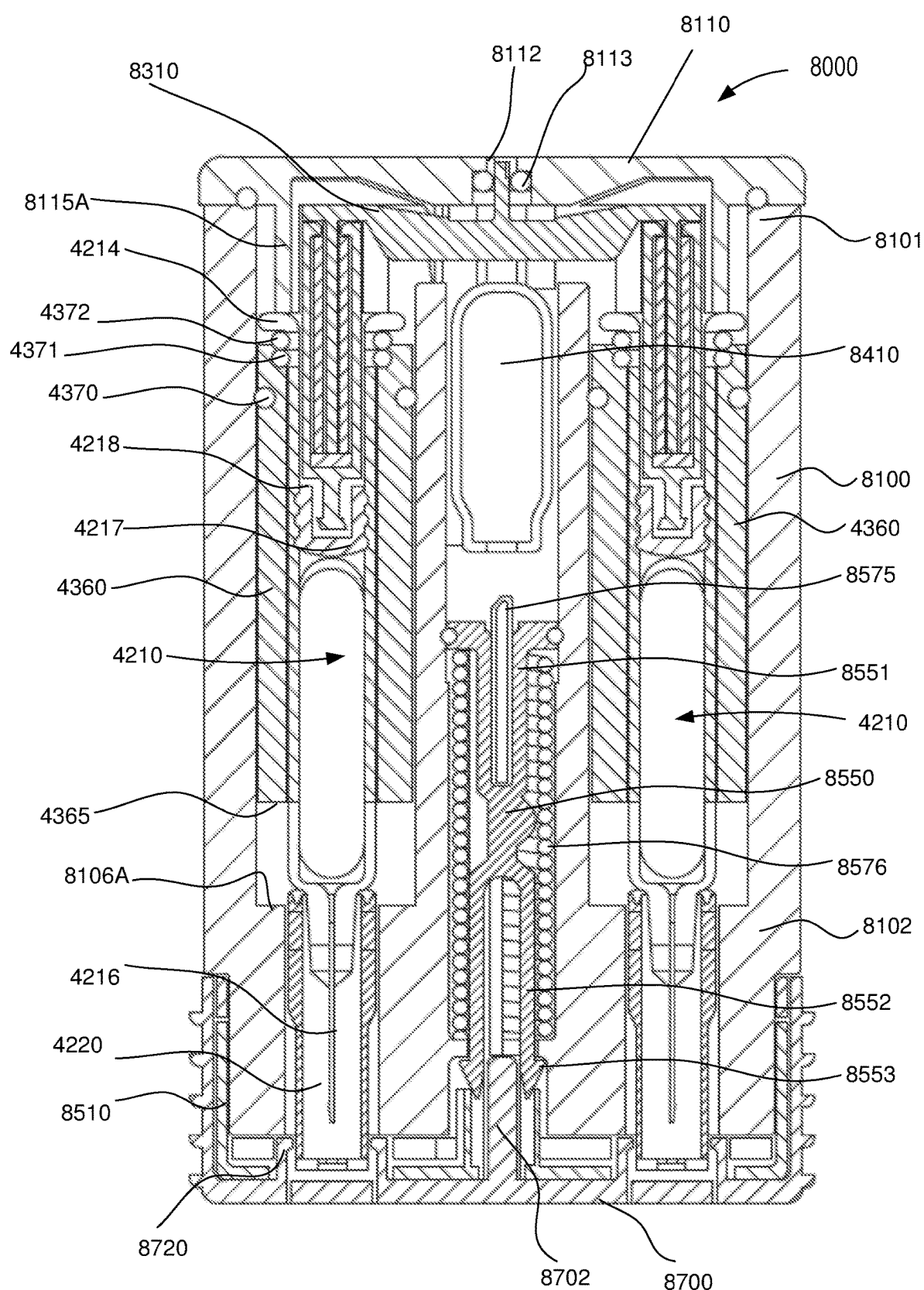
FIG. 67 is a front cross-sectional view of the medical injector shown in FIGS. 59 and 60, in the first configuration.

As shown in FIG. 67, the proximal cap 8110 also includes an O-ring 8113 and defines the vent opening 8112. As described herein, the vent opening 8112 provides the passageway through which pressurized gas is conveyed from the medicament cavity 8139A (or gas chamber portion of the medicament cavity 8139A) and the medicament cavity 8139B (or gas chamber portion of the medicament cavity 8139B) to a volume outside of the medical injector 8000. In this manner, the force produced by the pressurized gas on the medicament delivery mechanism 8300 and/or the medicament container assemblies 4200 can be reduced to allow needle retraction after the injection is completed. As shown in FIG. 68, the O-ring 8113, in conjunction with the valve portion 8345 of the gas vent assembly 8310, selectively seals the vent opening 8112 during needle insertion and delivery of the medicament.

The proximal cap 8110 includes a guide walls 8115A, 8115B within which the first (or proximal) member 8340 of the gas vent assembly 8310 moves. The guide walls 8115A, 8115B also each include an end surface 8117 (see FIG. 64) against which a flange 4214 of the container body 4210 rests when the medical injector 8000 is in its first configuration (i.e., the "storage" state).

As shown in FIG. 63, the distal end portion 8102 of the housing 8100 includes a first shoulder 8106A and a second shoulder 8106B and defines a first needle aperture 8105A and a second needle aperture 8105B. The distal end portion 8102 also includes base rail grooves 8114 and base retention recesses 8134 (see FIG. 62). The shoulders 8106A, 8106B are each configured to contact a corresponding surface 4365 of the carrier body 4360 (see e.g., FIG. 68) when the needle 4216 from each respective medicament container assembly 4200 has been inserted a desired distance. In this manner the shoulders 8106A, 8106B can act as an "end stop" or insertion limiting mechanism. The needle apertures 8105A, 8105B are the openings through which each needle 4216 is disposed when the medical injector 8000 is actuated, as described in further detail herein.

The distal end portion 8102 of the housing also includes a release member contact surface 8126, and defines the release member aperture. As shown in FIG. 67, the release member aperture 8145 receives a distal end portion 5152 of a release member 8550, such that the extensions 8553 of the release member 8550 engage with the release member contact surface to prevent activation of the medical injector 8000. The safety lock 8700, its components and functions are described in more detail below, and similar to the function of the safety lock 4700 described above.

The distal base retention recesses 8134 are configured to receive the base connection knobs 8518 of the actuator 8510 (also referred to herein as "base 8510," see e.g., FIG. 72) when the base 8510 is in a first position relative to the housing 8100. The proximal-most pair of base retention recesses 8134 are configured to receive the base connection knobs 8518 of the base 8510 when the base 8510 is in a second (i.e., actuated) position relative to the housing 8100. The base retention recesses 8134 have a tapered proximal sidewall and a non-tapered distal sidewall. This allows the base retention recesses 8134 to receive the base connection knobs 8518 such that the base 8510 can move proximally relative to the housing 8100, but cannot move distally relative to the housing 8100. Said another way, the distal-most set of base retention recesses 8134 are configured to prevent the base 8510 from moving distally when the base 8510 is in a first position and the proximal-most set of base retention recesses 8134 are configured to prevent the base 8510 from moving distally when the base 8510 is in a second position. Similarly stated, the proximal base retention recesses 8134 and the base connection knobs 8518 cooperatively to limit movement of the base to prevent undesirable movement of the base 8510 after the medical injector 8000 is actuated. The proximal base retention recesses 8134 and the base connection knobs 8518 also provide a visual cue to the user that the medical injector 8000 has been used.

The base rail grooves 8114 receive the guide members of the base 8510. The guide members of the base 8510 and the base rail grooves 8114 of the housing 8100 engage each other in a way that allows the guide members of the base 8510 to slide in a proximal and/or distal direction within the base rail grooves 8114 while limiting lateral movement of the guide members. This arrangement allows the base 8510 to move in a proximal and/or distal direction with respect to the housing 8100 but prevents the base 8510 from moving in a lateral direction with respect to the housing 8100.

The medicament container assemblies 4200 of the medical injector 8000 are the same as those described above with reference to the medical injector 4000. The attachment of the elastomeric members 4217 to the distal member 8320 of the gas venting assembly 8310 is similar to that described above with reference to the medical injector 4000, and is therefore not described in detail below.

The delivery mechanism 8300 includes a gas vent assembly 8310 (also referred to as an expandable assembly), but does not rely on a piston or rigid member to move the elastomeric members 4217 within the container bodies 4210 to inject the medicament. Rather, the elastomeric members 4217 are moved by the force produced by the pressurized gas within the gas chambers (or medicament cavities 8139A, 8139B). Accordingly, the stroke length and/or the dosage amount can be set by the expanded length of the gas vent assembly 8310. In this manner, the length of the medicament container assemblies 4200 and the length of the gas vent assembly 8310 can be configured such the desired dosage amount is delivered. Moreover, because the gas vent assembly 8310 moves from a collapsed to an expanded configuration, the medicament delivery mechanism 8300 can fit within the same housing 8100 regardless of the fill volume, the delivery volume and/or the ratio of the fill volume to the delivery volume. In this manner, the same housing and production tooling can be used to produce devices having various dosages of the medicament. For example, in a first embodiment (e.g., having a fill volume to delivery volume ratio of 0.4), the medicament container has a first length and the second movable member has a first length. In a second embodiment (e.g., having a fill volume to delivery volume ratio of 0.6), the medicament container has a second length shorter than the first length, and the second movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

In some embodiments, the device 8000 is configured such that a ratio of the housing length $H_L$ to the container length $H_C$ is less than about 1.5. In other embodiments, the device 8000 is configured such that a ratio of the housing length $H_L$ to the container length $H_C$ is less than about 1.25. In yet other embodiments, the device 8000 is configured such that a ratio of the housing length $H_L$ to the container length $H_C$ is less than about 1.1.

In some embodiments, the device 8000 is configured such that a ratio of the housing length $H_L$ to a sum of the container length $H_C$, the carrier distance, and the stroke is less than about 1.1. In other embodiments, the device 8000 is configured such that a ratio of the housing length $H_L$ to a sum of the container length $H_C$, the carrier distance, and the stroke is less than about 1.0. In yet other embodiments, the device 8000 is configured such that a ratio of the housing length $H_L$ to a sum of the container length $H_C$, the carrier distance, and the stroke is less than about 0.9.

Figure 73:
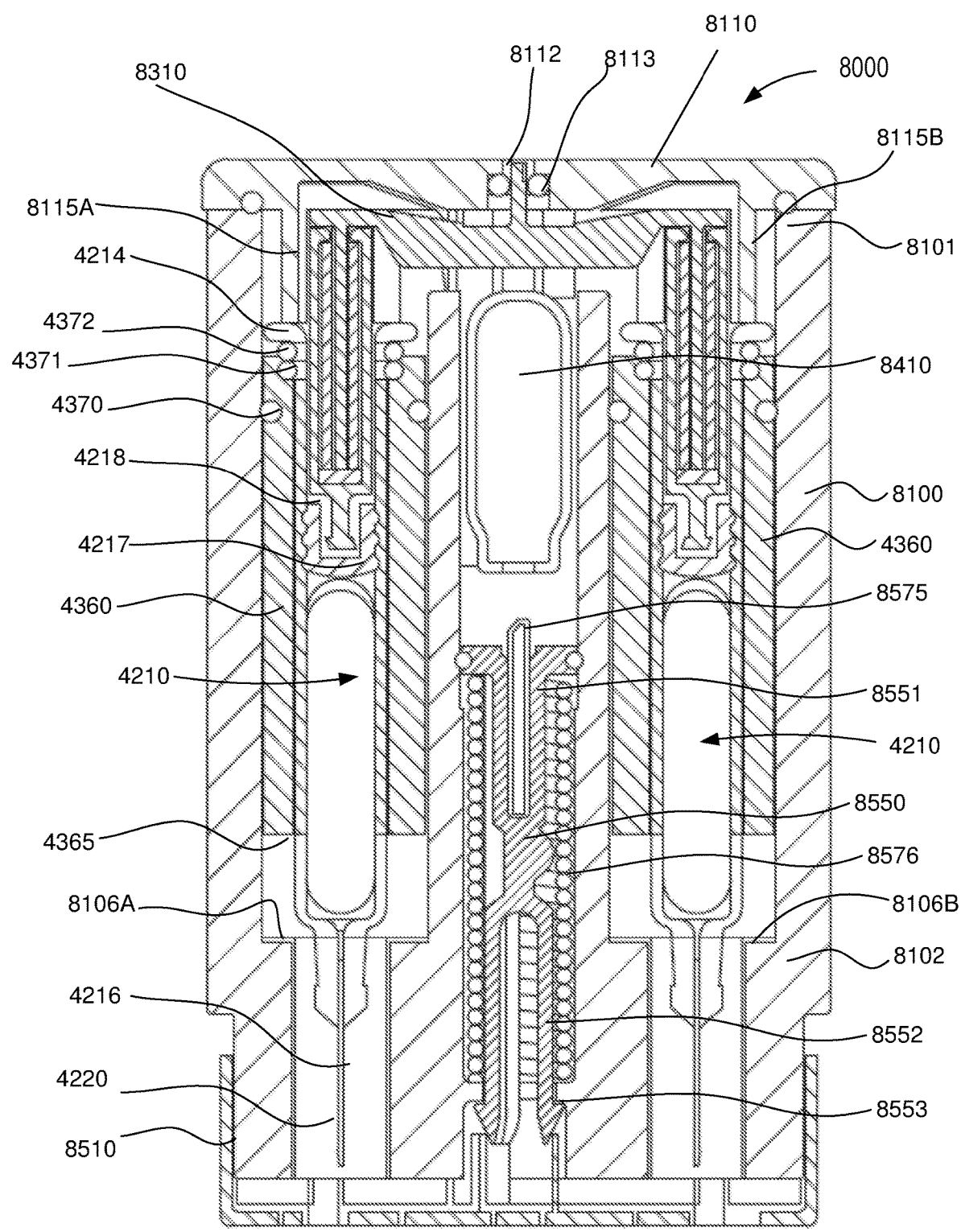
FIG. 73 is a front cross-sectional view of the medical injector shown in FIGS. 59 and 60, in a second configuration (safety lock removed).
Figure 74:
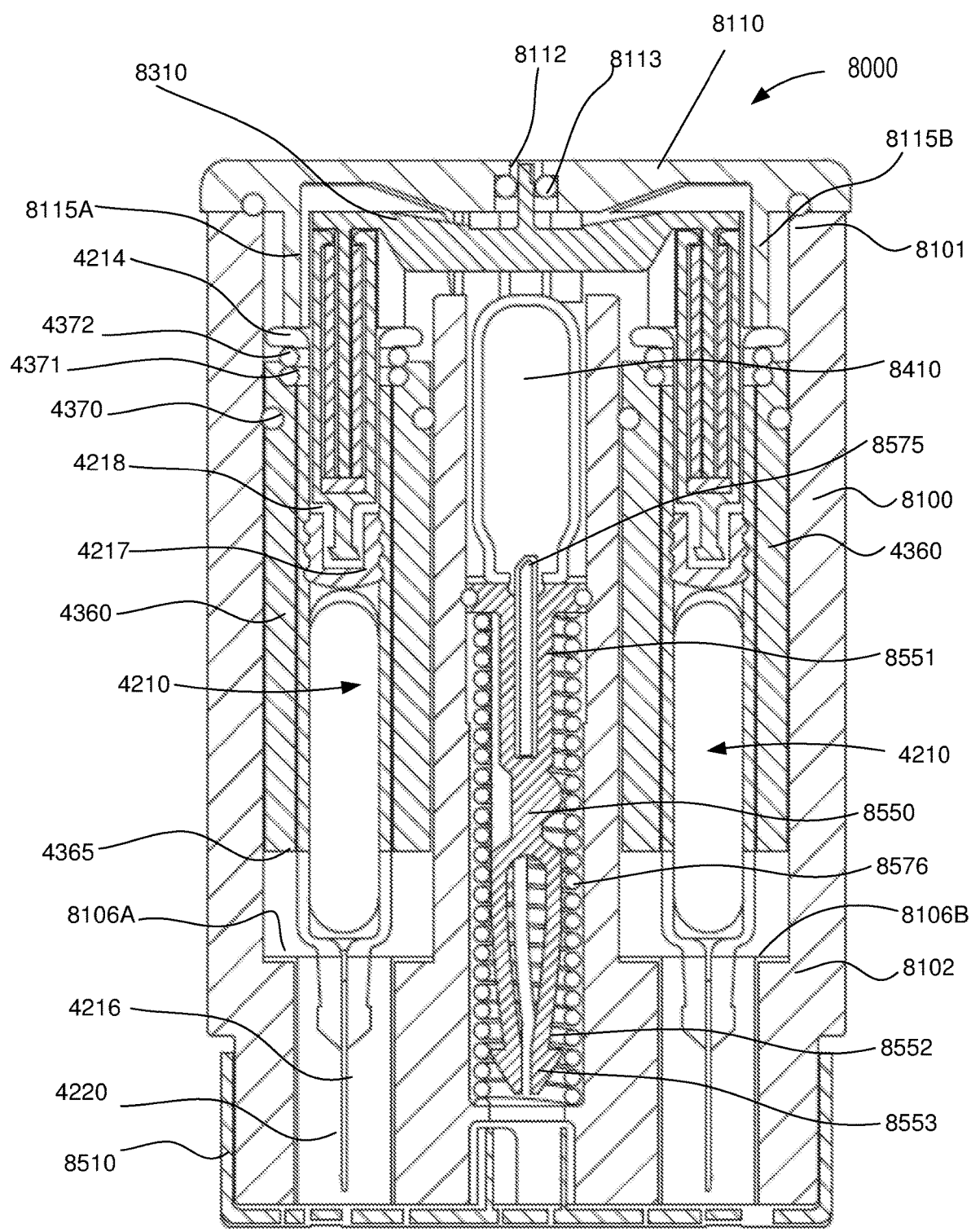
FIG. 74 is a front cross-sectional view of the medical injector shown in FIGS. 59 and 60, in a third configuration (actuated).

As shown in FIGS. 65 and 73, the system actuator assembly 8500 includes the base 8510, a release member 8550 and a spring 8576. FIG. 65 shows certain internal components of the medical injector 8000 without the base 8510 and the safety lock 8700 so that the release member 8550 can be more clearly shown. The release member 8550 has a proximal end portion 8551 and a distal end portion 8552, and is movably disposed within the distal end portion of the gas container cavity 8151. The proximal end portion of the release member 8550 includes a sealing member 8574 and a puncturer 8575. The sealing member 8574 is configured to engage the sidewall of the housing 8100 defining the gas container cavity 8151 such that the proximal end portion of the gas container cavity 8151 is fluidically isolated from the distal end portion of the gas container cavity 8151. In this manner, when gas is released from the gas container 8410, the gas contained in the proximal end portion of the gas container cavity 8151 is unable to enter the distal end portion of the gas container cavity 8151. The puncturer 8575 of the release member 8550 is configured to contact and puncture a frangible seal 8413 on the gas container 8410 when the release member 8550 moves proximally within the gas container cavity 8151.

The distal end portion 8552 of the release member 8550 includes extensions 8553. The extensions 8553 have projections that include tapered surfaces and engagement surfaces. Further, the extensions 8553 define an opening between the adjacent extensions 8553. The engagement surfaces are configured to extend through the release member aperture and contact the release member contact surface of the housing 8100, as shown in FIG. 73. In this manner, the engagement surfaces limit proximal movement of the release member 8550.

The opening defined by the extensions 8553 is configured to receive the safety lock protrusion 8702 of the safety lock 8700 (see e.g., FIGS. 70 and 71) when the safety lock 8700 is coupled to the housing 8100 and/or the base 8510. The safety lock protrusion 8702 is configured to prevent the extensions 8553 from moving closer to each other. Said another way, the safety lock protrusion 8702 is configured to ensure that the extensions 8553 remain spaced apart and the engagement surfaces remain in contact with the release member contact surface of the housing 8100. In some embodiments, for example, the release member 8550 and/or the extensions 8553 can be constructed from any suitable material configured to withstand deformation that may occur when exposed to a load over an extended period of time.

The tapered surfaces of the extensions 8553 are configured to contact corresponding tapered surfaces 8557 of the base 8510 when the base 8510 is moved proximally relative to the housing 8100. Accordingly, when the base 8510 is moved proximally relative to the housing 8100, the extensions 8553 are moved together by the tapered surfaces. The inward movement of the extensions 8553 causes the release member 8550 to disengage the release member contact surface 8126 of the housing 8100, thereby allowing the release member 8550 to be moved proximally along its longitudinal axis as the spring 8576 expands (see FIG. 37).

The gas container 8410 includes a distal end portion 8411 and a proximal end portion 8412, and is configured to contain and/or produce a pressurized gas. The distal end portion 8411 of the gas container 8410 contains a frangible seal 8413 configured to break when the puncturer 8575 of the release member 8550 contacts the frangible seal 8413. The gas container retention member 8180 of the proximal cap 8110 of the housing 8100 is configured to receive and/or retain the proximal end portion 8412 of the gas container 8410. Said another way, the position of the gas container 8410 within the gas container cavity 8151 is maintained by the gas container retention member 8180. As shown in FIGS. 16 and 17, the length of the gas container retention member 8180 and the length of the release member 8550 collectively determine the distance between the puncturer 8575 and the frangible seal 8413 when the medical injector 8000 is in the storage configuration. Accordingly, this distance, which is the distance through which the puncturer 8575 travels when the medical injector 8000 is actuated, can be adjusted by changing the length of the gas container retention member 8180 and/or the length of the release member 8550. In some embodiments, the actuation time and/or the force exerted by the puncturer 8575 on the frangible seal 8413 can be adjusted by changing the distance between the puncturer 8575 and the frangible seal 8413.

The medicament delivery mechanism 8300 includes two carrier assemblies 4390 and a gas vent assembly 8310. The carrier assemblies 4390 and the gas vent assembly 8310 are each movably disposed within the medicament cavities 8139A, 8139B of the housing 8100. The carrier assemblies 4390 included within the medical injector 8000 are substantially the same as those described above with reference to the medical injector 4000, and therefore are not described in detail herein. For example, as described above with reference to the medical injector 4000, each carrier body 4360 has a proximal surface 4376, forms a portion of the boundary of its respective gas chamber (i.e., the portion of the respective medicament cavity 1139A, 1139B within which the pressurized gas flows). In this manner, the pressurized gas produces a force on the proximal surfaces 4376, which moves each carrier assembly 4390 distally within the housing 8110.

Further, as described above, each carrier assembly 4390 includes a retraction spring 4380 that is disposed within the spring pocket 4363 defined by the outer surface of each carrier body 4360, as shown in FIG. 24. Thus, each of the carrier assemblies 4390 within the medical injector 8000 is separately retracted (i.e., is retracted independently from the other carrier assembly therein). In other embodiments, however, the medical injector 8000 can include a single retraction spring and/or biasing mechanism to retract both carrier assemblies therein.

The gas vent assembly 8310 is configured to expand and/or change configurations during operation of the medical injector 8100, and selectively produces a pathway through which pressurized gas escapes the medicament cavities 8139A, 8139B after delivery of the medicament. By releasing or removing the force from the carrier bodies 4360 and/or the medicament container assemblies 4200, the retraction springs 4380 can move the carrier bodies 4360 proximally to retract the needles 4216. Notably, the gas vent assembly 8310 does not exert a distal force on the elastomeric members 4217, but rather, is carried distally by each elastomeric member 4217 during delivery of the medicament. Thus, this arrangement is considered a "pistonless" delivery system, because the force for insertion and medicament delivery is provided by the pressurized gas acting directly upon the medicament container assemblies 4200 (e.g., the proximal surface 4218 of the elastomeric member 4217) and/or the carrier assemblies 4390 (e.g., the proximal surface 4376 of the carrier body 4360).

Figure 69:
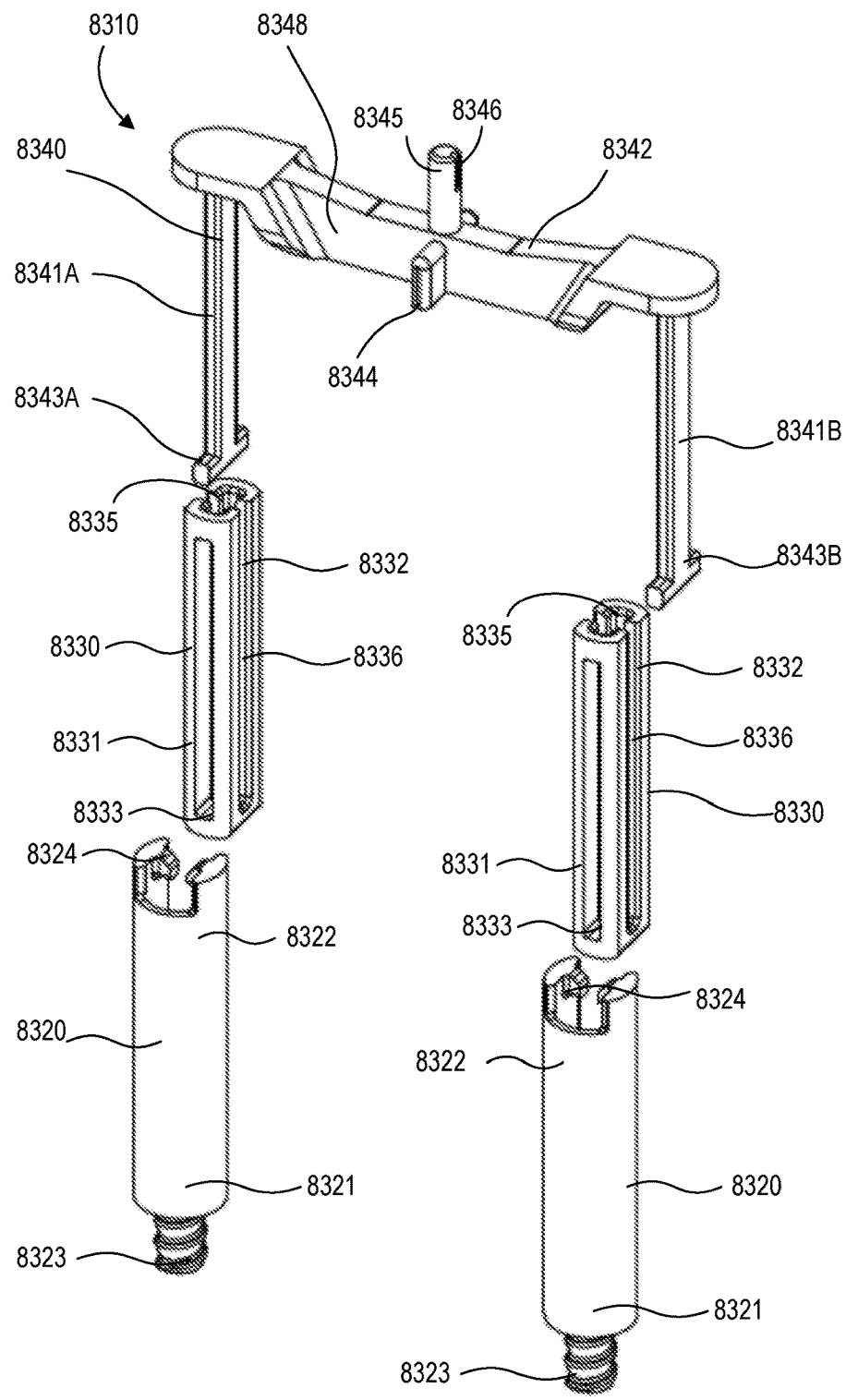
FIG. 69 is an exploded views of the gas vent assembly of the medical injector shown in FIGS. 59 and 60.

As shown in FIG. 69, the gas vent assembly 8310 includes two first (or distal) members 8320, two second (or central) members 8330, and a third (or proximal) member 8340. These components are nested together such that the gas vent assembly 8310 can be transitioned from a collapsed configuration to an expanded configuration, and a series of partially expanded configurations therebetween. When the gas vent assembly 8310 is in the expanded configuration (FIG. 77, after delivery of the medicament), the opening 8112, the O-ring 8113 and the passageway 8346 collectively allow the gas to escape the medicament cavities 8139A, 8139B, such that needle retraction can occur.

The first member 8320 includes a proximal end portion 8322 and a distal end portion 8321. The distal end portion 8321 includes a protrusion 8323 configured to matingly engage the elastomeric member 4217. In this manner, movement of the elastomeric member 4217 distally causes movement of first member 8320 distally. The proximal end portion 8322 includes a pair of retention walls 8324 configured to engage a corresponding distal end surface 8333 of the second (or central) member 8330. More particularly, the first member 8320 defines an opening within which the second member 8330 can slide. The retention walls 8324 limit movement of the second member 8330.

The second member 8330 includes a proximal end portion 8332 and a distal end portion 8331. The distal end portion 8331 includes the distal end surface 8333 that engages the first member 8320. The second member defines an opening 8335 and a pair of side grooves 8336. The third (or proximal) member 8340 is movably disposed within the opening 8335. In particular, the distal protrusions 8343A, 8343B of the third member 8340 slide within the side grooves 8336 and contact the proximal end portion 8332 to limit movement of the third member 8340 within the second member 8330.

The third member 8340 includes a proximal end portion 8342 and two distal end legs 8341A, 8341B. The distal end leg 8341A includes the distal protrusions 8343A that engage one of the second members 8320. The distal end leg 8341B includes the distal protrusions 8343B that engage the other second member 8320. The proximal end portion 8342 includes a guide surface 8344, a central portion 8348, and a valve portion 8345. The guide surface 8344 slides within the slots 8116 of the guide wall 8115. The central portion 8348 connects each of the two distal end legs 8341A, 8341A. The valve portion 8345 defines a passageway 8346.

Figure 70:
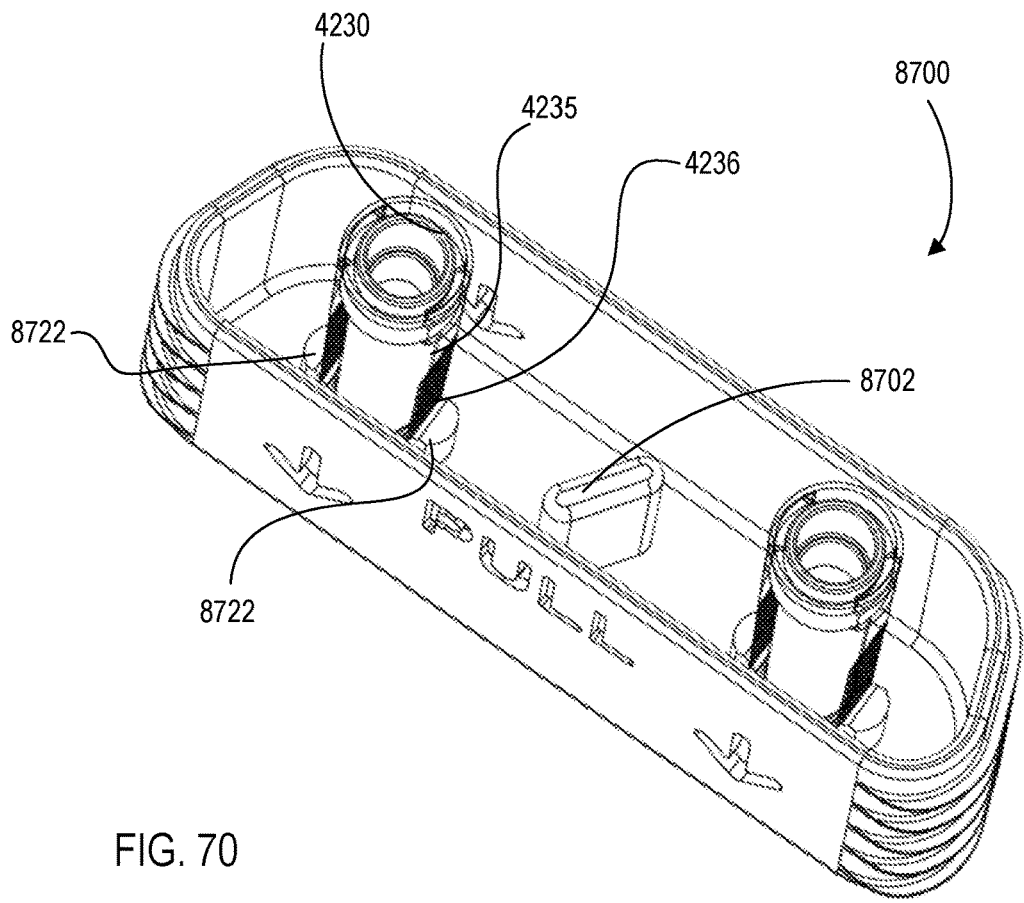
FIGS. 70 and 71 are perspective views of a safety lock of the medical injector shown in FIGS. 59 and 60.
Figure 71:
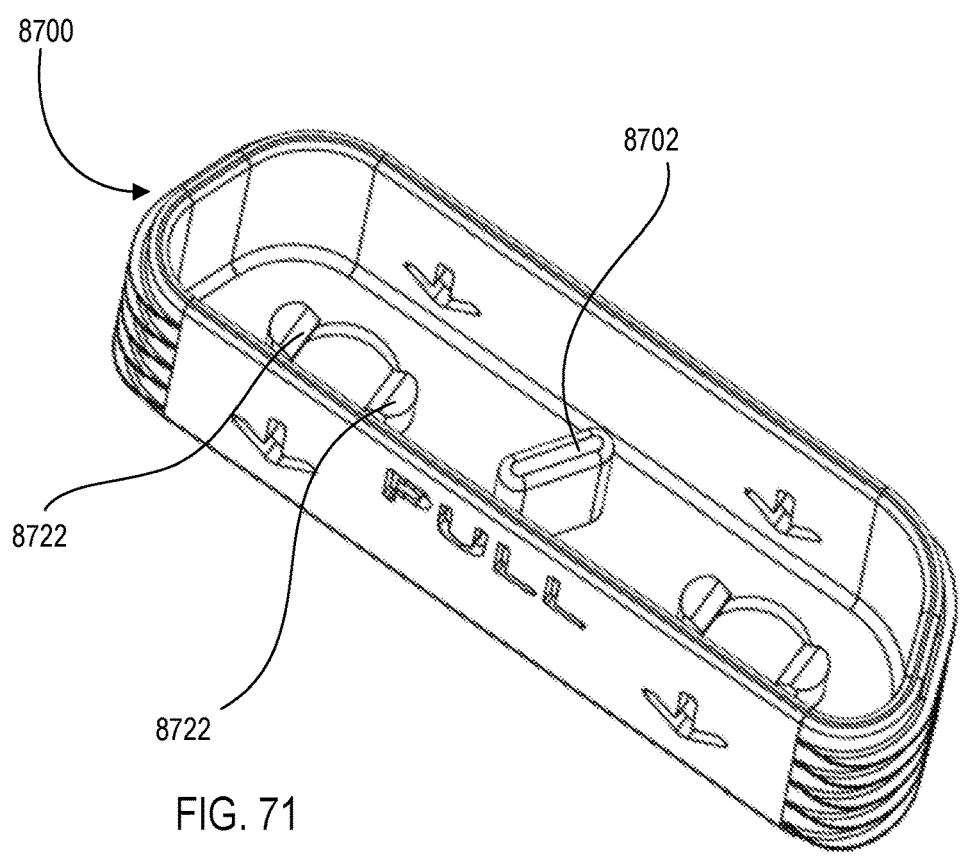

As shown in FIGS. 70 and 71, the safety lock 8700 includes a safety lock protrusion 8702 and an engagement portion 8720. As described above, when the safety lock 8700 is in a first (locked) position, the safety lock protrusion 8702 is configured to be disposed in the opening defined by the extensions 8553 of the release member 8550. Accordingly, the safety lock protrusion 8702 is configured to prevent the extensions 8553 from moving closer to each other, thereby preventing proximal movement of the release member 8550 and/or delivery of the medicament.

The safety lock 8700 includes engagement tabs 8722 that extend from a surface of the engagement members. The tabs 8722 engage the ribs 4236 of the sheath cover 4235 to limit relative movement between the safety lock 8700 and the needle sheath assembly 4220, as described above. In this manner, the needle sheath assembly 4220 can protect the user from the needle 4216 and/or can keep the needle 4216 sterile before the user actuates the medical injector 8000, and the needle sheath assembly 4220 can be removed from about the needle 4216 when the safety lock 8700 is removed.

The outer surface of the safety lock 8700 include a grip portion (lateral ribs) and indicia thereon. The grip portion provides an area for the user to grip and/or remove the safety lock 8700 from about the housing 8100. The indicia provide instruction on how to remove the safety lock 8700. In some embodiments, for example, indicia can indicate the direction the user should pull the safety lock 8700 to remove the safety lock 8700.

Figure 72:
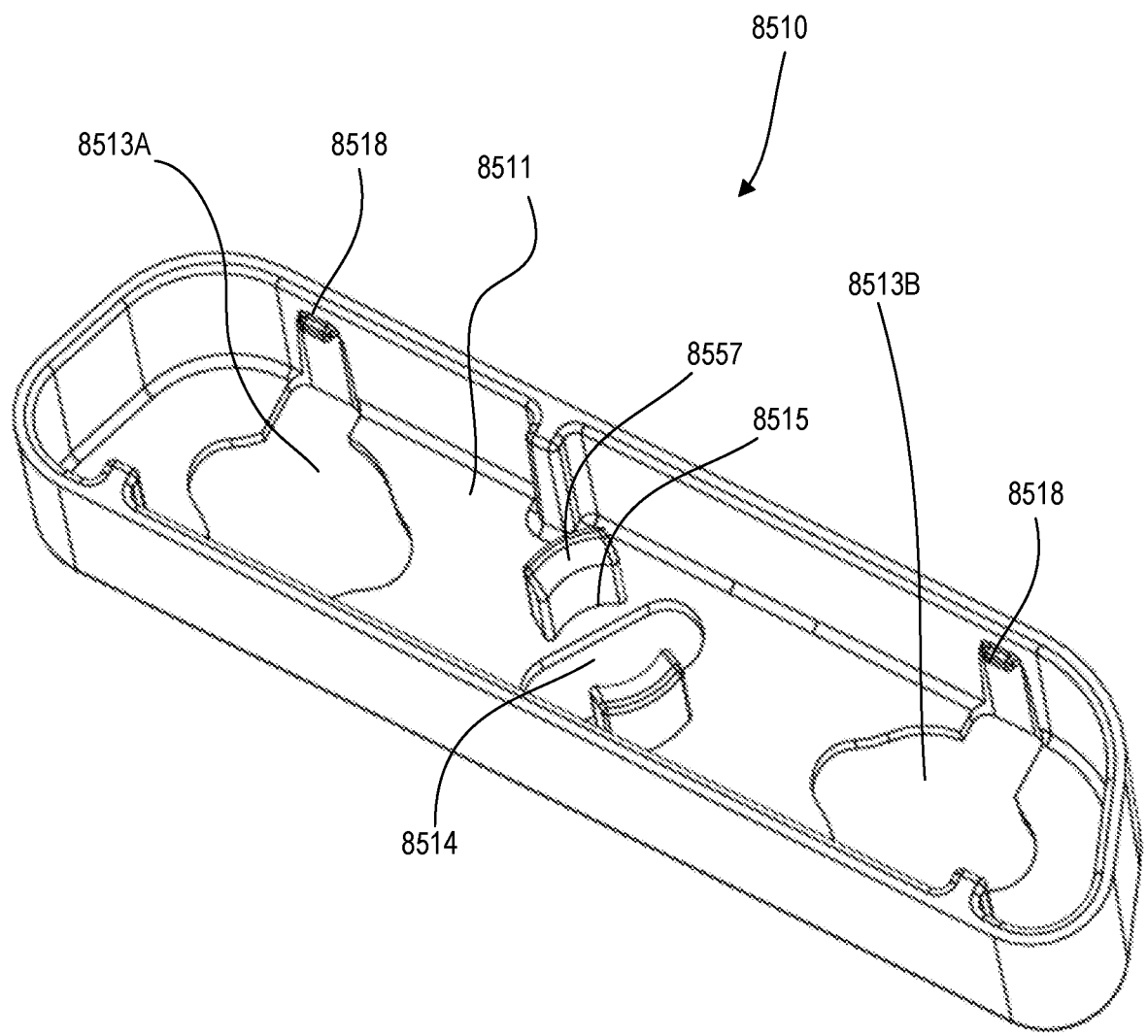
FIG. 72 is a perspective view of a system actuator of the medical injector shown in FIGS. 59 and 60.

FIG. 72 shows the base (or actuator) 8510 of the medical injector 8000. The base 8510 includes a proximal (or inner) surface 8511, a distal (or outer) surface, and base connection knobs 8518. The distal surface is disposed against a target surface (not shown) during use of the injector 8000. As described below, the housing 8100 is moved distally relative to the base 8510 and/or the distal surface, thereby causing the base 8510 to move proximally relative to the housing 8100 to actuate the medical injector 8000. The base 8510 defines two needle apertures 8513A, 8513B, and a safety lock protrusion aperture 8514. The needle aperture 8513 is configured to receive the needle 8216 when the medical injector 8000 is actuated. The safety lock protrusion aperture 8514 of the base 8510 receives the safety lock protrusion 8702 of the safety lock 8700 when the safety lock 8700 is coupled to the housing 8100 and/or the base 8510.

The proximal surface 8511 of the base 8510 includes guide members (not shown) and protrusions 8515. The guide members of the base 8510 engage and/or slide within the base rail grooves 8114 of the housing 8100, as described above. The protrusions 8515 of the base 8510 engage the tapered surfaces of the extensions 8553 of the release member 8550. As described in further detail herein, when the safety lock 8700 is removed and the base 8510 is moved in a proximal direction with respect to the housing 8100, the protrusions 8515 of the base 8510 are configured to move the extensions 8553 of the release member 8550 closer to each other, actuating the medicament delivery mechanism 8300. As described above, the base connection knobs 8518 engage the base retention recesses 8134 in a way that allows proximal movement of the base 8510 but limits distal movement of the base 8510.

Figure 66:
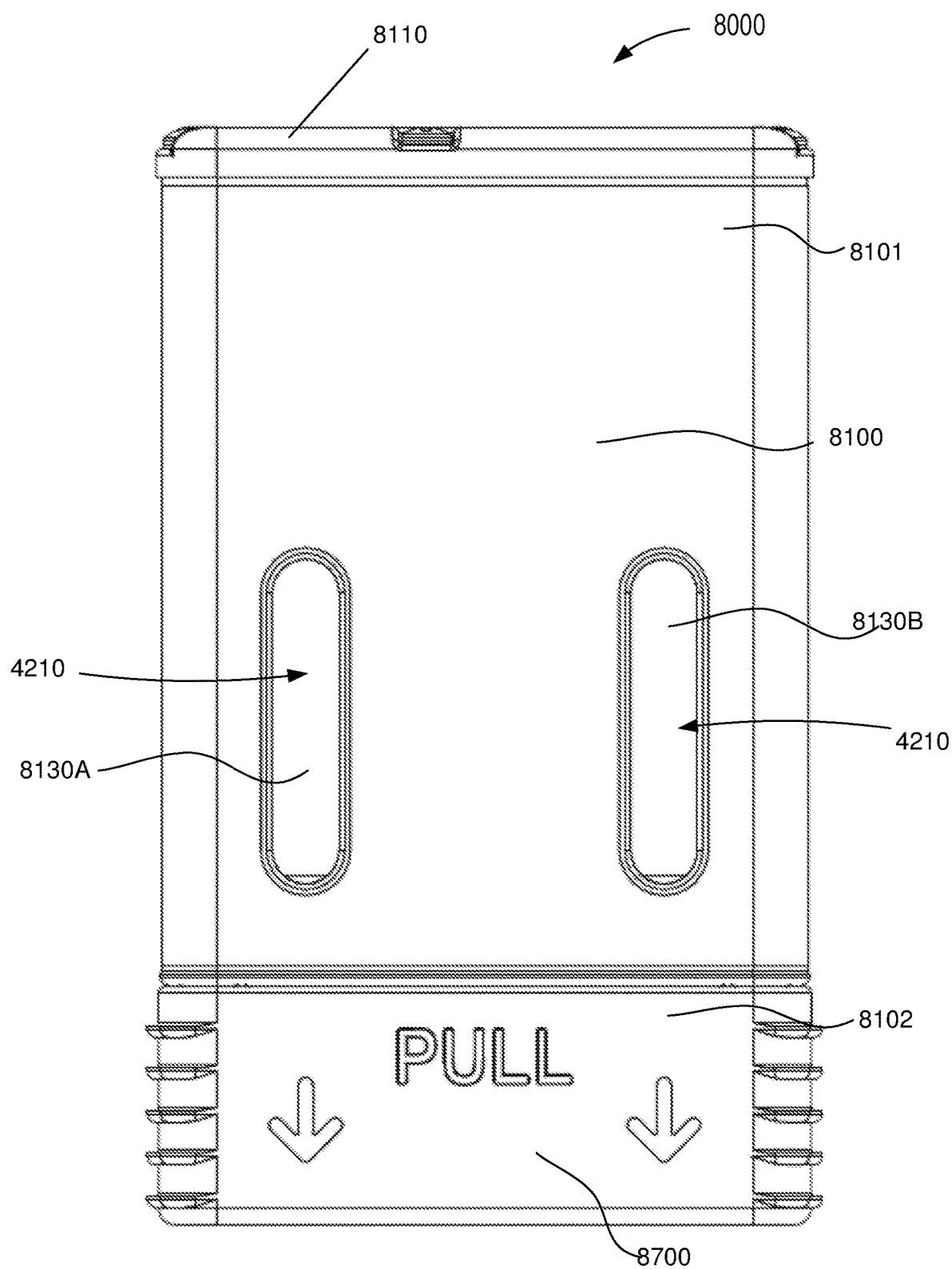
FIG. 66 is a front view of the medical injector shown in FIGS. 59 and 60, in the first configuration.

The medical injector 8000 can be moved from the first configuration (FIGS. 66 and 67) to a second configuration (FIG. 73) by moving the safety lock 8700 from a first position to a second position. The safety lock 8700 is moved from a first position to a second position by moving and/or removing the safety lock 8700 distally with respect to the housing 8100. When the safety lock 8700 is moved from the first position to the second position, the safety lock protrusion 8702 is removed from between the extensions 8553 of the release member 8550, thereby enabling the medicament delivery mechanism 8300. As shown in FIG. 66, prior to actuation, a portion of the medicament container assemblies 4200 can be viewed via the status apertures 8130A, 8130B. Specifically, the container bodies 4210 and the contents therein (e.g., the medicament) can be viewed. As described above, in some embodiments, the housing 8100 can include a label or other indicia providing a color strip (against which the medicament can be compared), instructions for viewing or the like. Although not shown in FIG. 18, in some embodiments, a portion of the elastomeric members 4217 are visible via the status apertures 8130A, 8130B.

After the safety lock 8700 is moved from the first position to the second position, the medical injector 8000 can be moved from the second configuration (FIG. 73) to a third configuration (FIG. 74) by moving the base 8510 from a first position to a second position. Similarly stated, the medical injector 8000 can be actuated by the system actuator assembly 8500 by moving the base 8510 proximally relative to the housing 8100. The base 8510 is moved from its first position to its second position by placing the medical injector 8000 against the body of the patient and moving the base 8510 with respect to the housing 8100. Specifically, as described above the base includes a "contact portion" (i.e., the distal surface) that can be placed against and/or in contact with the target location. Moving the base 8510 from the first position to the second position causes the base 8510 to engage the extensions 8553 of the release member 8550, thereby moving the extensions 8553 together. The inward movement of the extensions 8553 causes engagement surface of the release member 8550 to become disengaged from the housing 8100, thereby allowing the release member 8550 to be moved proximally along its longitudinal axis as the spring 8576 expands.

Figure 75:
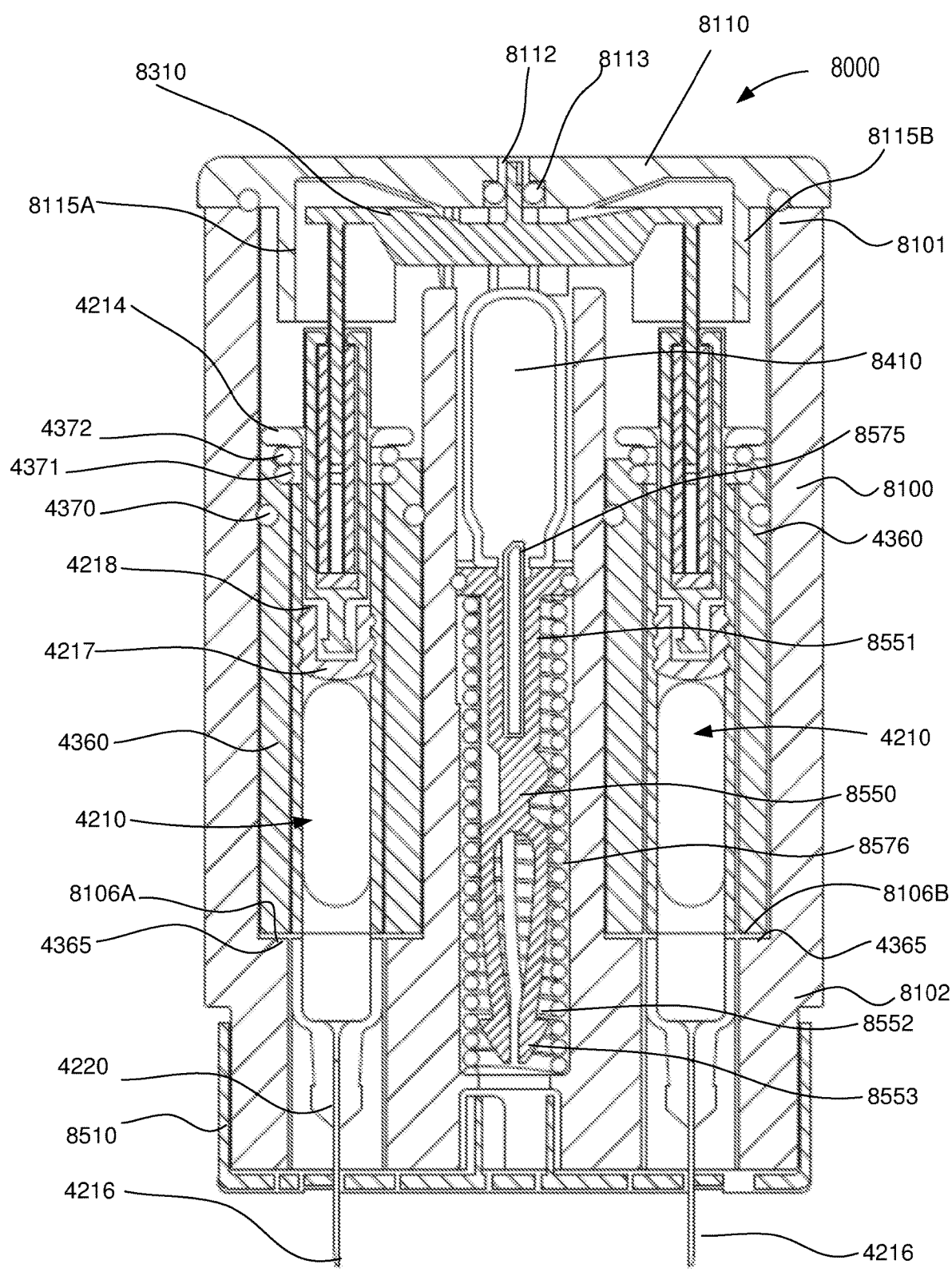
FIG. 75 is a front cross-sectional view of the medical injector shown in FIGS. 59 and 60, in the fourth configuration (needle inserted).

When the base 8510 is moved from the first position to the second position, the system actuator assembly 8500 actuates the medicament delivery mechanism 8300, thereby placing the medical injector 8000 in its fourth configuration (i.e., the needle insertion configuration), as shown in FIG. 75. More particularly, when the medical injector 8000 is in its fourth configuration, the puncturer 8575 of the release member 8550 is in contact with and/or disposed through the frangible seal 8413 of the gas container 8410.

After the frangible seal 8413 has been punctured, an actuating portion of a compressed gas flows from the gas container 8410, via the gas passageway and into the medicament cavity 8139A and the medicament cavity 8139B. The gas applies gas pressure to flanges 4214 of the medicament containers and/or the top surface of the carrier bodies 4360. Because the seals 4371, 4372 and the outer seal 4370 maintain their respective medicament cavities 8139A, 8139B fluidically isolated from the exterior of the device, the gas pressure exerts a force to move each carrier assembly 4390 distally within the respective medicament cavities 8139A, 8139B, as shown in FIG. 75. In this manner, the movement of the needles 4216 in a distal direction causes the distal end portion of each needle 4216 to exit the housing 8100 and enter the body of a patient prior to administering the medicament.

As shown in FIG. 75, when the device moves from the third configuration to the fourth configuration, the gas vent assembly expands from its collapsed configuration (FIGS. 66, 73) to a partially expanded configuration. Notably, in the partially expanded configuration, the valve portion 8345 is maintained in a sealed position within the opening 8112 and the O-ring 8113. Thus, the medicament cavities 8139A, 8139B are maintained in fluidic isolation.

When the needles 4216 have extended by a desired distance, the distal surfaces 4365A, 4365B of each carrier body 4360 contacts their respective end surfaces 8106A, 8106B of the housing 8100 to limit further distal movement of the carrier assemblies 4390 within the housing 8100. When the distal movement of the carrier assemblies 4390 is prevented, the gas within the medicament cavities 8139A, 8139B (i.e., the gas chamber) continues to apply gas pressure to the respective elastomeric members 4217. This causes the elastomeric members 4217 (and therefore the respective first members 8320 of the gas vent assembly 8310) to move in the distal direction with the medicament container bodies 4210. Distal movement of the elastomeric members 4217 generates a pressure upon the medicament contained within the medicament container assemblies 4200, thereby allowing at least a portion of the medicament to flow out of each medicament container 4200 via its needle 4216. The medicament is delivered to a body of a user via the medicament delivery path defined by the medicament container 4200 and the needle 4216. At the end of injection, the medical injector is in its fifth configuration (FIG. 76).

Figure 76:
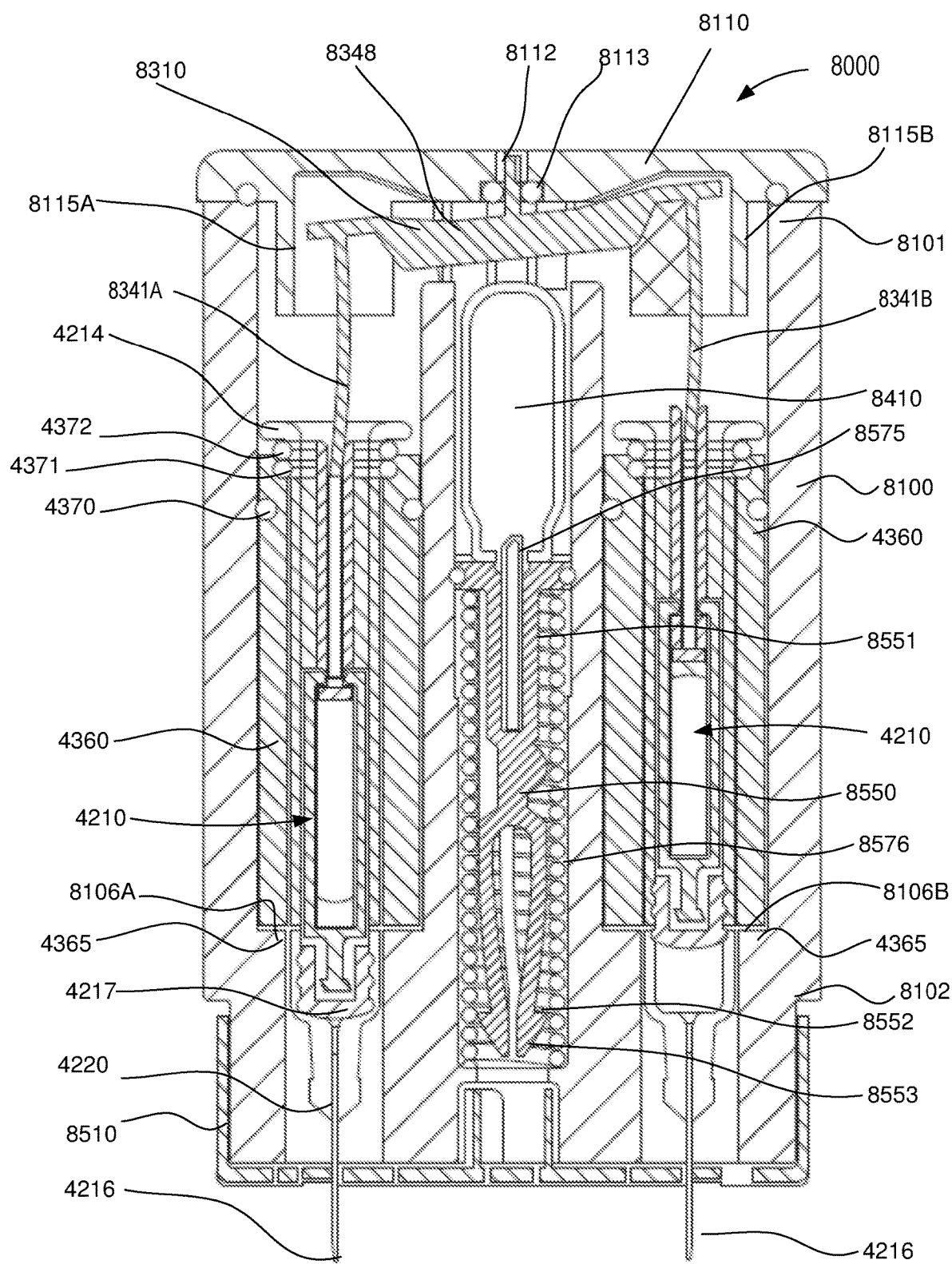
FIG. 76 is a front cross-sectional view of the medical injector shown in FIGS. 59 and 60, in the fifth configuration (medicament delivered).

Moreover, as shown in FIG. 76, the distal legs 8341A, 8341B are flexible and thus allow the vent assembly 8310 to expand in a manner in which the two elastomeric members 4217 are not moving at substantially the same location in within their respective container bodies 4210. This arrangement allows for the vent assembly 8310 to expand without being over-constrained. In other embodiments, however, the medicament can be injected substantially simultaneously.

When the medical injector 8000 is in its fifth configuration, a portion of the medicament container assemblies 4200, a portion of the carrier bodies 4360, and a portion of the gas vent assembly 8310 can be viewed via the status apertures 8130A, 8130B. As described above, in some embodiments, the housing 8100 can include a label or other indicia providing a color strip to assist the user in identifying the carrier, providing instructions for viewing, or the like. In some embodiments, a portion of the elastomeric members 4217 are visible via the status apertures 8130A, 8130B when the medical injector 8000 is in its fifth configuration.

Figure 77:
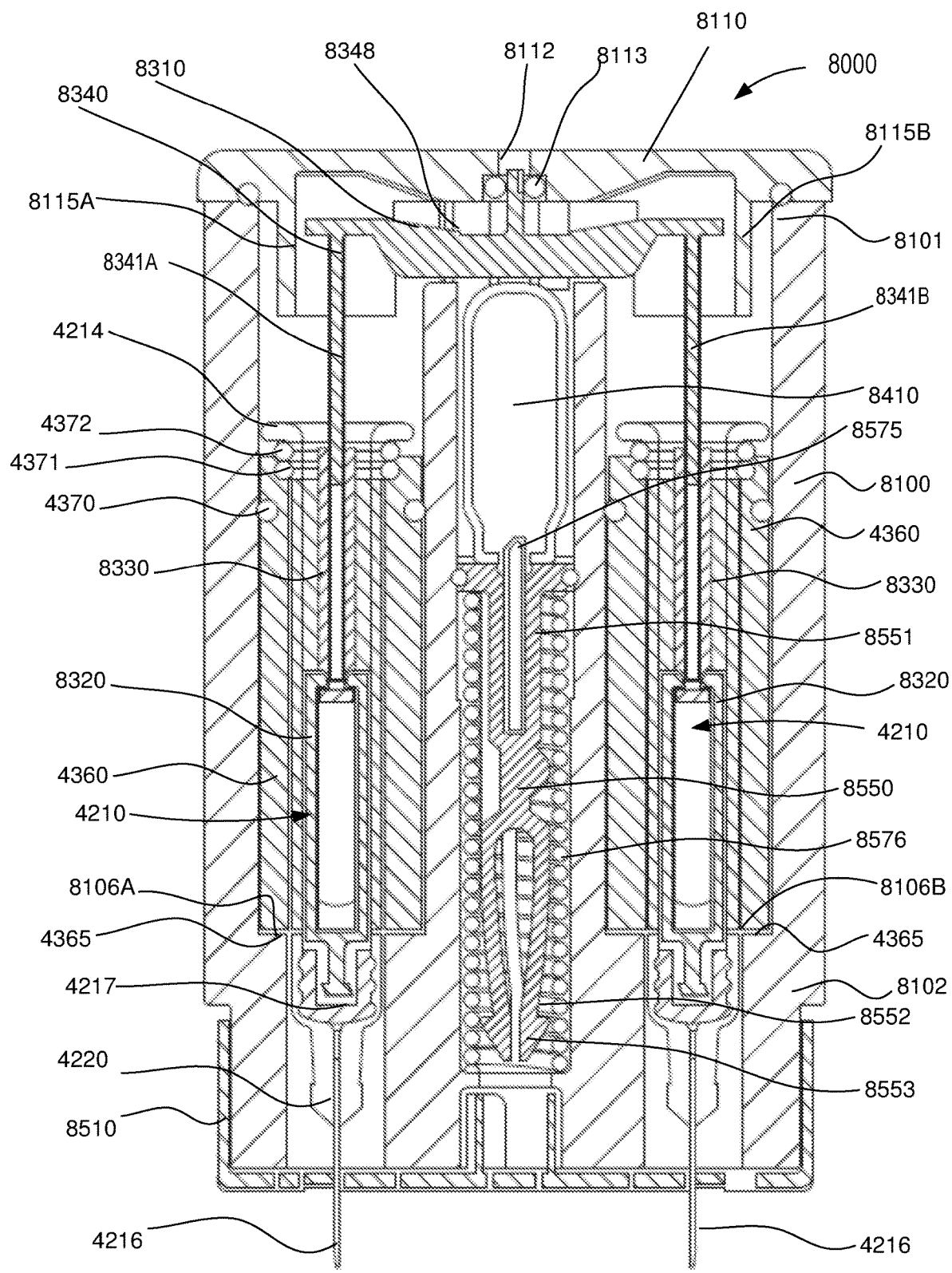
FIG. 77 is a perspective cross-sectional view of the medical injector shown in FIGS. 59 and 60, in the fifth configuration (medicament delivered).
Figure 78:
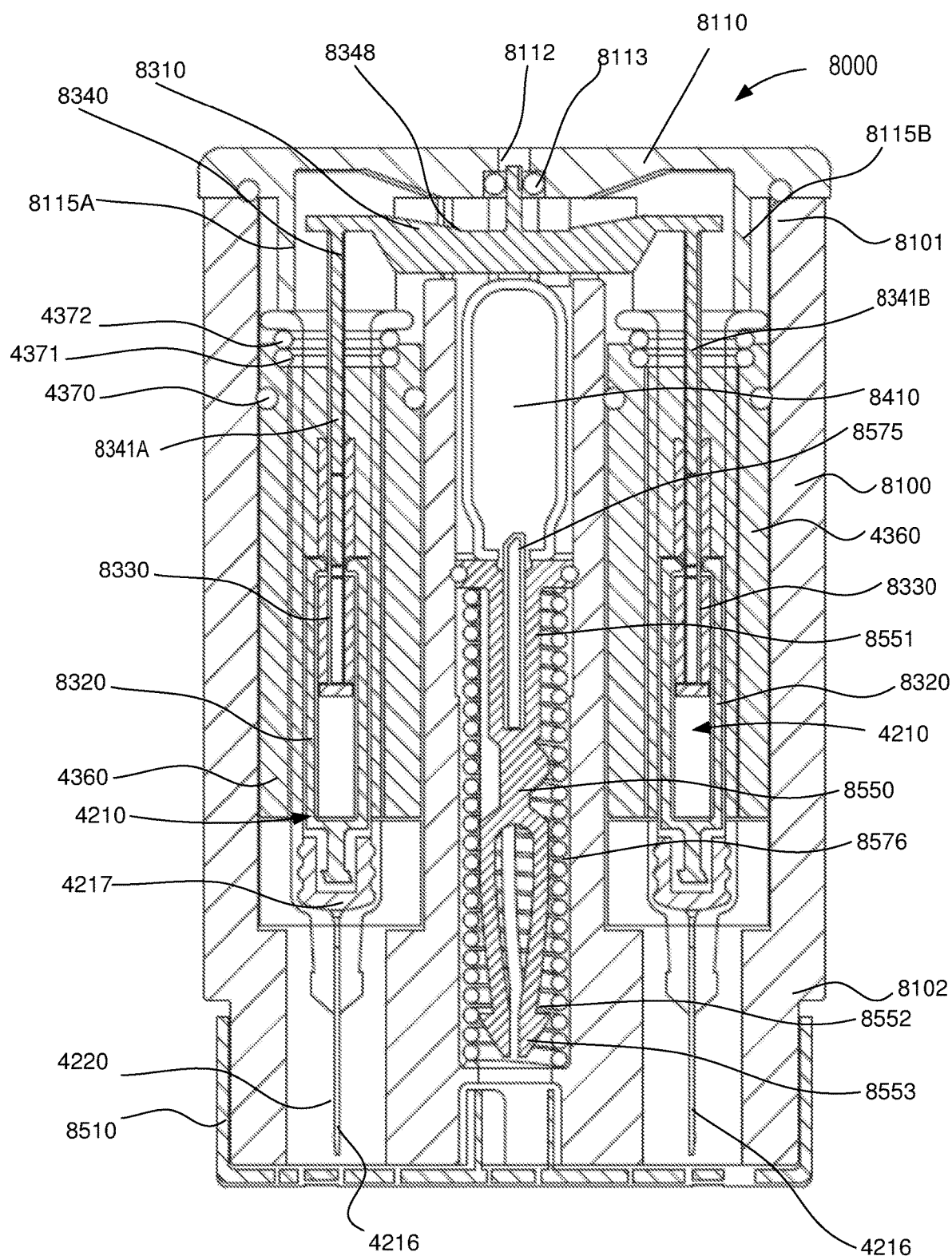
FIG. 78 is a front cross-sectional view of the medical injector shown in FIGS. 59 and 60, in a sixth configuration (needle retracted).

As shown in FIGS. 76 and 77, as the elastomeric members 4217 move distally, the gas vent assembly 8310 continues to move to its fully expanded configuration. After the elastomeric members 4217 has moved a predetermined distance within their respective medicament container body 4210 (corresponding to the desired dose), the valve portion 8345 is moved from within the opening 8112 thereby allowing the pressurized gas contained within the gas chambers (i.e., the volume within the medicament cavities 8139A, 8139B between the proximal end of the housing 8100 and the surface of the respective carrier 4360) to escape via the passageway 8346 and the opening 8112. After the gas pressure within the medicament cavities 8139A, 8139B decreases below a certain level, the force exerted by the retraction springs 4380 on each carrier body 4360 is sufficient to cause each carrier body 4360 to move proximally within the housing 8100 (i.e., to retract). This places the medical injector in its sixth configuration (FIG. 78).

When the medical injector 8000 is in its sixth configuration, a portion of each medicament container assembly 4200 can be viewed via the status apertures 8130A, 8130B. For example, the container body 4210 and a portion of the elastomeric member 4217 can be visible via the status apertures 8130A. 8130B. As described above, in some embodiments, the housing 8100 can include a label or other indicia providing a color strip to assist the user in identifying the elastomeric member, providing instructions for viewing, or the like. In some embodiments, a portion of the carriers 4360 can be visible via the status apertures 8130A, 8130B when the medical injector 8000 is in its sixth configuration.

Figure 80:
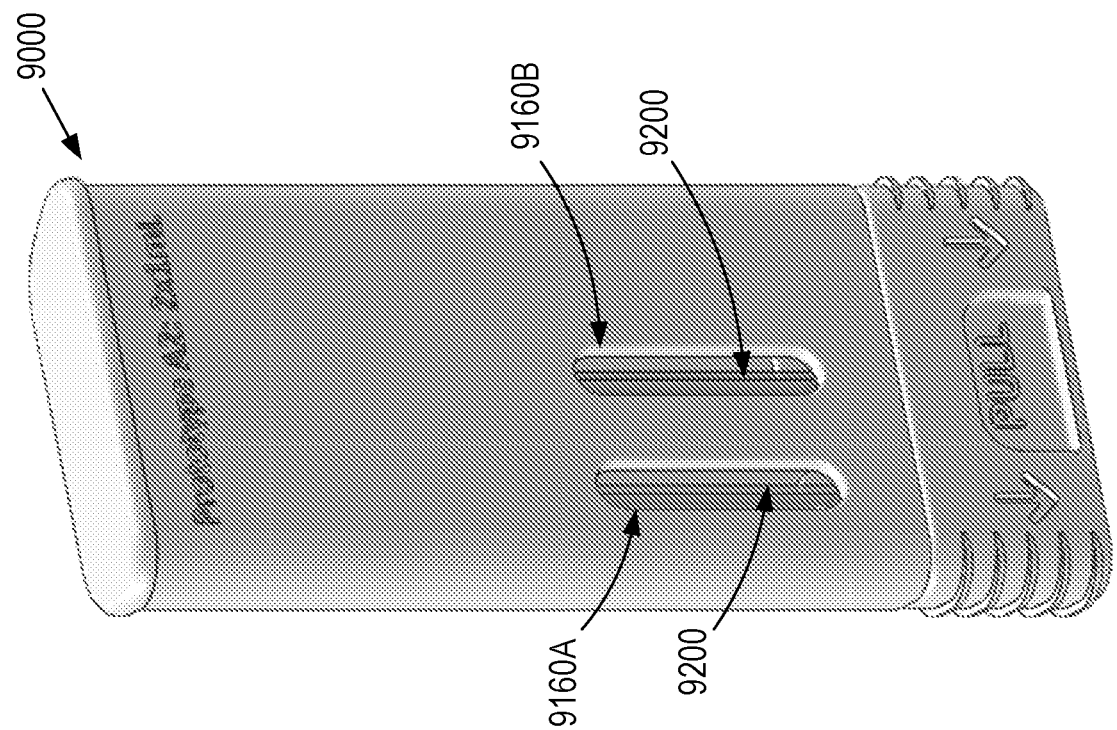
FIGS. 79 and 80 are a front view and a perspective view, respectively of a medical injector according to an embodiment.
Figure 79:
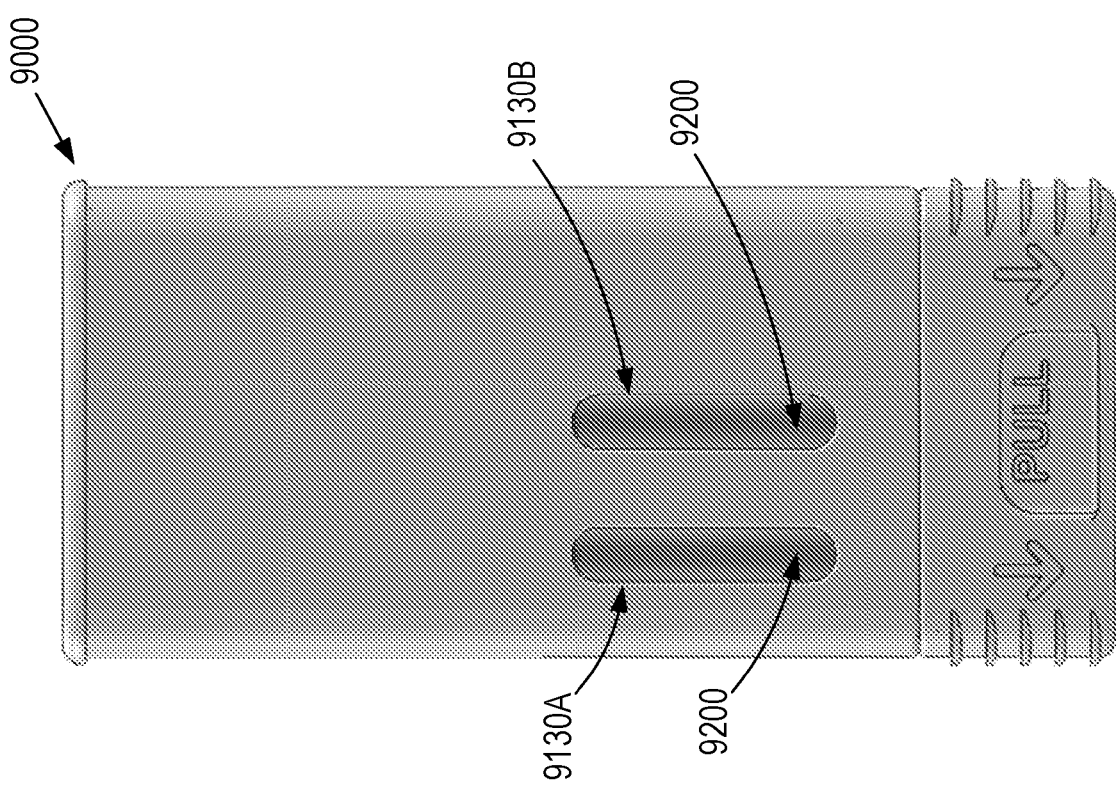
Figure 81:
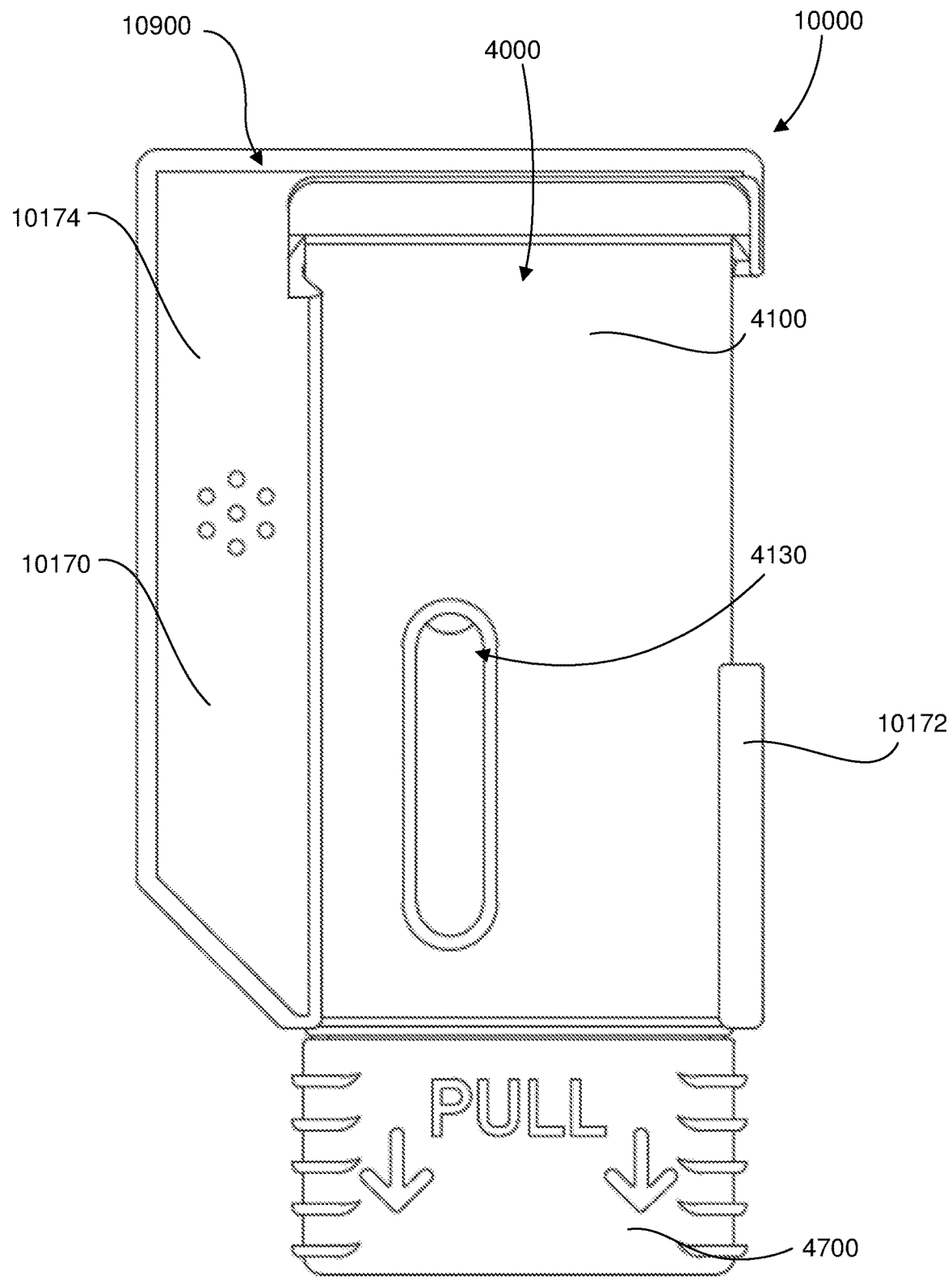
FIGS. 81 and 82 are a front view and a rear view, respectively of a medical injector including an electronic circuit system, according to an embodiment.
Figure 82:
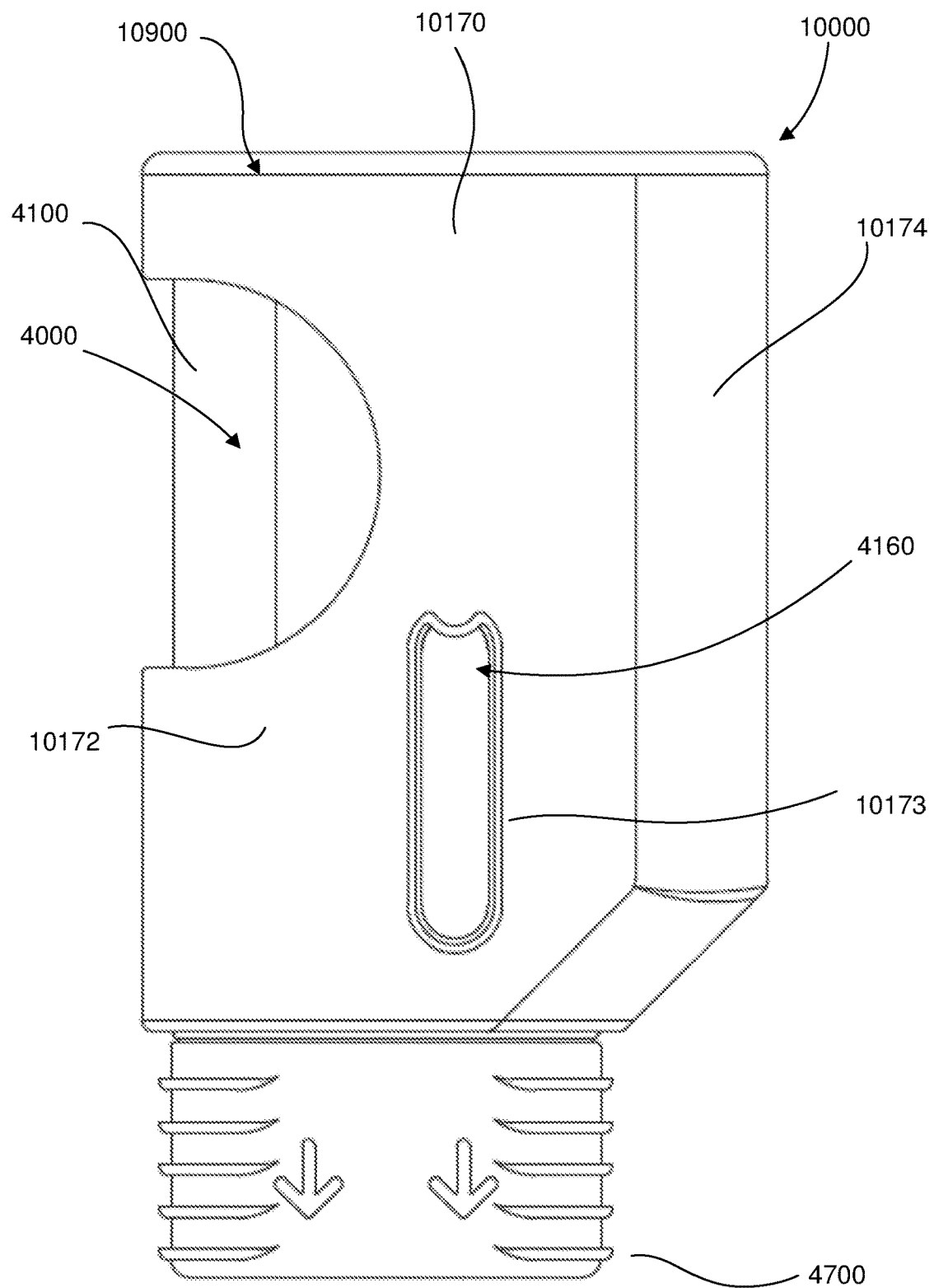
Figure 83:
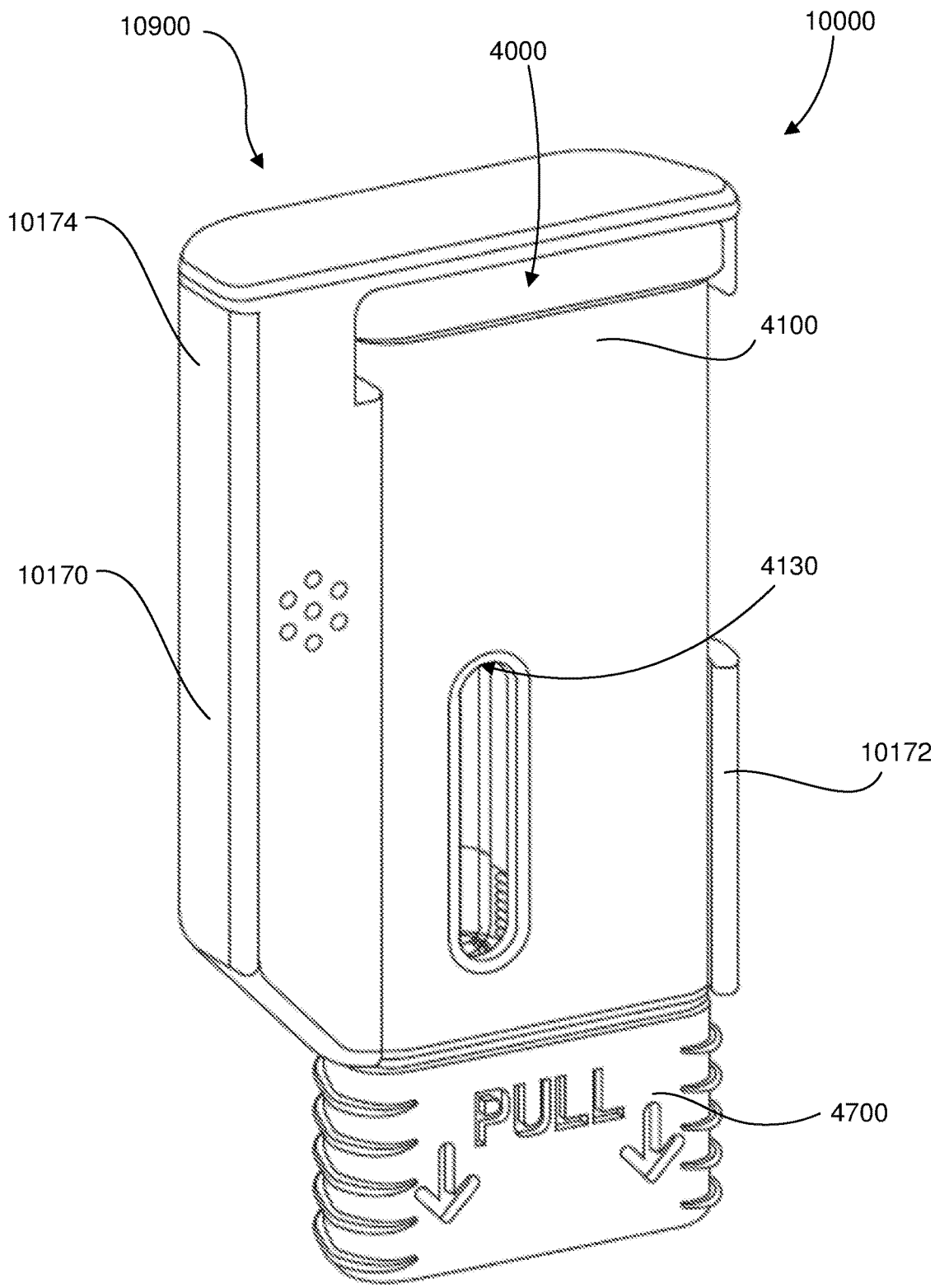
FIGS. 83 and 84 are front perspectives view of the medical injector including the electronic circuit system shown in FIGS. 81 and 82.
Figure 84:
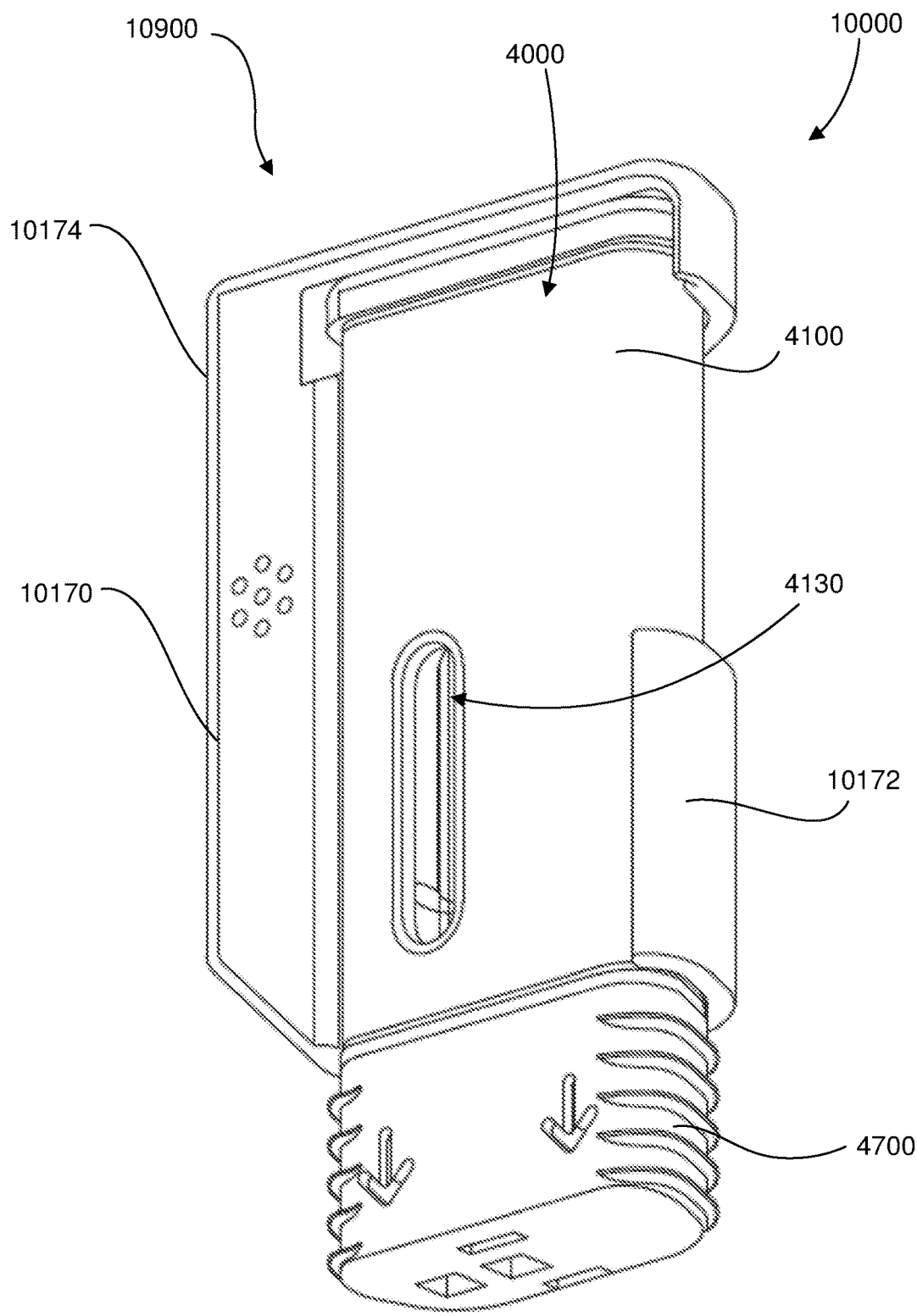
Figure 85:
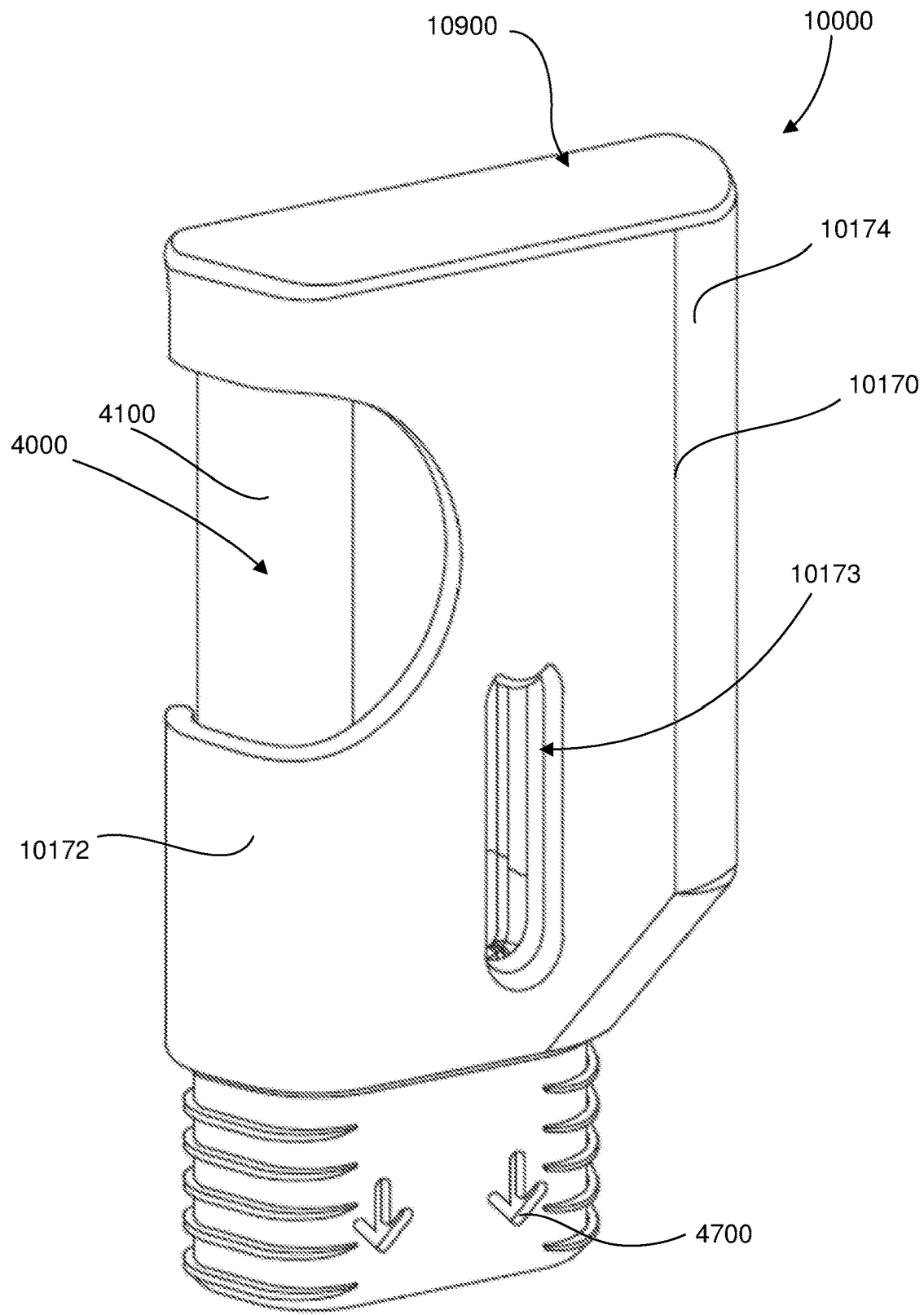
FIG. 85 is a rear perspective view of the medical injector including the electronic circuit system shown in FIGS. 81 and 82.
Figure 86:
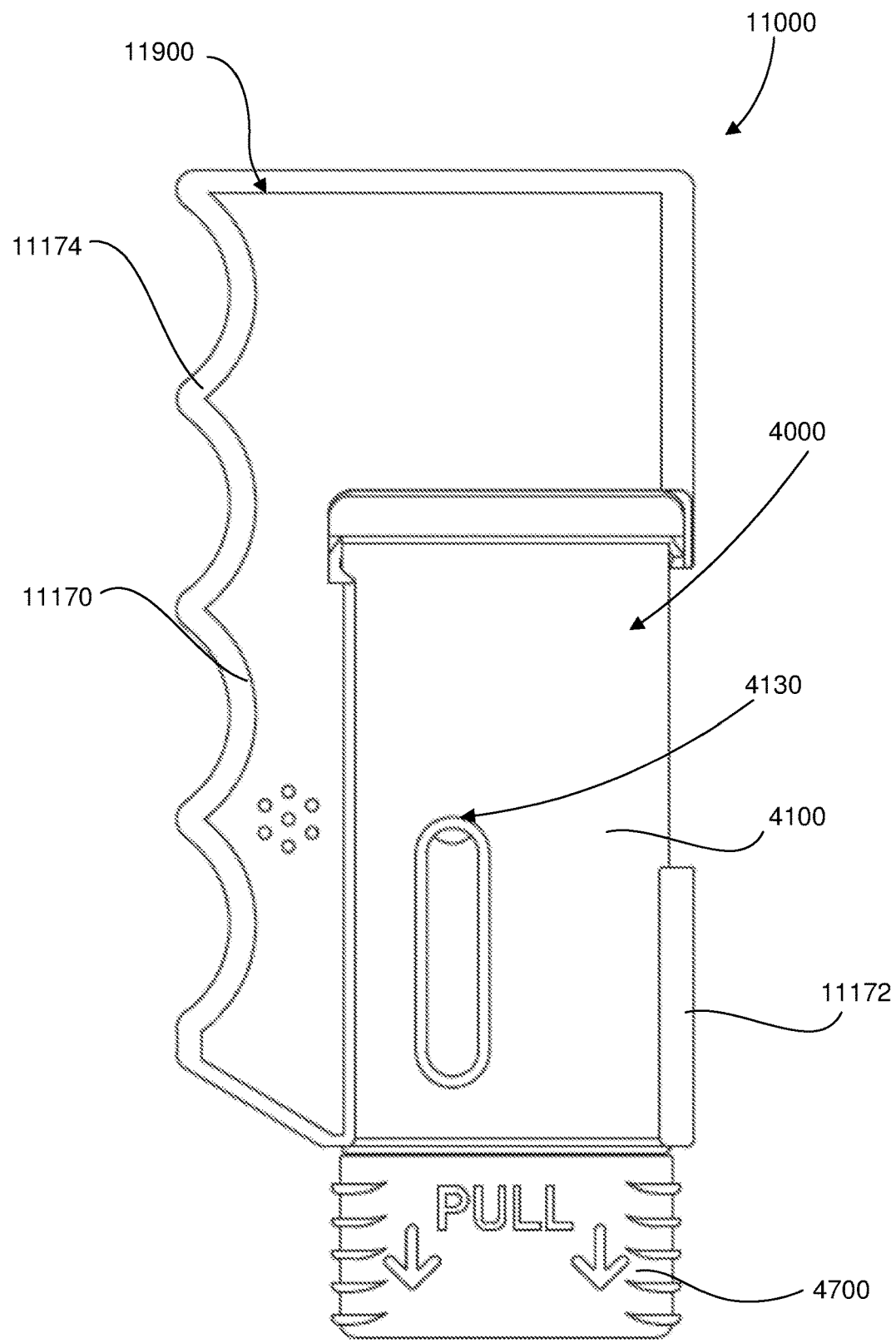
FIGS. 86 and 87 are a front view and a rear view, respectively of a medical injector including an electronic circuit system, according to an embodiment.
Figure 87:
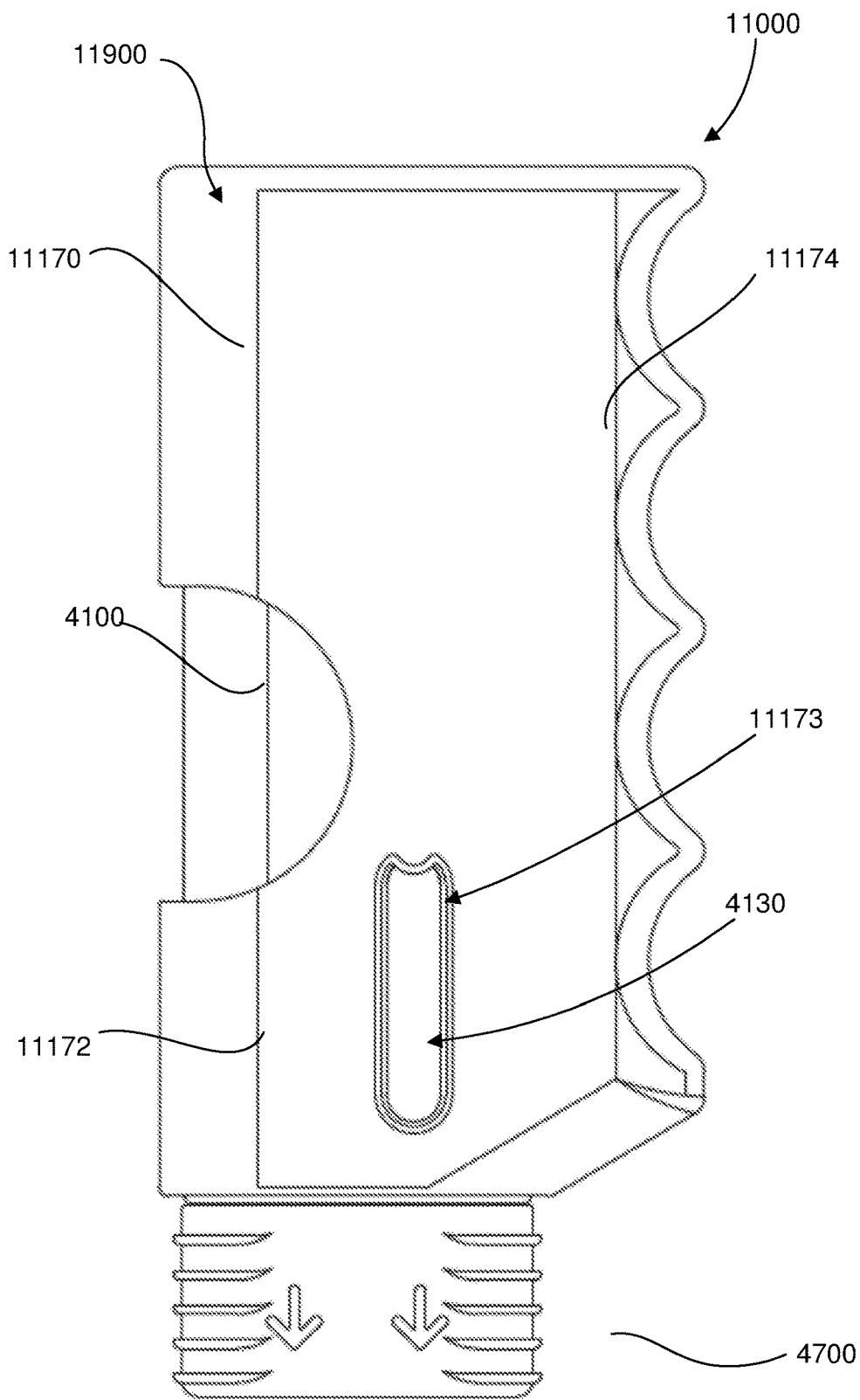
Figure 88:
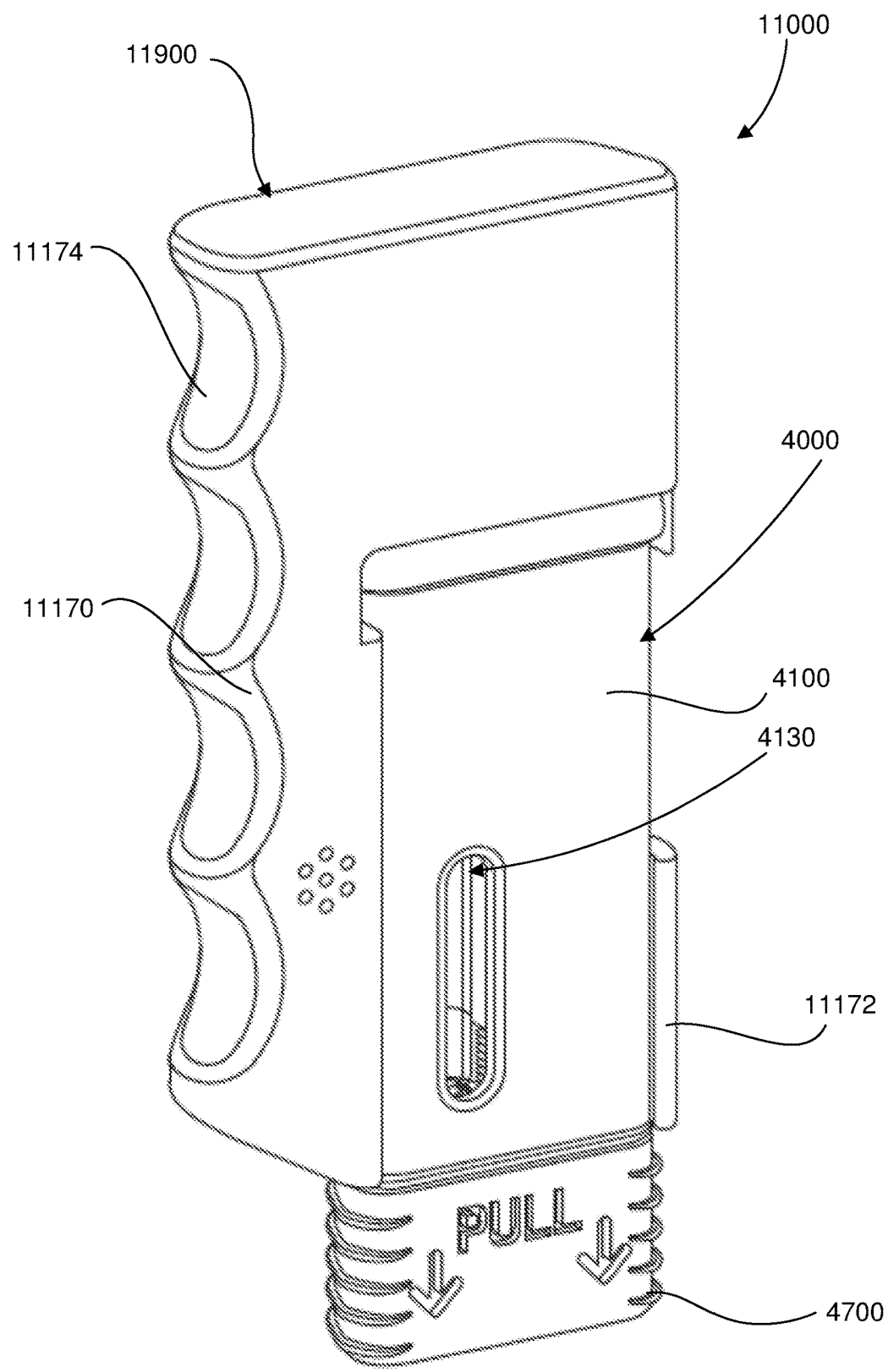
FIGS. 88 and 89 are front perspective views of the medical injector including the electronic circuit system shown in FIGS. 86 and 87.
Figure 89:
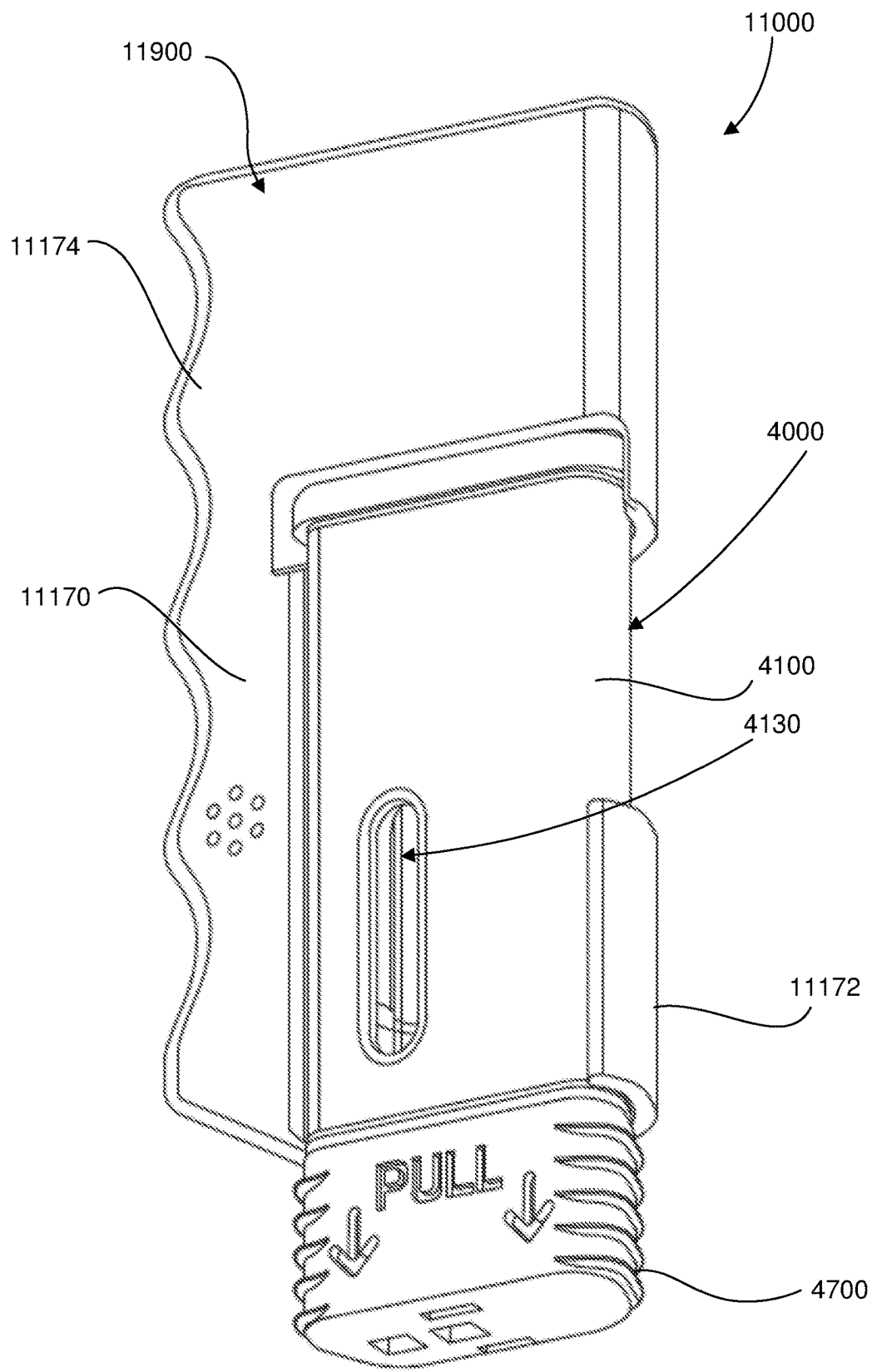

FIGS. 79 and 80 are perspective views of a medical injector 9000 according to an embodiment. The medical injector 9000 is characterized by having front status windows 9130A, 9130B and rear status windows 9160A, 9160B through which the medicament containers 9200 therein can be viewed. The operation of, and certain components within, the medical injector 9000 are similar in many respects to that of the medical injector 8000, and thus certain aspects are not described in detail herein. One way that the medical injector 9000 differs from the medical injector 8000 is that the dual-container medical injector 9000 includes the energy storage member on one side of the injector and the two medicament container assemblies 9200 on the other side of the injector.

Although the medical injector 5000' and the medical injector 5000 are shown and described as including an electronic circuit system integrated within the housing of the device, in other embodiments, the electronic circuit system can be an external, discrete component that is affixed to the device. For example, FIGS. 81-85 are various views of a medical injector assembly 10000 according to an embodiment. The medical injector assembly 10000 includes a medical injector 4000 and an electronic circuit system 10900. The electronic circuit system includes an electronics housing 10170 within which the electrical components and/or circuitry is disposed. The electronic circuit system 10900 can include any suitable electronic components (e.g., printed circuit boards, sensors, resistors, capacitors, inductors, switches, microcontrollers, microprocessors and/or the like) operatively coupled to produce and/or output the desired electronic signals and/or to perform the functions described herein. For example, the electronic circuit system can include any of the features of and/or perform any of the functions of any of the electronic circuit systems disclosed U.S. Pat. No. 8,226,610, entitled "Medical Injector with Compliance Tracking and Monitoring," U.S. Pat. No. 8,361,026, entitled "Apparatus and Methods for Self-administration of Vaccines and Other Medicaments," and U.S. Patent Publication No. 2014/0243749, filed on Dec. 27, 2013 and entitled "Devices, Systems and Methods for Locating and Interacting with Medicament Delivery Systems," the entirety of each of which is incorporated by reference herein.

The electronic housing 10170 includes a coupling portion 10172, a grip portion 10174, and a status aperture 10173. The coupling portion 10172 is configured to be removably coupled to the housing 4100 of the medical injector 4000. In this manner, the medical injector 4000 can be distributed separately and the electronic circuit system 10900 can be later coupled to the medical injector. This also allows for the electronic circuit system 10900 to be reused (i.e., used with more than one different delivery device). The coupling portion 10172 can include any suitable protrusions, recesses, and other features to suitably be coupled to the medical injector 4000. Moreover, when the electronic housing 10170 is coupled to the medical injector 4000, the front status window 4130 of the medical injector 4000 is viewed. Additionally, the electronic housing 10170 defines the status aperture 10173, which is aligned with the rear status window 4160 of the medical injector 4000.

The grip portion 10174 provides a location at which a user can grasp the electronic housing 10170 to manipulate the medical injector 4000.

FIGS. 86-89 are various views of a medical injector assembly 11000 according to an embodiment. The medical injector assembly 11000 includes a medical injector 4000 and an electronic circuit system 11900. The electronic circuit system includes an electronics housing 11170 within which the electrical components and/or circuitry is disposed. The electronic circuit system 11900 can include any suitable electronic components (e.g., printed circuit boards, sensors, resistors, capacitors, inductors, switches, microcontrollers, microprocessors and/or the like) operatively coupled to produce and/or output the desired electronic signals and/or to perform the functions described herein. For example, the electronic circuit system can include any of the features of and/or perform any of the functions of any of the electronic circuit systems disclosed U.S. Pat. No. 8,226,610, entitled "Medical Injector with Compliance Tracking and Monitoring," U.S. Pat. No. 8,361,026, entitled "Apparatus and Methods for Self-administration of Vaccines and Other Medicaments," and U.S. Patent Publication No. 2014/0243749, filed on Dec. 27, 2013 and entitled "Devices, Systems and Methods for Locating and Interacting with Medicament Delivery Systems," the entirety of each of which is incorporated by reference herein.

The electronic housing 11170 includes a coupling portion 11172, a grip portion 11174, and a status aperture 11173. The coupling portion 11172 is configured to be removably coupled to the housing 4100 of the medical injector 4000. In this manner, the medical injector 4000 can be distributed separately and the electronic circuit system 11900 can be later coupled to the medical injector. This also allows for the electronic circuit system 11900 to be reused (i.e., used with more than one different delivery device). The coupling portion 11172 can include any suitable protrusions, recesses, and other features to suitably be coupled to the medical injector 4000. Moreover, when the electronic housing 11170 is coupled to the medical injector 4000, the front status window 4130 of the medical injector 4000 is viewed. Additionally, the electronic housing 11170 defines the status aperture 11173, which is aligned with the rear status window 4160 of the medical injector 4000.

The grip portion 11174 provides a location at which a user can grasp the electronic housing 11170 to manipulate the medical injector 4000.

Although the medical injector assemblies 10000 and 11000 are shown and described as including the medical injector 4000, in other embodiments, the medical injector assemblies 10000 and 11000 can include any suitable medicament delivery device of the types shown and described herein. Similarly stated, the electronic circuit system 10900 can be used with and/or coupled to any of the medicament delivery devices shown and described herein.

Figure 90:
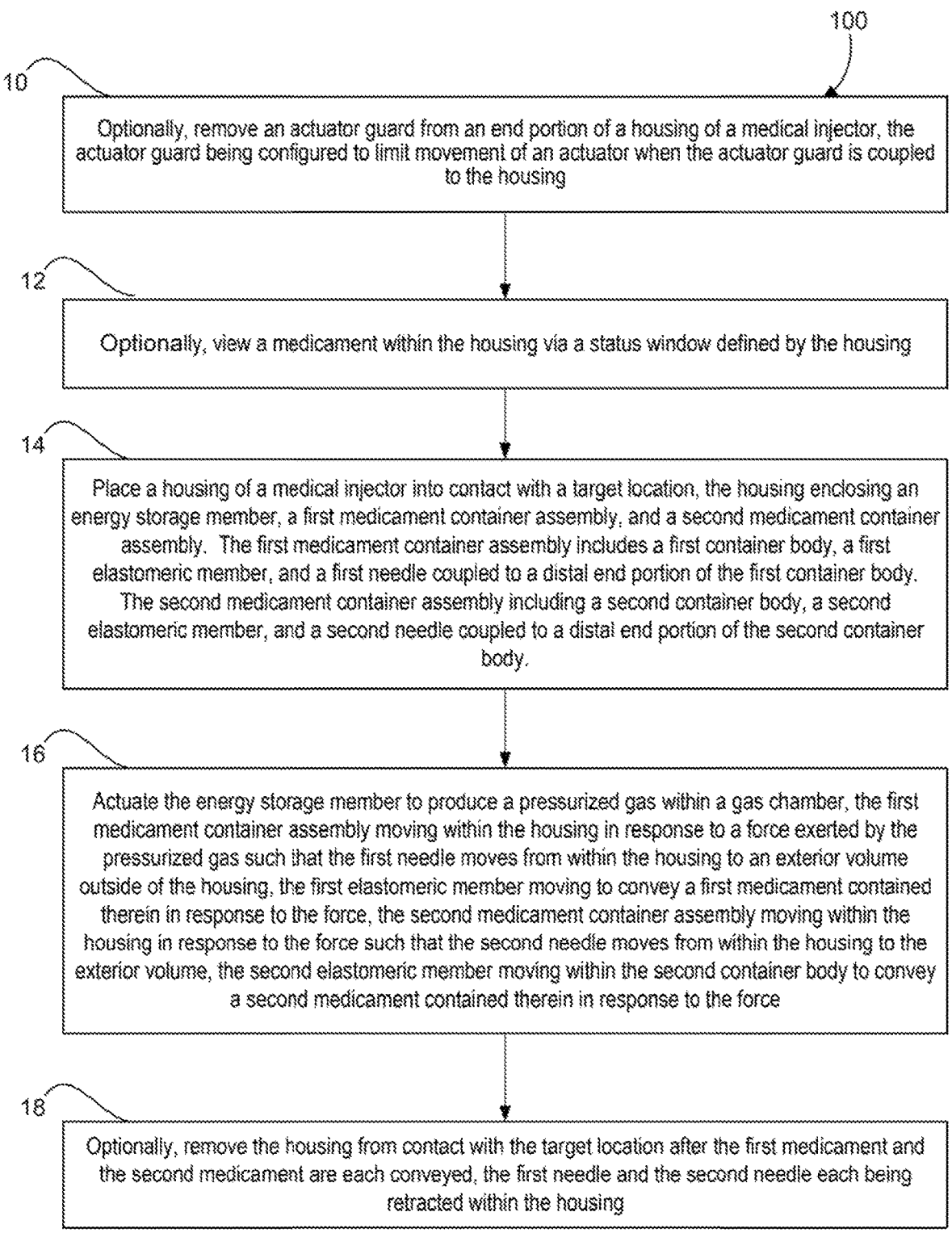
FIG. 90 is a flow chart of a method of delivering a medicament according to an embodiment.
Figure 91:
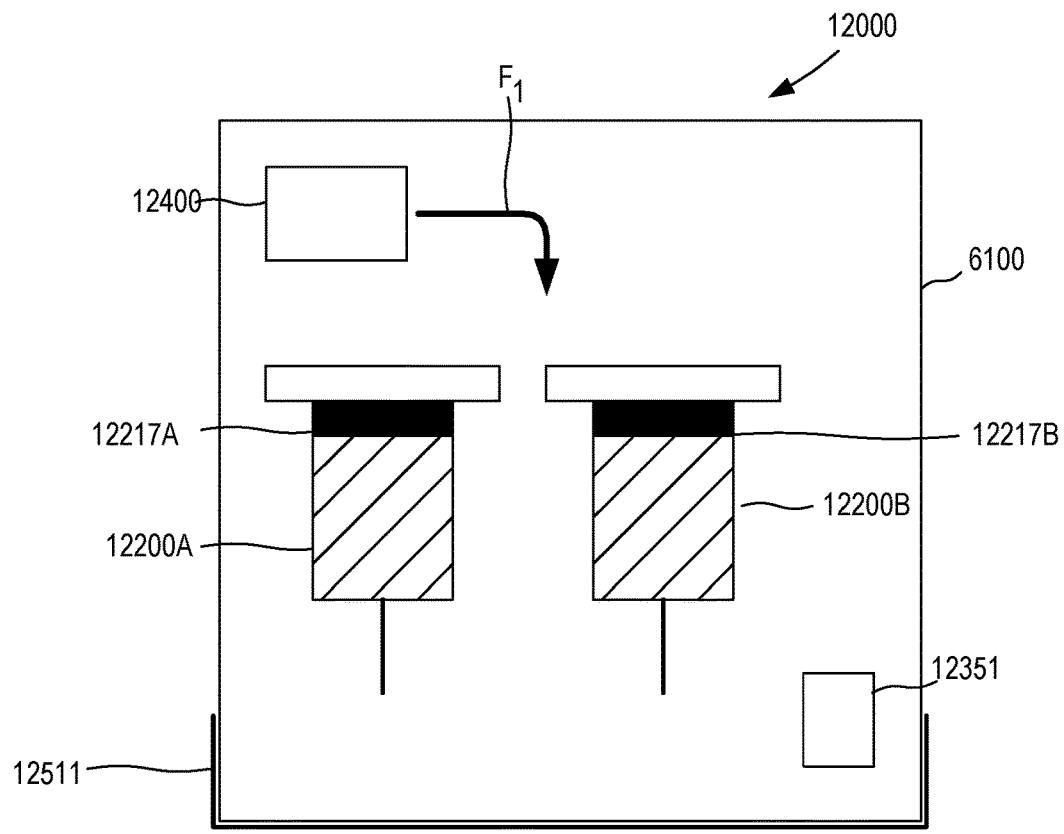
FIGS. 91-94 are schematic illustrations of a medicament delivery device according to an embodiment, in a first, second, third and fourth configuration, respectively.

In some embodiments, any of the devices shown and described herein can be used to deliver a medicament. For example, FIG. 90 is a flow chart of a method 100 of delivering a medicament via a "dual container" device, according to an embodiment. The method includes placing a housing of a medical injector into contact with a target location, 14. The housing defines a gas chamber, and encloses an energy storage member, a first medicament container assembly, and a second medicament container assembly. The first medicament container assembly includes a first container body, a first elastomeric member disposed within the first container body, and a first needle coupled to a distal end portion of the first container body. The first needle is disposed within the housing. The second medicament container assembly includes a second container body, a second elastomeric member disposed within the second container body, and a second needle coupled to a distal end portion of the second container body. The second needle is disposed within the housing. The medical injector can be any of the medical injectors shown and described herein, such as, for example, the medical injector 8000.

In some embodiments, the method 100 optionally includes removing, before the placing, an actuator guard from an end portion of the housing, 10. The actuator guard, which can be an of the guards or safety locks described herein (e.g., safety lock 8700) is configured to limit movement of the actuator when the actuator guard is coupled to the housing.

In some embodiments, the method 100 optionally includes viewing, before the placing, the first medicament within the first container body via a first status window defined by the housing, 12.

The method includes actuating the energy storage member to produce a pressurized gas within the gas chamber of the housing, 16. The first medicament container assembly moves within the housing in response to a force exerted by the pressurized gas such that the first needle moves from within the housing to an exterior volume outside of the housing. The first elastomeric member moves within the first container body to convey a first medicament contained therein in response to the force. The second medicament container assembly moves within the housing in response to the force exerted by the pressurized gas such that the second needle moves from within the housing to the exterior volume. The second elastomeric member moves within the second container body to convey a second medicament contained therein in response to the force.

In some embodiments, the method optionally includes removing the housing from contact with the target location after the first medicament and the second medicament are each conveyed, 18. This allows the first needle and the second needle to each be retracted within the housing, as described above.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, any of the devices shown and described herein can include an electronic circuit system to provide user instruction and/or feedback. In some embodiments the electronic circuit system can be integral to the device (e.g., included within the housing, such as the housing 1100). In other embodiments, the electronic circuit system can be an external, discrete component that is affixed to the device.

For example, any of the elastomeric members described herein can be constructed from any suitable material or combination of different materials. For example, in some embodiments, at least a portion of any of the elastomeric members described herein (e.g., the elastomeric members 1217, 2217, 3217, 4217) can be coated. Such coatings can include, for example, polydimethylsiloxane. In some embodiments, at least a portion of any of the elastomeric members described herein can be coated with polydimethylsiloxane in an amount of between approximately 0.02 $mg/cm^2$ and approximately 0.80 $mg/cm^2$.

Any of the medicament container assemblies described herein can have any suitable size (e.g., length and/or diameter) and can contain any suitable volume of the medicament. In some embodiments, any of the medicament container assemblies described herein (including the medicament container assemblies 1200, 2200, 3200, 4200, 5200, 6200, and 7200) can be a prefilled (or prefillable) syringe, such as those manufactured by Becton Dickinson, Gerresheimer, Ompi Pharma or others. For example, in some embodiments, the medicament container assembly 1200 (and any of the medicament container assemblies described herein) can be a Becton Dickinson "BD Hypak Physiolis" prefillable syringe containing any of the medicaments described herein. Moreover, any of the medicament delivery devices and/or medical injectors described herein can be configured to inject any suitable dosage such as, for example, a dose of up to 1 mL of any of the medicaments described herein. In other embodiments, any of the medicament delivery devices and/or medical injectors described herein can be configured to inject a dose of up to 2 mL, 3 mL, 4 mL, 5 mL, or more of any of the medicaments described herein.

Any of the container bodies described herein can be constructed from glass, and can be fitted and/or coupled to any suitable needle. For example, in some embodiments, any of the container bodies described herein (including the container bodies 1210, 2210, 3210, 4210, 5210, 6210, and 7210) can be coupled to a needle having any suitable size. Any of the medicament container assemblies and/or prefilled syringes described herein can be coupled to a needle having a gauge size of 21 gauge, 22 gauge, 23 gauge, 24 gauge, 25 gauge, 26 gauge, 27 gauge, 28 gauge, 29 gauge, 30 gauge, or 31 gauge. Any of the medicament container assemblies and/or prefilled syringes described herein can be coupled to a needle having any suitable length, such as, for example, a length of about 0.2 inches, about 0.27 inches, about 0.38 inches, about 0.5 inches, about 0.63 inches, about 0.75 inches, or more. In some embodiments, any of the medicament containers and/or prefilled syringes described herein can be coupled to a 29 gauge, needle having a length of approximately 0.5 inches. Moreover, any of the medicament containers and/or prefilled syringes described herein can include a staked needle at the distal end thereof.

Although the dual container devices shown and described herein (e.g., the medical injector 8000), are shown as including two substantially identical medicament container assemblies (e.g., the container assembly 4200), in other embodiments, a dual container delivery device can include two different medicament containers, each containing a different substance, having a different size, and/or having a different needle (different needle length, needle gauge or the like).

For example, although the medical injector 4000 is shown as having a carrier assembly 4390 that includes multiple O-ring seals, in other embodiments, any suitable sealing mechanism can be included. For example, in some embodiments, a carrier assembly can include an overmolded portion to form a seal with the housing and/or the medicament container body. In some embodiments, a carrier assembly need only include one seal between the flange of the medicament container body and the inner surface of the carrier body.

For example, any of the medical injectors shown and described herein can include a base (or distal actuator) having a mechanism for cooling the surface of the target injection site. By cooling the target injection site, patient comfort during an injection operation can be improved. Such cooling mechanisms can include, for example, an electronic cooler (e.g., a thermo-electric cooler) that is triggered upon removal of a safety guard, a chemical or spray that is emitted by the base upon removal of the safety guard, or any other suitable mechanism.

Any of the medical injectors shown and described herein can include a base (or distal actuator) having a mechanism for expanding, stretching or otherwise pulling taut a patient's skin at or near an injection site. In other embodiments, the base (or distal actuator) of any of the injectors described herein can include a mechanism that increases the surface area of the base (or distal actuator) against the injection site. For example, in some embodiments a base can include a series of grips, protrusions, microneedles, or the like that can grip the skin and expand to stretch the surface prior to actuation and/or injection or allow for a large surface area of contact against the skin for added stability for injectate administration. In other embodiments, a base can include a series of grips, protrusions, microneedles, or the like that can grip the skin and pinch the surface together prior to actuation and/or injection. Such a base can include a dome or other structure to pinch certain portions of the anatomy, such as, for example, the abdomen.

Although the medicament injectors shown and described above include a delivery mechanism (e.g., 1300) including the release of a pressurized gas, in other embodiments, a medicament delivery device can include any suitable method of delivery of a medicament disposed within. For example, in some embodiments, any of the devices described herein can include a mechanical energy storage (e.g. spring, gears, racks, pinions, pulleys, or the like) member, rather than a compressed gas container. In other embodiments, any of the devices described herein can include any other suitable energy storage member (e.g., magnetic, electrical, propellant based, chemical reaction based, or the like).

While the medical injectors herein are described as being "pistonless" gas-powered auto-injectors, in other embodiments, any of the medical injectors can include any suitable energy storage member configured to produce a force directly on a medicament container and/or a carrier (as described, for example, in the '849 patent). For example, in some embodiments, a medical injector can include one or more bias members, springs, and/or any other suitable mechanical drives (as described above) configured to exert a force on one or more medicament containers. By way of example, a medical injector can include a first spring configured to produce a force on a first medicament container and a second spring configured to produce a force, substantially equal to the force produced by the first spring, on a second medicament container. Moreover, the first spring and the second spring can be actuated substantially concurrently and/or via the same actuation event such that the first spring and second spring move the first medicament container and the second medicament container substantially concurrently.

Although some of the "dual container" injectors have been described above as being moved in response to a force produced by a single energy storage and/or the same type of energy storage member, in other embodiments, a medicament container can include any suitable combination of energy storage members. For example, in some embodiments, a medical injector can include a first compressed gas container configured to release a volume of compressed gas to move a first medicament container relative to a housing, and a second compressed gas container configured to release a volume of compressed gas to move a second medicament container relative to the housing. In other embodiments, a medical injector can include a compressed gas container configured to release a volume of compressed gas and a spring configured to transition from a first configuration to a second configuration. In such embodiments, for example, the first medicament container can be moved in response to a force associated with the expansion of the compressed gas while the second medicament container can be moved in response to a force associated with the transitioning of the spring from the first configuration to the second configuration (or vice versa). In other embodiments, the forces produced by the expansion of the compressed gas and the transitioning of the spring can be collectively exerted on both the first medicament container and the second medicament container.

Although the "dual container" injector 8000 has been described above as including a compressed gas container, in other embodiments, the medical injector 8000 and any of the injectors described herein, can use any suitable energy storage member of the types shown and described herein.

Although the embodiments have been particularly described above as moving the medicament containers in a substantially concurrent injection event, in other embodiments, a medical injector can be configured for a "staged" (or sequential) injection event. For example, in some embodiments, a medical injector can include a first energy storage member (such as any of those described herein) configured to exert a force on a first medicament container and a second energy storage member (similar to or different from the first energy storage member) configured to exert a force on a second medicament container. In such embodiments, actuation of the medical injector can result in the first energy storage member exerting the force on the first medicament container to initiate a first injection event, while the second energy storage member remains in a configuration associated with a greater potential energy (e.g., unactuated or the like). After a predetermined time after the actuation of the medical injector, the second energy storage member can exert the force on the second medicament container to initiate a second injection event. By way of example, a medical injector can include a first compressed gas storage container configured to release a volume of compressed gas to initiate an injection event associated with a first medicament container and a second compressed gas storage container configured to release a volume of compressed gas to initiate an injection event associated with a second medicament container. In such embodiments, actuation of the medical injector can result in (1) the first gas storage container being punctured (or actuated) at a first time to initiate the injection event associated with the first medicament container and (2) the second gas storage container being punctured (or actuated) at a second time, after the first time, to initiate the injection event associated with the second medicament container.

In other embodiments, the second energy storage member can exert the force on the second medicament container in response to a second actuation event. For example, a medical injector can include an actuator (e.g., a base or the like) configured to be actuated (e.g., moved) a first amount and a second amount after the first amount. By way of example, a medical injector can include a base actuator configured to be moved a first distance to actuate a first energy storage and a second distance to actuate a second energy storage member. In such embodiments, the movement of the base actuator can be substantially continuous. That is to say, the base actuator can be moved the second distance in a single continuous motion and, while moving through a distance substantially equal to the first distance, can trigger an actuation of the first energy storage member. In other embodiments, the movement of the base actuator the first amount can be a discrete operation and the movement of the base actuator the second amount can be a discrete operation.

In still other embodiments, the medical injector can include a first actuator configured to actuate the first energy storage member and a second actuator configured to actuate the second energy storage member. For example, in some embodiments, a user can manipulate the medical injector to actuate the first actuator (e.g., by moving a base or the like, as described above), which in turn actuates the first energy storage member. After the first actuator is actuated, the user can manipulate the second actuator, which in turn actuates the second energy storage member. In some embodiments, the first actuator can be configured to actuate the second actuator after an actuation event. In other embodiments, the second actuator can be discretely and/or otherwise independently actuated by the user. For example, in some embodiments, a medical injector can include a first actuator disposed on or at a first end portion of the medical injector and can include a second actuator disposed on or at a second end portion of the medical injector opposite the first end portion. In some such embodiments, the first actuator and the second actuator can be actuated and/or moved in response to forces exerted in the same direction while the medical injector is in a substantially constant orientation.

In other embodiments, a user can actuate the first actuator while the medical injector is in a first orientation and after an injection event associated with the first medicament container is complete, the user can flip the medical injector to a second orientation, substantially opposite the first orientation, to actuate the second actuator. In this manner, a needle of a first medicament container can be configured to extend from a first end of the medical injector while a needle of a second medicament container can be configured to extend from a second end of the medical injector opposite the first end. In some embodiments, the second actuator can be in a locked configuration or the like until completion of a retraction event of the first medicament container. Similarly, once the medical injector is reoriented, the first medicament container can be placed in a locked configuration. Moreover, when the medical injector is reoriented, the second actuator and/or second medicament container can be transitioned to an unlocked configuration to allow actuation of the second actuator and thus, an injection event associated with the second medicament container.

Although the medicament containers are described above as being actuated (either concurrently or independently) to perform an injection event of a medicament directly into a patient, in other embodiments, an injection event of a first medicament container or a second medicament container need not result in direct injection of the medicament into the patient. For example, in some embodiments, a medical injector can include a first medicament container including a needle coupled to a distal end portion of the first medicament container, and a second medicament container in fluid communication with the first medicament container. In such embodiments, actuation of the medical injector can result in, for example, an injection event in which the second medicament container injects a volume of medicament contained therein into the first medicament container. Moreover, in a substantially simultaneous process, the first medicament container can be moved to insert the needle into the patient. This arrangement can be such that a complete insertion of the needle into the patient substantially corresponds with and/or occurs substantially at the same time as an injection of the medicament from the second medicament container into the first medicament container.

Although particular injection events, mechanisms, devices, and/or components have been described herein, it is to be understood that they have been presented by way of example and not limitation. That is to say, an auto-injector can include more than one medicament container and can be configured to deliver at least one dose of a medicament to a patient in response any suitable actuation event and/or the like.

Any of the devices and/or medicament containers shown and described herein can be constructed from any suitable material. Such materials include glass, plastic (including thermoplastics such as cyclic olefin copolymers), or any other material used in the manufacture of prefilled syringes containing medications.

Any of the devices and/or medicament containers shown and described herein can contain and/or deliver a wide array of large or macromolecular injectables that include carbohydrate-derived formulations, lipids, nucleic acids, proteins/peptides (e.g. monoclonal antibodies) and other biotechnologically-derived medicaments. For example, anti-tumor necrosis factor agents such as infliximab, etanercept, adalimumab, golimumab, natalizumab, vedolizumab, and certolizumab can be administered using the described auto-injector heroin, Other macromolecular injectable medications that can be administered using the device and/or medicament containers shown and described herein include viscous medicaments that target pro-inflammatory cytokines (e.g. IL-1, IL-2, IL-4, IL-5, IL-6, IL-12, IL-13, IL-23, IL-17, IL-21 and associated receptors) including dupilumab, sarilumab, mepolizumab, benralizumab, reslizumab, lebrikizumab, ustekinumab, anrunkinzumab, bertilimumab, and tralokinumab. Large anti-adhesion molecules to treat a variety of diseases may be administered using the device and/or medicament containers shown and described herein including etrolizumab and vatelizumab. Still other large and viscous monoclonal antibodies that may be administered using the device and/or medicament containers shown and described herein include tezepelumab, anifrolumab, omalizumab, and proprotein convertase subtilisin kexin type 9 (PCSK9) inhibitors including alirocumab and evolocumab.

Any of the devices and/or medicament containers shown and described herein can include any suitable medicament or therapeutic agent. In some embodiments, the medicament contained within any of the medicament containers shown herein can be a vaccine, such as, for example, an influenza vaccine, a hepatitis vaccine, a *haemophilus* influenza Type B (HiB) vaccine, a measles vaccine, a mumps vaccine, a rubella vaccine, or combination vaccine (e.g. measles, mumps and rubella, quadrivalent, or hexavalent vaccines), a polio vaccine, a human papilloma virus (HPV) vaccine, a tetanus vaccine, a diphtheria vaccine, a *pertussis* vaccine, a bubonic plague vaccine, a yellow fever vaccine, a cholera vaccine, a malaria vaccine, a smallpox vaccine, a pneumococcal vaccine, a rotavirus vaccine, a varicella vaccine, a dengue fever vaccine, a rabies vaccine and/or a meningococcus vaccine. In other embodiments, the medicament contained within any of the medicament containers shown herein can be a catecholamine, such as epinephrine. In other embodiments, the medicament contained within any of the medicament containers shown herein can be an opioid receptor antagonist, such as naloxone, including any of the naloxone formulations described in U.S. Pat. No. 8,627,816, entitled "Medicament Delivery Device for Administration of Opioid Antagonists Including Formulation for Naloxone," filed on Feb. 28, 2011. In yet other embodiments, the medicament contained within any of the medicament containers shown herein can include peptide hormones such as insulin and glucagon; human growth hormone (HGH); sumatriptan; a corticosteroid such as dexamethasone; ondansetron; an opioid agonist receptor modulators such as fentanyl; a partial agonist opioid receptor modulators such as buprenorphine; a mixed agonist/antagonist opioid receptor modulator such as nalbuphine; a benzodiazepine such as diazepam, midazolam or lorazepam; erythropoiesis-stimulating agents (ESA) such as darbepoetin alfa; immunoglobulins including dual-variable domain immunoglobulins; interferons; anti-tumor; recombinant human granulocyte colony-stimulating factor (GCSF) such as pegfilgrastim; and other therapies suitable for injection in mammals. In yet other embodiments, the medicament contained within any of the medicament containers shown herein can be a placebo substance (i.e., a substance with no active ingredients), such as water.

The medicament containers and/or medicament delivery devices disclosed herein can contain any suitable amount of any medicament. For example, in some embodiments, a medicament delivery device as shown herein can be a single-dose device containing an amount medicament to be delivered of approximately 0.4 mg, 0.8 mg, 1 mg, 1.6 mg or 2 mg. As described above, the fill volume can be such that the ratio of the delivery volume to the fill volume is any suitable value (e.g., 0.4, 0.6 or the like). In some embodiments, an electronic circuit system can include "configuration switch" that, when actuated during the assembly of the delivery device, can select an electronic output corresponding to the dose contained within the medicament container.

Any of the medicament containers described herein can include any suitable elastomeric member and/or plunger. For example, an elastomeric member can be formulated to be compatible with the medicament contained within a medicament container. Moreover, a medicament container can include any number of elastomeric members. For example, in some embodiments, a medicament container can include a dry portion of a medicament and a fluid portion of the medicament, configured to be mixed before injection. The piston portion of the medicament delivery mechanism can be configured to engage multiple elastomeric members associated with the portions of the medicament. In this manner, multiple elastomeric members can be engaged to mix the dry portion with the fluid portion of the medicament before the completion of an injection event. In some embodiments, for example, any of the devices shown and described herein can include a mixing actuator similar to the mixing actuators shown and described in U.S. Pat. No. 9,173,999, entitled "Devices and Methods for Delivering Medicaments from a Multi-Chamber Container," filed Jan. 25, 2012, which is incorporated herein by reference in its entirety.

Although the injectors described herein have been shown and described as including mechanisms for needle retraction, in other embodiments any of the injectors shown and described herein can include a needle shield that extends distally after the injection to cover the exposed needle. Such a design may be used, for example, in a "pistonless" design as discussed above. For example, in some embodiments, a base of a medical injector (e.g. the base 4510 or the base 8510) can be (or include) an extending portion that, upon completion of the injection, extends distally to cover the needle. In some such embodiments, the gas vent assembly can divert all or a portion of the pressurized gas to a volume within the housing such that the diverted gas exerts a force on the base (or a portion of the base) to cause the base (or portion of the base) to extend distally to cover the needle. In other such embodiments, a spring, biasing member, or retraction member can propel the base (or portion of the base) distally.

For example, FIGS. 91-94 show schematic illustrations of a "dual container" device 12000 according to an embodiment in a first, second, third and fourth configuration, respectively. The medicament delivery device 12000 includes a housing 12100, two medicament containers 12200A and 12200B, an energy storage member 12400, a needle shield 12511, and a vent member 12351. The housing 12100 defines a gas chamber 12139 that receives a pressurized gas from the energy storage member 12400. The gas chamber 12139 can be of any suitable size and shape, and can be, for example, a portion of the volume defined by the housing 12100 within which a portion of the first medicament container 12200A and/or the second medicament container 12200B are disposed. The vent member (or mechanism) 12351 can be an opening or valve, of the types shown and described herein (e.g., with respect to the device 1000 and the device 4000). In this manner, the gas pressure within the gas chamber 12139 can be reduced upon completion of the injection event. The gas pressure can also be used to move the needle shield 12511.

The housing 12100 can be any suitable size, shape, or configuration and can be made of any suitable material. For example, in some embodiments, the housing 12100 is an assembly of multiple parts formed from a plastic material and defines a substantially rectangular shape when assembled. In other embodiments, the housing 12100 can have a substantially cylindrical shape.

The medicament containers 12200A, 12200B each have a container body that defines a volume that contains (i.e., is filled with or partially filled with) a medicament. The distal end portion of each medicament container 12200A, 12200B is coupled to a needle 12216A, 12216B, respectively, through which the medicament can be delivered. In some embodiments, the medicament container 12200A and the medicament container 12200B can each be a prefilled syringe having the needle 12216A, 12216B, respectively, staked thereto. Such prefilled syringes can be any of the types shown and described herein.

The medicament container 12200A and the medicament container 12200B each include an elastomeric member 1217A, 1217B, respectively, that seals the medicament within the container body. The elastomeric members 1217A, 1217B are configured to move within the container body to inject the medicament from the medicament container assembly 1200. The elastomeric members 1217A, 1217B can be of any design or formulation suitable for contact with the medicament, of the types shown and described herein.

Although the medicament container 12200A and the medicament container 12200B are shown as being parallel to and noncoaxial with each other, in other embodiments, the medicament container 12200A and the medicament container 12200B can be arranged in any suitable manner within the housing 12100. Moreover, although the medicament container 12200A and the medicament container 12200B are shown as being disposed within the housing 12100 without a carrier, in other embodiments, the medicament container 12200A and the medicament container 12200B can each be disposed within a carrier (or set of carriers) to facilitate movement within the housing 12100.

The energy storage member 12400 is disposed within the housing 12100, and is configured to convey a pressurized gas into the gas chamber 12139 produce a force $F_1$ (see FIGS. 51-53) to convey the contents of the two medicament containers 12200A and 12200B when the energy storage member 12400 is actuated. The energy storage member 12400 can be any suitable member or device that stores potential energy and, when actuated, produces the pressurized gas. For example, the energy storage member 12400 (and any of the energy storage members described herein) can be any of a device containing compressed gas, a device containing a vapor pressure-based propellant or the like.

Thus, when actuated the energy storage member 12400 produces a force $F_1$ to deliver the medicament contained within the medicament containers 12200A, 12200B. More specifically, the energy storage member 12400 produces the force $F_1$ that moves the medicament containers 12200A, 12200B from a first position to a second position in a first direction indicated by the arrow AA in FIG. 92 and/or that moves the plungers 12217A, 12217B from a first plunger position to a second plunger position as shown by the arrows BB in FIG. 93. By including a single energy storage member 12400, a user can initiate delivery from both medicament containers via a single actuation operation.

In some embodiments, the energy storage member 12400 can be configurable to include various amounts of stored energy without changing the size of the energy storage member. In such embodiments, therefore, a high force (e.g., to inject viscous medicaments) can be achieved in the same packaging that is used for lower viscosity medicaments. For example, in some embodiments, the energy storage member 12400 can be a compressed gas cylinder having any desired pressure (and thus, mass) of gas therein. Accordingly, the pressure and/or force (e.g., force $F_1$) can be achieved to complete the operations described herein, regardless of the medicament.

As shown, the energy storage member 12400 is operably coupled (e.g., via the gas chamber 12139) to the medicament containers 12200A, 12200B and/or the medicament therein such that the force $F_1$ delivers the medicament. In some embodiments, for example, the force $F_1$ can be transmitted to the medicament containers and/or the medicament therein via a carrier or movable member (not shown). When the medicament delivery device 12000 is actuated to produce the force $F_1$, the medicament containers 12200A, 12200B move from the first position (see FIG. 91, which corresponds to the first configuration of the medicament delivery device 12000) to the second position (see FIG. 92, which corresponds to the second configuration of the medicament delivery device 12000). As shown, the movement of the medicament containers 12200A, 12200B within the housing 12100 results in a needle insertion operation.

When the medicament containers 12200A, 12200B are in their respective second positions, the pressure within the gas chamber continues to exert a force on the elastomeric members 12217A, 12217B. This causes each elastomeric member 12217A, 12217B to move within its respective container body to expel the medicament therefrom, as shown by the arrows BB in FIG. 93. The movement of the elastomeric member 12217A, 12217B places the medicament delivery device 12000 in a third configuration.

Figure 92:
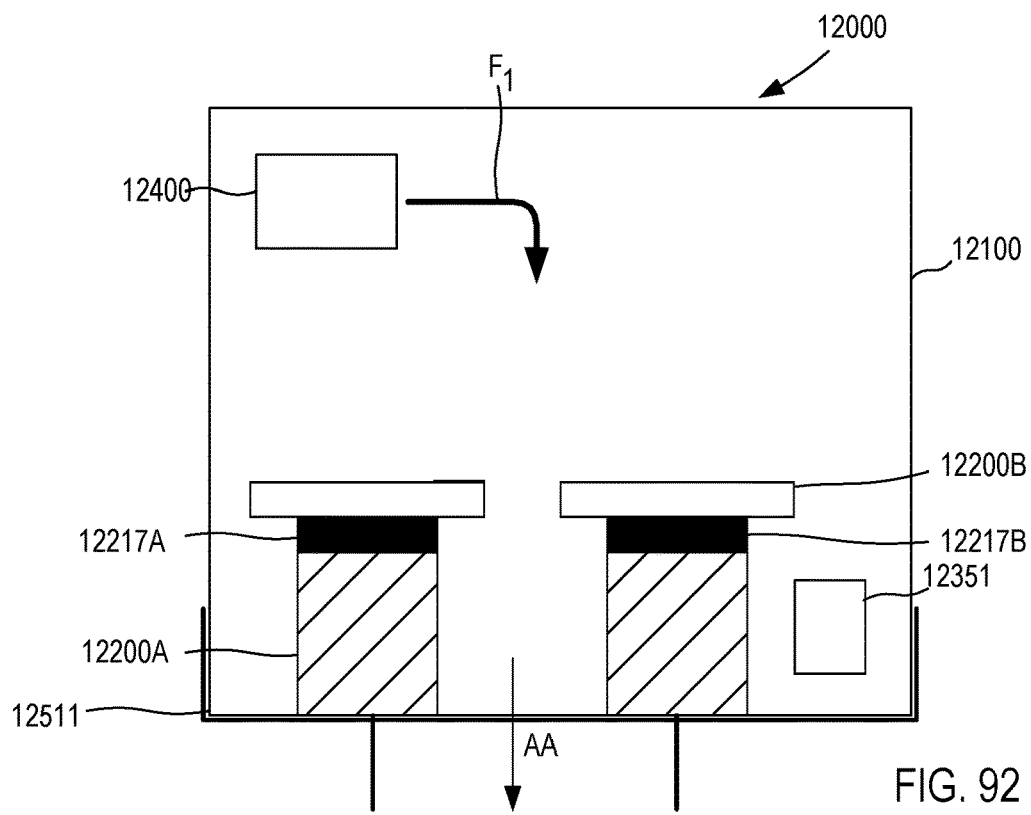
Figure 93:
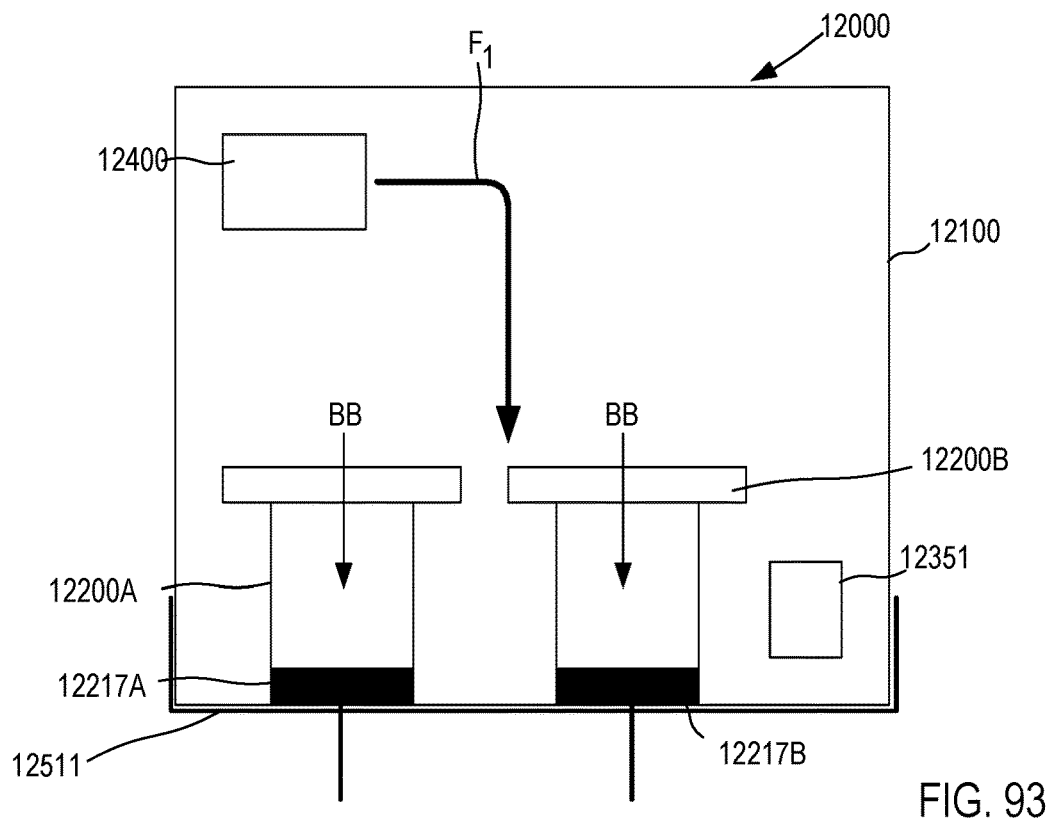
Figure 94:
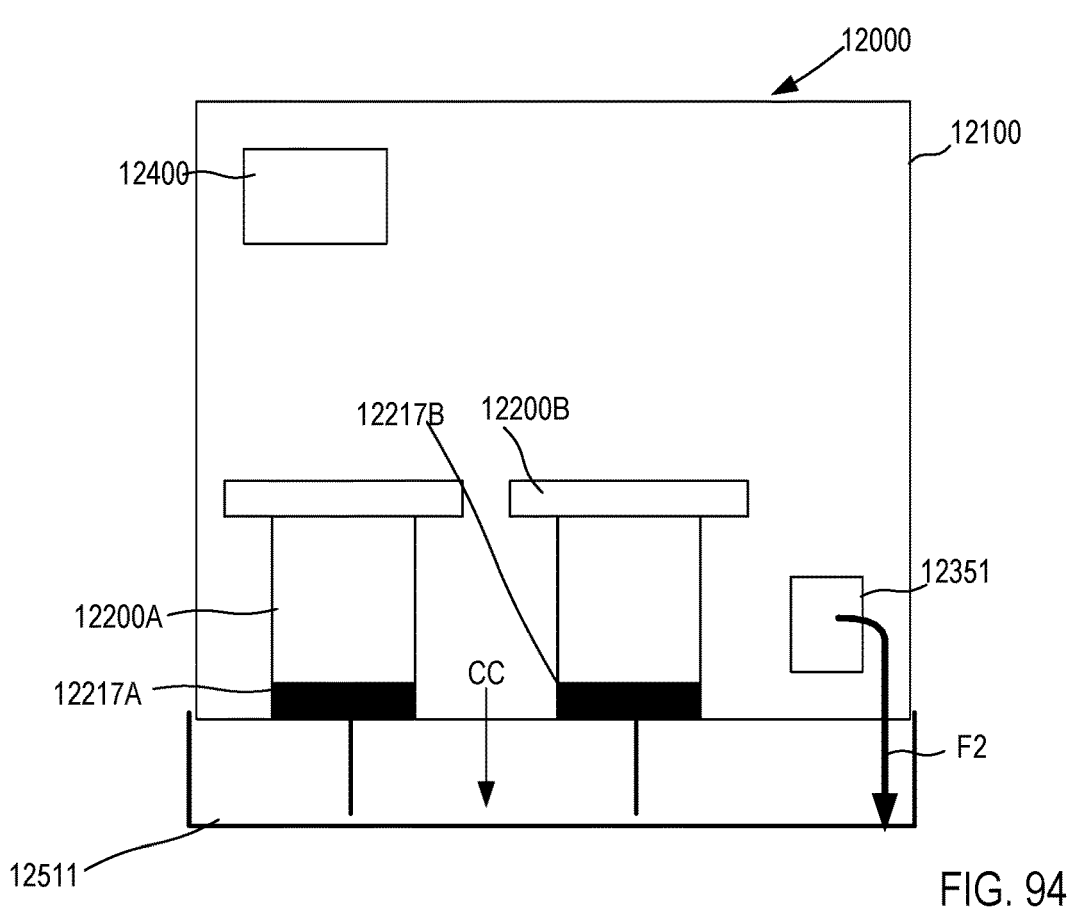

After the medicament is delivered, the vent member 12351 diverts and/or releases a portion of the pressurized gas towards the needle shield 12511. This produces an extension force $F_2$ on the needle shield 12511, which moves the needle shield 12511 to cover the needles (e.g., the second and third configuration, as shown in FIGS. 92 and 93) in the direction of the arrow CC.

In other embodiments, a portion of a needle sheath can be configured to remain within the housing during actuation, and then can be moved distally to cover the exposed needle after completion of the delivery event.

Although the gas vent assemblies 4310 and 8310 are shown and described herein as moving a valve portion relative to a seal to selectively place an internal gas chamber in fluid communication with an external volume, in other embodiments, any of the gas vent assemblies disclosed herein can be operable to vent all or a portion of the pressurized gas to a second region within the housing. Further, any of the gas vent assemblies disclosed herein can include any suitable valve arrangement. For example, in some embodiments a gas vent assembly and/or a portion a housing can include a tear-through seal that is punctured or torn when a portion of a medicament carrier or a portion of an elastomeric member moves past a specific point during a delivery event. In other embodiments, a gas vent assembly and/or a portion a housing can include a movable valve member (e.g., a poppet, ball, or the like) that is moved to release pressure when a portion of a medicament carrier or a portion of an elastomeric member moves past a specific point during a delivery event.

Although the housings are described herein as having a rectangular or cylindrical shape, in other embodiments, any of the housings described herein can have any suitable shape. For example, any of the housings described herein can have a substantially oval shape. Moreover, any of the housings described herein can be made of any suitable material, such as polymers, metallic materials, or the like. Moreover, in some embodiments, the gas chamber portion of the housing can be constructed from a metallic material to withstand the pressure exerted therein. For example, in some embodiments a portion of a medicament cavity or gas chamber can include a steel sleeve.

Although the medical injector 4000 and the medical injector 8000 are shown and described as being actuated from the distal end via the base 4510 and the base 8510, respectively, in other embodiments, any of the medicament delivery devices can be actuated in any suitable manner. For example, in some embodiments, any of the medical injectors described herein can include an actuator on a side portion of the housing that is depressed or moved inward relative to the housing to actuate the energy storage member. Such embodiments can be similar to the side actuation mechanisms (e.g., the mechanism 7450) shown and described in U.S. Pat. No. 7,648,482, entitled "Devices, Systems, and Methods for Medicament Delivery," the entire disclosure of which is incorporated herein by reference in its entirety. In other embodiments, any of the medical injectors described herein can include an actuator on a proximal of the housing that is depressed or moved inward relative to the housing to actuate the energy storage member.

In some embodiments, any of the medical injectors described herein can include a sensor-based actuator that is not moved relative to the housing to actuate the energy storage member. In such embodiments, the actuator can include a sensor that detects being disposed at an appropriate target location, and that produces a signal that is used to actuate the energy storage member.

Although the safety lock 4700 and the safety lock 8700 are shown and described as being removed from their respective housings in a distal direction, in other embodiments, any of the safety locks shown and described herein can be moved in any suitable manner to "arm" the device for use. For example, in some embodiments, a medicament delivery device can include a safety lock that remains attached to the housing (i.e., that is not removed during use). In other embodiments, the "arming" procedure can include multiple steps: first, the needle sheath can be removed, and second, a safety lock can be moved in any direction. For example, in some embodiments, any of the safety locks described herein can be a "side pull" safety lock, such as those shown and described in U.S. Pat. No. 7,648,482, entitled "Devices, Systems, and Methods for Medicament Delivery," the entire disclosure of which is incorporated herein by reference in its entirety. In other embodiments, any of the safety locks described herein can be twisted or rotated relative to the housing to enable the actuator to be moved.

In some embodiments, a safety lock initiate the removal of a needle sheath assembly without being a distal-pull safety lock. For example, in some embodiments, any of the safety locks described herein can be a "side pull" or proximally located safety lock that interacts with a needle sheath (or sheath assembly). Upon movement relative to the housing, the needle sheath (or sheath assembly) can be released from the medicament container assembly, and can fall from the device, thereby exposing the needle for use.

In some embodiments, the electronic circuit system of the types described herein can be used in either an actual medicament delivery device or a simulated medicament delivery device. A simulated medicament delivery device can, for example, correspond to an actual medicament delivery device and can, for example, facilitate training a user in the operation of the corresponding actual medicament delivery device.

The simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

Although various embodiments have been described as having particular features and/or combinations of components, other embodiments are possible having a combination of any features and/or components from any of embodiments where appropriate. For example, any of the devices shown and described herein can include an electronic circuit system as described herein.

What is claimed is:

1. An apparatus, comprising:
    a housing defining a gas chamber, a side wall of the housing defining an opening configured to selectively place the gas chamber in fluid communication with an exterior volume;
    a carrier configured to be movably disposed within the housing, the carrier configured to be coupled to a medicament container, a proximal surface of the carrier defining a portion of a boundary of the gas chamber; and
    an expandable assembly having a first member and a second member, the first member coupled to an elastomeric member disposed within the medicament container, the second member including a valve portion, the expandable assembly configured to transition from a collapsed configuration to an expanded configuration when the elastomeric member moves within the medicament container, the valve portion configured to move relative to the opening when the expandable assembly transitions from the collapsed configuration to the expanded configuration to place the gas chamber in fluid communication with the exterior volume.

2. The apparatus of claim 1, wherein the valve portion of the second member defines a gas release path, the valve portion disposed within the opening of the housing such that the gas release path is fluidically isolated from the gas chamber via a seal member when the expandable assembly is in the collapsed configuration.

3. The apparatus of claim 1, wherein:
    the carrier is configured to move from a first carrier position to a second carrier position in response to a pressurized gas being conveyed into the gas chamber such that a needle coupled to the medicament container moves from a first needle position, in which the needle is disposed within the housing, to a second needle position, in which a portion of the needle extends from the housing.

4. The apparatus of claim 3, wherein:
the housing includes a first stop surface and a second stop surface, the first stop surface configured to limit proximal movement of the carrier when the carrier is in the first carrier position, the second stop surface configured to limit distal movement of the carrier when the carrier is in the second carrier position.

5. The apparatus of claim 1, wherein an outer surface of the carrier includes a seal in sliding contact with an inner surface of the housing, the seal fluidically isolating the gas chamber from the exterior volume.

6. The apparatus of claim 1, further comprising:
the medicament container, the medicament container being a prefilled syringe having a needle staked to a distal end portion of a container body.

7. The apparatus of claim 6, wherein the medicament container contains the medicament, the medicament being any one of a drug or a biologic product.

8. The apparatus of claim 1, wherein the expandable assembly has a first length when in the collapsed configuration and a second length when in the expanded configuration, a ratio of the second length to the first length being greater than about 2.0.

9. The apparatus of claim 1, wherein:
the elastomeric member is configured to move a stroke distance within medicament container to expel a medicament contained therein in response to a pressurized gas being conveyed into the gas chamber; and
the expandable assembly has a first length when in the collapsed configuration, a ratio of the first length to the stroke distance being less than about 1.2.

10. The apparatus of claim 1, wherein:
the first member and the second member are each rigid; and
the first member defines an opening within which a portion of the second member slides when the expandable assembly moves from the collapsed configuration to the expanded configuration.

11. An apparatus, comprising:
a housing defining a gas chamber;
an energy storage member disposed within the housing, the energy storage member configured to produce a pressurized gas within the gas chamber;
a medicament container assembly disposed within the housing, the medicament container assembly including a container body and an elastomeric member disposed within the container body, the medicament container assembly including a needle coupled to a distal end portion of the container body; and
a carrier coupled to the medicament container assembly, a proximal surface of the carrier defining a portion of a boundary of the gas chamber, the carrier configured to move within the housing from a first carrier position to a second carrier position in response to a force exerted by the pressurized gas on the proximal surface of the carrier, the carrier including a first seal member and a second seal member, the first seal member in sliding contact with an inner surface of the housing to fluidically isolate the gas chamber, the second seal member in contact with a proximal end portion of the container body, the first seal member in a fixed position relative to the second seal member.

12. The apparatus of claim 11, wherein the first seal member is disposed about an outer surface of the carrier distally from the second seal member.

13. The apparatus of claim 11, wherein
a proximal end portion of the container body includes a flange; and
the second seal member is an o-ring disposed between a shoulder of the carrier and the flange.

14. The apparatus of claim 11, wherein:
the carrier defines a first groove surrounding an outer surface of the carrier and a second groove surrounding an inner surface of the carrier;
a proximal end portion of the container body includes a flange;
the first seal member is disposed within the first groove; and
the second seal member is disposed within the second groove between the proximal surface of the carrier and the flange.

15. The apparatus of claim 11, wherein the needle moves from a first needle position, in which the needle is disposed within the housing, to a second needle position, in which a portion of the needle extends from the housing, when the carrier moves from the first carrier position to the second carrier position.

16. The apparatus of claim 11, further comprising:
a retraction spring configured to move the carrier towards the first carrier position in response to the pressurized gas being conveyed out of the gas chamber via an opening defined by the housing.

17. The apparatus of claim 11, wherein the carrier defines an opening within which a portion of the medicament container assembly is disposed.

18. The apparatus of claim 11, wherein the medicament container assembly is a prefilled syringe, the needle being staked to the distal end portion of the container body.

19. The apparatus of claim 11, wherein the housing defines an opening configured to selectively place the gas chamber in fluid communication with an exterior volume, the apparatus further comprising:
an expandable assembly having a first member and a second member, the first member coupled to the elastomeric member disposed within the container body, the second member including a valve portion, the expandable assembly configured to transition from a collapsed configuration to an expanded configuration when the elastomeric member moves within the container body, the valve portion configured to move relative to the opening when the expandable assembly transitions from the collapsed configuration to the expanded configuration to place the gas chamber in fluid communication with the exterior volume.

20. The apparatus of claim 11, wherein:
the housing includes a first stop surface and a second stop surface, the first stop surface configured to limit proximal movement of the carrier when the carrier is in the first carrier position, the second stop surface configured to limit distal movement of the carrier when the carrier is in the second carrier position.

* * * * *